United States Patent
Crescenzi et al.

(10) Patent No.: US 7,217,713 B2
(45) Date of Patent: May 15, 2007

(54) N-SUBSTITUTED HYDROXYPYRIMIDINONE CARBOXAMIDE INHIBITORS OF HIV INTEGRASE

(75) Inventors: Benedetta Crescenzi, Rome (IT); Cristina Gardelli, Ariccia (IT); Ester Muraglia, Rome (IT); Emanuela Nizi, Siena (IT); Federica Orvieto, Rome (IT); Paola Pace, Rome (IT); Giovanna Pescatore, Cosenza (IT); Alessia Petrocchi, Rome (IT); Marco Poma, Grosseto (IT); Michael Rowley, Axa (IT); Rita Scarpelli, Rome (IT); Vincenzo Summa, Velletri (IT)

(73) Assignee: Istituto Di Richerche Di Biologia Molecolare P. Angeletti S.p.A., Pomezia (Rome) (IT)

( * ) Notice: Subject to any disclaimer, the term of this patent is extended or adjusted under 35 U.S.C. 154(b) by 0 days.

(21) Appl. No.: 11/491,815

(22) Filed: Jul. 24, 2006

(65) Prior Publication Data

US 2006/0258860 A1    Nov. 16, 2006

Related U.S. Application Data

(62) Division of application No. 10/493,280, filed as application No. PCT/GB02/004743 on Oct. 21, 2002.

(60) Provisional application No. 60/362,191, filed on Mar. 6, 2002, provisional application No. 60/339,658, filed on Oct. 26, 2001.

(51) Int. Cl.
*A61K 31/515* (2006.01)
*C07D 239/54* (2006.01)

(52) U.S. Cl. ............... 514/235.8; 514/252.14; 514/269; 544/122; 544/295; 544/319

(58) Field of Classification Search ............... 544/123, 544/295, 319; 514/235.8, 252.14, 269
See application file for complete search history.

(56) References Cited

U.S. PATENT DOCUMENTS

| | | | |
|---|---|---|---|
| 5,420,129 A | 5/1995 | Breu et al. | |
| 5,654,311 A | 8/1997 | Kurtz et al. | |
| 6,306,891 B1 | 10/2001 | Selnick et al. | |
| 6,333,323 B1 | 12/2001 | Fujishita et al. | |
| 6,506,787 B2 | 1/2003 | Fujishita et al. | |
| 6,620,841 B1 | 9/2003 | Fujishita et al. | |
| 6,645,956 B1 | 11/2003 | Fujishita et al. | |
| 6,716,605 B2 | 4/2004 | Fujishita et al. | |
| 6,841,558 B2 | 1/2005 | Anthony et al. | |
| 6,919,351 B2 | 7/2005 | Anthony et al. | |
| 7,091,209 B2 | 8/2006 | Gardelli et al. | |
| 2002/0019434 A1 | 2/2002 | Fujishita et al. | |
| 2003/0055071 A1 | 3/2003 | Anthony et al. | |
| 2003/0181499 A1 | 9/2003 | Fujishita et al. | |
| 2004/0002485 A1 | 1/2004 | Fujishita et al. | |
| 2004/0110804 A1 | 6/2004 | Walker et al. | |
| 2004/0127708 A1 | 7/2004 | Fuji et al. | |
| 2004/0204498 A1 | 10/2004 | Walker et al. | |
| 2004/0229892 A1 | 11/2004 | Naidu et al. | |
| 2004/0229909 A1 | 11/2004 | Kiyama et al. | |
| 2005/0010048 A1 | 1/2005 | Zhuang et al. | |
| 2005/0075356 A1 | 4/2005 | Di Francesco et al. | |

FOREIGN PATENT DOCUMENTS

| | | |
|---|---|---|
| CA | 2339272 A1 | 3/2000 |
| EP | 1422218 A1 | 5/2004 |
| EP | 601386 A1 | 6/2004 |
| WO | WO 99/32117 A1 | 7/1999 |
| WO | WO 99/62520 A1 | 12/1999 |

(Continued)

OTHER PUBLICATIONS

Miles, Medline Abstract (Community Pract, vol. 78, Issue 8, pp. 292-294) Aug. 2005.*

(Continued)

*Primary Examiner*—Deepak Rao
(74) *Attorney, Agent, or Firm*—Kenneth R. Walton; Valerie J. Camara

(57) ABSTRACT

N-substituted 5-hydroxypyrimidin-6-one-4-carboxamides of formula:

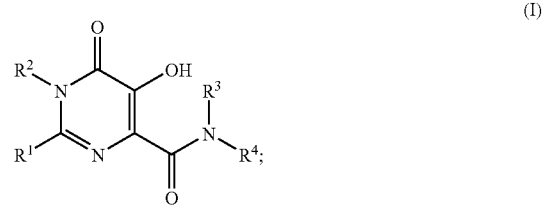

(I)

are described as inhibitors of HIV integrase and inhibitors of HIV replication, wherein $R^1$, $R^2$, $R^3$ and $R^4$ are defined herein. These compounds are useful in the prevention and treatment of infection by HIV and in the prevention, delay in the onset, and treatment of AIDS. The compounds are employed against HIV infection and AIDS as compounds per se or in the form of pharmaceutically acceptable salts. The compounds and their salts can be employed as ingredients in pharmaceutical compositions, optionally in combination with other antivirals, immunomodulators, antibiotics or vaccines. Methods of preventing, treating or delaying the onset of AIDS and methods of preventing or treating infection by HIV are also described.

12 Claims, No Drawings

FOREIGN PATENT DOCUMENTS

| WO | WO 99/62897 A1 | 12/1999 |
|---|---|---|
| WO | WO 00/51990 A1 | 9/2000 |
| WO | WO 01/00578 A1 | 1/2001 |
| WO | WO 01/85700 A2 | 11/2001 |
| WO | WO 02/06246 A1 | 1/2002 |
| WO | WO 2004/004657 A1 | 1/2004 |
| WO | WO 2004/062613 A2 | 7/2004 |

OTHER PUBLICATIONS van Heeswijk et al., PubMed Abstract (Antivir Ther. 6(4):201-29) Dec. 2001.*

Marcus et al., PubMed Abstract (Intervirology 45(4-6):260-6) 2002.*

Ratner, L., et al., "Complete Nucleotide Sequence of the AIDS Virus, HTLV-III", Nature, vol. 313, pp. 277-284, (1985).

Toh, H., et al., "Close Structural Resemblance Between Putative Polymerase of a Drosophila Transposable Genetic Element 17.6 and Pol Gene Product of Moloney Murine Leukemia Virus", EMBO Journal, vol. 4, No. 5, pp. 1267-1272, (1985).

Power, M.D., et al., "Nucleotide Sequence of SRV-1, a Type D Simian Acquired Immune Deficiency Syndrome Retrovirus", Science, vol. 231, pp. 1567-1572, (1986).

Pearl, L.H., et al., "A Structural Model for the Retroviral Proteases", Nature, vol. 329, pp. 351-354, (1987).

Ivin, B.A., et al., "Unsaturated Hydantoin Derivatives, XI.", Chemistry of Heterocyclic Compounds, vol. 10, No. 11, pp. 1342-1535 (1976) Translated from Khimiya Geterotsiklicheskikh Soedineii, No. 11, pp. 1527-1535 (1974).

Culbertson, Townley P., et al., "Synthesis of 5,6-Dihydroxy-2-phenyl-4-pyrimidinecarboxylic Acid, Methyl Ester, a Corrected Structure", Journal of Heterocyclic Chemistry, vol. 16, pp. 1423-1424, (1979).

CAPLUS No. 1992:571466, "Preparation of 2-Phenylpyrimidines as Agrochemical Fungicides", 1992, Abstract of DE4029654, plus compunds therein indexed in the CAS Registry File.

Derwent Abstract No. 2000-237546, "Antiviral Agent Containing New or Known Pyrazine, Pyrimidine, Pyridazine or Triazine Caboxamide", 2000, Abstract of WO 00/10569 (See Cite No. 13—CA2339272).

Derwent Abstract No. 2003-505255/47, "HIV Integrase Inhibitor Comprises New and Known Cyclic Compounds," 2003, Abstract of WO 03/47564.

Sunderland, Christopher, et al., "6-Carboxamido-5,4-Hydroxypyrimidinones: A New Class of Heterocyclic Ligands and Their Evaluation as Gadolinium Chelating Agents", Inorganic Chemistry, vol. 40, No. 26, pp. 6746-6756 (2001).

Mauss, S., et al., "Influence of HIV Protease Inhibitors on Hepatitis C Viral Load in Individuals with HIV and HCV Coinfection", Program and Abstracts of the Interscience Conference on Antimicrobial Agents and Chemotherapy, p. 218 (1997).

Derwent Abstract No. 2004-440941/41, "4-Oxoquinoline compounds with inhibitory activity specific to HIV integrase, useful as anti-HIV agents in preventives or remedies for AIDS particularly efficacious when in combination with e.g. protease inhibitor", 2004, Abstract of WO 2004/046115.

* cited by examiner

N-SUBSTITUTED HYDROXYPYRIMIDINONE CARBOXAMIDE INHIBITORS OF HIV INTEGRASE

This application is a divisional of pending U.S. Ser. No. 10/493,280, filed Apr. 20, 2004, which is the National Stage of International Application No. PCT/GB02/004743, filed on Oct. 21, 2002, which claims the benefit under 35 U.S.C. 119(e) of U.S. Provisional Application Nos. 60/339,658 filed on Oct. 26, 2001 and 60/362,191 filed on Mar. 6, 2002.

FIELD OF THE INVENTION

The present invention is directed to N-substituted 5-hydroxy-6-oxo-1,6-dihydropyrimidine-4-carboxamides and pharmaceutically acceptable salts thereof, their synthesis, and their use as inhibitors of the HIV integrase enzyme. The compounds and pharmaceutically acceptable salts thereof of the present invention are useful for preventing or treating infection by HIV and for treating or delaying the onset of AIDS.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhbitors such as indinavir and nelfinavir. The compounds of this invention are inhibitors of HIV integrase and inhibitors of HIV replication. The inhibition of integrase in vitro and HIV replication in cells is a direct result of inhibiting the strand transfer reaction catalyzed by the recombinant integrase in vitro in HIV infected cells. The particular advantage of the present invention is highly specific inhibition of HIV integrase and HIV replication.

SUMMARY OF THE INVENTION

The present invention is directed to novel hydroxypyrimidinone carboxamides. These compounds are useful in the inhibition of HIV integrase, the prevention of infection by HIV, the treatment of infection by HIV and in the prevention, treatment, and delay in the onset of AIDS and/or ARC, either as compounds or their pharmaceutically acceptable salts or hydrates (when appropriate), or as pharmaceutical composition ingredients, whether or not in combination with other HIV/AIDS antivirals, anti-infectives, immunomodulators, antibiotics or vaccines. More particularly, the present invention includes a compound of Formula (I):

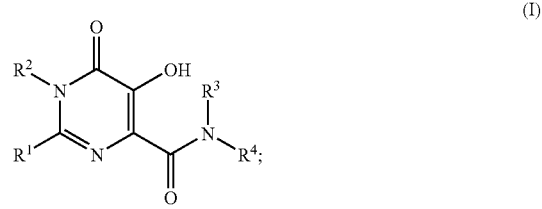

(I)

wherein
R¹ is
(1) —H,
(2) —$C_{1-6}$ alkyl, which is optionally substituted with one or more substituents (e.g., optionally from 1 to 6, or 1 to 5, or 1 to 4, or 1 to 3, or 1 or 2 substituents; or is optionally mono-substituted) each of which is independently halogen, —OH, —CN, —O—$C_{1-6}$ alkyl, —O—$C_{1-6}$ haloalkyl, —C(=O)$R^a$, —$CO_2R^a$, —$SR^a$, —S(=O)$R^a$, —N($R^aR^b$), —C(=O)—$C_{0-6}$ alkyl-N($R^aR^b$), N($R^a$)—C(=O)—$C_{0-6}$ alkyl-N($R^bR^c$), —$SO_2R^a$, —N($R^a$)$SO_2R^b$, —$SO_2N(R^aR^b)$, —N($R^a$)—C(=O)$R^b$,

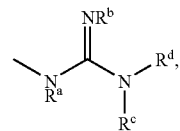

or —N($R^2$)C(=O)C(=O)N($R^aR^b$),
(3) —$R^k$,
(4) —$C_{1-6}$ alkyl-$R^k$, wherein:
  (i) the alkyl is optionally substituted with one or more substituents(e.g., optionally from 1 to 6, or 1 to 5, or 1 to 4, or 1 to 3, or 1 or 2 substituents; or is optionally mono-substituted) each of which is independently halogen, —OH, —CN, —O—$C_{1-6}$ alkyl, —O—$C_{1-6}$ haloalkyl, —N($R^aR^b$), —N($R^a$)$CO_2R^b$, —N($R^a$)C(=O)—$C_{0-6}$ alkyl-N($R^bR^c$), or —N($R^a$)—$C_{2-6}$ alkyl-OH with the proviso that the —OH is not attached to the carbon alpha to N($R^a$); and
  (ii) the alkyl is optionally mono-substituted with —$R^s$, —$C_{1-6}$ alkyl-$R^s$, —N($R^a$)—C(=O)—$C_{0-6}$ alkyl-$R^s$, —N($R^a$)—$C_{0-6}$ alkyl-$R^s$, —O—$C_{0-6}$ alkyl-$R^s$, or —N($R^a$)—C(=O)—$C_{0-6}$ alkyl-$R^s$; wherein $R^s$ is
    (a) aryl which is optionally substituted with one or more substituents (e.g., optionally from 1 to 5, or 1 to 4, or 1 to 3, or 1 or 2 substituents; or is optionally mono-substituted) each of which is independently halogen, —OH, —$C_{1-6}$ alkyl, —$C_{1-6}$ alkyl-$OR^a$, —$C_{1-6}$ haloalkyl, —O—$C_{1-6}$ alkyl, —O—$C_{1-6}$ haloalkyl, methylenedioxy attached to two adjacent carbon atoms, or aryl;

(b) a 4- to 8-membered saturated heterocyclic ring containing from 1 to 4 heteroatoms independently selected from N, O and S; wherein the saturated heterocyclic ring is optionally substituted with one or more substituents (e.g., optionally from 1 to 6, or 1 to 5, or 1 to 4, or 1 to 3, or 1 or 2 substituents; or is optionally mono-substituted) each of which is independently halogen, —$C_{1-6}$ alkyl, —$C_{1-6}$ alkyl-$OR^a$, —$C_{1-6}$ haloalkyl, —O—$C_{1-6}$ alkyl, —O—$C_{1-6}$ haloalkyl, —C(=O)$R^a$, —$CO_2R^a$, —C(=O)—$C_{0-6}$ alkyl-N($R^aR^b$), —$SO_2R^a$, oxo, aryl, or —$C_{1-6}$ alkyl-aryl; or (c) a 5- to 7-membered heteroaromatic ring containing from 1 to 4 heteroatoms independently selected from N, O and S; wherein the heteroaromatic ring is optionally substituted with one or more substituents (e.g., optionally 1 to 5, or 1 to 4, or 1 to 3, or 1 or 2 substituents; or is optionally mono-substituted) each of which is independently halogen, —$C_{1-6}$ alkyl, —$C_{1-6}$ alkyl-$OR^a$, —$C_{1-6}$ haloalkyl, —O—$C_{1-6}$ alkyl, —O—$C_{1-6}$ haloalkyl, oxo, or aryl;

(5) —$C_{0-6}$ alkyl-O—$C_{0-6}$ alkyl-$R^k$,
(6) —$C_{0-6}$ alkyl-S(O)$_n$—$C_{0-6}$ alkyl-$R^k$,
(7) —O—$C_{1-6}$ alkyl-$OR^k$,
(8) —O—$C_{1-6}$ alkyl-O—$C_{1-6}$ alkyl-$R^k$,
(9) —O—$C_{1-6}$ alkyl-S(O)$_nR^k$,
(10) —$C_{0-6}$ alkyl-N($R^a$)—$R^k$,
(11) —$C_{0-6}$ alkyl-N($R^a$)—$C_{1-6}$ alkyl-$R^k$,
(12) —$C_{0-6}$ alkyl-N($R^a$)—$C_{1-6}$ alkyl-$OR^k$,
(13) —$C_{0-6}$ alkyl-C(=O)—$R^k$,
(14) —$C_{0-6}$ alkyl-C(=O)N($R^a$)—$C_{0-6}$ alkyl-$R^k$,
(15) —$C_{0-6}$ alkyl-N($R^a$)C(=O)—$C_{0-6}$ alkyl-$R^k$,
(16) —$C_{0-6}$ alkyl-N($R^a$)C(=O)—O—$C_{0-6}$ alkyl-$R^k$, or
(17) —$C_{0-6}$ alkyl-N($R^a$)C(=O)C(=O)$R^k$;

$R^2$ is —$C_{1-6}$ alkyl which is optionally substituted with one or more substituents (e.g., optionally from 1 to 6, or 1 to 5, or 1 to 4, or 1 to 3, or 1 or 2 substituents; or is optionally mono-substituted) each of which is independently (1) halogen,
(2) —OH,
(3) —CN,
(4) —O—$C_{1-6}$ alkyl,
(5) —O—$C_{1-6}$ haloalkyl,
(6) —C(=O)$R^a$,
(7) —$CO_2R^a$,
(8) —$SR^a$,
(9) —S(=O)$R^a$,
(10) —N($R^aR^b$),
(11) —C(=O)N($R^aR^b$),
(12) —N($R^a$)—C(=O)—$C_{1-6}$ alkyl-N($R^bR^c$),
(13) —$SO_2R^a$,
(14) —N($R^a$)$SO_2R^b$,
(15) —$SO_2$N($R^aR^b$),
(16) —N($R^a$)—C($R^b$)=O,
(17) —$C_{3-8}$ cycloalkyl,
(18) aryl, wherein the aryl is optionally substituted with one or more substituents (e.g., optionally from 1 to 5, or 1 to 4, or 1 to 3, or 1 or 2 substituents; or is optionally mono-substituted) each of-which is independently halogen, —$C_{1-6}$ alkyl, —$C_{1-6}$ haloalkyl, —O—$C_{1-6}$ alkyl, —O—$C_{1-6}$ haloalkyl, —$C_{0-6}$ alkyl-N($R^aR^b$), or —$C_{1-6}$ alkyl substituted with a 5- or 6-membered saturated heterocyclic ring containing from 1 to 4 heteroatoms independently selected from N, O and S; wherein the saturated heterocyclic ring is optionally substituted with from 1 to 3 substituents each of which is independently —$C_{1-6}$ alkyl, oxo, or a 5- or 6-membered heteroaromatic ring containing from 1 to 4 heteroatoms independently selected from N, O and S; or

(19) a 5- to 8-membered monocyclic heterocycle which is saturated or unsaturated and contains from 1 to 4 heteroatoms independently selected from N, O and S; wherein the heterocycle is optionally substituted with one or more substituents (e.g., optionally from 1 to 6, or 1 to 5, or 1 to 4, or 1 to 3, or 1 or 2 substituents; or is optionally mono-substituted) each of which is independently —$C_{1-6}$ alkyl, —O—$C_{1-6}$ alkyl, oxo, phenyl, or naphthyl;

$R^3$ is —H or —$C_{1-6}$ alkyl;
$R^4$ is
(1) H,
(2) $C_{1-6}$ alkyl which is optionally substituted with one or more substituents (e.g., optionally from 1 to 6, or 1 to 5, or 1 to 4, or 1 to 3, or 1 or 2 substituents; or is optionally mono-substituted) each of which is independently halogen, —OH, O—$C_{1-6}$ alkyl, —O—$C_{1-6}$ haloalkyl, —$NO_2$, —N($R^aR^b$), —C(=O)$R^a$, —$CO_2R^a$, —$SR^a$, —S(=O)$R^a$, —$SO_2R^a$, or —N($R^a$)$CO_2R^b$, (3) $C_{1-6}$ alkyl which is optionally substituted with one or more substituents (e.g., optionally from 1 to 6, or 1 to 5, or 1 to 4, or 1 to 3, or 1 or 2 substituents; or is optionally mono-substituted) each of which is independently halogen, —OH, or O—$C_{1-4}$ alkyl, and which is substituted with 1 or 2 substituents each of which is independently:
(i) $C_{3-8}$ cycloalkyl,
(ii) aryl,
(iii) a fused bicyclic carbocycle consisting of a benzene ring fused to a $C_{5-7}$ cycloalkyl,
(iv) a 5- or 6-membered saturated heterocyclic ring containing from 1 to 4 heteroatoms independently selected from N, O and S,
(v) a 5- or 6-membered heteroaromatic ring containing from 1 to 4 heteroatoms independently selected from N, O and S, or
(vi) a 9- or 10-membered fused bicyclic heterocycle containing from 1 to 4 heteroatoms independently selected from N, O and S, wherein at least one of the rings is aromatic, (4) $C_{2-5}$ alkynyl optionally substituted with aryl,
(5) $C_{3-8}$ cycloalkyl optionally substituted with aryl,
(6) aryl,
(7) a fused bicyclic carbocycle consisting of a benzene ring fused to a $C_{5-7}$ cycloalkyl,
(8) a 5- or 6-membered saturated heterocyclic ring containing from 1 to 4 heteroatoms independently selected from N, O and S,
(9) a 5- or 6-membered heteroaromatic ring containing from 1 to 4 heteroatoms independently selected from N, O and S, or
(10) a 9- or 10-membered fused bicyclic heterocycle containing from 1 to 4 heteroatoms independently selected from N, O and S, wherein at least one of the rings is aromatic;

wherein
each aryl in (3)(ii) or the aryl (4), (5) or (6) or each fused carbocycle in (3)(iii) or the fused carbocycle in (7) is optionally substituted with one or more substituents (e.g., optionally from 1 to 5, or 1 to 4, or 1 to 3, or 1 or 2 substituents; or is optionally mono-substituted) each of which is independently halogen, —OH, —$C_{1-6}$ alkyl, —$C_{1-6}$ alkyl-$OR^a$, —$C_{1-6}$ haloalkyl, —O—$C_{1-6}$ alkyl, —O—$C_{1-6}$ haloalkyl, —CN, —$NO_2$, —$N(R^aR^b)$, —$C_{1-6}$ alkyl-$N(R^aR^b)$, —$C(=O)N(R^aR^b)$, —$C(=O)R^a$, —$CO_2R^a$, —$C_{1-6}$ alkyl-$CO_2R^a$, —$CO_2R^a$, —$SR^a$, —$S(=O)R^a$, —$SO_2R^a$, —$N(R^a)SO_2R^b$, —$SO_2N(R^aR^b)$, $N(R^a)C(=O)R^b$, —$N(R^a)CO_2R^b$, —$C_{1-6}$ alkyl-$N(R^a)CO_2R^b$, aryl, —$C_{1-6}$ alkyl-aryl, —O-aryl, or —$C_{0-6}$ alkyl-het wherein het is a 5- or 6-membered heteroaromatic ring containing from 1 to 4 heteroatoms independently selected from N, O and S, and het is optionally fused with a benzene ring, and is optionally substituted with one or more substituents (e.g., optionally from 1 to 5, or 1 to 4, or 1 to 3, or 1 or 2 substituents; or is optionally mono-substituted) each of which is independently —$C_{1-6}$ alkyl, —$C_{1-6}$ haloalkyl, —O—$C_{1-6}$ alkyl, —O—$C_{1-6}$ haloalkyl, oxo, or —$CO_2R^a$;

each saturated heterocyclic ring in (3)(iv) or the saturated heterocyclic ring in (8) is optionally substituted with one or more substituents (e.g., optionally from 1 to 6, or 1 to 5, or 1 to 4, or 1 to 3, or 1 or 2 substituents; or is optionally mono-substituted) each of which is independently halogen, —$C_{1-6}$ alkyl, —$C_{1-6}$ haloalkyl, —O—$C_{1-6}$ alkyl, —O—$C_{1-6}$ haloalkyl, oxo, aryl, or a 5- or 6-membered heteroaromatic ring containing from 1 to 4 heteroatoms independently selected from N, O and S; and each heteroaromatic ring in (3)(v) or the heteroaromatic ring in (9) or each fused bicyclic heterocycle in (3)(vi) or the fused bicyclic heterocycle in (10) is optionally substituted with one or more substituents (e.g., optionally from 1 to 6, or 1 to 5, or 1 to 4, or 1 to 3, or 1 or 2 substituents; or is optionally mono-substituted) each of which is independently halogen, —$C_{1-6}$ alkyl, —$C_{1-6}$ haloalkyl, —O—$C_{1-6}$ alkyl, —O—$C_{1-6}$ haloalkyl, oxo, aryl, or —$C_{1-6}$ alkyl-aryl;

or alternatively $R^3$ and $R^4$ together with the N to which both are attached form a $C_{3-7}$ azacycloalkyl which is optionally substituted with one or more substituents (e.g., optionally from 1 to 6, or 1 to 5, or 1 to 4, or 1 to 3, or 1 or 2 substituents; or is optionally mono-substituted) each of which is independently —$C_{1-6}$ alkyl or oxo;

each $R^a$, $R^b$, $R^c$, and $R^d$ is independently —H or —$C_{1-6}$ alkyl;

$R^k$ is carbocycle or heterocycle, wherein the carbocycle or heterocycle is optionally substituted with one or more substituents (e.g., optionally from 1 to 7, or 1 to 6, or 1 to 5, or 1 to 4, or 1 to 3, or 1 or 2 substituents; or is optionally mono-substituted) each of which is independently (1) halogen,
(2) —OH,
(3) —CN,
(4) —$C_{1-6}$ alkyl, which is optionally substituted with one or more substituents (e.g., optionally from 1 to 6, or 1 to 5, or 1 to 4, or 1 to 3, or 1 or 2 substituents; or is optionally mono-substituted) each of which is independently halogen, —OH, —CN, —O—$C_{1-6}$ alkyl, —O—$C_{1-6}$ haloalkyl, —$C(=O)R^a$, —$CO_2R^a$, —$SR^a$, —$S(=O)R^a$, —$N(R^aR^b)$, —$C(=O)—(CH_2)_{0-2}N(R^aR^b)$, $N(R^a)—C(=O)—(CH_2)_{0-2}N(R^bR^c)$, —$SO_2R^a$, —$N(R^a)SO_2R^b$, —$SO_2N(R^aR^b)$, or —$N(R^a)—C(R^b)=O$,
(5) —O—$C_{1-6}$ alkyl, which is optionally substituted with one or more substituents (e.g., optionally from 1 to 6, or 1 to 5, or 1 to 4, or 1 to 3, or 1 or 2 substituents; or is optionally mono-substituted) each of which is independently halogen, —OH, —CN, —O—$C_{1-6}$ alkyl, —O—$C_{1-6}$ haloalkyl, —$C(=O)R^a$, —$CO_2R^a$, —$SR^a$, —$S(=O)R^a$, —$N(R^aR^b)$, —$C(=O)—(CH_2)_{0-2}N(R^aR^b)$, $N(R^a)—C(=O)—(CH_2)_{0-2}N(R^bR^c)$, —$SO_2R^a$, —$N(R^a)SO_2R^b$, —$SO_2N(R^aR^b)$, or —$N(R^a)—C(R^b)=O$,
(6) —$NO_2$,
(7) oxo,
(8) —$C(=O)R^a$,
(9) —$CO_2R^a$,
(10) —$SR^a$,
(11) —$S(=O)R^a$,
(12) —$N(R^aR^b)$,
(13) —$C(=O)N(R^aR^b)$,
(14) —$C(=O)$—$C_{1-6}$ alkyl-$N(R^aR^b)$,
(15) —$N(R^a)C(=O)R^b$,
(16) —$SO_2R^a$,
(17) —$SO_2N(R^aR^b)$,
(18) —$N(R^a)SO_2R^b$,
(19) —$R^m$,
(20) —$C_{1-6}$ alkyl-$R^m$, wherein the alkyl is optionally substituted with one or more substituents (e.g., optionally from 1 to 6, or 1 to 5, or 1 to 4, or 1 to 3, or 1 or 2 substituents; or is optionally mono-substituted) each of which is independently halogen, —OH, —CN, —$C_{1-6}$ haloalkyl, —O—$C_{1-6}$ alkyl, —O—$C_{1-6}$ haloalkyl, —$C(=O)R^a$, —$CO_2R^a$, —$SR^a$, —$S(=O)R^a$, —$N(R^aR^b)$, —$N(R^a)CO_2R^b$, —$SO_2R^a$, —$N(R^a)SO_2R^b$, —$SO_2N(R^aR^b)$, or —$N(R^a)—C(R^b)=O$,
(21) —$C_{0-6}$ alkyl-$N(R^a)$—$C_{0-6}$ alkyl-$R^m$,
(22) —$C_{0-6}$ alkyl-O—$C_{0-6}$ alkyl-$R^m$,
(23) —$C_{0-6}$ alkyl-S—$C_{0-6}$ alkyl-$R^m$,
(24) —$C_{0-6}$ alkyl-$C(=O)$—$C_{0-6}$ alkyl-$R^m$,
(25) —$C(=O)$—O—$C_{0-6}$ alkyl-$R^m$,
(26) —$C(=O)N(R^a)$—$C_{0-6}$ alkyl-$R^m$,
(27) —$N(R^a)C(=O)$—$R^m$,
(28) —$N(R^a)C(=O)$—$C_{1-6}$ alkyl-$R^m$, wherein the alkyl is optionally substituted with one or more substituents (e.g., optionally from 1 to 6, or 1 to 5, or 1 to 4, or 1 to 3, or 1 or 2 substituents; or is optionally mono-substituted) each of which is independently halogen, —OH, —CN, —$C_{1-6}$ haloalkyl, —O—$C_{1-6}$ alkyl, —O—$C_{1-6}$ haloalkyl, —$C(=O)R^a$, —$CO_2R^a$, —$SR^a$, —$S(=O)R^a$, —$N(R^aR^b)$, —$N(R^a)CO_2R^b$, —$SO_2R^a$, —$N(R^a)SO_2R^b$, —$SO_2N(R^aR^b)$, or —$N(R^a)—C(R^b)=O$,
(29) —$N(R^a)$—$C(=O)$—$N(R^b)$—$C_{0-6}$ alkyl-$R^m$,
(30) —$N(R^a)$—$C(=O)$—O—$C_{0-6}$ alkyl-$R^m$,
(31) —$N(R^a)$—$C(=O)$—$N(R^b)$—$SO_2$—$C_{0-6}$ alkyl-$R^m$,
(32) —$C(=O)$—$C(=O)$—$N(R^aR^b)$,
(33) —$C(=O)$—$C_{1-6}$ alkyl-$SO_2R^a$, or
(34) —$C(=O)$—$C(=O)R^m$;

carbocycle in $R^k$ is (i) a $C_3$ to $C_8$ monocyclic, saturated or unsaturated ring, (ii) a $C_7$ to $C_{12}$ bicyclic ring system, or (iii) a $C_{11}$ to $C_{1-6}$ tricyclic ring system, wherein each ring in (ii) or (iii) is independent of or fused to the other ring or rings and each ring is saturated or unsaturated;

heterocycle in $R^k$ is (i) a 4- to 8-membered, saturated or unsaturated monocyclic ring, (ii) a 7- to 12-membered bicyclic ring system, or (iii) an 11 to 16-membered tricyclic ring system; wherein each ring in (ii) or (iii) is independent of or fused to the other ring or rings and each ring is saturated or unsaturated; the monocyclic ring, bicyclic ring system, or tricyclic ring system contains from 1 to 6 heteroatoms selected from N, O and S and a balance of carbon atoms; and wherein any one or more of the nitrogen and sulfur heteroatoms is optionally be oxidized, and any one or more of the nitrogen heteroatoms is optionally quaternized;

each $R^m$ is independently $C_{3-8}$ cycloalkyl; aryl; a 5- to 8-membered monocyclic heterocycle which is saturated or unsaturated and contains from 1 to 4 heteroatoms independently selected from N, O and S; or a 9- to 10-membered bicyclic heterocycle which is saturated or unsaturated and contains from 1 to 4 heteroatoms independently selected from N, O and S; wherein any one or more of the nitrogen and sulfur heteroatoms in the heterocycle or bicyclic heterocycle is optionally oxidized and any one or more of the nitrogen heteroatoms is optionally quaternized; and wherein the cycloalkyl or the aryl defined in $R^m$ is optionally substituted with one or more substituents (e.g., optionally from 1 to 5, or 1 to 4, or 1 to 3, or 1 or 2 substituents; or is optionally mono-substituted) each of which is independently halogen, —$C_{1-6}$ alkyl optionally substituted with —O—$C_{1-4}$ alkyl, —$C_{1-6}$ haloalkyl, —O—$C_{1-6}$ alkyl, —O—$C_{1-6}$ haloalkyl, —N($R^aR^b$), aryl, or —$C_{1-6}$ alkyl-aryl; and the monocyclic or bicyclic heterocycle defined in $R^m$ is optionally substituted with one or more substituents (e.g., optionally from 1 to 6, or 1 to 5, or 1 to 4, or 1 to 3, or 1 or 2 substituents; or is optionally mono-substituted) each of which is independently halogen, —$C_{1-6}$ alkyl, —$C_{1-6}$ haloalkyl, —O—$C_{1-6}$ alkyl, —O—$C_{1-6}$ haloalkyl, oxo, aryl, —$C_{1-6}$ alkyl-aryl, —C(=O)-aryl, —$CO_2$-aryl, —$CO_2$—$C_{1-6}$ alkyl-aryl, a 5- or 6-membered saturated heterocyclic ring containing from 1 to 4 heteroatoms independently selected from N, O and S, or a 5- or 6-membered heteroaromatic ring containing from 1 to 4 heteroatoms independently selected from N, O and S; and each n is independently an integer equal to zero, 1 or 2;

or a pharmaceutically acceptable salt thereof.

The present invention also includes pharmaceutical compositions containing a compound of the present invention and methods of preparing such pharmaceutical compositions. The present invention further includes methods of treating AIDS, methods of delaying the onset of AIDS, methods of preventing AIDS, methods of preventing infection by HIV, and methods of treating infection by HIV.

Other embodiments, aspects and features of the present invention are either further described in or will be apparent from the ensuing description, examples and appended claims.

DETAILED DESCRIPTION OF THE INVENTION

The present invention includes the N-substituted hydroxypyrimidinone carboxamides of Formula (I) above. These compounds and pharmaceutically acceptable salts thereof are HIV integrase inhibitors.

An embodiment of the present invention is a compound of Formula (I) exactly as defined above, except that in the definition of $R^k$, $R^k$ is optionally substituted with one or more substituents each of which is independently one of the substituents (1) to (18), and is optionally mono-substituted with one of the substituents (19) to (34).

Another embodiment of the present invention is a compound of Formula (I) as originally defined above, except that the definition of $R^2$ includes a proviso that none of the following optional substituents is attached to the carbon atom in the —$C_{1-6}$ alkyl group that is attached to the ring nitrogen: halogen, —OH, —O—$C_{1-6}$ alkyl, —O—$C_{1-6}$ haloalkyl, —$SR^a$, —S(=O)$R^a$, or —N($R^a$)—C($R^b$)=O. Stated another way, none of these substituents is attached to the carbon atom alpha to the ring nitrogen.

Another embodiment of the present invention is a compound of Formula (I) as originally defined above except that in the definition of $R^1$, $R^1$ is one of substitutents (1) to (16) and in the definition of $R^k$, $R^k$ is optionally substituted with one or more substituents (e.g., optionally from 1 to 7, or 1 to 6, or 1 to 5, or 1 to 4, or 1 to 3, or 1 to 2 substituents, or is optionally monosubstituted) each of which is independently one of substitutents (1) to (31).

Another embodiment of the present invention is a compound of Formula (I), wherein $R^1$ is:

(1) —H, (2) —$C_{1-6}$ alkyl, which is optionally substituted with one or more substituents each of which is independently halogen, —OH, —CN, —O—$C_{1-6}$ alkyl, —O—$C_{1-6}$ haloalkyl, —C(=O)$R^a$, —$CO_2R^a$, —$SR^a$, —S(=O)$R^a$, —N($R^aR^b$), —C(=O)—(CH$_2$)$_{0-3}$—N($R^aR^b$), N($R^a$)—C(=O)—(CH$_2$)$_{0-3}$—N($R^bR^c$), —$SO_2R^a$, —N($R^a$)$SO_2R^b$, —$SO_2$N($R^aR^b$), —N($R^a$)—C(=O)$R^b$,

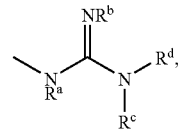

or —N($R^2$)C(=O)C(=O)N($R^aR^b$), (3) $R^k$, (4) —(CH$_2$)$_{1-3}$—$R^k$, wherein:

(i) the —(CH$_2$)$_{1-3}$— moiety is optionally substituted with one or more substituents each of which is independently halogen, —OH, —CN, —O—$C_{1-6}$ alkyl, —O—$C_{1-6}$ haloalkyl, —N($R^aR^b$), —N($R^a$)$CO_2R^b$, —N($R^a$)C(=O)—(CH$_2$)$_{0-3}$—N($R^bR^c$), or —N($R^a$)—(CH$_2$)$_{2-3}$—OH with the proviso that the —OH is not attached to the carbon alpha to N($R^a$); and (ii) the —(CH$_2$)$_{1-3}$— moiety is optionally mono-substituted with —$R^s$, —$C_{1-6}$ alkyl-$R^s$, —N($R^a$)—C(=O)—(CH$_2$)$_{0-3}$—$R^s$, —N($R^a$)—(CH$_2$)$_{0-3}$—$R^s$, —O—(CH$_2$)$_{0-3}$—$R^s$, or —N($R^a$)—C(=O)—(CH$_2$)$_{0-3}$—$R^s$; wherein $R^s$ is (a) aryl which is optionally substituted with one or more substituents each of which is independently halogen, —OH, —$C_{1-6}$ alkyl, —$C_{1-6}$ alkyl-$OR^a$, —$C_{1-6}$ haloalkyl, —O—$C_{1-6}$ alkyl, —O—$C_{1-6}$ haloalkyl, methylenedioxy attached to two adjacent carbon atoms, or aryl;

(b) a 4- to 8-membered saturated heterocyclic ring containing from 1 to 4 heteroatoms independently selected from N, O and S; wherein the saturated heterocyclic ring is optionally substituted with one or more substituents each of which is independently halogen, —$C_{1-6}$ alkyl, —$C_{1-6}$ alkyl-$OR^a$, —$C_{1-6}$ haloalkyl, —O—$C_{1-6}$ alkyl, —O—$C_{1-6}$ haloalkyl, —C(=O)$R^a$, —$CO_2R^a$, —C(=O)—(CH$_2$)$_{0-3}$—N($R^aR^b$), —$SO_2R^a$, oxo, aryl, or —(CH$_2$)$_{1-3}$-aryl; or (c) a 5- to 7-membered heteroaromatic ring containing from 1 to 4 heteroatoms independently selected from N, O and S; wherein the heteroaromatic ring is optionally substituted with one or more substituents each of which is independently halogen, —$C_{1-6}$ alkyl, —$C_{1-6}$ alkyl-$OR^a$, —$C_{1-6}$ haloalkyl, —O—$C_{1-6}$ alkyl, —O—$C_{1-6}$ haloalkyl, oxo, or aryl;

(5) —$(CH_2)_{0-3}$—O—$(CH_2)_{0-3}$—$R^k$,
(6) —$(CH_2)_{0-3}$—S(O)$_n$—$(CH_2)_{0-3}$—$R^k$,
(7) —$(CH_2)_{1-3}$—$OR^k$,
(8) —$(CH_2)_{1-3}$—O—$(CH_2)_{1-3}$—$R^k$,
(9) —O—$(CH_2)_{1-3}$—S(O)$_n R^k$,
(10) —$(CH_2)_{0-3}$—N($R^a$)—$R^k$,
(11) —$(CH_2)_{0-3}$—N($R^a$)—$(CH_2)_{1-3}$—$R^k$,
(12) —$(CH_2)_{0-3}$—N($R^a$)—$(CH_2)_{1-3}$—$OR^k$,
(13) —$(CH_2)_{0-3}$—C(=O)—$R^k$,
(14) —$(CH_2)_{0-3}$—C(=O)N($R^a$)—$(CH_2)_{0-3}$—$R^k$,
(15) —$(CH_2)_{0-3}$—N($R^a$)C(=O)—$(CH_2)_{0-3}$—$R^k$,
(16) —$(CH_2)_{0-3}$—N($R^a$)C(=O)—O—$(CH_2)_{0-3}$—$R^k$,
(17) —C($CH_3$)$_2$N($R^a$)C(=O)$R^b$,
(18) —C($CH_3$)$_2$N($R^a$)C(=O)$R^k$, or
(19) —C($CH_3$)$_2$N($R^a$)C(=O)C(=O)N($R^b R^c$);

and all other variables are as originally defined above;
or a pharmaceutically acceptable salt thereof.

In an aspect of this embodiment, $R^1$ is one of groups (1) to (16).

Another embodiment of the present invention is a compound of Formula (I), wherein $R^1$ is:

(1) —H,
(2) —$C_{1-4}$ alkyl, which is optionally substituted with from 1 to 4 substituents each of which is independently halogen, —OH, —CN, —O—$C_{1-4}$ alkyl, —O—$C_{1-4}$ haloalkyl, —C(=O)$R^a$, —$CO_2 R^a$, —$SR^a$, —S(=O)$R^a$, —N($R^a R^b$), —C(=O)—$C_{0-4}$ alkyl-N($R^a R^b$), N($R^a$)—C(=O)—$C_{0-4}$ alkyl-N($R^b R^c$), —$SO_2 R^a$, —N($R^a$)$SO_2 R^b$, —$SO_2$N($R^a R^b$), —N($R^a$)—C(=O)$R^b$,

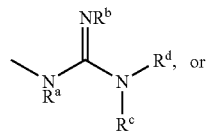

—N($R^2$)C(=O)C(=O)N($R^a R^b$),
(3) —$R^k$,
(4) —$C_{1-4}$ alkyl-$R^k$, wherein:
  (i) the alkyl is optionally substituted with from 1 to 4 substituents each of which is independently halogen, —OH, —CN, —O—$C_{1-4}$ alkyl, —O—$C_{1-4}$ haloalkyl, —N($R^a R^b$), —N($R^a$)$CO_2 R^b$, —N($R^a$)C(=O)—$C_{0-4}$ alkyl-N($R^b R^c$), or —N($R^a$)—$(CH_2)_{2-4}$—OH; and
  (ii) the alkyl is optionally mono-substituted with —$R^s$, —N($R^a$)—C(=O)—$C_{0-4}$ alkyl-$R^s$, —N($R^a$)—$C_{0-4}$ alkyl-$R^s$, —O—$C_{0-4}$ alkyl-$R^s$, or —N($R^a$)—C(=O)—$C_{0-4}$ alkyl-$R^s$; wherein $R^s$ is
    (a) aryl which is optionally substituted with from 1 to 3 substituents each of which is independently halogen, —OH, —$C_{1-4}$ alkyl, —$C_{1-4}$ alkyl-$OR^a$, —$C_{1-4}$ haloalkyl, —O—$C_{1-4}$ alkyl, —O—$C_{1-4}$ haloalkyl, methylenedioxy attached to two adjacent carbon atoms, or phenyl;
    (b) a 5- or 6-membered heteroaromatic ring containing from 1 to 4 heteroatoms independently selected from N, O and S; wherein the heteroaromatic ring is optionally substituted with from 1 to 3 substituents each of which is independently halogen, —$C_{1-4}$ alkyl, —$C_{1-4}$ alkyl-$OR^a$, —$C_{1-4}$ haloalkyl, —O—$C_{1-4}$ alkyl, —O—$C_{1-4}$ haloalkyl, oxo, or phenyl; or
    (c) a 5- or 6-membered saturated heterocyclic ring containing from 1 to 4 heteroatoms independently selected from N, O and S; wherein the saturated heterocyclic ring is optionally substituted with from 1 to 3 substituents each of which is independently halogen, —$C_{1-4}$ alkyl, —$C_{1-4}$ alkyl-$OR^a$, —$C_{1-4}$ haloalkyl, —O—$C_{1-4}$ alkyl, —O—$C_{1-4}$ haloalkyl, —C(=O)$R^a$, —$CO_2 R^a$, —C(=O)—$C_{0-4}$ alkyl-N($R^a R^b$), —$SO_2 R^a$, oxo, or phenyl,
(5) —$(CH_2)_{0-3}$—C(=O)N($R^a$)—$(CH_2)_{0-3}$—$R^k$,
(6) —C($C_{1-4}$ alkyl)$_2$N($R^a$)C(=O)$R^b$,
(7) —C($C_{1-4}$ alkyl)$_2$N($R^a$)C(=O)$R^k$, or
(8) —C($C_{1-4}$ alkyl)$_2$N($R^a$)C(=O)C(=O)N($R^b R^c$);
and all other variables are as originally defined above;
or a pharmaceutically acceptable salt thereof.

In an aspect of this embodiment, $R^1$ is one of groups (1) to (5).

Another embodiment of the present invention is a compound of Formula (I), wherein $R^1$ is:

(1) —H,
(2) —$C_{1-4}$ alkyl, which is optionally substituted with from 1 to 3 substituents each of which is independently halogen, —O—$C_{1-4}$ alkyl, —O—$C_{1-4}$ haloalkyl, —C(=O)$R^a$, —$CO_2 R^a$, —N($R^a R^b$), or —C(=O)—$(CH_2)_{0-2}$-N($R^a R^b$),
(3) —$R^k$,
(4) —$(CH_2)_{1-4}$—$R^k$, wherein:
  (i) the —$(CH_2)_{1-4}$— moiety is optionally substituted with 1 or 2 substituents each of which is independently halogen, —OH, —O—$C_{1-4}$ alkyl, —O—$C_{1-4}$ haloalkyl, or —N($R^a R^b$); and
  (ii) the —$(CH_2)_{1-4}$— moiety is optionally mono-substituted with —$R^s$ or —N($R^a$)—$(CH_2)_{1-2}$—$R^s$; wherein $R^s$ is
    (a) phenyl which is optionally substituted with from 1 to 3 substituents each of which is independently halogen, —$C_{1-4}$ alkyl, —$C_{1-4}$ alkyl-$OR^a$, —$C_{1-4}$ haloalkyl, —O—$C_{1-4}$ alkyl, or —O—$C_{1-4}$ haloalkyl; or
    (b) a 5- or 6-membered heteroaromatic ring containing from 1 to 4 heteroatoms independently selected from N, O and S; wherein the heteroaromatic ring is optionally substituted with from 1 to 3 substituents each of which is independently halogen, —$C_{1-4}$ alkyl, —$C_{1-4}$ alkyl-$OR^a$, —$C_{1-4}$ haloalkyl, —O—$C_{1-4}$ alkyl, or —O—$C_{1-4}$ haloalkyl; or
    (c) a 5- or 6-membered saturated heterocyclic ring containing from 1 to 4 heteroatoms independently selected from N, O and S; wherein the saturated heterocyclic ring is optionally substituted with from 1 to 3 substituents each of which is independently halogen, —$C_{1-4}$ alkyl, —$C_{1-4}$ alkyl-$OR^a$, —$C_{1-4}$ haloalkyl, —O—$C_{1-4}$ alkyl, —O—$C_{1-4}$ haloalkyl, —C(=O)$R^a$, or —$CO_2 R^a$,
(5) —C(=O)N($R^a$)—$(CH_2)_{0-3}$—$R^k$,
(6) —C($CH_3$)$_2$N($R^a$)C(=O)$R^b$,
(7) —C($CH_3$)$_2$N($R^a$)C(=O)$R^k$,
(8) —C($CH_3$)$_2$N($R^a$)C(=O)C(=O)N($R^b R^c$);
and all other variables are as originally defined above;
or a pharmaceutically acceptable salt thereof.

In an aspect of this embodiment, $R^1$ is one of groups (1) to (5).

Another embodiment of the present invention is a compound of Formula (I), wherein
$R^k$ is $C_{3-8}$ cycloalkyl; aryl selected from phenyl and naphthyl; a bicyclic carbocycle selected from indanyl and tetrahydronaphthyl; a 5- or 6-membered saturated heterocyclic ring containing from 1 to 4 heteroatoms independently selected from N, O and S; a 5- or 6-membered heteroaromatic ring containing from 1 to 4 heteroatoms independently selected from N, O and S; or a bicyclic heterocycle which is a benzene ring fused to a 5- or 6-membered saturated or unsaturated heterocyclic ring containing from 1 to 3 heteroatoms independently selected from N, O and S;

wherein the cycloalkyl, aryl, bicyclic carbocycle, saturated heterocyclic ring, heteroaromatic ring, or bicyclic heterocycle is optionally substituted with from 1 to 4 substituents each of which is independently (1) halogen,
(2) —OH,
(3) —CN,
(4) —$C_{1-4}$ haloalkyl,
(5) —$C_{1-4}$ alkyl, which is optionally substituted with from 1 to 3 substituents each of which is independently —OH, —CN, —O—$C_{1-4}$ alkyl, —O—$C_{1-4}$ haloalkyl, —C(=O)$R^a$, —CO$_2R^a$, —S$R^a$, —S(=O)$R^a$, —N($R^aR^b$), —C(=O)—(CH$_2$)$_{0-2}$N($R^aR^b$), N($R^a$)—C(=O)—(CH$_2$)$_{0-2}$N($R^bR^c$), —SO$_2R^a$, —N($R^a$)SO$_2R^b$, —SO$_2$N($R^aR^b$), or —N($R^a$)—C($R^b$)=O,
(6) —O—$C_{1-4}$ haloalkyl
(7) —O—$C_{1-4}$ alkyl, which is optionally substituted with from 1 to 3 substituents each of which is independently —OH, —CN, —O—$C_{1-6}$ alkyl, —O—$C_{1-6}$ haloalkyl, —C(=O)$R^a$, —CO$_2R^a$, —S$R^a$, —S(=O)$R^a$, —N($R^aR^b$), —C(=O)—(CH$_2$)$_{0-2}$N($R^aR^b$), N($R^a$)—C(=O)—(CH$_2$)$_{0-2}$N($R^bR^c$), —SO$_2R^a$, —N($R^a$)SO$_2R^b$, —SO$_2$N($R^aR^b$), or —N($R^a$)—C($R^b$)=O,
(8) —NO$_2$,
(9) oxo,
(10) —C(=O)$R^a$,
(11) —CO$_2R^a$,
(12) —S$R^a$,
(13) —S(=O)$R^a$,
(14) —N($R^aR^b$),
(15) —C(=O)N($R^aR^b$),
(16) —C(=O)—$C_{1-6}$ alkyl-N($R^aR^b$),
(17) —N($R^a$)C(=O)$R^b$,
(18) —SO$_2R^a$,
(18) —SO$_2$N($R^aR^b$),
(19) —N($R^a$)SO$_2R^b$,
(20) —$R^m$,
(21) —$C_{1-4}$ alkyl-$R^m$,
(22) —(CH$_2$)$_{0-2}$—N($R^a$)—(CH$_2$)$_{0-2}$—$R^m$,
(23) —(CH$_2$)$_{0-2}$—O—(CH$_2$)$_{0-2}$—$R^m$,
(24) —(CH$_2$)$_{0-2}$—S—(CH$_2$)$_{0-2}$—$R^m$,
(25) —(CH$_2$)$_{0-2}$—C(=O)—(CH$_2$)$_{0-2}$—$R^m$,
(26) —C(=O)—O—(CH$_2$)$_{0-2}$—$R^m$,
(27) —C(=O)N($R^a$)—$R^m$, or
(28) —C(=O)—C(=O)N($R^aR^b$);
and all other variables are as originally defined above;
or a pharmaceutically acceptable salt thereof.

In an aspect of this embodiment, the cycloalkyl, aryl, bicyclic carbocycle, saturated heterocyclic ring, heteroaromatic ring, or bicyclic heterocycle is optionally substituted with from 1 to 4 substituents each of which is independently selected from the groups (1) to (27).

In an aspect of this embodiment, $R^k$ (i.e., the cycloalkyl, aryl, bicyclic carbocycle, saturated heterocyclic ring, heteroaromatic ring, or bicyclic heterocycle) is optionally substituted with from 1 to 4 substituents each of which is independently one of the substituents (1) to (19), and is optionally mono-substituted with one of the substituents (20) to (28). In a feature of this aspect, $R^k$ is optionally substituted with from 1 to 4 substituents each of which is independently one of the substituents (1) to (19), and is mono-substituted with one of the substituents (20) to (28).

In another aspect of this embodiment, each $R^m$ is independently $C_{3-7}$ cycloalkyl; aryl selected from phenyl and naphthyl; a 5- or 6-membered saturated heterocyclic ring containing from 1 to 4 heteroatoms independently selected from N, O and S; a 5- or 6-membered heteroaromatic ring containing from 1 to 4 heteroatoms independently selected from N, O and S, wherein any N is optionally oxidized to form an N-oxide; or a bicyclic heterocycle which is a benzene ring fused to a 5- or 6-membered, saturated or unsaturated heterocyclic ring containing from 1 to 3 heteroatoms selected from N, O and S; wherein the cycloalkyl or the aryl defined in $R^m$ is optionally substituted with from 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, —N($R^aR^b$), phenyl, or —(CH$_2$)$_{1-2}$-phenyl;

the saturated heterocyclic ring defined in $R^m$ is optionally substituted with from 1 to 4 substituents each of which is independently —$C_{1-4}$ alkyl optionally substituted with —O—$C_{1-4}$ alkyl, —$C_{1-4}$ haloalkyl, —O—$C_{1-4}$ alkyl, —O—$C_{1-4}$ haloalkyl, oxo, phenyl, —(CH$_2$)$_{1-2}$-phenyl, —C(=O)-phenyl, —CO$_2$-phenyl, —CO$_2$—(CH$_2$)$_{1-2}$-phenyl, a 5- or 6-membered saturated heterocyclic ring containing from 1 to 4 heteroatoms independently selected from N, O and S, or a 5- or 6-membered heteroaromatic ring containing from 1 to 4 heteroatoms independently selected from N, O and S; and the heteroaromatic ring or the bicyclic heterocycle defined in $R^m$ is optionally substituted with from 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, oxo, phenyl, or —(CH$_2$)$_{1-2}$-phenyl.

Another embodiment of the present invention is a compound of Formula (I), wherein $R^k$ is phenyl; a 5- or 6-membered saturated heterocyclic ring containing 1 or 2 heteroatoms selected from 1 or 2 N atoms, 0 or 1 O atoms, and 0 or 1 S atoms; a 5- or 6-membered heteroaromatic ring containing 1 or 2 heteroatoms selected from 1 or 2 N atoms, 0 or 1 O atoms, and 0 or 1 S atoms; or a bicyclic heterocycle which is a benzene ring fused to a 5- or 6-membered saturated heterocyclic ring containing 1 or 2 nitrogen atoms; and all other variables are as originally defined;
or a pharmaceutically acceptable salt thereof.

In an aspect of this embodiment,
(a) the phenyl, the saturated heterocyclic ring, heteroaromatic ring, or bicyclic heterocycle is optionally substituted with from 1 to 3 substituents each of which is independently
(1) fluoro,
(2) chloro,
(3) bromo,
(4) —OH
(5) —CF$_3$,
(6) —$C_{1-4}$ alkyl, which is optionally substituted with 1 or 2 substituents each of which is independently —OH, —CN, —O—$C_{1-4}$ alkyl, —OCF$_3$, —N($R^aR^b$), —C(=O)N($R^aR^b$), or N($R^a$)—C(=O)—(CH$_2$)$_{0-2}$N($R^bR^c$),
(7) —OCF$_3$, (8) —O—$C_{1-4}$ alkyl
(9) —C(=O)$R^a$,
(10) —$CO_2R^a$,
(11) —$SR^a$,
(12) —$SR^a$,
(13) —N($R^aR^b$),
(14) —C(=O)N($R^aR^b$),
(15) —C(=O)—$(CH_2)_{1-2}$—N($R^aR^b$),
(16) —N($R^a$)C(=O)$R^b$, or
(17) —$SO_2R^a$;
(b) the phenyl is optionally mono-substituted with
(1) —$(CH_2)_{1-2}$—$R^m$, or
(2) —$(CH_2)_{0-2}$—N($R^a$)—$(CH_2)_{0-2}$—$R^m$; and
(c) the saturated heterocyclic ring, heteroaromatic ring, or bicyclic heterocycle is optionally mono- or di-substituted with
(1) oxo
(2) —$(CH_2)_{1-2}$—$R^m$,
(3) —O—$(CH_2)_{1-2}$—$R^m$, or
(4) —$(CH_2)_{0-1}$—C(=O)—$(CH_2)_{0-2}$—$R^m$.

In a feature of the preceding aspect, each $R^m$ is independently cyclopropyl; phenyl; a 5- or 6-membered saturated heterocyclic ring selected from pyrrolidinyl, imidazolidinyl, pyrazolidinyl, piperidinyl, piperazinyl, and morpholinyl; or a 5- or 6-membered heteroaromatic ring selected from thienyl, pyridyl optionally in the form of an N-oxide, imidazolyl, pyrrolyl, pyrazolyl, thiazolyl, isothiazolyl, oxazolyl, isooxazolyl, oxadiazolyl, thiadiazolyl, pyrazinyl, pyrimidinyl, triazolyl, tetrazolyl, furanyl, and pyridazinyl; wherein
the cyclopropyl is unsubstituted;
the phenyl is optionally substituted with from 1 to 3 substituents each of which is independently halogen, —$C_{1-4}$ alkyl, —$CF_3$, —O—$C_{1-4}$ alkyl, —$OCF_3$, or —N($R^aR^b$);
the saturated heterocyclic ring is optionally substituted with 1 or 2 substituents each of which is independently —$C_{1-4}$ alkyl, —$CF_3$, —O—$C_{1-4}$ alkyl, —$OCF_3$, oxo, phenyl, —$(CH_2)_{1-2}$-phenyl, —C(=O)-phenyl, —$CO_2$-phenyl, or —$CO_2$—$CH_2$-phenyl; and
the heteroaromatic ring is optionally substituted with 1 or 2 substituents each of which is independently —$C_{1-4}$ alkyl, —$CF_3$, —O—$C_{1-4}$ alkyl, —$OCF_3$, oxo, phenyl, or —$(CH_2)_{1-2}$-phenyl.

Another embodiment of the present invention is a compound of Formula (I), wherein $R^2$ is:
(1) —$C_{1-6}$ alkyl,
(2) —$C_{1-6}$ alkyl substituted with —N($R^aR^b$),
(3) —$C_{1-6}$ alkyl substituted with phenyl, wherein the phenyl is:
(a) optionally substituted with from 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, or —$C_{0-4}$ alkyl-N($R^aR^b$); and
(b) optionally mono-substituted with —$C_{1-4}$ alkyl substituted with a 5- or 6-membered saturated heterocyclic ring containing from 1 to 3 heteroatoms selected from 1 or 2 N atoms, 0 or 1 O atoms, and 0 or 1 S atoms;
wherein the heterocyclic ring is optionally substituted with from 1 to 3 substituents each of which is independently —$C_{1-6}$ alkyl, oxo, or a 5- or 6-membered heteroaromatic ring containing from 1 to 3 heteroatoms selected from 1 to 3 N atoms, 0 or 1 O atom, and 0 or 1 S atom; or
(4) —$C_{1-6}$ alkyl optionally substituted with —OH and substituted with a 5- or 6-membered saturated monocyclic heterocycle which contains from 1 to 3 heteroatoms selected from 1 to 3 N atoms, 0 or 1 O atoms, and 0 or 1 S atoms; wherein the heterocycle is optionally substituted with from 1 to 4 substituents each of which is independently —$C_{1-6}$ alkyl, —O—$C_{1-6}$ alkyl, oxo, or phenyl; or
(5) —$C_{1-6}$ alkyl substituted with a 5- or 6-membered heteroaromatic ring which contains from 1 to 3 heteroatoms selected from 1 to 3 N atoms, 0 or 1 O atoms, and 0 or 1 S atoms; wherein the heteroaromatic ring is optionally substituted with from 1 to 4 substituents each of which is independently —$C_{1-6}$ alkyl, —O—$C_{1-6}$ alkyl, oxo, or phenyl;
and all other variables are as originally defined above;
or a pharmaceutically acceptable salt thereof.

Another embodiment of the present invention is a compound of Formula (I) exactly as defined in the immediately preceding embodiment, except that when $R^2$ is —$C_{1-6}$ alkyl substituted with —N($R^aR^b$), it is with the proviso that —N($R^aR^b$) is not attached to the carbon atom in the —$C_{1-6}$ alkyl group that is attached to the ring nitrogen (i.e., that the —N($R^aR^b$) group is not attached to the carbon atom alpha to the ring nitrogen).

Another embodiment of the present invention is a compound of Formula (I), wherein $R^2$ is methyl;
and all other variables are as originally defined above;
or a pharmaceutically acceptable salt thereof.

Another embodiment of the present invention is a compound of Formula (I), wherein $R^3$ is —H or —$C_{1-4}$ alkyl;
and all other variables are as originally defined above;
or a pharmaceutically acceptable salt thereof.

In an aspect of this embodiment, $R^3$ is —H or methyl. In another aspect of this embodiment, $R^3$ is —H.

Another embodiment of the present invention is a compound of Formula (I), wherein $R^4$ is $C_{1-4}$ alkyl substituted with an aryl, which is optionally substituted with from 1 to 4 substituents each of which is independently halogen, —OH, —$C_{1-4}$ alkyl, —$C_{1-4}$ alkyl-$OR^a$, —$C_{1-4}$ haloalkyl, —O—$C_{1-4}$ alkyl, —O—$C_{1-4}$ haloalkyl, —CN, —$NO_2$, —N($R^aR^b$), —$C_{1-4}$ alkyl-N($R^aR^b$), —C(=O)N($R^aR^b$), —C(=O)$R^a$, —$CO_2R^a$, —$C_{1-4}$ alkyl-$CO_2R^a$, —$OCO_2R^a$, —$SR^a$, —S(=O)$R^a$, —$SO_2R^a$, —N($R^a$)$SO_2R^b$, —$SO_2$N($R^aR^b$), —N($R^a$)C(=O)$R^b$, —N($R^a$)$CO_2R^b$, —$C_{1-4}$ alkyl-N($R^a$)$CO_2R^b$, methylenedioxy attached to two adjacent ring carbon atoms, phenyl, —$C_{1-4}$ alkyl-phenyl, —O—phenyl, or —$(CH_2)_{0-2}$-het;
wherein het is a 5- or 6-membered heteroaromatic ring containing from 1 to 4 heteroatoms independently selected from N, O and S, and het is optionally fused with a benzene ring, and is optionally substituted with 1 or 2 substituents each of which is independently —$C_{1-4}$ alkyl, —$C_{1-4}$ haloalkyl, —O—$C_{1-4}$ alkyl, —O—$C_{1-4}$ haloalkyl, or —$CO_2R^a$;
and all other variables are as originally defined above;
or a pharmaceutically acceptable salt thereof.

Another embodiment of the present invention is a compound of Formula (I), wherein $R^4$ is —$CH_2$-phenyl, wherein the phenyl is optionally substituted with from 1 to 3 substituents each of which is independently fluoro, bromo, chloro, —OH, —$C_{1-4}$ alkyl, —$C_{1-4}$ fluoroalkyl, —O—$C_{1-4}$ alkyl, —O—$C_{1-4}$ fluoroalkyl, —$(CH_2)_{1-2}$—N($R^aR^b$), —$SO_2R^a$, —$(CH_2)_{0-2}$—$CO_2R^a$, —$(CH_2)_{0-2}$—N($R^a$)$CO_2R^b$, —$NO_2$, —$SR^a$, —N($R^aR^b$) or phenyl;
each $R^a$ and $R^b$ is independently is H or —$C_{1-4}$ alkyl;
and all other variables are as originally defined above;
or a pharmaceutically acceptable salt thereof.

In an aspect of the preceding embodiment, $R^4$ is —$CH_2$-phenyl, wherein the phenyl is optionally substituted with from 1 to 3 substituents, each of which is independently —F, —Br, —Cl, —OH, —$C_{1-4}$ alkyl, —$C_{1-4}$ fluoroalkyl, —O—$C_{1-4}$ alkyl, —$SO_2$—$C_{1-4}$ alkyl, —S—$C_{1-4}$ alkyl, —N($CH_3$)$_2$ or —O—$C_{1-4}$ fluoroalkyl. In another aspect of the preceding embodiment, $R^4$ is p-fluorobenzyl or 2,3-dimethoxybenzyl.

In another aspect of the preceding embodiment, the phenyl is optionally substituted with from 1 to 3 substituents each of which is independently fluoro, bromo, chloro, —OH, —$C_{1-4}$ alkyl, —$C_{1-4}$ fluoroalkyl, —O—$C_{1-4}$ alkyl, —O—$C_{1-4}$ fluoroalkyl, —($CH_2$)$_{1-2}$—N($R^aR^b$), —$SO_2R^a$, —($CH_2$)$_{0-2}$—$CO_2R^a$, —($CH_2$)$_{0-2}$—N($R^a$)$CO_2R^b$, —$NO_2$, or phenyl.

In an aspect of the preceding embodiment, the phenyl is optionally substituted with from 1 to 3 substituents, each of which is independently —F, —Br, —Cl, —OH, —$C_{1-4}$ alkyl, —$C_{1-4}$ fluoroalkyl, —O—$C_{1-4}$ alkyl, or —O—$C_{1-4}$ fluoroalkyl. In another aspect of the preceding embodiment, $R^4$ is p-fluorobenzyl or 2,3-dimethoxybenzyl.

A class of compounds of the present invention includes any compound of Formula (1), wherein
$R^1$ is —$R^k$;
$R^k$ is phenyl which is
(a) optionally substituted with from 1 to 3 substituents each of which is independently:
  (1) halogen,
  (2) —$C_{1-6}$ alkyl, which is optionally substituted with 1 or 2 substituents each of which is independently —O—$C_{1-6}$ alkyl, —O—$C_{1-6}$ haloalkyl, —C(=O)$R^a$, —$CO_2R^a$, —$SR^a$, —S(=O)$R^a$, —N($R^aR^b$), —C(=O)—($CH_2$)$_{0-2}$N($R^aR^b$), N($R^a$)—C(=O)—($CH_2$)$_{0-2}$N($R^bR^c$), —$SO_2R^a$, —N($R^a$)$SO_2R^b$, —$SO_2$N($R^aR^b$), or —N($R^a$)—C($R^b$)=O,
  (3) —$C_{1-6}$ haloalkyl,
  (4) —O—$C_{1-6}$ haloalkyl,
  (5) —C(=O)$R^a$,
  (6) —$CO_2R^a$,
  (7) —C(=O)N($R^aR^b$), or
  (8) —C(=O)—$C_{1-6}$ alkyl-N($R^aR^b$); and
(b) optionally mono-substituted with
  (1) —$C_{1-4}$ alkyl-$R^m$, or
  (2) —$C_{0-4}$ alkyl-N($R^a$)—$C_{0-4}$ alkyl-$R^m$;
wherein $R^m$ is aryl selected from phenyl and naphthyl; a 5- or 6-membered saturated heterocyclic ring containing from 1 to 3 heteroatoms independently selected from N, O and S; or a 5- or 6-membered heteroaromatic ring containing from 1 to 3 heteroatoms independently selected from N, O and S; wherein
the aryl defined in $R^m$ is optionally substituted with from 1 to 3 substituents each of which is independently halogen, —$C_{1-4}$ alkyl, —$CF_3$, —O—$C_{1-4}$ alkyl, —$OCF_3$, or —N($R^aR^b$);
the saturated heterocyclic ring defined in $R^m$ is optionally substituted with from 1 to 3 substituents each of which is independently —$C_{1-4}$ alkyl or oxo, and is additionally optionally mono-substituted with phenyl, —($CH_2$)$_{1-2}$-phenyl, —C(=O)-phenyl, —$CO_2$-phenyl, —$CO_2$—($CH_2$)$_{1-2}$-phenyl, or a 5- or 6-membered heteroaromatic ring containing from 1 to 3 heteroatoms independently selected from N, O and S; and
the heteroaromatic ring defined in $R^m$ is optionally substituted with 1 or 2 substituents each of which is independently —$C_{1-4}$ alkyl or oxo;
and all other variables are as originally defined above; or a pharmaceutically acceptable salt thereof.

A sub-class of the preceding class of compounds of the present invention includes any compounds of Formula (I), wherein
$R^2$ is methyl;
$R^3$ is —H;
$R^4$ is:
(1) —$CH_2$-phenyl, wherein the phenyl is optionally substituted with from 1 to 3 substituents each of which is independently fluoro, bromo, chloro, —OH, —$C_{1-4}$ alkyl, —$C_{1-4}$ fluoroalkyl, —O—$C_{1-4}$ alkyl, —O—$C_{1-4}$ fluoroalkyl, —($CH_2$)$_{1-2}$—N($R^aR^b$), —$SO_2R^a$, —($CH_2$)$_{0-2}$—$CO_2R^a$, —($CH_2$)$_{0-2}$—N($R^a$)$CO_2R^b$, —$NO_2$, —$SR^a$, —N($R^aR^b$) or phenyl; or
(2) a fused bicyclic carbocycle selected from

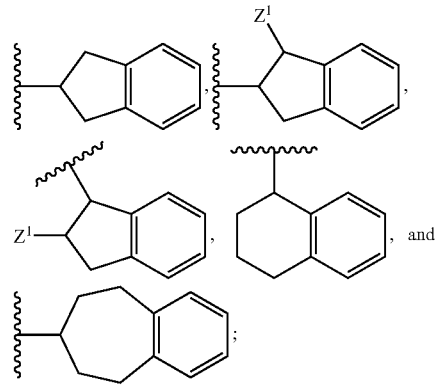

wherein $Z^1$ is —H or —OH; and
each $R^a$ and $R^b$ is independently is H or —$C_{1-4}$ alkyl;
and all other variables are as defined in the class;
or a pharmaceutically acceptable salt thereof.

Another sub-class of the preceding class of compounds of the present invention includes any compounds of Formula (I), wherein $R^4$ is 4-fluorobenzyl or 2,3-dimethoxybenzyl; and all other variables are as defined in the class; or a pharmaceutically acceptable salt thereof.

Still another sub-class of the preceding class of compounds of the present invention includes any compounds of Formula (I), wherein $R^2$ is methyl; $R^3$ is —H; $R^4$ is 4-fluorobenzyl or 2,3-dimethoxybenzyl; each $R^a$ and $R^b$ is independently is H or —$C_{1-4}$ alkyl; and all other variables are as defined in the class; or a pharmaceutically acceptable salt thereof.

Another class of the present invention includes any compound of Formula (II):

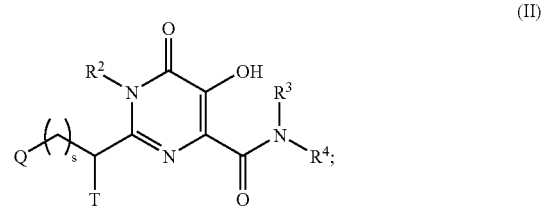

(II)

wherein
Q is:
(1) methyl which is optionally substituted with 1 or 2 of —O—$C_{1-4}$ alkyl, (2) phenyl which is optionally substituted with from 1 to 3 substituents each of which is independently —F, ≦Cl, Br, —$C_{1-4}$ alkyl, —$CF_3$, —O—$C_{1-4}$ alkyl, —$OCF_3$, methylenedioxy attached to two adjacent carbon atoms, or phenyl; or (3) a 5- or 6-membered saturated heterocyclic ring containing from 1 to 3 heteroatoms independently selected from N, O and S; wherein the saturated heterocyclic ring is optionally substituted with 1 or 2 substituents each of which is independently —F, —Cl, —Br, —$C_{1-4}$ alkyl, oxo, phenyl, or —C(=O)-phenyl;

T is:
(1) —H,
(2) —OH,
(3) methyl or ethyl, optionally substituted with —OH or —O—$C_{1-4}$ alkyl,
(4) —O—$C_{1-4}$ alkyl
(5) —N($R^a R^b$),
(6) —N($R^a$)—($CH_2$)2—OH,
(7) —N($R^a$)—$CO_2 R^b$,
(8) —N($R^a$)—C(=O)—($CH_2$)$_{1-2}$—N($R^a R^b$),
(9) —$R^s$,
(10) —($CH_2$)$_{1-2}$—$R^s$, or
(11) —($CH_2$)$_{0-2}$—N($R^a$)—($CH_2$)$_{0-3}$—$R^s$;

$R^s$ is:
(1) phenyl optionally substituted with from 1 to 4 substituents each of which is independently halogen, —$C_{1-4}$ alkyl, —$C_{1-4}$ alkyl-$OR^a$, —$C_{1-4}$ haloalkyl, —O—$C_{1-4}$ alkyl, —O—$C_{1-4}$ haloalkyl, or —N($R^a R^b$);
(2) a 5- or 6-membered saturated heterocyclic ring containing from 1 to 3 heteroatoms independently selected from N, O and S; which is optionally substituted with from 1 to 4 substituents each of which is independently —$C_{1-4}$ alkyl, —$C_{1-4}$ alkyl-$OR^a$, —$C_{1-4}$ haloalkyl, —O—$C_{1-4}$ alkyl, —O—$C_{1-4}$ haloalkyl, —C(=O)$R^a$, oxo, phenyl, or —$CH_2$-phenyl; or
(3) a 5- or 6-membered heteroaromatic ring containing from 1 to 3 heteroatoms independently selected from N, O and S; which is optionally substituted with from 1 to 4 substituents each of which is independently —$C_{1-4}$ alkyl, —$C_{1-4}$ alkyl-$OR^a$, —$C_{1-4}$ haloalkyl, —O—$C_{1-4}$ alkyl, —O—$C_{1-4}$ haloalkyl, or oxo;

$R^2$ is
(1) —$C_{1-4}$ alkyl,
(2) —$C_{1-4}$ alkyl substituted with —N($R^a R^b$), or
(3) —$C_{1-4}$ alkyl substituted with a 5- or 6-membered saturated monocyclic heterocycle which contains from 1 to 3 heteroatoms selected from 1 to 3 N atoms, 0 or 1 O atoms, and 0 or 1 S atoms; wherein the saturated heterocycle is optionally substituted with from 1 to 4 substituents each of which is independently a —$C_{1-4}$ alkyl;

$R^3$ is —H or —$C_{1-4}$ alkyl;

$R^4$ is —$CH_2$-phenyl, wherein the phenyl is optionally substituted with from 1 to 3 substituents each of which is independently fluoro, bromo, chloro, —OH, —$C_{1-4}$ alkyl, —$C_{1-4}$ fluoroalkyl, —O—$C_{1-4}$ alkyl, —O—$C_{1-4}$ fluoroalkyl, —($CH_2$)$_{1-2}$—N($R^a R^b$), —$SO_2 R^a$, —($CH_2$)$_{0-2}$—$CO_2 R^a$, —($CH_2$)$_{0-2}$—N($R^a$)$C_{0-2} R^b$, —$NO_2$, —$SR^a$, —N($R^a R^b$) or phenyl;

each $R^a$ and $R^b$ is independently is H or —$C_{1-4}$ alkyl; and s is an integer equal to zero, 1, or 2;
or a pharmaceutically acceptable salt thereof.

In an aspect of this class, $R^4$ is —$CH_2$-phenyl, wherein the phenyl is optionally substituted with from 1 to 3 substituents each of which is independently fluoro, bromo, chloro, —OH, —$C_{1-4}$ alkyl, —$C_{1-4}$ fluoroalkyl, —O—$C_{1-4}$ alkyl, —O—$C_{1-4}$ fluoroalkyl, —($CH_2$)$_{1-2}$—N($R^a R^b$), —$SO_2 R^a$, —($CH_2$)$_{0-2}$—$CO_2 R^a$, —($CH_2$)$_{0-2}$—N($R^a$)$CO_2 R^b$, —$NO_2$, or phenyl A sub-class of the preceding class of compounds of the present invention includes any compounds of Formula (II) exactly as defined in the preceding class, except that when $R^2$ is —$C_{1-4}$ alkyl substituted with —N($R^a R^b$), it is with the proviso that —N($R^a R^b$) is not attached to the carbon atom in the —$C_{1-4}$ alkyl group that is attached to the ring nitrogen (i.e., that the —N($R^a R^b$) group is not attached to the carbon atom alpha to the ring nitrogen).

Another sub-class of the preceding class of compounds of the present invention includes any compounds of Formula (II), wherein
Q is phenyl;
T is:
(1) —H,
(2) —N($R^a R^b$),
(3) a 5- or 6-membered saturated heterocyclic ring containing from 1 to 3 heteroatoms independently selected from N, O and S; which is optionally substituted with 1 or 2 substituents each of which is independently —$C_{1-4}$ alkyl or —C(=O)$R^a$, or
(4) —N($R^a$)—($CH_2$)$_{1-2}$-heteroaromatic, wherein the heteroaromatic is a 5- or 6-membered ring containing 1 or 2 N atoms;

$R^2$ is methyl;
$R^3$ is —H; and
$R^4$ is —$CH_2$-phenyl, wherein the phenyl is optionally substituted with 1 or 2 substituents each of which is independently —F, —Cl, —Br, —$C_{1-4}$ alkyl, —$CF_3$, —O—$C_{1-4}$ alkyl, —$SO_2 CH_3$, —$SCH_3$, —N($CH_3$)$_2$ or —$OCF_3$;
each $R^a$ and $R^b$ is independently —H, methyl or ethyl; and s is an integer equal to zero or 1;
or a pharmaceutically acceptable salt thereof.

In an aspect of this subclass, $R^4$ is —$CH_2$-phenyl, wherein the phenyl is optionally substituted with 1 or 2 substituents each of which is independently —F, —Cl, —Br, —$C_{1-4}$ alkyl, —$CF_3$, —O—$C_{1-4}$ alkyl, or —$OCF_3$.

Another class of compounds of the present invention includes any compound of Formula (I), wherein
$R^1$ is —$R^k$;
$R^k$ is (i) a 5- or 6-membered saturated heterocyclic ring containing from 0 to 1 oxygen atoms and from 1 to 3 nitrogen atoms or (ii) a bicyclic heterocycle which is a benzene ring fused to a 5- or 6-membered saturated heterocyclic ring containing from 0 to 1 oxygen atoms and from 1 to 3 nitrogen atoms;
wherein the saturated heterocyclic ring or bicyclic heterocycle is optionally substituted with from 1 to 3 substituents each of which is independently
(1) —$C_{1-4}$ alkyl, which is optionally substituted with from 1 to 4 substituents each of which is independently halogen, —O—$C_{1-4}$ alkyl, —O—$C_{1-4}$ haloalkyl, —C(=O)$R^a$, —$CO_2 R^a$, —$SR^a$, —S(=O)$R^a$, —N($R^a R^b$), —C(=O)—($CH_2$)$_{0-2}$N($R^a R^b$), N($R^a$)—C(=O)—($CH_2$)$_{0-2}$N($R^b R^c$), —$SO_2 R^a$, —N($R^a$)$SO_2 R^b$, —$SO_2$N($R^a R^b$), or —N($R^a$)—C($R^b$)=O,
(2) —OH,
(3) —C(=O)$R^a$,
(4) —$CO_2 R^a$,
(5) —C(=O)N($R^a R^b$),
(6) —C(=O)—$C_{1-6}$ alkyl-N($R^a R^b$),
(7) —$SR^a$,
(8) —S(=O)$R^a$,
(9) —$SO_2 R^a$,

(10) —N(R$^a$R$^b$),

(11) —R$^m$,

(12) —C$_{1-4}$ alkyl-R$^m$, wherein the alkyl is optionally substituted with from 1 to 4 substituents each of which is independently halogen, —OH, —CN, —C$_{1-4}$ haloalkyl, —O—C$_{1-4}$ alkyl, —O—C$_{1-4}$ haloalkyl, —C(=O)R$^a$, —CO$_2$R$^a$, —SR$^a$, —S(=O)R$^a$, —N(R$^a$R$^b$), —N(R$^a$)CO$_2$R$^b$, —SO$_2$R$^a$, —N(R$^a$)SO$_2$R$^b$, —SO$_2$N(R$^a$R$^b$), or —N(R$^a$)—C(R$^b$)=O,

(13) —C$_{0-4}$ alkyl-N(R$^a$)—C$_{0-4}$ alkyl-R$^m$,

(14) —C$_{0-4}$ alkyl-O—C$_{0-4}$ alkyl-R$^m$,

(15) —C$_{0-4}$ alkyl-S—C$_{0-4}$ alkyl-R$^m$,

(16) —C$_{0-4}$ alkyl-C(=O)—C$_{0-4}$ alkyl-R$^m$,

(17) —C(=O)—O—C$_{0-4}$ alkyl-R$^m$, or

(18) —C(=O)N(R$^a$)—C$_{0-4}$ alkyl-R$^m$;

wherein each R$^m$ is independently —C$_{3-6}$ cycloalkyl; aryl selected from phenyl and naphthyl; a 5- or 6-membered saturated heterocyclic ring containing from 1 to 3 heteroatoms independently selected from N, O and S; or a 5- or 6-membered heteroaromatic ring containing from 1 to 3 heteroatoms independently selected from N, O and S, wherein any N is optionally oxidized to form an N-oxide; wherein the aryl is optionally substituted with from 1 to 3 substituents each of which is independently halogen, —C$_{1-4}$ alkyl, —CF$_3$, —O—C$_{1-4}$ alkyl, —OCF$_3$, or —N(R$^a$R$^b$);

the saturated heterocyclic ring is optionally substituted with from 1 to 3 substituents each of which is independently —C$_{1-4}$ alkyl or oxo, and is additionally optionally mono-substituted with phenyl, —(CH$_2$)$_{1-2}$-phenyl, —C(=O)-phenyl, —CO$_2$-phenyl, or —CO$_2$—(CH$_2$)$_{1-2}$-phenyl; and the heteroaromatic ring is optionally substituted with 1 or 2 substituents each of which is independently halogen, —C$_{1-4}$ alkyl, or oxo;

and all other variables are as originally defined above;

or a pharmaceutically acceptable salt thereof.

A sub-class of the preceding class of compounds of the present invention includes any compounds of Formula (I), wherein R$^1$ is:

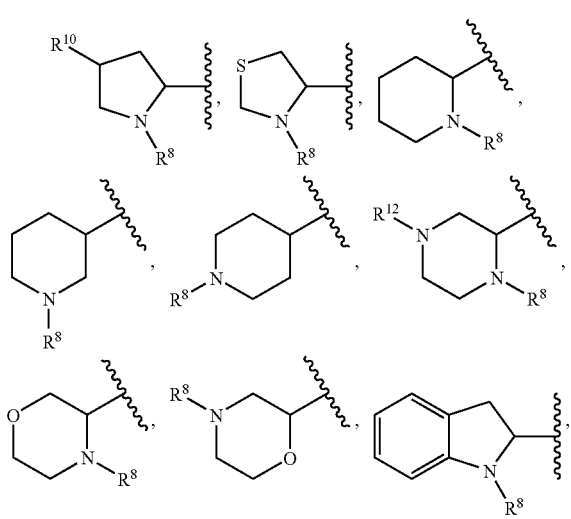

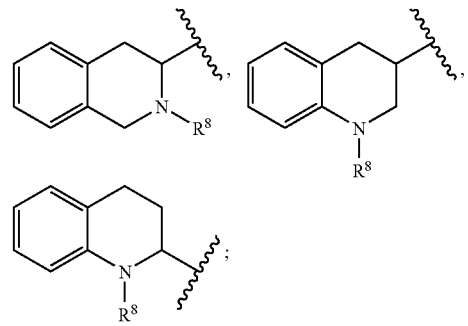

R$^8$ is:
(1) —H,
(2) —C$_{1-4}$ alkyl, which is optionally substituted with 1 or 2 substituents each of which is independently —OH, —O—C$_{1-4}$ alkyl, —OCF$_3$, —C(=O)R$^a$, —CO$_2$R$^a$, —SR$^a$, —N(R$^a$R$^b$), or —C(=O)N(R$^a$R$^b$),
(3) —C(=O)R$^a$,
(4) —CO$_2$R$^a$,
(5) —C(=O)N(R$^a$R$^b$),
(6) —C(=O)—(CH$_2$)$_{1-2}$—N(R$^a$R$^b$),
(7) —SO$_2$R$^a$,
(8) —(CH$_2$)$_{1-2}$—R$^m$,
(9) —(CH$_2$)$_{0-2}$—C(=O)—(CH$_2$)$_{0-2}$—R$^m$,
(10) —C(=O)—O—(CH$_2$)$_{0-2}$—R$^m$, or
(11) —C(=O)N(R$^a$)—(CH$_2$)$_{0-2}$—R$^m$;

R$^{10}$ is —H, —OH, —C$_{1-4}$ alkyl, —O—C$_{1-4}$ alkyl, —N(R$^a$R$^b$), or —O—(CH$_2$)$_{1-2}$—R$^m$;

R$^{12}$ is
(1) —H,
(2) —C$_{1-4}$ alkyl, which is optionally substituted with 1 or 2 substituents each of which is independently —OH, —O—C$_{1-4}$ alkyl, —OCF$_3$, —C(=O)R$^a$, —CO$_2$R$^a$, —SR$^a$, —N(R$^a$R$^b$), or —C(=O)N(R$^a$R$^b$),
(3) —C(=O)R$^a$,
(4) —CO$_2$R$^a$,
(5) —C(=O)—(CH$_2$)$_{1-2}$—N(R$^a$R$^b$), or
(6) —SO$_2$R$^a$;

R$^2$ is methyl;

R$^3$ is —H or methyl;

R$^4$ is —CH$_2$-phenyl, wherein the phenyl is optionally substituted with from 1 to 3 substituents each of which is independently fluoro, bromo, chloro, —OH, —C$_{1-4}$ alkyl, —C$_{1-4}$ fluoroalkyl, —O—C$_{1-4}$ alkyl, —O—C$_{1-4}$ fluoroalkyl, —(CH$_2$)$_{1-2}$—N(R$^a$R$^b$), —SO$_2$R$^a$, —(CH$_2$)$_{0-2}$—CO$_2$R$^a$, —(CH$_2$)$_{0-2}$—N(R$^a$)CO$_2$R$^b$, —NO$_2$, —SR$^a$, —N(R$^a$R$^b$) or phenyl; and each R$^a$ and R$^b$ is independently —H or —C$_{1-4}$ alkyl;

or a pharmaceutically acceptable salt thereof.

In an aspect of this subclass, R$^4$ is —CH$_2$-phenyl, wherein the phenyl is optionally substituted with from 1 to 3 substituents each of which is independently fluoro, bromo, chloro, —OH, —C$_{1-4}$ alkyl, —C$_{1-4}$ fluoroalkyl, —O—C$_{1-4}$ alkyl, —O—C$_{1-4}$ fluoroalkyl, —(CH$_2$)$_{1-2}$—N(R$^a$R$^b$), —SO$_2$R$^a$, —(CH$_2$)$_{0-2}$—CO$_2$R$^a$, —(CH$_2$)$_{0-2}$—N(R$^a$)CO$_2$R$^b$, —NO$_2$, or phenyl.

Another class of the present invention includes any compound of Formula (III):

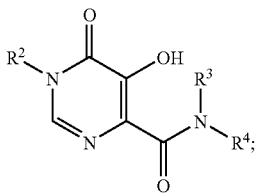

(III)

wherein R² is:
(1) —C₁₋₆ alkyl,
(2) —C₁₋₆ alkyl substituted with —N(RᵃRᵇ),
(3) —C₁₋₆ alkyl substituted with phenyl which is:
   (a) optionally substituted with from 1 to 4 substituents each of which is independently halogen, —C₁₋₄ alkyl, —C₁₋₄ haloalkyl, —O—C₁₋₄ alkyl, —O—C₁₋₄ haloalkyl, or —C₀₋₆ alkyl-N(RᵃRᵇ); and
   (b) optionally mono-substituted with —C₁₋₄ alkyl substituted with a 5- or 6-membered saturated heterocyclic ring containing from 1 to 3 heteroatoms selected from 1 or 2 N atoms, 0 or 1 O atoms, and 0 or 1 S atoms;
   wherein the heterocyclic ring is optionally substituted with from 1 to 3 substituents each of which is independently —C₁₋₆ alkyl, oxo, or a 5- or 6-membered heteroaromatic ring containing from 1 to 3 heteroatoms selected from 1 to 3 N atoms, 0 or 1 O atom, and 0 or 1 S atom;
(4) —C₁₋₆ alkyl optionally substituted with —OH and substituted with a 5- or 6-membered saturated monocyclic heterocycle which contains from 1 to 3 heteroatoms selected from 1 to 3 N atoms, 0 or 1 O atoms, and 0 or 1 S atoms; wherein the heterocycle is optionally substituted with from 1 to 4 substituents each of which is independently —C₁₋₆ alkyl, —O—C₁₋₆ alkyl, oxo, or phenyl; or
(5) —C₁₋₆ alkyl substituted with a 5- or 6-membered heteroaromatic ring which contains from 1 to 3 heteroatoms selected from 1 to 3 N atoms, 0 or 1 O atoms, and 0 or 1 S atoms; wherein the heteroaromatic ring is optionally substituted with from 1 to 4 substituents each of which is independently —C₁₋₆ alkyl, —O—C₁₋₆ alkyl, oxo, or phenyl;

and all other variables are as originally defined above;
or a pharmaceutically acceptable salt thereof.

A sub-class of the preceding class of compounds of the present invention includes any compounds of Formula (III) exactly as defined in the preceding class, except that when R² is —C₁₋₆ alkyl substituted with —N(RᵃRᵇ), it is with the proviso that —N(RᵃRᵇ) is not attached to the carbon atom in the —C₁₋₆ alkyl group that is attached to the ring nitrogen (i.e., that the —N(RᵃRᵇ) group is not attached to the carbon atom alpha to the ring nitrogen).

Another sub-class of the preceding class of compounds of the present invention includes any compounds of Formula (III), wherein
R² is:
(1) —C₁₋₄ alkyl,
(2) —(CH₂)₁₋₃—N(RᵃRᵇ),
(3) —(CH₂)₁₋₃-phenyl, wherein the phenyl is:
   (a) optionally substituted with from 1 to 3 substituents each of which is independently fluoro, chloro, bromo, —C₁₋₄ alkyl, —CF₃, —O—C₁₋₄ alkyl, —O—CF₃, or —(CH₂)₁₋₃—N(RᵃRᵇ); and
   (b) optionally mono-substituted with —(CH₂)₁₋₃-saturated heterocycle which is a 5- or 6-membered saturated heterocyclic ring containing from 1 to 3 heteroatoms selected from 1 or 2 N atoms, 0 or 1 O atoms, and 0 or 1 S atoms, wherein the heterocyclic ring is optionally substituted with from 1 to 3 substituents each of which is independently —C₁₋₄ alkyl or pyridyl;
(4) —(CH₂)₁₋₃-saturated heterocycle, wherein the —(CH₂)₁₋₃— moiety is optionally substituted with an —OH and the saturated heterocycle is a 5- or 6-membered saturated monocyclic heterocycle which contains from 1 to 3 heteroatoms selected from 1 to 3 N atoms, 0 or 1 O atoms, and 0 or 1 S atoms; wherein the heterocycle is optionally substituted with from 1 to 3 substituents each of which is independently a —C₁₋₄ alkyl; or
(5) —(CH₂)₁₋₃-pyridyl;
R³ is —H or methyl;
R⁴ is —CH₂-phenyl, wherein the phenyl is optionally substituted with from 1 to 3 substituents each of which is independently fluoro, bromo, chloro, —OH, —C₁₋₄ alkyl, —C₁₋₄ fluoroalkyl, —O—C₁₋₄ alkyl, —O—C₁₋₄ fluoroalkyl, —(CH₂)₁₋₂—N(RᵃRᵇ), —SO₂Rᵃ, —(CH₂)₀₋₂—CO₂Rᵃ, —(CH₂)₀₋₂—N(Rᵃ)CO₂Rᵇ, —NO₂, —SRᵃ, —N(RᵃRᵇ) or phenyl and;
each Rᵃ and Rᵇ is independently is H or —C₁₋₄ alkyl;
or a pharmaceutically acceptable salt thereof.

In an aspect of this subclass, R⁴ is —CH₂-phenyl, wherein the phenyl is optionally substituted with from 1 to 3 substituents each of which is independently fluoro, bromo, chloro, —OH, —C₁₋₄ alkyl, —C₁₋₄ fluoroalkyl, —O—C₁₋₄ alkyl, —O—C₁₋₄ fluoroalkyl, —(CH₂)₁₋₂—N(RᵃRᵇ), —SO₂Rᵃ, —(CH₂)₀₋₂—CO₂Rᵃ, —(CH₂)₀₋₂—N(Rᵃ)CO₂Rᵇ, —NO₂, or phenyl.

Another class of compounds of the present invention includes any compound of Formula (I), wherein
R¹ is —C(=O)NH—(CH₂)₁₋₂—Rᵏ; and
Rᵏ is (i) a 5- or 6-membered saturated heterocyclic ring containing from 1 to 3 heteroatoms independently selected from N, O and S, or (ii) a 5- or 6-membered heteroaromatic ring containing from 1 to 3 heteroatoms independently selected from N, O and S;
and all other variables are as originally defined above;
or a pharmaceutically acceptable salt thereof.

A sub-class of the preceding class of compounds of the present invention includes any compounds of Formula (I), wherein
R¹ is —C(=O)NH—(CH₂)₁₋₂—Rᵏ; and
Rᵏ is (i) a 5- or 6-membered saturated heterocyclic ring containing from 1 to 3 heteroatoms independently selected from N, O and S, or (ii) a 5- or 6-membered heteroaromatic ring containing from 1 to 3 heteroatoms independently selected from N, O and S;
R² is methyl;
R³ is —H or methyl;
R⁴ is —CH₂-phenyl, wherein the phenyl is optionally substituted with from 1 to 3 substituents each of which is independently fluoro, bromo, chloro, —OH, —C₁₋₄ alkyl, —C₁₋₄ fluoroalkyl, —O—C₁₋₄ alkyl, —O—C₁₋₄ fluoroalkyl, —(CH₂)₁₋₂—N(RᵃRᵇ), —SO₂Rᵃ, —(CH₂)₀₋₂—CO₂Rᵃ, —(CH₂)₀₋₂—N(Rᵃ)CO₂Rᵇ, —NO₂, —SRᵃ, —N(RᵃRᵇ) or phenyl; and
each Rᵃ and Rᵇ is independently —H or —C₁₋₄ alkyl;
or a pharmaceutically acceptable salt thereof.

In an aspect of this subclass, R⁴ is —CH₂-phenyl, wherein the phenyl is optionally substituted with from 1 to 3 substituents each of which is independently fluoro, bromo, chloro, —OH, —C$_{1-4}$ alkyl, —C$_{1-4}$ fluoroalkyl, —O—C$_{1-4}$ alkyl, —O—C$_{1-4}$ fluoroalkyl, —(CH$_2$)$_{1-2}$—N(R$^a$R$^b$), —SO$_2$R$^a$, —(CH$_2$)$_{0-2}$—CO$_2$R$^a$, —(CH$_2$)$_{0-2}$—N(R$^a$)CO$_2$R$^b$, —NO$_2$, or phenyl.

It is to be understood that additional embodiments of the present invention include, but are not limited to, compounds of Formula I wherein each of two or three or more of R$^1$, R$^2$, R$^3$, R$^4$, R$^a$, R$^b$, R$^c$, R$^d$, R$^k$ and R$^m$ is independently defined in accordance with its definition in one of the embodiments or an aspect thereof as set forth above, or in accordance with its definition in one of the foregoing classes set forth above or a sub-class or feature thereof. Any and all possible combinations of these variables in Formula I are additional embodiments within the scope of the present invention.

An aspect of the present invention is a compound selected from the group consisting of N-(2-ethoxybenzyl)-5-hydroxy-1-methyl-2-(4-methylphenyl)-6-oxo-1,6-dihydropyrimidine-4-carboxamide;

N-(2,3-dimethoxybenzyl)-5-hydroxy-1-methyl-2-(4-methylphenyl)-6-oxo-1,6-dihydropyrimidine-4-carboxamide;

N-(2,3-dimethoxybenzyl)-2-{4-[(dimethylamino)methyl]phenyl}-5-hydroxy-1-methyl-6-oxo-1,6-dihydropyrimidine-4-carboxamide;

N-(4-fluorobenzyl)-2-{4-[(dimethylamino)methyl]phenyl}-5-hydroxy-1-methyl-6-oxo-1,6-dihydropyrimidine-4-carboxamide;

N-(2,3-dimethoxybenzyl)-5-hydroxy-1-methyl-6-oxo-2-[4-(pyrrolidin-1-ylmethyl)phenyl]-1,6-dihydropyrimidine-4-carboxamide;

N-(4-fluorobenzyl)-5-hydroxy-1-methyl-6-oxo-2-[4-(pyrrolidin-1-ylmethyl)phenyl]-1,6-dihydropyrimidine-4-carboxamide;

N-(4-fluorobenzyl)-5-hydroxy-1-methyl-6-oxo-2-[4-(piperidin-1-ylmethyl)phenyl]-1,6-dihydropyrimidine-4-carboxamide;

N-(2,3-dimethoxybenzyl)-5-hydroxy-1-methyl-2-[4-(morpholin-4-ylmethyl)phenyl]-6-oxo-1,6-dihydropyrimidine-4-carboxamide;

N-(4-fluorobenzyl)-5-hydroxy-1-methyl-2-[4-(morpholin-4-ylmethyl)phenyl]-6-oxo-1,6-dihydropyrimidine-4-carboxamide;

N-(4-fluorobenzyl)-5-hydroxy-1-methyl-2-{4-[(4-methylpiperazin-1-yl)methyl]phenyl}-6-oxo-1,6-dihydropyrimidine-4-carboxamide;

2-{4-[(diethylamino)methyl]phenyl}-N-(2,3-dimethoxybenzyl)-5-hydroxy-1-methyl-6-oxo-1,6-dihydropyrimidine-4-carboxamide;

2-{4-[(diethylamino)methyl]phenyl}-N-(4-fluorobenzyl)-5-hydroxy-1-methyl-6-oxo-1,6-dihydropyrimidine-4-carboxamide;

2-[(dimethylamino)(phenyl)methyl]-N-(4-fluorobenzyl)-5-hydroxy-1-methyl-6-oxo-1,6-dihydropyrimidine-4-carboxamide;

N-(4-fluorobenzyl)-2-[(4-formylpiperazin-1-yl)(phenyl)methyl]-5-hydroxy-1-methyl-6-oxo-1,6-dihydropyrimidine-4-carboxamide;

N-(4-fluorobenzyl)-5-hydroxy-1-methyl-6-oxo-2-{phenyl[(pyridin-3-ylmethyl)amino]methyl}-1,6-dihydropyrimidine-4-carboxamide;

2-benzyl-1-[2-(dimethylamino)ethyl]-N-(4-fluorobenzyl)-5-hydroxy-6-oxo-1,6-dihydropyrimidine-4-carboxamide;

1-[2-(dimethylamino)ethyl]-N-(4-fluorobenzyl)-5-hydroxy-2-(2-methylphenyl)-6-oxo-1,6-dihydropyrimidine-4-carboxamide;

N-(4-fluorobenzyl)-5-hydroxy-1-methyl-2-(4-methylphenyl)-6-oxo-1,6-dihydropyrimidine-4-carboxamide;

2-benzyl-N-(2,3-dimethoxybenzyl)-1-[2-(dimethylamino)ethyl]-5-hydroxy-6-oxo-1,6-dihydropyrimidine-4-carboxamide;

2-{4-[(4-ethylpiperazin-1-yl)methyl]phenyl}-N-(4-fluorobenzyl)-5-hydroxy-1-methyl-6-oxo-1,6-dihydropyrimidine-4-carboxamide;

N-(4-fluorobenzyl)-5-hydroxy-1-methyl-6-oxo-2-{4-[(2-pyridin-3-ylpiperidin-1-yl)methyl]phenyl}-1,6-dihydropyrimidine-4-carboxamide;

N-(4-fluorobenzyl)-5-hydroxy-1-methyl-6-oxo-1,6-dihydropyrimidine-4-carboxamide;

N-(2,3-dimethoxybenzyl)-5-hydroxy-1-methyl-6-oxo-1,6-dihydropyrimidine-4-carboxamide;

N-[4-fluoro-2-(trifluoromethyl)benzyl]-5-hydroxy-1-methyl-6-oxo-1,6-dihydropyrimidine-4-carboxamide;

N-(3-chloro-4-methylbenzyl)-5-hydroxy-1-methyl-6-oxo-1,6-dihydropyrimidine-4-carboxamide;

5-hydroxy-N-[(1R,2S)-2-hydroxy-2,3-dihydro-1H-inden-1-yl]-1-methyl-2-{4-[(4-methylpiperazin-1-yl)methyl]phenyl}-6-oxo-1,6-dihydropyrimidine-4-carboxamide;

N-(4-fluorobenzyl)-5-hydroxy-2-(4-{[(2R)-2-(methoxymethyl)pyrrolidin-1-yl]methyl}phenyl)-1-methyl-6-oxo-1,6-dihydropyrimidine-4-carboxamide;

N-(4-fluorobenzyl)-5-hydroxy-2-(4-{[(2S)-2-(methoxymethyl)pyrrolidin-1-yl]methyl}phenyl)-1-methyl-6-oxo-1,6-dihydropyrimidine-4-carboxamide;

N-(4-fluorobenzyl)-2-(4-{[(4-fluorobenzyl)amino]methyl}phenyl)-5-hydroxy-1-methyl-6-oxo-1,6-dihydropyrimidine-4-carboxamide;

2-benzyl-N-(4-fluorobenzyl)-5-hydroxy-1-(2-morpholin-4-ylethyl)-6-oxo-1,6-dihydropyrimidine-4-carboxamide;

1-[2-(dimethylamino)ethyl]-N-(4-fluorobenzyl)-5-hydroxy-6-oxo-1,6-dihydropyrimidine-4-carboxamide;

N-(4-fluorobenzyl)-5-hydroxy-6-oxo-1-(pyridin-3-ylmethyl)-1,6-dihydropyrimidine-4-carboxamide;

2-benzyl-N-(4-fluorobenzyl)-5-hydroxy-6-oxo-1-(2-pyrrolidin-1-ylethyl)-1,6-dihydropyrimidine-4-carboxamide;

2-benzyl-N-(4-fluorobenzyl)-5-hydroxy-6-oxo-1-(2-piperidin-1-ylethyl)-1,6-dihydropyrimidine-4-carboxamide;

2-(1-benzylpiperidin-2-yl)-N-(4-fluorobenzyl)-5-hydroxy-1-methyl-6-oxo-1,6-dihydropyrimidine-4-carboxamide;

N-(4-fluorobenzyl)-5-hydroxy-1-methyl-2-(1-methylpiperidin-2-yl)-6-oxo-1,6-dihydropyrimidine-4-carboxamide;

2-(1-benzylpiperidin-3-yl)-N-(4-fluorobenzyl)-5-hydroxy-1-methyl-6-oxo-1,6-dihydropyrimidine-4-carboxamide;

1-{3-[(dimethylamino)methyl]benzyl}-N-(4-fluorobenzyl)-5-hydroxy-6-oxo-1,6-dihydropyrimidine-4-carboxamide;

N-(2,3-dimethoxybenzyl)-1-[2-(dimethylamino)ethyl]-5-hydroxy-6-oxo-1,6-dihydropyrimidine-4-carboxamide;

N-(2,3-dimethoxybenzyl)-5-hydroxy-6-oxo-1-(pyridin-3-ylmethyl)-1,6-dihydropyrimidine-4-carboxamide;

N4-(4-fluorobenzyl)-5-hydroxy-1-methyl-N2-(2-morpholin-4-ylethyl)-6-oxo-1,6-dihydropyrimidine-2,4-dicarboxamide;

N-(4-fluorobenzyl)-5-hydroxy-6-oxo-1-[3-(pyrrolidin-1-ylmethyl)benzyl]-1,6-dihydropyrimidine-4-carboxamide;

N-(4-fluorobenzyl)-5-hydroxy-1-[3-(morpholin-4-ylmethyl)benzyl]-6-oxo-1,6-dihydropyrimidine-4-carboxamide;

N-(4-fluorobenzyl)-5-hydroxy-1-{3-[(4-methylpiperazin-1-yl)methyl]benzyl}-6-oxo-1,6-dihydropyrimidine-4-carboxamide;

N-(4-fluorobenzyl)-5-hydroxy-6-oxo-1-{3-[(4-pyridin-2-ylpiperazin-1-yl)methyl]benzyl}-1,6-dihydropyrimidine-4-carboxamide;

N-(4-fluorobenzyl)-5-hydroxy-1-[2-(morpholin-4-ylm-ethyl)benzyl]-6-oxo-1,6-dihydropyrimidine-4-carboxamide;

N-(4-fluorobenzyl)-5-hydroxy-6-oxo-1-{2-[(4-pyridin-2-ylpiperazin-1-yl)methyl]benzyl}-1,6-dihydropyrimidine-4-carboxamide;

N-(4-fluorobenzyl)-5-hydroxy-1-methyl-6-oxo-2-pyrrolidin-2-yl-1,6-dihydropyrimidine-4-carboxamide;

N4-(4-fluorobenzyl)-5-hydroxy-1-methyl-6-oxo-N2-(pyridin-2-ylmethyl)-1,6-dihydropyrimidine-2,4-dicarboxamide;

N-(4-fluorobenzyl)-5-hydroxy-1-(2-hydroxy-3-morpholin-4-ylpropyl)-6-oxo-1,6-dihydropyrimidine-4-carboxamide;

N-(4-fluorobenzyl)-5-hydroxy-1-[4-(morpholin-4-ylmethyl)benzyl]-6-oxo-1,6-dihydropyrimidine-4-carboxamide;

N-(4-fluorobenzyl)-5-hydroxy-1-methyl-2-(2-morpholin-4-ylethyl)-6-oxo-1,6-dihydropyrimidine-4-carboxamide;

2-(2,2-dimethoxyethyl)-N-(4-fluorobenzyl)-5-hydroxy-1-methyl-6-oxo-1,6-dihydropyrimidine-4-carboxamide;

2-(2,3-dihydro-1H-indol-2-yl)-N-(4-fluorobenzyl)-5-hydroxy-1-methyl-6-oxo-1,6-dihydropyrimidine-4-carboxamide;

2-[2-(4-benzoylpiperazin-1-yl)ethyl]-N-(4-fluorobenzyl)-5-hydroxy-1-methyl-6-oxo-1,6-dihydropyrimidine-4-carboxamide;

2-[1-(N,N-dimethylglycyl)piperidin-2-yl]-N-(4-fluorobenzyl)-5-hydroxy-1-methyl-6-oxo-1,6-dihydropyrimidine-4-carboxamide;

N-(4-fluorobenzyl)-5-hydroxy-1-methyl-2-(1-methyl-2,3-dihydro-1H-indol-2-yl)-6-oxo-1,6-dihydropyrimidine-4-carboxamide;

N-(4-fluorobenzyl)-5-hydroxy-1-methyl-6-oxo-2-(1,2,3,4-tetrahydroquinolin-2-yl)-1,6-dihydropyrimidine-4-carboxamide;

N-(4-fluorobenzyl)-5-hydroxy-1-methyl-2-(1-methyl-1,2,3,4-tetrahydroquinolin-2-yl)-6-oxo-1,6-dihydropyrimidine-4-carboxamide;

tert-butyl (2S,4R)-4-(benzyloxy)-2-(4-{[(4-fluorobenzyl)amino]carbonyl}-5-hydroxy-1-methyl-6-oxo-1,6-dihydropyrimidin-2-yl)pyrrolidine-1-carboxylate;

tert-butyl (2S,4R)-2-(4-{[(4-fluorobenzyl)amino]carbonyl}-5-hydroxy-1-methyl-6-oxo-1,6-dihydropyrimidin-2-yl)-4-hydroxypyrrolidine-1-carboxylate;

2-[(2S,4R)-4-(benzyloxy)pyrrolidin-2-yl]-N-(4-fluorobenzyl)-5-hydroxy-1-methyl-6-oxo-1,6-dihydropyrimidine-4-carboxamide;

N-(4-fluorobenzyl)-5-hydroxy-2-[(2S,4R)-4-hydroxypyrrolidin-2-yl]-1-methyl-6-oxo-1,6-dihydropyrimidine-4-carboxamide;

N-(4-fluorobenzyl)-5-hydroxy-2-[(2S,4R)-4-hydroxy-1-methylpyrrolidin-2-yl]-1-methyl-6-oxo-1,6-dihydropyrimidine-4-carboxamide;

2-[(2S,4R)-4-(benzyloxy)-1-methylpyrrolidin-2-yl]-N-(4-fluorobenzyl)-5-hydroxy-1-methyl-6-oxo-1,6-dihydropyrimidine-4-carboxamide;

2-[(2S,4R)-1-benzoyl-4-(benzyloxy)pyrrolidin-2-yl]-N-(4-fluorobenzyl)-5-hydroxy-1-methyl-6-oxo-1,6-dihydropyrimidine-4-carboxamide;

2-[1-(N,N-dimethylglycyl)-2,3-dihydro-1H-indol-2-yl]-N-(4-fluorobenzyl)-5-hydroxy-1-methyl-6-oxo-1,6-dihydropyrimidine-4-carboxamide;

2-(1-benzoyl-2,3-dihydro-1H-indol-2-yl)-N-(4-fluorobenzyl)-5-hydroxy-1-methyl-6-oxo-1,6-dihydropyrimidine-4-carboxamide;

N-(4-fluorobenzyl)-5-hydroxy-1-methyl-6-oxo-2-[1-(pyridin-2-ylcarbonyl)-2,3-dihydro-1H-indol-2-yl]-1,6-dihydropyrimidine-4-carboxamide;

tert-butyl 3-(4-{[(4-fluorobenzyl)amino]carbonyl}-5-hydroxy-1-methyl-6-oxo-1,6-dihydropyrimidin-2-yl)-4-methylpiperazine-1-carboxylate;

N-(4-fluorobenzyl)-5-hydroxy-1-methyl-2-(4-methylmorpholin-3-yl)-6-oxo-1,6-dihydropyrimidine-4-carboxamide;

(+)-N-(4-fluorobenzyl)-5-hydroxy-1-methyl-2-(4-methylmorpholin-3-yl)-6-oxo-1,6-dihydropyrimidine-4-carboxamide (−)-N-(4-fluorobenzyl)-5-hydroxy-1-methyl-2-(4-methylmorpholin-3-yl)-6-oxo-1,6-dihydropyrimidine-4-carboxamide 2-(1-ethyl-2,3-dihydro-1H-indol-2-yl)-N-(4-fluorobenzyl)-5-hydroxy-1-methyl-6-oxo-1,6-dihydropyrimidine-4-carboxamide;

2-(1-benzoylpiperidin-2-yl)-N-(4-fluorobenzyl)-5-hydroxy-1-methyl-6-oxo-1,6-dihydropyrimidine-4-carboxamide;

N-(4-fluorobenzyl)-5-hydroxy-1-methyl-6-oxo-2-[1-(pyridin-2-ylcarbonyl)piperidin-2-yl]-1,6-dihydropyrimidine-4-carboxamide;

N-(4-fluorobenzyl)-5-hydroxy-1-methyl-2-(2-methyl-1,2,3,4-tetrahydroisoquinolin-3-yl)-6-oxo-1,6-dihydropyrimidine-4-carboxamide;

2-(1-benzoylpyrrolidin-2-yl)-N-(4-fluorobenzyl)-5-hydroxy-1-methyl-6-oxo-1,6-dihydropyrimidine-4-carboxamide;

N-(4-fluorobenzyl)-5-hydroxy-1-methyl-6-oxo-2-[1-(pyridin-2-ylcarbonyl)pyrrolidin-2-yl]-1,6-dihydropyrimidine-4-carboxamide;

N-(4-fluorobenzyl)-5-hydroxy-1-methyl-2-(1-methylpyrrolidin-2-yl)-6-oxo-1,6-dihydropyrimidine-4-carboxamide;

2-[(2S,4R)-4-(benzyloxy)-1-(pyridin-2-ylcarbonyl)pyrrolidin-2-yl]-N-(4-fluorobenzyl)-5-hydroxy-1-methyl-6-oxo-1,6-dihydropyrimidine-4-carboxamide;

2-[1-(dimethylamino)-2-phenylethyl]-N-(4-fluorobenzyl)-5-hydroxy-1-methyl-6-oxo-1,6-dihydropyrimidine-4-carboxamide;

2-[(2S,4R)-1-benzoyl-4-hydroxypyrrolidin-2-yl]-N-(4-fluorobenzyl)-5-hydroxy-1-methyl-6-oxo-1,6-dihydropyrimidine-4-carboxamide;

N-(4-fluorobenzyl)-5-hydroxy-2-(1-isobutyl-2,3-dihydro-1H-indol-2-yl)-1-methyl-6-oxo-1,6-dihydropyrimidine-4-carboxamide;

N-(4-fluorobenzyl)-5-hydroxy-2-(1-isopropyl-2,3-dihydro-1H-indol-2-yl)-1-methyl-6-oxo-1,6-dihydropyrimidine-4-carboxamide;

2-[1-(N,N-dimethylglycyl)pyrrolidin-2-yl]-N-(4-fluorobenzyl)-5-hydroxy-1-methyl-6-oxo-1,6-dihydropyrimidine-4-carboxamide;

2-{1-[(6-bromopyridin-2-yl)carbonyl]pyrrolidin-2-yl}-N-(4-fluorobenzyl)-5-hydroxy-1-methyl-6-oxo-1,6-dihydropyrimidine-4-carboxamide;

N-(4-fluorobenzyl)-5-hydroxy-1-methyl-2-(1-methylpiperazin-2-yl)-6-oxo-1,6-dihydropyrimidine-4-carboxamide;

2-(1-benzoyl-4-methylpiperazin-2-yl)-N-(4-fluorobenzyl)-5-hydroxy-1-methyl-6-oxo-1,6-dihydropyrimidine-4-carboxamide;

N-(4-fluorobenzyl)-5-hydroxy-1-methyl-6-oxo-2-[1-(pyridin-2-ylcarbonyl)-1,2,3,4-tetrahydroquinolin-2-yl]-1,6-dihydropyrimidine-4-carboxamide;

2-(1-acetylpyrrolidin-2-yl)-N-(4-fluorobenzyl)-5-hydroxy-1-methyl-6-oxo-1,6-dihydropyrimidine-4-carboxamide;

2-[1-(cyclopropylcarbonyl)pyrrolidin-2-yl]-N-(4-fluorobenzyl)-5-hydroxy-1-methyl-6-oxo-1,6-dihydropyrimidine-4-carboxamide;

N-(4-fluorobenzyl)-5-hydroxy-1-methyl-2-[1-(methylsulfonyl)pyrrolidin-2-yl]-6-oxo-1,6-dihydropyrimidine-4-carboxamide;

N-(4-fluorobenzyl)-5-hydroxy-1-methyl-2-{1-[(4-methylmorpholin-3-yl)carbonyl]pyrrolidin-2-yl}-6-oxo-1,6-dihydropyrimidine-4-carboxamide;

2-(1,4-dimethylpiperazin-2-yl)-N-(4-fluorobenzyl)-5-hydroxy-1-methyl-6-oxo-1,6-dihydropyrimidine-4-carboxamide;

N-(4-fluorobenzyl)-5-hydroxy-1-methyl-6-oxo-2-[1-(pyridin-3-ylcarbonyl)pyrrolidin-2-yl]-1,6-dihydropyrimidine-4-carboxamide;

2-[(2S,4R)-1-acetyl-4-(benzyloxy)pyrrolidin-2-yl]-N-(4-fluorobenzyl)-5-hydroxy-1-methyl-6-oxo-1,6-dihydropyrimidine-4-carboxamide;

N-(4-fluorobenzyl)-5-hydroxy-2-(1-isonicotinoylpyrrolidin-2-yl)-1-methyl-6-oxo-1,6-dihydropyrimidine-4-carboxamide;

2-{1-[(ethylamino)carbonyl]pyrrolidin-2-yl}-N-(4-fluorobenzyl)-5-hydroxy-1-methyl-6-oxo-1,6-dihydropyrimidine-4-carboxamide;

N-(4-fluorobenzyl)-5-hydroxy-1-methyl-2-{1-[(1-methyl-1H-imidazol-2-yl)carbonyl]pyrrolidin-2-yl}-6-ox6-1,6-dihydropyrimidine-4-carboxamide;

2-[(2S,4R)-1-acetyl-4-hydroxypyrrolidin-2-yl]-N-(4-fluorobenzyl)-5-hydroxy-1-methyl-6-oxo-1,6-dihydropyrimidine-4-carboxamide;

2-[1-(anilinocarbonyl)pyrrolidin-2-yl]-N-(4-fluorobenzyl)-5-hydroxy-1-methyl-6-oxo-1,6-dihydropyrimidine-4-carboxamide;

2-(4-ethyl-1-methylpiperazin-2-yl)-N-(4-fluorobenzyl)-5-hydroxy-1-methyl-6-oxo-1,6-dihydropyrimidine-4-carboxamide;

N-(4-fluorobenzyl)-5-hydroxy-1-methyl-2-{1-[(1-oxidopyridin-2-yl)carbonyl]pyrrolidin-2-yl}-6-oxo-1,6-dihydropyrimidine-4-carboxamide;

N-(4-fluorobenzyl)-5-hydroxy-1-methyl-6-oxo-2-[1-(pyrazin-2-ylcarbonyl)pyrrolidin-2-yl]-1,6-dihydropyrimidine-4-carboxamide;

2-[(4R)-3-acetyl-1,3-thiazolidin-4-yl]-N-(4-fluorobenzyl)-5-hydroxy-1-methyl-6-oxo-1,6-dihydropyrimidine-4-carboxamide;

N-(4-fluorobenzyl)-5-hydroxy-1-methyl-2-[1-methyl-4-(methylsulfonyl)piperazin-2-yl]-6-oxo-1,6-dihydropyrimidine-4-carboxamide;

N-(4-fluorobenzyl)-5-hydroxy-1-methyl-2-(4-methylthiomorpholin-3-yl)-6-oxo-1,6-dihydropyrimidine-4-carboxamide;

N-[4-fluoro-2-(methylsulfonyl)benzyl]-5-hydroxy-1-methyl-6-oxo-2-[1-(pyrazin-2-ylcarbonyl)pyrrolidin-2-yl]-1,6-dihydropyrimidine-4-carboxamide;

2-(1-acetylpyrrolidin-2-yl)-N-[4-fluoro-2-(methylsulfonyl)benzyl]-5-hydroxy-1-methyl-6-oxo-1,6-dihydropyrimidine-4-carboxamide;

2-(3-acetyl-1,3-thiazolidin-2-yl)-N-(4-fluorobenzyl)-5-hydroxy-1-methyl-6-oxo-1,6-dihydropyrimidine-4-carboxamide;

2-[1-(acetylamino)-1-methylethyl]-N-(4-fluorobenzyl)-5-hydroxy-1-methyl-6-oxo-1,6-dihydropyrimidine-4-carboxamide;

2-(1-acetylpyrrolidin-2-yl)-N-(2-ethoxybenzyl)-5-hydroxy-1-methyl-6-oxo-1,6-dihydropyrimidine-4-carboxamide;

2-(4-acetyl-1-methylpiperazin-2-yl)-N-(4-fluorobenzyl)-5-hydroxy-1-methyl-6-oxo-1,6-dihydropyrimidine-4-carboxamide;

N-(4-fluorobenzyl)-5-hydroxy-1-methyl-2-[1-methyl-4-(pyrazin-2-ylcarbonyl)piperazin-2-yl]-6-oxo-1,6-dihydropyrimidine-4-carboxamide;

2-(1-acetylpyrrolidin-2-yl)-5-hydroxy-1-methyl-N-[2-(methylthio)benzyl]-6-oxo-1,6-dihydropyrimidine-4-carboxamide;

N-(4-fluorobenzyl)-5-hydroxy-2-{1-[(1H-imidazol-5-ylcarbonyl)amino]-1-methylethyl}-1-methyl-6-oxo-1,6-dihydropyrimidine-4-carboxamide;

2-[1-benzoyl-4-(pyrazin-2-ylcarbonyl)piperazin-2-yl]-N-(4-fluorobenzyl)-5-hydroxy-1-methyl-6-oxo-1,6-dihydropyrimidine-4-carboxamide;

2-(4-benzoyl-1-methylpiperazin-2-yl)-N-(4-fluorobenzyl)-5-hydroxy-1-methyl-6-oxo-1,6-dihydropyrimidine-4-carboxamide;

2-[4-(benzyloxy)-1-(pyrazin-2-ylcarbonyl)pyrrolidin-2-yl]-N-(4-fluorobenzyl)-5-hydroxy-1-methyl-6-oxo-1,6-dihydropyrimidine-4-carboxamide;

2-(1-acetylpyrrolidin-2-yl)-N-(2,3-dimethoxybenzyl)-5-hydroxy-1-methyl-6-oxo-1,6-dihydropyrimidine-4-carboxamide;

2-(1-acetylpyrrolidin-2-yl)-5-hydroxy-N-(2-methoxybenzyl)-1-methyl-6-oxo-1,6-dihydropyrimidine-4-carboxamide;

N1-[1-(4-{[(4-fluorobenzyl)amino]carbonyl}-5-hydroxy-1-methyl-6-oxo-1,6-dihydropyrimidin-2-yl)-1-methylethyl]-N2,N2-dimethylethanediamide;

2-(1-acetylpyrrolidin-2-yl)-N-[2-(dimethylamino)benzyl]-5-hydroxy-1-methyl-6-oxo-1,6-dihydropyrimidine-4-carboxamide;

2-[(2S)-1-acetylpyrrolidin-2-yl]-N-(4-fluorobenzyl)-5-hydroxy-1-methyl-6-oxo-1,6-dihydropyrimidine-4-carboxamide;

N-(4-fluorobenzyl)-5-hydroxy-2-[4-hydroxy-1-(pyrazin-2-ylcarbonyl)pyrrolidin-2-yl]-1-methyl-6-oxo-1,6-dihydropyrimidine-4-carboxamide;

N-[1-(4-{[(4-fluorobenzyl)amino]carbonyl}-5-hydroxy-1-methyl-6-oxo-1,6-dihydropyrimidin-2-yl)-1-methylethyl]imidazo[2,1-b][1,3]thiazole-6-carboxamide;

2-[(2S,4S)-1-acetyl-4-fluoropyrrolidin-2-yl]-N-(4-fluorobenzyl)-5-hydroxy-1-methyl-6-oxo-1,6-dihydropyrimidine-4-carboxamide;

N-(4-fluorobenzyl)-5-hydroxy-1-methyl-2-{1-methyl-4-[(1-methyl-1H-imidazol-2-yl)carbonyl]piperazin-2-yl}-6-oxo-1,6-dihydropyrimidine-4-carboxamide;

N-(4-fluorobenzyl)-5-hydroxy-1-methyl-2-(1-methyl-1-{[(5-methyl-1,3,4-oxadiazol-2-yl)carbonyl]amino}ethyl)-6-oxo-1,6-dihydropyrimidine-4-carboxamide;

N1-{1-[4-({[4-fluoro-2-(methylsulfonyl)benzyl]amino}carbonyl)-5-hydroxy-1-methyl-6-oxo-1,6-dihydropyrimidin-2-yl]-1-methylethyl}-N2,N2-dimethylethanediamide;

2-(4-acetyl-1,2-dimethylpiperazin-2-yl)-N-(4-fluorobenzyl)-5-hydroxy-1-methyl-6-oxo-1,6-dihydropyrimidine-4-carboxamide;

N-(4-fluorobenzyl)-5-hydroxy-1-methyl-6-oxo-2-[1-(pyrimidin-4-ylcarbonyl)pyrrolidin-2-yl]-1,6-dihydropyrimidine-4-carboxamide;

N-(4-fluorobenzyl)-5-hydroxy-1-methyl-6-oxo-2-[1-(pyrimidin-5-ylcarbonyl)pyrrolidin-2-yl]-1,6-dihydropyrimidine-4-carboxamide;

N-(4-fluorobenzyl)-5-hydroxy-1-methyl-2-{1-methyl-1-[(1H-pyrazol-5-ylcarbonyl)amino]ethyl}-6-oxo-1,6-dihydropyrimidine-4-carboxamide;

2-[(2R,4R)-1-acetyl-4-methoxypyrrolidin-2-yl]-N-(4-fluorobenzyl)-5-hydroxy-1-methyl-6-oxo-1,6-dihydropyrimidine-4-carboxamide;

2-{1-[(dimethylamino)(oxo)acetyl]pyrrolidin-2-yl }-N-(4-fluorobenzyl)-5-hydroxy-1-methyl-6-oxo-1,6-dihydropyrimidine-4-carboxamide;

N-{1-[4-({[4-fluoro-2-(methylsulfonyl)benzyl]amino }carbonyl)-5-hydroxy-1-methyl-6-oxo-1,6-dihydropyrimidin-2-yl]-1-methylethyl}imidazo[2, 1-b][1,3]thiazole-6-carboxamide;

2-[(2R,4R)-1-benzoyl-4-methoxypyrrolidin-2-yl]-N-(4-fluorobenzyl)-5-hydroxy-1-methyl-6-oxo-1,6-dihydropyrimidine-4-carboxamide;

N-(4-fluorobenzyl)-5-hydroxy-2-[4-(isopropylsulfonyl)-1-methylpiperazin-2-yl]-1-methyl-6-oxo-1,6-dihydropyrimidine-4-carboxamide;

2-[1,2-dimethyl-4-(methylsulfonyl)piperazin-2-yl]-N-(4-fluorobenzyl)-5-hydroxy-1-methyl-6-oxo-1,6-dihydropyrimidine-4-carboxamide;

N-(4-fluorobenzyl)-5-hydroxy-2-[(2S,4R)-4-methoxy-1-methylpyrrolidin-2-yl]-1-methyl-6-oxo-1,6-dihydropyrimidine-4-carboxamide;

N-(4-fluorobenzyl)-5-hydroxy-1-methyl-2-{1-[(methylsulfonyl)acetyl]pyrrolidin-2-yl}-6-oxo-1,6-dihydropyrimidine-4-carboxamide;

2-[(2S)-1-acetyl-4,4-difluoropyrrolidin-2-yl]-N-(4-fluorobenzyl)-5-hydroxy-1-methyl-6-oxo-1,6-dihydropyrimidine-4-carboxamide;

2-[(2R,4R)-1-acetyl-4-ethoxypyrrolidin-2-yl]-N-(4-fluorobenzyl)-5-hydroxy-1-methyl-6-oxo-1,6-dihydropyrimidine-4-carboxamide;

2-[(2S)-4,4-difluoro-1-methylpyrrolidin-2-yl]-N-(4-fluorobenzyl)-5-hydroxy-1-methyl-6-oxo-1,6-dihydropyrimidine-4-carboxamide;

N-(2,3-dimethoxybenzyl)-5-hydroxy-1-methyl-6-oxo-2-[1-(pyridazin-3-ylcarbonyl)pyrrolidin-2-yl]-1,6-dihydropyrimidine-4-carboxamide;

N-(4-fluorobenzyl)-5-hydroxy-1-methyl-2-(1-methyl-1-{[morpholin-4-yl(oxo)acetyl]amino}ethyl)-6-oxo-1,6-dihydropyrimidine-4-carboxamide;

2-{(2R,4R)-1-[(dimethylamino)(oxo)acetyl]-4-methoxypyrrolidin-2-yl}-N-(4-fluorobenzyl)-5-hydroxy-1-methyl-6-oxo-1,6-dihydropyrimidine-4-carboxamide;

2-[(2S)-4,4-difluoro-1-(pyrazin-2-ylcarbonyl)pyrrolidin-2-yl]-N-(4-fluorobenzyl)-5-hydroxy-1-methyl-6-oxo-1,6-dihydropyrimidine-4-carboxamide;

N-(4-fluorobenzyl)-5-hydroxy-1-methyl-2-{(2S,4S)-1-methyl-4-[(methylsulfonyl)amino]pyrrolidin-2-yl}-6-oxo-1, 6-dihydropyrimidine-4-carboxamide;

2-{1-[(dimethylamino)sulfonyl]pyrrolidin-2-yl}-N-(4-fluorobenzyl)-5-hydroxy-1-methyl-6-oxo-1,6-dihydropyrimidine-4-carboxamide;

2-{(2R,4R)-4-ethoxy-1-[(methylamino)(oxo)acetyl]pyrrolidin-2-yl}-N-(4-fluorobenzyl)-5-hydroxy-1-methyl-6-oxo-1,6-dihydropyrimidine-4-carboxamide;

2-[(2S)-4,4-difluoro-1-(pyridazin-3-ylcarbonyl)pyrrolidin-2-yl]-N-(4-fluorobenzyl)-5-hydroxy-1-methyl-6-oxo-1,6-dihydropyrimidine-4-carboxamide;

2-[(2S)-4,4-difluoro-1-(pyridin-2-ylcarbonyl)pyrrolidin-2-yl]-N-(4-fluorobenzyl)-5-hydroxy-1-methyl-6-oxo-1,6-dihydropyrimidine-4-carboxamide;

2-{(2S)-1-[(dimethylamino)(oxo)acetyl]4,4-difluoropyrrolidin-2-yl}-N-(4-fluorobenzyl)-5-hydroxy-1-methyl-6-oxo-1,6-dihydropyrimidine-4-carboxamide;

N-(4-fluorobenzyl)-5-hydroxy-1-methyl-2-{1-[morpholin-4-yl(oxo)acetyl]pyrrolidin-2-yl}-6-oxo-1,6-dihydropyrimidine-4-carboxamide;

2-{(2S)-1-[(dimethylamino)(oxo)acetyl]pyrrolidin-2-yl}-N-(4-fluorobenzyl)-5-hydroxy-1-methyl-6-oxo-1,6-dihydropyrimidine-4-carboxamide;

2-{(2S)-1-[(dimethylamino)(oxo)acetyl]pyrrolidin-2-yl}-N-(4-fluoro-2-methoxybenzyl)-5-hydroxy-1-methyl-6-oxo-1,6-dihydropyrimidine-4-carboxamide;

N1-[1-(4-{[(4-fluorobenzyl)amino]carbonyl}-5-hydroxy-1-methyl-6-oxo-1,6-dihydropyrimidin-2-yl)-1-methylethyl]-N1,N2,N2-trimethylethanediamide;

2-[(2S)-1-acetylpyrrolidin-2-yl]-N-(4-fluoro-2-methoxybenzyl)-5-hydroxy-1-methyl-6-oxo-1,6-dihydropyrimidine-4-carboxamide;

N-(4-fluorobenzyl)-2-[(2S,4S)-4-fluoro-1-methylpyrrolidin-2-yl]-5-hydroxy-1-methyl-6-oxo-1,6-dihydropyrimidine-4-carboxamide;

2-{(2S,4S)-1-[(dimethylamino)(oxo)acetyl]-4-fluoropyrrolidin-2-yl}-N-(4-fluorobenzyl)-5-hydroxy-1-methyl-6-oxo-1,6-dihydropyrimidine-4-carboxamide;

N1-[1-(4-{[(3-chloro4-fluorobenzyl)amino]carbonyl}-5-hydroxy-1-methyl-6-1,6-dihydropyrimidin-2-yl)-1-methylethyl]-N2,N2-dimethylethanediamide;

and pharmaceutically acceptable salts thereof.

Another aspect of the present invention is a compound selected from the group consisting of:

N-(4-fluorobenzyl)-5-hydroxy-1-methyl-6-oxo-2-[1-(pyrazin-2-ylcarbonyl)pyrrolidin-2-yl]-1,6-dihydropyrimidine-4-carboxamide;

2-[(2S,4R)-1-benzoyl-4-hydroxypyrrolidin-2-yl]-N-(4-fluorobenzyl)-5-hydroxy-1-methyl-6-oxo-1,6-dihydropyrimidine-4-carboxamide;

N-(4-fluorobenzyl)-5-hydroxy-1-methyl-2-{1-[(1-oxidopyridin-2-yl)carbonyl]pyrrolidin-2-yl}-6-oxo-1,6-dihydropyrimidine-4-carboxamide;

2-(1-acetylpyrrolidin-2-yl)-N-(4-fluorobenzyl)-5-hydroxy-1-methyl-6-oxo-1,6-dihydropyrimidine-4-carboxamide;

2-[(2S,4R)-4-(benzyloxy)-1-(pyridin-2-ylcarbonyl)pyrrolidin-2-yl]-N-(4-fluorobenzyl)-5-hydroxy-1-methyl-6-oxo-1,6-dihydropyrimidine-4-carboxamide;

N-(4-fluorobenzyl)-5-hydroxy-1-methyl-2-(4-methylmorpholin-3-yl)-6-oxo-1,6-dihydropyrimidine-4-carboxamide;

(+)-N-(4-fluorobenzyl)-5-hydroxy-1-methyl-2-(4-methylmorpholin-3-yl)-6-oxo-1,6-dihydropyrimidine-4-carboxamide (−)-N-(4-fluorobenzyl)-5-hydroxy-1-methyl-2-(4-methylmorpholin-3-yl)-6-oxo-1,6-dihydropyrimidine-4-carboxamide N-(4-fluorobenzyl)-5-hydroxy-1-methyl-6-oxo-2-[1-(pyridin-2-ylcarbonyl)pyrrolidin-2-yl]-1,6-dihydropyrimidine-4-carboxamide;

N-(4-fluorobenzyl)-5-hydroxy-1-methyl-6-oxo-2-[1-(pyridin-2-ylcarbonyl)-1,2,3,4-tetrahydroquinolin-2-yl]-1,6-dihydropyrimidine-4-carboxamide;

2-[(2S,4R)-1-benzoyl-4-(benzyloxy)pyrrolidin-2-yl]-N-(4-fluorobenzyl)-5-hydroxy-1-methyl-6-oxo-1,6-dihydropyrimidine-4-carboxamide;

2-[(2S,4R)-1-acetyl-4-(benzyloxy)pyrrolidin-2-yl]-N-(4-fluorobenzyl)-5-hydroxy-1-methyl-6-oxo-1,6-dihydropyrimidine-4-carboxamide;

N-(4-fluorobenzyl)-5-hydroxy-1-methyl-6-oxo-2-[1-(pyridin-3-ylcarbonyl)pyrrolidin-2-yl]-1,6-dihydropyrimidine-4-carboxamide;

N-(4-fluorobenzyl)-5-hydroxy-2-(1-isonicotinoylpyrrolidin-2-yl)-1-methyl-6-oxo-1,6-dihydropyrimidine-4-carboxamide;

2-(1,4-dimethylpiperazin-2-yl)-N-(4-fluorobenzyl)-5-hydroxy-1-methyl-6-oxo-1,6-dihydropyrimidine-4-carboxamide;

N-(4-fluorobenzyl)-5-hydroxy-1-methyl-2-{1-[(1-methyl-1H-imidazol-2-yl)carbonyl]pyrrolidin-2-yl}-6-oxo-1,6-dihydropyrimidine-4-carboxamide;

2-(1-benzoylpyrrolidin-2-yl)-N-(4-fluorobenzyl)-5-hydroxy-1-methyl-6-oxo-1,6-dihydropyrimidine-4-carboxamide;

N-(4-fluorobenzyl)-5-hydroxy-1-methyl-2-[1-(methylsulfonyl)pyrrolidin-2-yl]-6-oxo-1,6-dihydropyrimidine-4-carboxamide;

2-[(4R)-3-acetyl-1,3-thiazolidin4-yl]-N-(4-fluorobenzyl)-5-hydroxy-1-methyl-6-oxo-1,6-dihydropyrimidine-4-carboxamide;

2-{1-[(ethylamino)carbonyl]pyrrolidin-2-yl}-N-(4-fluorobenzyl)-5-hydroxy-1-methyl-6-oxo-1,6-dihydropyrimidine-4-carboxamide;

2-(4-ethyl-1-methylpiperazin-2-yl)-N-(4-fluorobenzyl)-5-hydroxy-1-methyl-6-oxo-1,6-dihydropyrimidine-4-carboxamide;

2-[(2S,4R)-4-(benzyloxy)-1-methylpyrrolidin-2-yl]-N-(4-fluorobenzyl)-5-hydroxy-1-methyl-6-oxo-1,6-dihydropyrimidine-4-carboxamide;

N-(4-fluorobenzyl)-5-hydroxy-1-methyl-6-oxo-2-[1-(pyridin-2-ylcarbonyl)-2,3-dihydro-1H-indol-2-yl]-1,6-dihydropyrimidine-4-carboxamide;

N-(4-fluorobenzyl)-5-hydroxy-1-methyl-2-(1-methyl-1,2,3,4-tetrahydroquinolin-2-yl)-6-oxo-1,6-dihydropyrimidine-4-carboxamide;

N-(4-fluorobenzyl)-5-hydroxy-1-methyl-2-(2-methyl-1,2,3,4-tetrahydroisoquinolin-3-yl)-6-oxo-1,6-dihydropyrimidine-4-carboxamide;

2-[1-(dimethylamino)-2-phenylethyl]-N-(4-fluorobenzyl)-5-hydroxy-1-methyl-6-oxo-1,6-dihydropyrimidine-4-carboxamide;

2-[(dimethylamino)(phenyl)methyl]-N-(4-fluorobenzyl)-5-hydroxy-1-methyl-6-oxo-1,6-dihydropyrimidine-4-carboxamide;

N-(2,3-dimethoxybenzyl)-5-hydroxy-1-methyl-2-[4-(morpholin-4-ylmethyl)phenyl]-6-oxo-1,6-dihydropyrimidine-4-carboxamide;

and pharmaceutically acceptable salts thereof.

Other embodiments of the present invention include the following:

(a) A pharmaceutical composition comprising a compound of Formula (I) and a pharmaceutically acceptable carrier.

(b) A pharmaceutical composition which comprises the product prepared by combining (e.g., mixing) an effective amount of a compound of Formula (I) and a pharmaceutically acceptable carrier.

(c) The pharmaceutical composition of (a) or (b), further comprising a therapeutically effective amount of an HIV infection/AIDS treatment agent selected from the group consisting of HIV/AIDS antiviral agents, immunomodulators, and anti-infective agents.

(d) The pharmaceutical composition of (c), wherein the HIV infection/AIDS treatment agent is an antiviral selected from the group consisting of HIV protease inhibitors, non-nucleoside HIV reverse transcriptase inhibitors, and nucleoside HIV reverse transcriptase inhibitors.

(e) A combination useful for inhibiting HIV integrase, for treating or preventing infection by HIV, or for preventing, treating or delaying the onset of AIDS, which is a therapeutically effective amount of a compound of Formula (I) and a therapeutically effective amount of an HIV infection/AIDS treatment agent selected from the group consisting of HIV/AIDS antiviral agents, immunomodulators, and anti-infective agents.

(f) The combination of (e), wherein the HIV infection/AIDS treatment agent is an antiviral selected from the group consisting of HIV protease inhibitors, non-nucleoside HIV reverse transcriptase inhibitors and nucleoside HIV reverse transcriptase inhibitors.

(g) A method of inhibiting HIV integrase in a subject in need thereof which comprises administering to the subject a therapeutically effective amount of a compound of Formula (I).

(h) A method of preventing or treating infection by HIV in a subject in need thereof which comprises administering to the subject a therapeutically effective amount of a compound of Formula (I).

(i) The method of (h), wherein the compound of Formula (I) is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors.

(j) A method of preventing, treating or delaying the onset of AIDS in a subject in need thereof which comprises administering to the subject a therapeutically effective amount of a compound of Formula (I).

(k) The method of (j), wherein the compound is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors (l) A method of inhibiting HIV integrase in a subject in need thereof which comprises administering to the subject the pharmaceutical composition of (a), (b), (c) or (d) or the combination of (e) or (f).

(m) A method of preventing or treating infection by HIV in a subject in need thereof which comprises administering to the subject the pharmaceutical composition of (a), (b), (c) or (d) or the combination of (e) or (f).

(n) A method of preventing, treating or delaying the onset of AIDS in a subject in need thereof which comprises administering to the subject the pharmaceutical composition of (a), (b), (c) or (d) or the combination of (e) or (f).

The present invention also includes a compound of the present invention (i) for use in, (ii) for use as a medicament for, or (iii) for use in the preparation of a medicament for: (a) inhibiting HIV protease, (b) preventing or treating infection by HIV, or (c) preventing, treating or delaying the onset of AIDS. In these uses, the compounds of the present invention can optionally be employed in combination with one or more HIV/AIDS treatment agents selected from HIV/AIDS antiviral agents, anti-infective agents, and immunomodulators.

Additional embodiments of the invention include the pharmaceutical compositions, combinations and methods set forth in (a)–(n) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt.

As used herein, the term "$C_{1-6}$ alkyl" (or "$C_1$–$C_6$ alkyl") means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl.

The term "$C_0$" as employed in expressions such as "$C_{0-6}$ alkyl" means a direct covalent bond. For example, when $R^1$ in Compound I is —$C_{0-6}$ alkyl-O—$C_{0-6}$ alkyl-$R^k$, then $R^1$ is —O—$R^k$ when both alkyl groups are $C_0$ alkyl. Similarly, when an integer defining the presence of a certain number of atoms in a group is equal to zero, it means that the atoms adjacent thereto are connected directly by a bond. For example, the compound of Formula (II) has

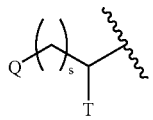

as a substituent at the 2-position of the pyrimidinone ring, wherein s is an integer equal to zero, 1 or 2. When s is zero, the substituent has the following structure:

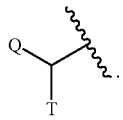

The term "—$C_{1-6}$ alkyl-" refers to a $C_1$ to $C_6$ linear or branched alkyl group as just defined which is bivalent. It can alternatively be referred to as "$C_{1-6}$ alkylene" or "$C_{1-6}$ alkanediyl". A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—.

The term "$C_{2-5}$ alkynyl" (or "$C_2$–$C_5$ alkynyl") means linear or branched chain alkynyl groups having from 2 to 5 carbon atoms and includes all of the pentynyl isomers as well as 1-butynyl, 2-butynyl, 3-butynyl, 1-propynyl, 2-propynyl, and ethynyl (or acetylenyl). Similar terms such as "$C_{2-3}$ alkynyl" have an analogous meaning.

The term "$C_{3-8}$ cycloalkyl" (or "$C_3$–$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "$C_{3-7}$ azacycloalkyl" (or "$C_3$–$C_7$ azacycloalkyl") means a saturated cyclic ring consisting of one nitrogen and from three to seven carbon atoms (i.e., azetidinyl, pyrrolidinyl, piperidinyl, or azepanyl).

The term "halogen" (or "halo") refers to fluorine, chlorine, bromine and iodine (alternatively referred to as fluoro, chloro, bromo, and iodo).

The term "$C_{1-6}$ haloalkyl" (which may alternatively be referred to as "$C_1$–$C_6$ haloalkyl" or "halogenated $C_1$–$C_6$ alkyl") means a $C_1$ to $C_6$ linear or branched alkyl group as defined above with one or more halogen substituents. The term "$C_{1-4}$ haloalkyl" has an analogous meaning. The term "$C_{1-6}$ fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "carbocycle" (and variations thereof such as "carbocyclic" or "carbocyclyl") as used herein refers to (i) a $C_3$ to $C_8$ monocyclic, saturated or unsaturated ring, (ii) a $C_7$ to $C_{12}$ bicyclic ring system, or (iii) a $C_{11}$ to $C_{16}$ tricyclic ring system, wherein each ring in (ii) or (iii) is independent of or fused to the other ring or rings and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. Fused tricyclic carbocycles have an analogous meaning. A subset of the fused bicyclic carbocycles are those bicyclic carbocycles in which one ring is a benzene ring and the other ring is saturated or unsaturated, with attachment via any carbon atom that results in a stable compound. Representative examples of this subset include the following:

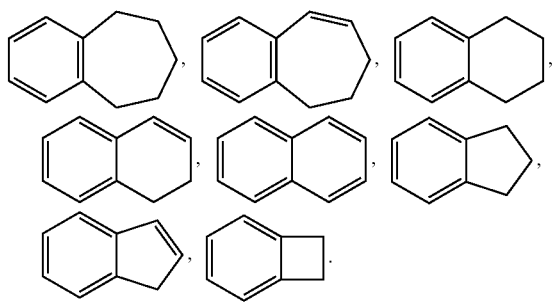

The term "aryl" refers to aromatic mono- and polycarbocyclic ring systems, wherein the individual carbocyclic rings in the polyring systems are fused or attached to each other via a single bond. Suitable aryl groups include phenyl, naphthyl, and biphenylenyl.

The term "heterocycle" (and variations thereof such as "heterocyclic" or "heterocyclyl") broadly refers to (i) a 4- to 8-membered, saturated or unsaturated monocyclic ring, (ii) a 7- to 12-membered bicyclic ring system, or (iii) an 11 to 16-membered tricyclic ring system; wherein each ring in (ii) or (iii) is independent of or fused to the other ring or rings and each ring is saturated or unsaturated, and the monocyclic ring, bicyclic ring system, or tricyclic ring system contains one or more heteroatoms (e.g., from 1 to 6 heteroatoms, or from 1 to 4 heteroatoms) selected from N, O and S and a balance of carbon atoms (the monocylic ring typically contains at least one carbon atom and the ring systems typically contain at least two carbon atoms); and wherein any one or more of the nitrogen and sulfur heteroatoms is optionally be oxidized, and any one or more of the nitrogen heteroatoms is optionally quaternized. The heterocyclic ring may be attached at any heteroatom or carbon atom, provided that attachment results in the creation of a stable structure. When the heterocyclic ring has substituents, it is understood that the substituents may be attached to any atom in the ring, whether a heteroatom or a carbon atom, provided that a stable chemical structure results.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring which consists of carbon atoms and one or more heteroatoms selected from N, O and S. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl

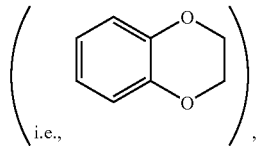

imidazo(2,1-b)(1,3)thiazole,

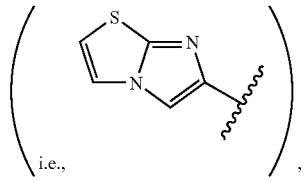

and benzo-1,3-dioxolyl

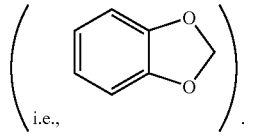

In certain contexts herein,

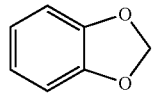

is alternatively referred to as phenyl having as a substituent methylenedioxy attached to two adjacent carbon atoms.

Representative examples of tricyclic heterocycles include phenothiazinyl, carbazolyl, beta-carbolinyl, tetrahydro-beta-carbolinyl, acridinyl, phenazinyl, and phenoxazinyl.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable (e.g., $R^a$, $R^b$, $R^c$, $R^k$, etc.) occurs more than one time in any constituent or in Formula I or in any other formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ;") includes mono- and poly-substitution by a named substituent to the extent such single and multiple substitution (including multiple substitution at the same site) is chemically allowed.

The compounds of the present invention may have asymmetric centers and may occur, except when specifically noted, as mixtures of stereoisomers or as individual diastereomers, or enantiomers, with all isomeric forms being included in the present invention.

The N-substituted hydroxypyrimidinone compounds of the present invention may also occur as tautomers thereof. It is understood that the present invention includes all tautomers of the hydroxypyrimidinone compounds of Formula I, both singly and in mixtures.

The compounds of the present invention are useful in the inhibition of HIV integrase, the prevention or treatment of infection by human immunodeficiency virus (HIV) and the prevention, treatment or the delay in the onset of consequent pathological conditions such as AIDS. Preventing AIDS, treating AIDS, delaying the onset of AIDS, or preventing or treating infection by HIV is defined as including, but not limited to, treatment of a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention are commercial products to be sold for these purposes.

Compounds representative of the present invention have been tested for inhibition in an assay for the strand transfer activity of integrase. The assay is conducted in accordance with Wolfe, A. L. et al., *J. Virol.* 1996, 70: 1424–1432, for recombinant integrase, except that: (i) the assay uses preassembled integrase strand transfer complexes; (ii) the strand transfer reaction is performed in the presence of inhibitor in 2.5 mM $MgCl_2$ using 0.5 to 5 nM of a 3' FITC labeled target DNA substrate as described in WO 02/30930 and (iii) strand transfer products are detected using an alkaline phosphatase conjugated anti-FITC antibody and a chemiluminescent alkaline phosphatase substrate. Representative compounds (e.g., the compounds set forth in Table 1 below) tested in the integrase assay demonstrated $IC_{50}$'s of about 5 micromolar or less.

Further description on conducting the assay using preassembled complexes is found in Hazuda et al., *J. Virol.* 1997, 71: 7005–7011; Hazuda et al., *Drug Design and Discovery* 1997, 15: 17–24; and Hazuda et al., *Science* 2000, 287: 646–650.

Certain compounds representative of the present invention have also been tested in an assay for inhibition of acute HIV infection of T-lymphoid cells, conducted in accordance with Vacca, J. P. et al., *Proc. Natl. Acad. Sci. USA* 1994, 91: 4096. These compounds demonstrated $IC_{95}$'s of about 20 micromolar or less.

The compounds of the present invention may be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. When the compounds of the invention carry an acidic moiety, suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

For the purpose of preventing or treating HIV infection or preventing, treating or delaying the onset of AIDS, the compounds of the present invention may be administered orally, parenterally (including subcutaneous injections, intravenous, intramuscular, intrasternal injection or infusion techniques), by inhalation spray, or rectally, in the form of a unit dosage of a pharmaceutical composition containing a therapeutically effective amount of the compound and conventional non-toxic pharmaceutically-acceptable carriers, adjuvants and vehicles.

The term "administration" and variants thereof (e.g., "administering" a compound) in reference to a compound of the invention mean providing the compound or a prodrug of the compound to the individual in need of treatment. When a compound of the invention or a prodrug thereof is provided in combination with one or more other active agents (e.g., antiviral agents useful for treating HIV infection or AIDS), "administration" and its variants are each understood to include concurrent and sequential provision of the compound or prodrug and other agents.

As used herein, the term "composition" is intended to encompass a product comprising the specified ingredients in the specified amounts, as well as any product which results, directly or indirectly, from combining the specified ingredients in the specified amounts.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated. When the active compound (i.e., active ingredient) is administered as the salt, references to the amount of active ingredient are to the free acid or free base form of the compound.

The pharmaceutical compositions may be in the form of orally-administrable suspensions or tablets or capsules, nasal sprays, sterile injectable preparations, for example, as sterile injectable aqueous or oleagenous suspensions or suppositories. These compositions can be prepared by methods and contain excipients which are well known in the art. Suitable methods and ingredients are described in *Remington's Pharmaceutical Sciences*, 18$^{th}$ edition, edited by A. R. Gennaro, Mack Publishing Co., 1990, which is herein incorporated by reference in its entirety.

The compounds of this invention can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of the HIV integrase inhibitor compounds of the present invention with one or more agents useful in the treatment of HIV infection or ADS. For example, the compounds of this invention may be effectively administered, whether at periods of pre-exposure and/or post-exposure, in combination with effective amounts of one or more of the HIV/AIDS antivirals, immunomodulators, antiinfectives, or vaccines useful for treating HIV infection or AIDS. Suitable antiviral agents include those listed in the following Table:

| | ANTIVIRALS | |
|---|---|---|
| Drug Name | Manufacturer (Tradename and/or Location) | Indication (Activity) |
| abacavir GW 1592 1592U89 | Glaxo Welcome (ZIAGEN ®) | HIV infection, AIDS, ARC (nRTI) |
| abacavir + lamivudine + zidovudine | GlaxoSmithKline (TRIZIVIR ®) | HIV infection, AIDS, ARC (nnRTI) |
| acemannan | Carrington Labs (Irving, TX) | ARC |

-continued

ANTIVIRALS

| Drug Name | Manufacturer (Tradename and/or Location) | Indication (Activity) |
|---|---|---|
| ACH 126443 | Achillion Pharm. | HIV infections, AIDS, ARC (nucleoside reverse transcriptase inhibitor) |
| acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| adefovir dipivoxil GS 840 | Gilead | HIV infection, AIDS, ARC (RTI) |
| AL-721 | Ethigen (Los Angeles, CA) | ARC, PGL, HIV positive, AIDS |
| alpha interferon | Glaxo Wellcome | Kaposi's sarcoma, HIV, in combination w/Retrovir |
| AMD3100 | AnorMed | HIV infection, AIDS, ARC (CXCR4 antagonist) |
| amprenavir 141 W94 GW 141 VX478 (Vertex) | Glaxo Wellcome (AGENERASE ®) | HIV infection, AIDS, ARC (PI) |
| ansamycin LM 427 | Adria Laboratories (Dublin, OH) Erbamont (Stamford, CT) | ARC |
| antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| atazanavir (BMS 232632) | Bristol-Myers-Squibb (ZRIVADA ®) | HIV infection, AIDS, ARC (PI) |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (PI) |
| BMS-234475 (CGP-61755) | Bristol-Myers Squibb/ Novartis | HIV infection, AIDS, ARC (PI) |
| capravirine (AG-1549, S-1153) | Pfizer | HIV infection, AIDS, ARC (nnRTI) |
| CI-1012 | Warner-Lambert | HIV-1 infection |
| cidofovir | Gilead Science | CMV retinitis, herpes, papillomavirus |
| curdlan sulfate | AJI Pharma USA | HIV infection |
| cytomegalovirus immune globin | MedImmune | CMV retinitis |
| cytovene ganciclovir | Syntex | sight threatening CMV peripheral CMV retinitis |
| delavirdine | Pharmacia-Upjohn (RESCRIPTOR ®) | HIV infection, AIDS, ARC (nnRTI) |
| dextran Sulfate | Ueno Fine Chem. Ind. Ltd. (Osaka, Japan) | AIDS, ARC, HIV positive asymptomatic |
| ddC (zalcitabine, dideoxycytidine) | Hoffman-La Roche (HIVID ®) | HIV infection, AIDS, ARC (nRTI) |
| ddI Dideoxyinosine | Bristol-Myers Squibb (VIDEX ®) | HIV infection, AIDS, ARC; combination with AZT/d4T (nRTI) |
| DPC 681 & DPC 684 | DuPont | HIV infection, AIDS, ARC (PI) |
| DPC 961 & DPC 083 | DuPont | HIV infection AIDS, ARC (nnRTRI) |
| emvirine | Triangle Pharmaceuticals (COACTINON ®) | HIV infection, AIDS, ARC (non-nucleoside reverse transcriptase inhibitor) |
| EL10 | Elan Corp, PLC (Gainesville, GA) | HIV infection |
| efavirenz (DMP 266) | DuPont (SUSTIVA ®) Merck (STOCRIN ®) | HIV infection, AIDS, ARC (nnRTI) |
| famciclovir | Smith Kline | herpes zoster, herpes simplex |
| emtricitabine FTC | Triangle Pharmaceuticals (COVIRACIL ®) Emory University | HIV infection, AIDS, ARC (nRTI) |

ANTIVIRALS -continued

| Drug Name | Manufacturer (Tradename and/or Location) | Indication (Activity) |
|---|---|---|
| emvirine | Triangle Pharmaceuticals (COACTINON ®) | HIV infection, AIDS, ARC (non-nucleoside reverse transcriptase inhibitor) |
| HBY097 | Hoechst Marion Roussel | HIV infection, AIDS, ARC (nnRTI) |
| hypericin | VIMRx Pharm. | HIV infection, AIDS, ARC |
| recombinant human interferon beta | Triton Biosciences (Almeda, CA) | AIDS, Kaposi's sarcoma, ARC |
| interferon alfa-n3 | Interferon Sciences | ARC, AIDS |
| indinavir | Merck (CRIXIVAN ®) | HIV infection, AIDS, ARC, asymptomatic HIV positive, also in combination with AZT/ddI/ddC (PI) |
| ISIS 2922 | ISIS Pharmaceuticals | CMV retinitis |
| JE2147/AG1776 | Agouron | HIV infection, AIDS, ARC (PI) |
| KNI-272 | Nat'l Cancer Institute | HIV-assoc. diseases |
| lamivudine, 3TC | Glaxo Wellcome (EPIVIR ®) | HIV infection, AIDS, ARC; also with AZT (nRTI) |
| lobucavir | Bristol-Myers Squibb | CMV infection |
| lopinavir (ABT-378) | Abbott | HIV infection, AIDS, ARC (PI) |
| lopinavir + ritonavir (ABT-378/r) | Abbott (KALETRA ®) | HIV infection, AIDS, ARC (PI) |
| mozenavir (DMP-450) | AVID (Camden, NJ) | HIV infection, AIDS, ARC (PI) |
| nelfinavir | Agouron (VIRACEPT ®) | HIV infection, AIDS, ARC (PI) |
| nevirapine | Boeheringer Ingleheim (VIRAMUNE ®) | HIV infection, AIDS, ARC (nnRTI) |
| novapren | Novaferon Labs, Inc. (Akron, OH) | HIV inhibitor |
| pentafusaide T-20 | Trimeris | HIV infection, AIDS, ARC (fusion inhibitor) |
| peptide T octapeptide sequence | Peninsula Labs (Belmont, CA) | AIDS |
| PRO 542 | Progenics | HIV infection, AIDS, ARC (attachment inhibitor) |
| PRO 140 | Progenics | HIV infection, AIDS, ARC (CCR5 co-receptor inhibitor) |
| trisodium phosphonoformate | Astra Pharm. Products, Inc | CMV retinitis, HIV infection, other CMV infections |
| PNU-140690 | Pharmacia Upjohn | HIV infection, AIDS, ARC (PI) |
| probucol | Vyrex | HIV infection, AIDS |
| RBC-CD4 | Sheffield Med. Tech (Houston TX) | HIV infection, AIDS, ARC |
| ritonavir (ABT-538) | Abbott (RITONAVIR ®) | HIV infection, AIDS, ARC (PI) |
| saquinavir | Hoffmann-LaRoche (FORTOVASE ®) | HIV infection, AIDS, ARC (PI) |
| stavudine; d4T didehydrodeoxythymidine | Bristol-Myers Squibb (ZERIT ®) | HIV infection, AIDS, ARC (nRTI) |
| T-1249 | Trimeris | HIV infection, AIDS, ARC (fusion inhibitor) |
| TAK-779 | Takeda | HIV infection, AIDS, ARC (injectable CCR5 receptor antagonist) |
| tenofovir | Gilead (VIREAD ®) | HIV infection, AIDS, ARC (nRTI) |
| tipranavir (PNU-140690) | Boehringer Ingelheim | HIV infection, AIDS, ARC (PI) |
| TMC-120 & TMC-125 | Tibotec | HIV infections, AIDS, ARC (nnRTI) |
| TMC-126 | Tibotec | HIV infection, AIDS, ARC (PI) |
| valaciclovir | Glaxo Wellcome | genital HSV & CMV infections |
| virazole | Viratek/ICN (Costa | asymptomatic HIV positive, |

| | -continued | |
|---|---|---|
| | ANTIVIRALS | |
| Drug Name | Manufacturer (Tradename and/or Location) | Indication (Activity) |
| ribavirin | Mesa, CA) | LAS, ARC |
| zidovudine; AZT | Glaxo Wellcome (RETROVIR ®) | HIV infection, AIDS, ARC, Kaposi's sarcoma in combination with other therapies (nRTI) |

PI = protease inhibitor
nnRTI = non-nucleoside reverse transcriptase inhibitor
nRTI = nucleoside reverse transcriptase inhibitor A compound of the present invention can also be administered in combination with another HIV integrase inhibitor such as a compound described in WO 99/62513, WO 99/62520, or WO 99/62897. A compound of the present invention can also be administered in combination with a CCR5 receptor antagonist, such as a compound described in WO 99/04794, WO 99/09984, WO 99/38514, WO 00/59497, WO 00/59498, WO 00/59502, WO 00/59503, WO 00/76511, WO 00/76512, WO 00/76513, WO 00/76514, WO 00/76792, or WO 00/76793. The compounds of this invention may be effectively administered, whether at periods of pre-exposure and/or post-exposure, in combination with effective amounts of one or more HIV/AIDS antivirals, immunomodulators, antiinfectives, or vaccines useful for treating HIV infection or ADS disclosed in the Table in WO 01/38332, which is herein incorporated by reference in its entirety.

It will be understood that the scope of combinations of the compounds of this invention with HIV/AIDS antivirals, immunomodulators, anti-infectives or vaccines is not limited to those listed above or listed in the above-referenced Table in WO 01/38332, but includes in principle any combination with any pharmaceutical composition useful for the treatment of AIDS. The HIV/AIDS antivirals and other agents will typically be employed in these combinations in their conventional dosage ranges and regimens as reported in the art, including the dosages described in the *Physicians' Desk Reference*, 54$^{th}$ edition, Medical Economics Company, 2000. The dosage ranges for a compound of the invention in these combinations are the same as those set forth above.

Abbreviations used in the instant specification, particularly the Schemes and Examples, include the following:
AIDS=acquired immunodeficiency syndrome
ARC=AIDS related complex
BOC or Boc=t-butyloxycarbonyl
Bn=benzyl
Bz=benzoyl
CBZ or Cbz=carbobenzoxy (alternatively, benzyloxycarbonyl)
DMAD=dimethylacetylenedicarboxylate
DMAP=dimethylaminopyridine
DMF=N,N-dimethylformamide
Et=ethyl
EtOAc=ethyl acetate
FIA-MS=flow injection analysis mass spectrometry
HIV=human immunodeficiency virus
HPLC=high performance liquid chromatography
m-CPBA=meta-chloroperbenzoic acid
Me=methyl
NMP=N-methyl pyrrolidinone
NMR=nuclear magnetic resonance
Ph=phenyl
TFA=trifluoroacetic acid
THF=tetrahydrofuran The compounds of the present invention can be readily prepared according to the following reaction schemes and examples, or modifications thereof, using readily available starting materials and reagents. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

The compounds of the present invention can be prepared by coupling suitable substituted alkyl 1-alkyl-1,6-dihydro-5-hydroxy-6-oxopyrimidine-4-carboxylates (or carboxylic acids or halides) with the appropriate amines, as represented by Scheme 1. In the scheme, P is H or a protective group, typically an ester (e.g., benzoate or pivalate) that is normally removed under the conditions employed to convert the the methyl ester to the amide. The ester protective group is typically used to purify the 2-substituted-5,6 dihydroxypyrimidine-4-carboxylates after their synthesis when the unprotected product cannot be crystallized from the reaction crude and/or for synthetic reasons.

Scheme 1

Methods for coupling carboxylic acid derivatives with amines to form carboxamides are well known in the art. Suitable methods are described, for example, in Jerry March, *Advanced Organic Chemistry*, 3rd edition, John Wiley & Sons, 1985, pp. 370–376. Amines of formula 1-1 can be prepared using the methods described in Richard Larock, Comprehensive Organic Transformations, VCH Publishers Inc, 1989, pp. 385–438, or routine variations thereof.

Methyl 1-alkyl-1,6-dihydro-5-hydroxy-6-oxopyrimidine-4-carboxylates of formula 1-2 can be prepared as shown in Scheme 2, wherein amidoxime 2-1 can be reacted with DMAD in an appropriate solvent and at a suitable temperature to give the intermediate dihydroxypyrimidine 2-2, followed by protection of the 5-hydroxy group in 2-2 with a suitable protecting agent such as benzoate or pivalate to give 2-3, and then alkylation of nitrogen-1 to afford 1-2. This procedure is described in the literature [Culbertson et al., *J Heterocycl. Chem.* 1979, 16 (7): 1423–24]. Dihydroxypyrimidine 2-2 can be isolated or directly protected to give 2-3. The alkyl group can be introduced on N, by reaction of 2-3 with an alkylating agent in the presence of an inorganic base (e.g., cesium carbonate). If a mixture of N— and O-alkylated derivatives results, the desired N-alkylated product 1-2 can be separated by flash chromatography. Scheme 2 is exemplified in Example 1.

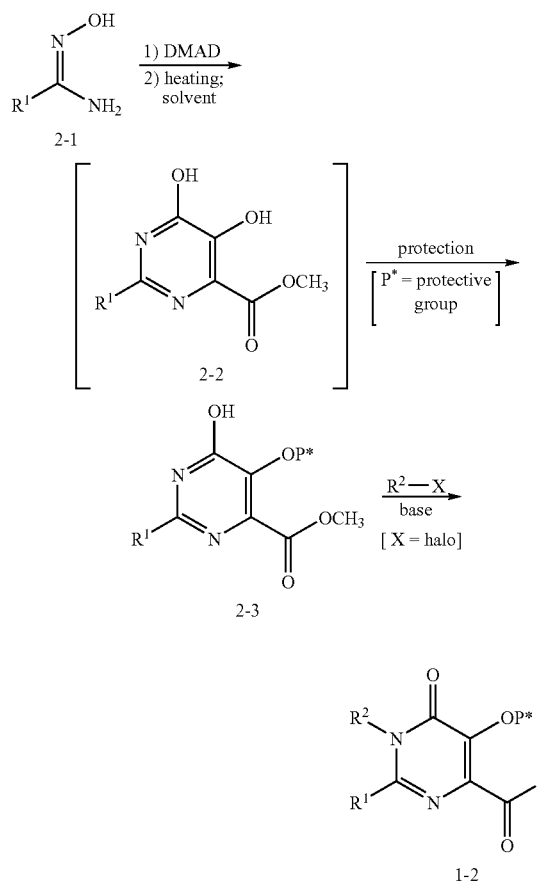

Methyl 1-alkyl-1,6-dihydro-5-hydroxy-6-oxopyrimidine-4-carboxylates of formula 1-2 can be prepared as shown in Scheme 3, wherein an N-alkylamidoxime 3-1 can be reacted with dimethylacetylenedicarboxylate to give the unprotected 1-2 (P=H). The unprotected compound can be isolated as such or it can be converted to 1-2 by reaction with a suitable protecting group. Scheme 3 is exemplified in Example 2.

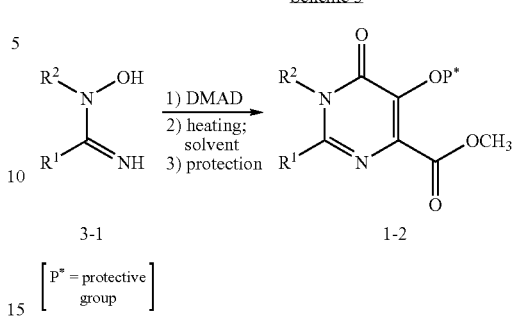

Amidoximes 2-1 and 3-1 are prepared from the corresponding nitriles 15 by chemistry described herein (see Example 1, Step 1 and Example 2, Step 2). Nitriles can be prepared from carboxylic acids by various procedures known in the art, including, for example, conversion to carboxamides by the procedure of of Pozdnev (*Tetrahedron Lett.* 1989, 30: 5193) (see also, Example 6, Step 2), and dehydration of the amide by the procedure of Waldmann (*Tetrahedron* 1994, 50: 11865) (see also, Example 6, Step 3).

Compounds of the present invention of general formula 3-3 or 3-6 can be prepared in accordance with Scheme 3, Parts 1 and 2, wherein haloderivative 3-1 or 3–4 can be synthesized by the bromination or chlorination of a suitable substrate affording a —CH$_2$Br, —CH$_2$Cl, —CHBr—, or —CHCl— group, followed by displacement of the halogen with a nucleophile ("Nu") such as an amine, thiol, or alcoholate to obtain the nucleophile-substituted methyl ester intermediate 3-2 or 3-5, which need not be isolated. Elaboration of the methyl ester functionality into the carboxamide will afford the final product 3-3 or 3–6. Scheme 3 is exemplified in Example 5.

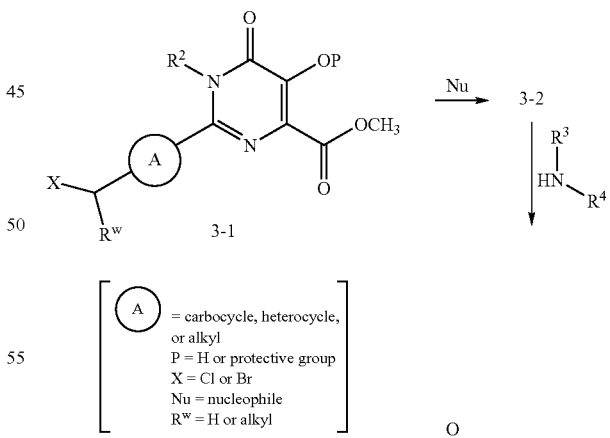

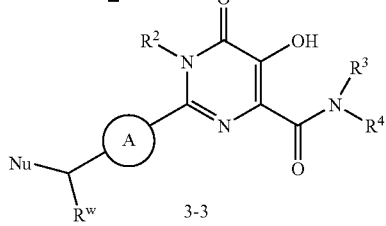

Scheme 3 - Part 2

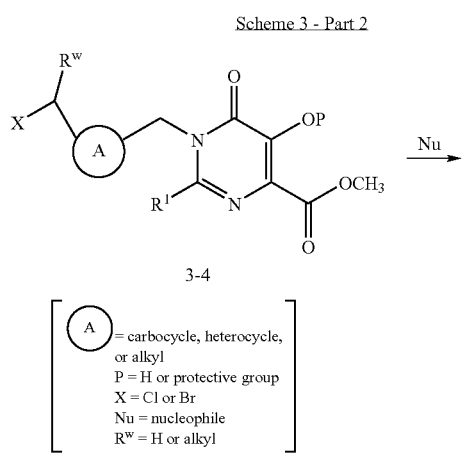

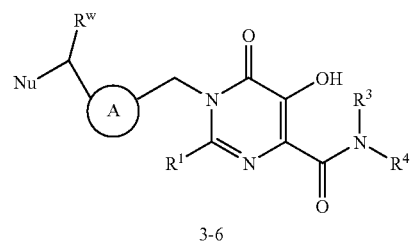

Scheme 4 depicts the preparation of compounds of the invention that contain an alkylated aliphatic amine in the substituent at the 2 position. Nitrogen alkylation is achieved via a reductive amination or alkylation. The nitrogen alkylation can be performed before formation of the amide (via 4-3) or after formation of the amide (via 4-2) depending on the substrate, with suitable deprotection as necessary. Scheme 4 is exemplified in Examples 6 to 8 below.

Scheme 4

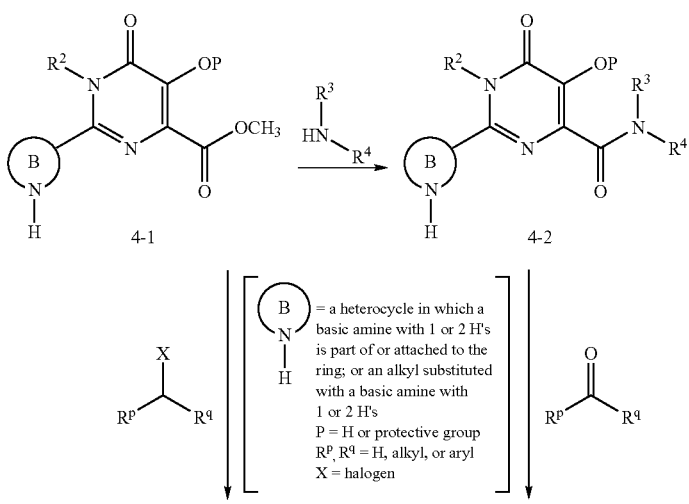

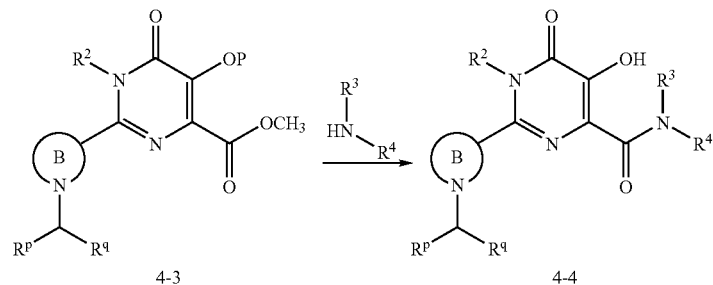

Compounds of the present invention with general formula 5-3 containing an acylated nitrogen or sulfonylated nitrogen in the substituent at the 2-position, can be prepared following Scheme 5. Acylation or sulfonylation of the nitrogen in the 2-substituent of the pyrimidine core provides compound 5-2, which can be elaborated into the final amide 5-3 by reaction of a suitable amine in a polar solvent. Scheme 5 is exemplified in Examples 9 to 12 below.

Scheme 5

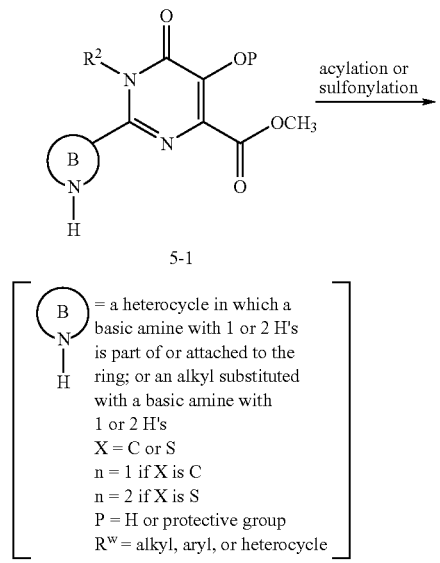

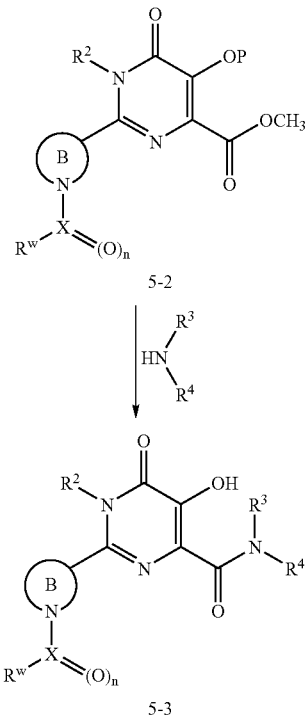

The preparation of compounds that feature a carboxamide at the 2 position of the pyrimidine core can be achieved as shown in Scheme 6, wherein a starting material bearing a 2-ethyl- and a 4-methylcarboxylate functionality (6-1) is employed. This strategy will allow the regioselective elaboration of the 4-methyl ester into the carboxamide by reaction with a suitable amine. The other ester bond in the 2 position can then be further elaborated. Scheme 6 is exemplified in Example 13 below.

Scheme 6

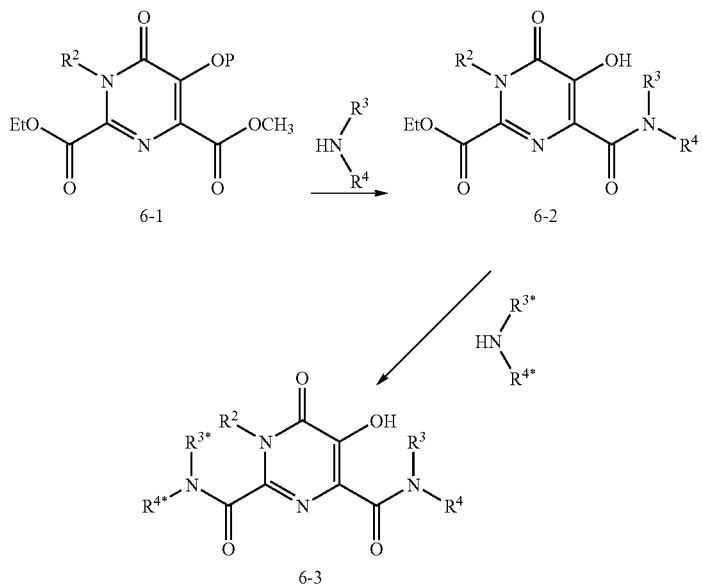

Compounds of the present invention of formula 7-2 can be prepared by reaction of aldehydes or ketones 7-1 with suitable amines under reductive alkylation conditions, as shown in Scheme 7. Scheme 7 is exemplifed in Example 14 below.

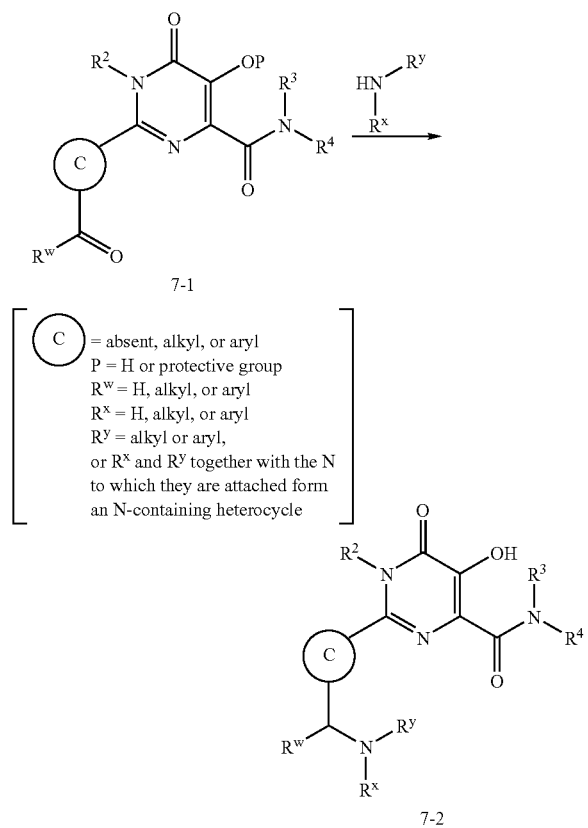

In the processes for preparing compounds of the present invention set forth in the foregoing schemes and exemplified in the examples below, functional groups in various moieties and substituents may be sensitive or reactive under the reaction conditions employed and/or in the presence of the reagents employed. Such sensitivity/reactivity can interfere with the progress of the desired reaction to reduce the yield of the desired product, or possibly even preclude its formation. Accordingly, it may be necessary or desirable to protect sensitive or reactive groups on any of the molecules concerned. Protection can be achieved by means of conventional protecting groups, such as those described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, 1991. The protecting groups can be removed at a convenient subsequent stage using methods known in the art. For example, in preparing the compounds of the invention it is sometimes necessary to protect one or more amino groups (e.g., amino groups present in substituents at the 2-position of the pyrimidinone ring) with, for example, a Boc or Cbz group or to protect hydroxy (e.g., the 5-hydroxy group on the pyrimidinone ring) with, for example, a benzoyl or benzyl group. The Boc group can be removed by acid treatment (e.g., TFA) either before or after formation of the final amide at C-6 of the pyrimidinone nucleus. The Cbz and benzyl groups are typically removed by catalytic hydrogenation or under strong acid conditions, either prior to or following formation of the final amide. The benzoyl group can be removed concurrently with the formation of the final amide. Examples 6 and 12 below illustrate the use of a Boc protective group and of Boc, benzoyl and benzyl protective groups in the preparation of compounds of the invention.

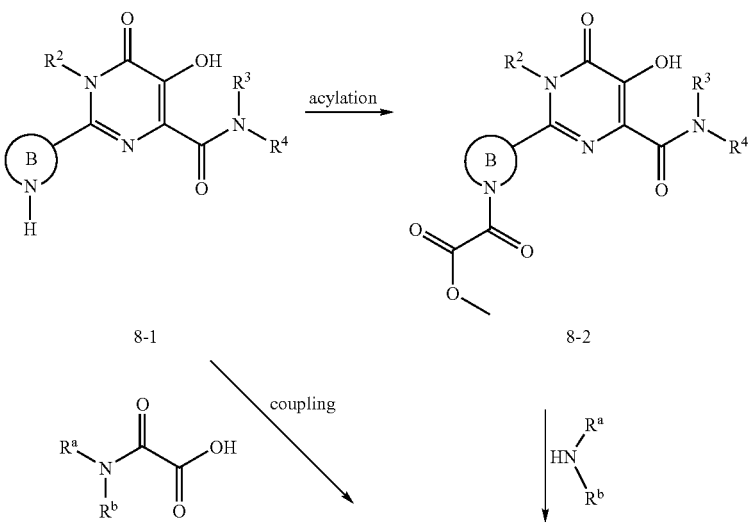

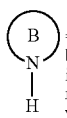
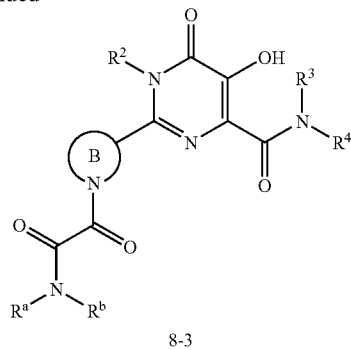

8-3

The preparation of compounds that feature a bis oxalamide at the 2 position of the pyrimidine core can be achieved as shown in Scheme 8, wherein a starting material bearing a basic nitrogen at the 2-position of the pyrimidine carboxyamide (8-1) is employed. This strategy will allow to obtain the final compound (8-3) following two possible procedures: by simple coupling of monoamide oxalic acid to the amine (8-1) or by the acylation of the basic nitrogen of (8-1) with dimethyl oxalate to give the ester intermediate (8-2) that is converted to the final compound by heating in presence of amine in appropriate solvent. Scheme 8 is exemplified in Examples 17, 18, and 20 below.

The following examples serve only to illustrate the invention and its practice. The examples are not to be construed as limitations on the scope or spirit of the invention.

EXAMPLE 1

Methyl 5-(benzoyloxy)-2-[1-(tert-butoxycarbonyl)pyrrolidin-2-yl]-1-methyl-6-oxo-1,6-dihydropyrimidine-4-carboxylate

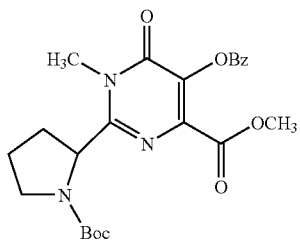

Step 1: Tert-butyl-2-[amino(hydroxyimino)methyl]pyrrolidine-1-carboxylate

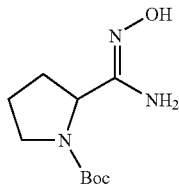

A solution of hydroxylamine hydrochloride (1.0 eq.) in MeOH was added at 0° C. to a solution of KOH (1.0 eq.) in MeOH. The resulting reaction mixture was filtered and added to a solution of tert-butyl-2-cyanopyrrolidine-1-carboxylate (1.0 eq.) in methanol and stirred at 40° C. for 2 h. The solvent was removed in vacuo and the residue treated with water; the solid was filtered and washed with a mixture of Et₂O: Petroleum Ether 1:1 to afford the title compound as a white solid as a mixture of rotamers by NMR.

¹H-NMR (DMSO-d₆, 400 MHz) δ 8.92 (s, 1H), 5.35 (s, 1H), 5.15 (s, 1H), 4.25 (bs, 0.5H), 4.10 (s, 0.5H), 3.40–3.30 (m, 1H), 2.10–1–70 (m, 4H), 1.40 (s, 4.5H), 1.35 (s, 4.5H), one signal is obscured by water.

Step 2: Methyl 5-(benzoyloxy)-2-[1-(tert-butoxycarbonyl)pyrrolidin-2-yl]-6-hydroxypyrimidine-4-carboxylate

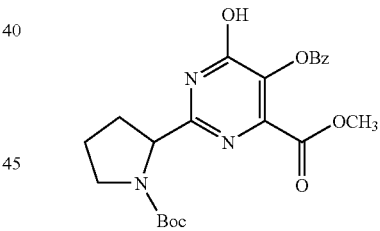

A solution of the product of Step 1 (1.0 eq.) and dimethyl acetylenedicarboxylate (1.05 eq.) in CHCl₃ was refluxed for 3 h. The reaction mixture was concentrated and the crude product was used directly in the next step without further purification. The crude product was dissolved in xylene and refluxed for 24 h. The solvent was removed in vacuo and the crude was dissolved in pyridine. Benzoic anhydride was added (1.5 eq.). The reaction mixture was stirred at room temperature until the starting material was consumed as determined by MS analysis. The reaction mixture was concentrated, and the resulting oil was diluted with ethyl acetate and washed with 1N HCl solutions saturated NaHCO₃ solution, saturated NaCl solution. The crude oil obtained after organic solvent evaporation was purified by flash chromatography to obtain the title compound as a yellow solid.

¹H-NMR (CDCl₃, 400 MHz) δ 12.08 (bs, 1H), 8.18 (d, J=7.6 Hz, 2H), 7.64 (t, J=7.4 Hz, 1H), 7.50 (t, J=7.6 Hz, 2H), 4.80–4.60 (m, 1H), 3.82 (s, 3H), 3.60–3.50 (m, 1H), 3.40–3.20 (m, 1H), 2.50–2.10 (m, 2H), 2.00–1.70 (m, 2H), 1.50 (s, 9H).

MS m/z 444 (M+H)+.

Step 3: Methyl 5-(benzoyloxy)-2-[1-(tert-butoxycarbonyl)pyrrolidin-2-yl]-1-methyl-6-oxo-1,6-dihydropyrimidine-4-carboxylate To a stirred solution of the product of Step 2 (1.0 eq.) in THF, Cs₂CO₃ was added (1.2 eq.) followed by the addition of CH₃I (2.0 eq.). The reaction was stirred at 40° C. until the starting material was consumed as determined by MS analysis. The reaction was concentrated and the residue taken up with EtOAc, washed with 1 N HCl, saturated solution of NaHCO₃ and brine. The organic phase was dried over anhydrous Na₂SO₄, filtered and concentrated. Reaction crude showed 3.4:1 ratio N (desired product) versus O methylation. The title product was purified by flash column chromatography (EtOAc: Petroleum Ether=1:1) and obtained as a 1: 1 mixture of rotamers by NMR.

¹H-NMR (CDCl₃, 400 MHz) δ 8.12 (d, J=7 Hz, 2H), 7.58 (t, J=7 Hz, 1H), 7.46 (t J=7 Hz, 2H), 4.97–4.95 (m, 0.5H), 4.87–4.83 (m, 0.5H), 3.74 (s, 1.5H), 3.72 (s, 1.5 H), 3.63 (s, 1.5H), 3.59 (s, 1.5H), 3.56–3.42 (m, 1H), 2.40–2.25 (m, 5H), 1.41 (s, 4.5 H), 1.25 (s, 4.5H).

MS m/z 458 (M+H)+.

Also obtained was the O-methylated compound of formula:

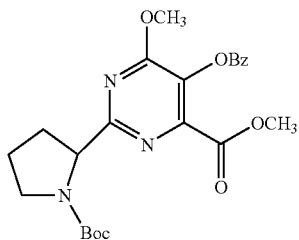

as a mixture of rotamers by NMR. ¹H-NMR (CDCl₃, 400 MHz) δ 8.21 (d, J=7.6 Hz, 2H), 7.72 (t, J=7.6 Hz, 1H), 7.56 (t, J=7.6 Hz, 2H), 5.10–5.05 (m, 0.3H), 5.00–4.95 (m, 0.7H), 4.01 (s, 3H), 3.87 (s, 3H), 3.80–3.60 (m, 2H), 2.50–2.40 (m, 1H), 2.15–2.00 (m, 2H), 2.00–1.85 (m, 1H), 1.61 (s, 2.7H), 1.40 (s, 6.3H).

MS m/z 458 (M+H)+.

EXAMPLE 2

Benzyl 2-[5-(benzoyloxy)-4-(methoxycarbonyl)-1-methyl-6-oxo-1,6-dihydropyrimidin-2-yl]indoline-1-carboxylate

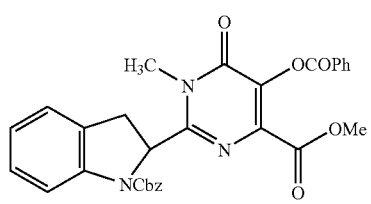

Step 1: Benzyl 2-[[hydroxy(methyl)amino](imino) methyl]indoline-1-carboxylate

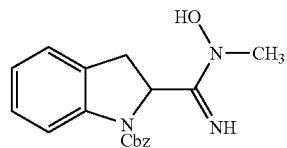

1-Benzyloxycarbonyl-2-cyanoindoline was added to a solution of triethylamine (2 eq.) and MeNHOH.HCl (2 eq.) in EtOH. After stirring overnight the reaction mixture was evaporated, dissolved in EtOAc, washed with water, dried over Na₂SO₄ and evaporated to afford the title compound.

¹H NMR (DMSO-d₆, 340K, 300 MHz) δ 7.68 (d, J=8.0 Hz, 1H), 7.41–7.30 (m, 5 H), 7.19 (t, J=7.5 Hz, 2H), 6.99 (t, J=7.6 Hz, 1H), 5.53 (dd, J=5.5, 10.9 Hz, 1H), 5.22 (s, 2H), 3.62 (dd, J=11.0, 16.6 Hz, 1H), 3.33 (s, 3H), 3.01 (dd, J=5.5 Hz, 16.6 Hz, 1H).

MS m/z 326 (M+H)+.

Step 2: Benzyl 2-[5-(benzoyloxy)-4-(methoxycarbonyl)-1-methyl-6-oxo-1,6-dihydropyrimidi-2-yl]indoline-1-carboxylate The product of Step 1 was dissolved in CHCl₃ and dimethylacetylenedicarboxylate was added dropwise (1.2 eq.) at room temperature. After 4 h the mixture was evaporated, and the residue was dissolved in xylene and stirred at 160° C. for 2 days. The solvent was then evaporated, and the residue was dissolved in pyridine, after which (PhCO)₂O (2 eq.) was added and the reaction mixture was stirred for 2 days. After evaporation, the resulting crude oil was diluted with EtOAc, washed with HCl 1N, dried over Na₂SO₄ and evaporated. The product was purified by flash chromatography on silica gel (EtOAc/petroleum ether, 1:4) to afford the title product.

¹H NMR (DMSO-d₆, 340 K, 400 MHz) δ 8.08 (d, J=7.3 Hz, 2H), 7.77 (t, J=7.4 Hz, 2H), 7.62 (t, J=7.6 Hz, 2H), 7.31–7.20 (m, 7H), 7.00 (t, J=7.3 Hz, 1H), 5.83 (dd, J=4.6 Hz, 11.0 Hz, 1H), 5.23–5.13 (m, 2H), 3.76 (dd, J=11.1, 16.6 Hz, 1H), 3.65 (s, 3H), 3.56 (s, 3H), 3.27 (dd, J=4.4 Hz, 16.6 Hz, 1H).

MS m/z 540 (M+H)+.

EXAMPLE 3

N-(4-Fluorobenzyl)-5-hydroxy-1-methyl-2-(4-methylphenyl)-6-oxo-1,6-dihydropyrimidine-4carboxamide

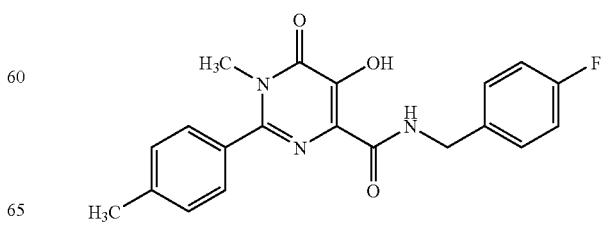

To a stirred solution of methyl 5-[(2,2-dimethylpropanoyl)oxy]-1-methyl-2-(4-methylphenyl)-6-oxo-1,6-dihydropyrimidine-4-carboxylate (prepared from 4-methylbenzonitrile by procedures similar to those set forth in Examples 2 or 3) in DMF 3 equivalents of 4-fluorobenzylamine were added and mixture was stirred at 90° C. for 2 h. The title product precipitated from the cooled reaction mixture after the addition of 2 N HCl, and was collected by filtration and washed with diethyl ether.

$^1$H NMR (DMSO-d$_6$, 400 MHz) δ 12.45 (s, 1H), 9.31 (bt, J=6.0 Hz, 1H), 7.62 (m, 2 H), 7.40–7.32 (m, 4H), 7.14 (t, J=8.8 Hz, 2H), 4.45 (d, J=6.0 Hz, 2H), 3.35 (s, 3 H), 2.48 (s, 3H).

MS m/z 368 (M+H)$^+$.

EXAMPLE 4

N-(4-fluorobenzyl)-5-hydroxy-1-methyl-6-oxo-1,6-dihydropyrimidine-4-carboxamide

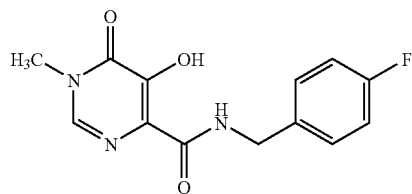

Step 1: 4,5-Dihydroxy-6-(methoxycarbonyl)pyrimidine-2-carboxylic acid

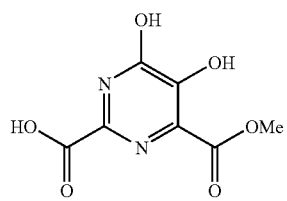

2-Ethoxycarbonyl-4,5-Dihydroxy-6-(methoxycarbonyl) pyrimidine [obtained from ethyl amino(hydroxyimino)ethanoate (Branco, P. S. et al, Tetrahedron 1992, 40: 6335) by procedures similar to those set forth in Example 1] was suspended in dioxane/FHF 2:1 and 1N NaOH was added. After 20 min the mixture was acidified with 1N HCl solution, concentrated and filtered to give the title product.

$^1$H-NMR (DMSO-d, 400 MHz) δ 13.10 (bs, 1H), 11.11 (bs, 1H), 3.82 (s, 3H).

MS m/z 213 (M–H)$^-$.

Step 2: Methyl 5,6-dihydroxypyrimidine-4-carboxylate

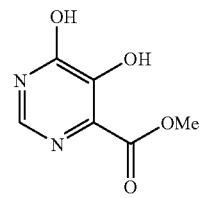

A solution of the product of Step 1 in HCl 1N solution was stirred for 6 hours at 90° C. Reaction mixture was filtered and the solid washed with HCl 1N. Evaporation of the filtrate afforded the title product as a solid.

$^1$H NMR (DMSO-d$_6$, 300 K, 400 MHz) δ 7.75 (s, 1H), 3.82 (s, 3H). $^{13}$C NMR (DMSO-d$_6$, 300 K, 400 MHz) δ 165.66, 158.20, 147.14, 139.00, 127.85, 52.16.

Step 3: Methyl 5-[(2,2-dimethylpropanoyl)oxy]-6-hydroxypyrimidine-4-carboxylate

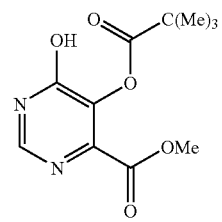

Pivaloyl chloride 1.1 eq. was added to a solution of the product of Step 2 in pyridine, and the mixture was heated to 40° C. for 10 minutes. HPLC showed the complete conversion of starting material. The reaction mixture was concentrated, the resulting oil was diluted with ethyl acetate and washed with 1 N HCl solution. The title product was obtained as a brown solid after evaporation of the organic phase and trituration with diethyl ether.

$^1$H NMR (DMSO-d$_6$, 400 MHz) δ 13.35 (s, 1H), 8.18 (s, 1H), 3.85 (s, 3H), 1.28 (s, 9 H).

Step 4: Methyl 5-[(2,2-dimethylpropanoyl)oxy]-1-methyl-6-oxo-1,6-dihydropyrimidine-4-carboxylate

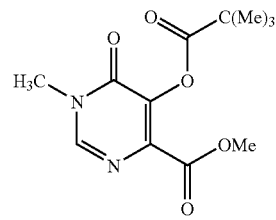

Dimethyl sulfate (1.5 eq.) was added to a solution of the product of Step 3 (1 eq.) in THF containing cesium carbonate (1.5 eq.). The reaction was carried out at 50° C. for thirty minutes. The solvent was evaporated and the resulting oil was dissolved in ethyl acetate, washed with 1N HCl solution. The crude title compound was recovered as yellow solid and used in the next step without purification.

¹H NMR (DMSO-d₆, 400 MHz) δ 8.43 (s, 1H), 3.81 (s, 3H), 3.45 (s, 3H), 1.30 (s, 9 H).

Step 5: N-(4-fluorobenzyl)-5-hydroxy-1-methyl-6-oxo-1,6-dihydropyrimidine-4-carboxamide 4-Fluorobenzylamine (3 eq.) was added to a solution of the crude product of Step 4 in DMF and the reaction mixture was heated to 90° C. for one hour. The title compound was obtained by RP-HPLC (C₁₈, eluting with water and acetonitrile containing 0.1% TFA).

¹H NMR (DMSO-d₆, 400 MHz) δ 12.5 (s, 1H), 9.54 (t, J=6.2 Hz, 1H), 8.05 (s, 1H), 7.36 (dd, J=6.2, 8.4 Hz, 2H), 7.14 (t, J=8.4 Hz, 2H), 4.45 (d, J=6.2 Hz, 2H), 3.44 (s, 3H). MS m/z 276 (M−H)⁻.

EXAMPLE 5

N-(4-Fluorobenzyl)-5-hydroxy-1-methyl-2-[4-(morpholin-4-ylmethyl)phenyl]-6-oxo-1,6-dihydropyrimidine-4-carboxamide

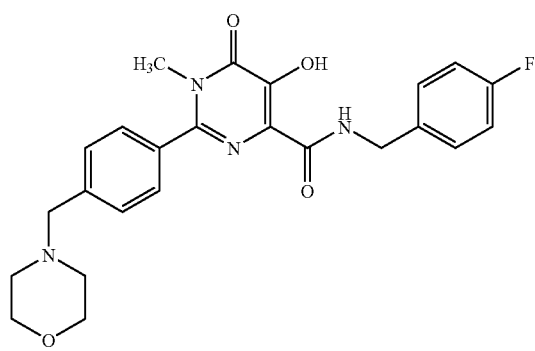

Step 1: Methyl 2-[4-(bromomethyl)phenyl]-5-[(2,2-dimethylpropanoyl)oxy]-1-methyl-6-oxo-1,6-dihydropyrimidine-4-carboxylate

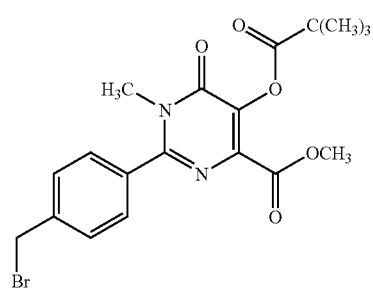

To a vigorously boiling solution of methyl 5-[(2,2-dimethylpropanoyl)oxy]-1-methyl-2-(4-methylphenyl)-6-oxo-1,6-dihydropyrimidine-4-carboxylate in carbon tetrachloride N-bromosuccinimide (1 eq.) and benzoyl peroxide (0.05 eq.) were added as dry powders. After 4 hr the mixture was allowed to reach room temperature and the precipitated succinimide was filtered off. The filtrate was evaporated under vacuum and the solid residue was used as such.

¹H NMR (DMSO-d₆, 400 MHz) δ 7.68–7.57 (m, 4H), 4.77 (s, 2H), 3.80 (s, 3H), 3.27 (s, 3H), 1.30 (s, 9H).

Step 2: N-(4-Fluorobenzyl)-5-hydroxy-1-methyl-2-[4-(morpholin-4-ylmethyl)phenyl]-6-oxo-1,6-dihydropyrimidine-4-carboxamide A THF solution of methyl 2-[4-(bromomethyl)phenyl]-5-[(2,2-dimethylpropanoyl)oxy]-1-methyl-6-oxo-1,6-dihydropyrimidine-4-carboxylate was reacted with 4 eq. of morpholine for 0.5 h at room temperature. After evaporation of volatiles, the oily residue was taken into DMF and treated with 3 eq. of 4-fluorobenzylamine at 90° C. for 2 h. Title product was isolated as its trifluoroacetate salt by RP-HPLC (C18, water/acetonitrile with 1% of TFA as eluant).

¹H-NMR (DMSO-d₆, 400 MHz) δ 12.45 (s, 1H), 10 (bs, 1H), 9.31 (bt, 1H), 7.74 (m, 2H), 7.62 (m, 2H), 7.35 (m, 2H), 7.14 (t, J=8.8 Hz, 2H), 4.54–4.38 (m, 4H), 4.1–3.9 (m, 2H), 3.9–3.7 (m, 2H), 3.68–3.51 (m, 2H), 3.31 (s, 3H), 3.2–3.1 (m, 2H).

MS: m/z 453 (M+H)⁺.

EXAMPLE 6

N-(4-fluorobenzyl)-5-hydroxy-1-methyl-2-(4-methylmorpholin-3-yl)-6-oxo-1,6-dihydropyrimidine-4-carboxamide

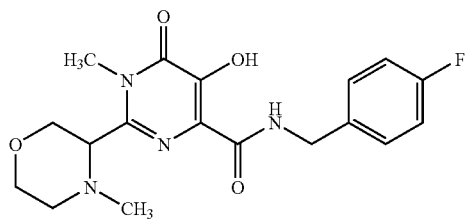

Step 1:
4-(tert-Butoxycarbonyl)morpholine-3-carboxylic acid

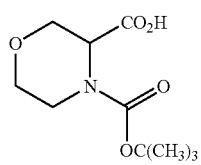

To a vigorously stirred solution of 3-morpholinecarboxylic acid and triethylamine (1.11 eq.) in MeOH (1.4 M) at 50° C. was added di-t-butyl dicarbonate (2 eq.). Stirring was continued at 50° C. for 5 min and at room temperature overnight. The reaction mixture was then concentrated to obtain an oily residue and suspended between EtOAc (500 ml) and saturated NaHCO₃ (500 ml). The organic layer was extracted with saturated NaHCO₃ (2×250 ml) and H₂O (250 ml). Combined aqueous layers were brought to pH=2.0 with 3 M HCl and immediately extracted with EtOAc (2×500 ml). The combined organic layers were washed with dilute HCl, dried, filtered and evaporated to give the title compound as a pale yellow oil, a 1:1 mixture of rotamers by NMR.

$^1$H NMR (400 MHz, DMSO-d$_6$) 12.93 (bs, 1H), 4.32 (s, 0.5H), 4.29 (s, 0.5H), 4.2–4.1 (m, 1H), 3.83–3.74 (m, 1H), 3.58–3.52 (m, 2H), 3.36–3.31 (m, 1H), 3.16 (t, J=11.4 Hz, 0.5H), 3.00 (t, J=11.4 Hz, 0.5H), 1.40 (s, 4.5H), 1.36 (s, 4.5H).

MS m/z 232 (M+H)$^+$.

Step 2: tert-Butyl 3-(aminocarbonyl)morpholine-4-carboxylate

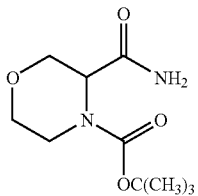

To a stirred solution of the compound prepared in Step 1 (1 eq.), pyridine (0.6 eq.) and di-t-butyl dicarbonate (1.3 eq.) in dioxane (0.6 M), NH$_4$HCO$_3$ (1.26 eq.) was added and the mixture was stirred at room temperature for 20 hours. Mixture was concentrated, taken up in EtOAc and washed with water and brine. Organics were dried over Na$_2$SO$_4$ and evaporated giving the title product as an oil which crystallized at room temperature.

$^1$H-NMR (DMSO-d$_6$, 300 MHz) δ 7.35 (bs, 1H), 7.06 (bs, 1H), 4.15 (bs, 2H), 3.76 (bs, 1H), 3.57–3.51 (m, 2H), 3.28 (m, 1H), 3.18 (m, 1H), 1.36 (s, 9H).

MS m/z 231 (M+H)$^+$.

Step 3: tert-Butyl 3-cyanomorpholine-4-carboxylate

A solution of the product of Step 2 (1 eq.) and triethylamine (2.1 eq.) in CH$_2$Cl$_2$ (0.1 M) was cooled to 0° C. and-trifluoroacetic anhydride (1.1 eq.) added dropwise under nitrogen. Stirring was continued 3.5 hours more at room temperature and volatiles removed in vacuo. Residues taken in EtOAc were washed with water, brine and dried over Na$_2$SO$_4$. Evaporation gave the title compound as a brown solid.

$^1$H NMR (DMSO-d$_6$, 400 MHz) δ 5.04 (d, J=2.7 Hz, 1H), 3.96 (d, J=12.2 Hz, 1H), 3.86 (dd, J=11.5, 2.6 Hz, 1H), 3.69 (d, J=12.4 Hz, 1H), 3.56 (dd, J=12.2, 3.2 Hz, 1 H), 3.40 (td, J=11.9, 2.89 Hz, 1H), 2.97 (m, 1H), 1.43 (s, 9H).

MS m/z 213 (M+H)$^+$.

Step 4: tert-Butyl 3-[(Z)-amino(hydroxyimino)methyl]morpholine4-carboxylate

A solution of of the product of Step 3 (1 eq.), hydroxylamine hydrochloride (1.4 eq.) and triethylamine (1.7 eq.) in EtOH (0.5 M) was refluxed under nitrogen for 5 hours. Mixture was concentrated and residues taken up in EtOAc and washed with water and brine. Combined organics were dried over Na$_2$SO$_4$ and evaporated giving the title compound as a yellow solid.

$^1$H NMR (DMSO-d$_6$, 400 MHz) δ 9.16 (bs, 1H), 5.32 (bs, 2H), 4.30 (bs, 1H), 4.08 (d, J=11.6 Hz, 1H), 3.75 (d, J=6.8 Hz, 1H), 3.50–3.33 (m, 4H), 1.38 (s, 9H).

MS: m/z 246 (M+H)$^+$.

Step 5: Dimethyl-2-({2-amino-2-[4-(tert-butoxycarbonyl)morpholin-3-yl]ethenyl}oxy)but-2-enedioate A solution of the product of Step 4 (1 eq.) and dimethylacetylenedicarboxylate (1.2 eq.) in CHCl$_3$ was refluxed for 1 hour under nitrogen and solution concentrated. Residue was purified by flash chromatography on silica gel, eluents petroleum ether/EtOAc 7:3→1:1, to give the desired product as a mixture of two isomers E/Z (76:14).

$^1$H NMR (DMSO-d$_6$, 400 MHz, 300K) δ 6.60 and 6.20 (2 bs, 2H), 5.58 and 5.41 (2s, 1H), 4.36 (bs, 1H), 4.04 (bs, 1H), 3.8 (bs, 1H), 3.76 and 3.72 (2 s, 3H), 3.63 and 3.58 (2 s, 3H), 3.53 (td, J=13.6, 3.7 Hz, 1H), 3.44 (t, J=10.4 Hz, 1H), 3.31 (m, 2 H), (s, 9H).

MS m/z 388 (M+H)$^+$.

Step 6: tert-Butyl-3-[4,5-dihydroxy-6-(methoxycarbonyl)pyrimidin-2-yl]morpholine-4-carboxylate

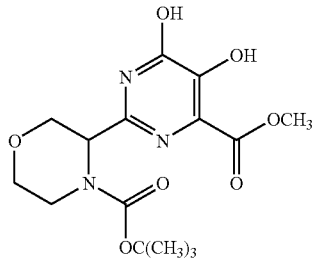

The adducts of Step 5 were refluxed in xylenes for 24 hours. Then the reaction was cooled down and concentrated in vacuo. Ethyl ether was added until precipitation of a solid that was filtered, washed with ethyl ether and dried to give the title pyrimidine as an orange solid.

$^1$H NMR (DMSO-$d_6$, 400 MHz, 340 K) δ 4.62 (s, 1H), 4.15 (d, J=12 Hz, 1H), 3.84 (bs, 1H), 3.82 (s, 3H), 3.70 (dd, J=12.3, 4 Hz, 1H), 3.61 (dd, J=12.2, 3.8 Hz, 1H), 3.56 (t, J=13 Hz, 1H), 3.43 (td, J=11.5, 3.4 Hz, 1H), 1.35 (s, 9H).

MS m/z $3^{56}$ (M+H)$^+$.

Step 7: tert-Butyl-3-[5-(benzoyloxy)-4-hydroxy-6-(methoxycarbonyl)pyrimidin-2-yl]morpholine-4-carboxylate

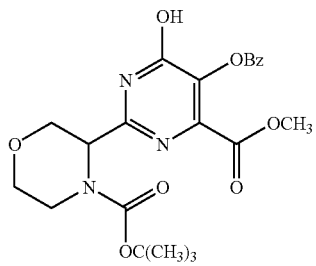

The pyrimidine from Step 6 in dry pyridine (0.2 M), was treated with benzoic anhydride (2 eq.) overnight at room temperature. The mixture was evaporated, taken in EtOAc and washed with HCl 1N, NaHCO$_3$ and brine. Organics were dried over Na$_2$SO$_4$, and filtered, evaporated and purified by flash chromatography on silica gel, eluents EtOAc/Petroleum Ether: 7/3.

$^1$H NMR (DMSO-$d_6$, 300 MHz, 340K) δ 13.3 (bs, 1H), 8.07 (d, J=7.5 Hz, 2H), 7.76 (t, J=7.5 Hz, 1H), 7.61 (t, J=7.5 Hz, 2H), 4.73 (s, 1H), 4.22 (d, J=12.4 Hz, 1H), 3.86 (d, J=11.0 Hz, 1H), 3.78 (dd, J=12.4, 3.9 Hz, 1H), 3.73 (s, 3H), 3.58 (t, J=13.9 Hz, 2H), 3.47 (td, J=10.7, 3.6, 1H), 1.36 (s; 9H).

MS m/z 600 (M+H)$^+$.

Step 8: Alkylated derivatives 8A and 8B

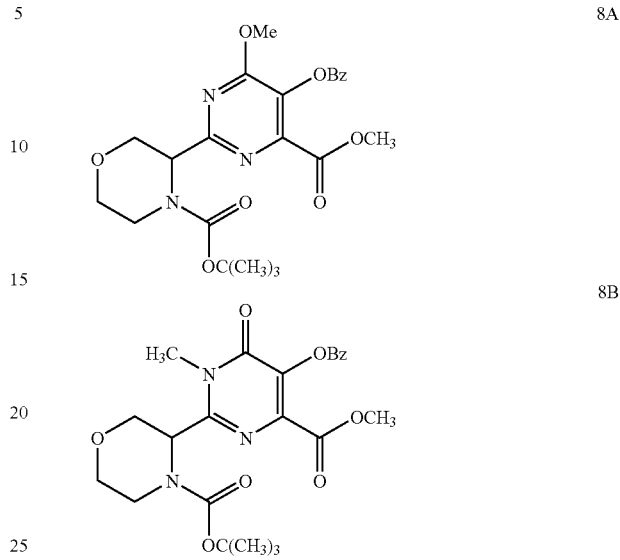

The pyrimidine product of Step 7 in dry THF (0.6 M) was treated with cesium carbonate (1.5 eq.) and dimethyl sulfate (1.5 eq.) at 50° C. for 1 hour. Solvent was removed in vacuo and residue taken in EtOAc, washed with HCl 1N and brine. Organics were dried over Na$_2$SO$_4$, filtered and evaporated to obtain a crude which was purified by flash chromatography on silica gel, (eluents EtOAc/Petroleum Ether: 3/7) to separate the two compounds 8A and 8B (ratio 8A/8B 1/0.85).

An alternative route was also employed as follows: The pyrimidine product of Step 7 was added to a suspension of LiH (1.1 eq) in dioxane at room temperature. The mixture was aged 45 min at 38° C. and was then cooled to room temperature. Dimethylsulfate (1.3 eq) was added and the mixture was warmed to 38° C. (4h) and 56° C. (4h). The reaction mixture was cooled to 16° C. and glacial acetic acid (0.1 eq) was added, followed by water and EtOAc. The aqueous layer was separated and extracted with EtOAc. The combined organic layer was dried (Na$_2$SO$_4$) and concentrated to an oil, which was chromatographed through silica gel, eluting with 50–55% EtOAc/hexanes to separated compound 8A from 8B. The fractions were evaporated to a foamy solid. This solid was dissolved in ether and re-evaporated to foamy solid that could be scraped out easily. This solid was dried in a vacuum oven overnight at 40° C. to afford 8B as a pale yellow solid. The ratio of 8A/8B is variable with this route, from 1:4 to 1:12.

tert-Butyl-3-[5-(benzoyloxy)-4-methoxy-6-(methoxycarbonyl)pyrimidin-2-yl]morpholine-4-carboxylate (8A)

$^1$NMR (300 MHz, DMSO-$d_6$+TFA, 330K) δ 8.10 (d, J=7.9 Hz, 2H), 7.77 (t, J=7.3 Hz, 1H), 7.61 (t, J=7.4 Hz, 2H), 4.94 (bs, 1H), 4.50 (d, J=1 1.6 Hz, 1H), 4.0 (s, 3H), 3.85–3.81 (m, 2H), 3.76 (s, 3H), 3.66 (d, J=10.4 Hz, 1H), 3.49–3.45 (m, 2H), 1.35 (bs, 9H).

MS m/z 474 (M+H)$^+$.

tert-Butyl-3-[5-(benzoyloxy)-4-(methoxycarbonyl)-1-methyl-6-oxo-1,6-dihydropyrimidin-2-yl]morpholine-4-carboxylate (8B)

$^1$H NMR (DMSO-$d_6$, 400 MHz, 330K,) δ 8.09 (d, J=7.3 Hz, 2H), 7.77 (t, J=7.5 Hz, 1H), 7.62 (t, J=7.8 Hz, 2H), 5.08 (d, J=3.4 Hz, 1H), 4.21 (d, J=12.3 Hz, 1 H), 3.95–3.85 (m, 3H), 3.76 (s, 3H), 3.58 (s, 3H), 3.55–3.50 (m, 2H), 1.34 (s, 9H).
MS m/z 474 (M+H)$^+$.

Step 9: tert-Butyl-3-(4-{[(4-fluorobenzyl)amino]carbonyl}-5-hydroxy-1-methyl-6-oxo-1,6-dihydropyrimidin-2-yl]-morpholine-4-carboxylate

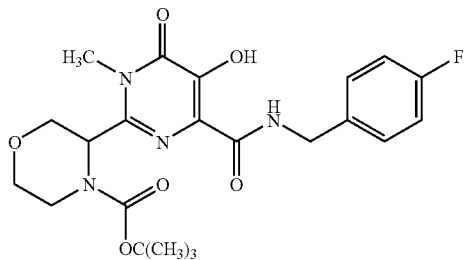

The methyl ester 8B in dry MeOH was treated with 4-fluorobenzylamine (2.5 eq.) at reflux for 2 hours. Solvent was removed in vacuo and residue triturated with Et$_2$O to obtain the title product.

$^1$H NMR (300 MHz, DMSO-$d_6$, 320K) δ 11.95 (bs, 1H), 8.32 (t, J=6.0 Hz, 1H), 7.39–7.35 (m, 2H), 7.19–7.13 (m, 2H), 4.96 (dd, J=4.25, 2.42 Hz, 1H), 4.62 (dd, J=14.9, 6.95 Hz, 1H), 4.49 (dd, J=14.9, 5.83 Hz, 1H), 4.16 (dd, J=12.2, 2.0 Hz, 1H), 3.87–3.79 (m, 2H), 3.70–3.64 (m, 1H), 3.55–3.45 (m, 5H), 1.23 (s, 9H).
MS m/z 463 (M+H)$^+$.

Step 10: N-(4-fluorobenzyl)-5-hydroxy-1-methyl-2-morpholin-3-yl-6-oxo-1,6-dihydropyrimidine-4-carboxamide

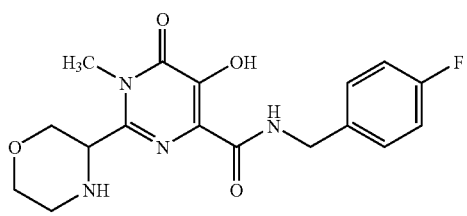

The compound from Step 9 was treated with a mixture of dichloromethane/TFA (2/1) for 1 hour at room temperature. Organics were removed in vacuo to give the title compound as a solid.

$^1$H NMR (300 MHz, DMSO-$d_6$, 300 K) δ 9.45 (bs, 1H), 7.39–7.36 (m, 2H), 7.19–7.15 (m, 2H), 4.93 (d, J=9.2 Hz, 1H), 4.64 (dd, J=15.4, 6.7 Hz, 1H), 4.55 (dd, J=15.4, 6.2 Hz, 1H), 4.35 (d, J=12.8 Hz, 1H), 4.08 (d, J=12.6 Hz, 1H), 3.77 (t, J=12.4 Hz, 1H), 3.55 (s, 3H), 3.55–3.46 (m, 2H), 3.40–3.34 (m, 1H).
MS m/z 363 (M+H)$^+$.

Step 11: N-(4-fluorobenzyl)-5-hydroxy-1-methyl-2-(4-methylmorpholin-3-yl)-6-oxo-1,6-dihydropyrimidine-4-carboxamide The compound from Step 10 was dissolved in MeOH and treated with triethylamine (1 eq.), sodium acetate (1.6 eq.), formaldehyde 37% w/w aq. soln. (3 eq.), and sodium cyanoborohydride (1.43 eq.). The mixture was left stirring at room temperature for 1 hour. The reaction mixture was concentrated and the title compound was obtained by RP-HPLC purification (C$_{18}$, eluting with water and acetonitrile containing 0.1% TFA), as its trifluoroacetate salt.

$^1$H NMR (400 MHz, DMSO-$d_6$+TFA) δ 12.33 (bs, 1H), 10.05 (bs, 1H), 9.48 (t, J=6.4 Hz, 1H), 7.35–7.33 (m, 2H), 7.15–7.12 (m, 2H), 4.98 (d, J=8.8 Hz, 1H), 4.57 (d, J=6.4 Hz, 2H), 4.36 (d, J=12.7 Hz, 1H), 4.13 (d, J=12.4 Hz, 1H), 3.77 (t, J=12.5 Hz, 1H), 3.69 (d, J=12.8 Hz, 1H), 3.54 (s, 3H), 3.48–3.41 (m, 2H), 2.83 (s, 3 H).
MS m/z 377 (M+H)$^+$.

N-(4-fluorobenzyl)-5-hydroxy-1-methyl-2-(4-methylmorpholin-3-yl)-6-oxo-1,6-dihydropyrimidine-4-carboxamide has been resolved into its enantiomers by semi preparative chiral HPLC using the following conditions:

Solvents: a mixture of 1:1 0.2% TFA in Hexanes: EtOH
Column: chiralpak AS column, 250×46 mm at 1.0 ml/min, collected by absorbtion at 260 nM The first eluate is the (+) enatiomer (MeOH, c=0.24, 25C): [α]$_D$=(+) 55.42.
The second eluate is the (−) enantiomer (MeOH, c=0.215, 25C) [α]$_D$=(−) 51.63.

EXAMPLE 7

2-(4-ethyl-1-methylpiperazin-2-yl)-N-(4-fluorobenzyl)-5-hydroxy-1-methyl-6-oxo-1,6-dihydropyrimidine-4-carboxamide

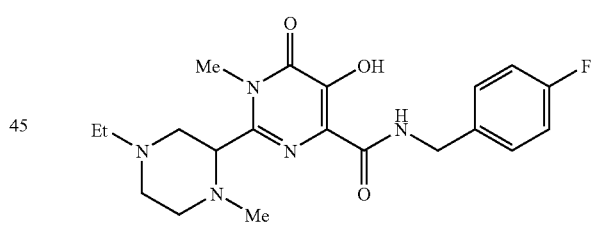

Step 1: Methyl 1-methyl-2-(4-tert-butoxycarbonylpiperazin-2-yl))-5-benzoyloxy-6-oxo-1,6-dihydropyrimidine-4-carboxylate

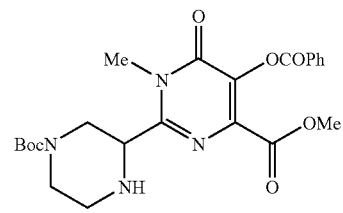

Methyl 1-methyl-2-(4-tert-butoxycarbonyl-1-benzyloxy-carbonylpiperazin-2-yl))-5-benzoyloxy-6-oxo-1,6-dihydro-pyrimidine-4-carboxylate (prepared from 1-[(benzyloxy)carbonyl]-4-(tert-butoxycarbonyl)piperazine-2-carboxylic acid (Bigge et al, *Tetrahedron Lett.* 1989, 30: 5193) by procedures similar to those set forth in Examples 2 or 3 in combination with a deprotection step) was dissolved in MeOH and hydrogenated at atm pressure on 10% Pd/C for 1 hour. The crude title product was obtained after filtration and evaporation.

Step 2: N-(4-fluorobenzyl) 1-methyl-2-(4-tert-butoxycarbonylpiperazin-2-yl))-5-hydroxy-6-oxo-1,6-dihydropyrimidine-4-carboxamide

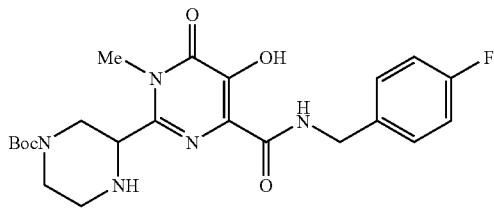

The crude product from Step 1 was dissolved in MeOH and 4-fluorobenzylamine (3.5 eq.) added. After being refluxed overnight, the precipitate was filtered and washed with Et$_2$O to afford the title product.

Step 3: N-(4-fluorobenzyl) 1-methyl-2-(4-tert-butoxycarbonyl-1-methylpiperazin-2-yl))-5-hydroxy-6-oxo-1,6-dihydropyrimidine-4-carboxamide

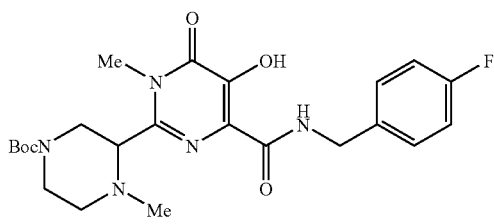

The solid product from Step 2 was dissolved in MeOH and NaCNBH$_3$ (1.4 eq.), AcONa (1.6 eq.), HCHO 37% (1 eq.) were added. The reaction mixture was stirred at room temperature for 2 days, and then evaporated to afford the crude title product.

$^1$H NMR (DMSOd$_6$+TFA, 340K, 400 MHz) δ 7.40–7.35 (m, 2H), 7.18–7.10 (m, 2H), 4.83 (d, J=7.3 Hz, 1H), 4.59 (d, J=6.3 Hz, 2H), 4.41 (d, J=14.9 Hz, 1H), 4.20–4.10 (m, 1H), 3.75–3.60 (m, 1H), 3.54 (s, 3H), 3.38–3.25 (m, 2H), 3.15–3.05 (m, 1H), 2.85 (s, 3H), 1.45 (s, 9H). MS (EI+) m/z=476 (M+H)$^+$.

Step 4: N-(4-fluorobenzyl)-5-hydroxy-1-methyl-2-(1-methylpiperazin-2-yl)-6-oxo-1,6-dihydropyrimidine-4-carboxamide

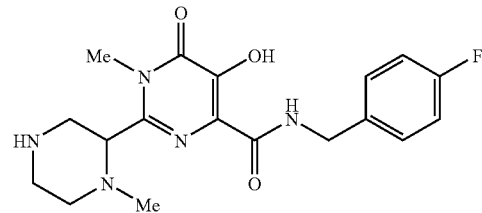

The crude product from Step 3 was stirred in CH$_2$Cl$_2$/TFA (1:1) for 2 hours to remove the Boc protective group from the piperazinyl nitrogen.

$^1$H NMR (DMSOd$_6$, 340K, 400 MHz) δ 12.25 (bs, 1H), 9.03 (bs, 1H), 7.42–7.35 (m, 2H), 7.20–7.10 (m, 2H), 4.62–4.45 (m, 2H), 4.14–4.09 (m, 1H), 3.62 (s, 3H), 3.62–3.52 (m, 1H), 3.48–3.32 (m, 1H), 3.25–3.15 (m, 1H), 3.15–3.05 (m, 2H), 2.44–2.32 (m, 1H), 2.34 (s, 3H).
MS (EI+) m/z=376 (M+H)$^+$.

Step 5: 2-(4-ethyl-1-methylpiperazin-2-yl)-N-(4-fluorobenzyl)-5-hydroxy-1-methyl-6-oxo-1,6-dihydropyrimidine-4-carboxamide Triethylamine (2 eq.), NaCNBH$_3$ (1.4 eq.), AcONa (1.6 eq.) and CH$_3$CHO (1 eq.) were added to a methanolic solution of the crude product obtained in step 4. The reaction was stirred at room temperature for 1 hour. The title product was obtained as its trifluroacetate salt by preparative RP-HPLC purification (C18, gradient of CH$_3$CN/H$_2$O+0.01% TFA).

$^1$H NMR (DMSO-d$_6$+TFA, 300 MHz) δ 9.40 (t, J=5.9 Hz, 1H), 7.34 (t, J=8.02 Hz, 2H), 7.14 (t, J=8.7 Hz, 2H), 5.00 (d, J=9.9 Hz, 1H), 4.54 (d, J=6.1 Hz, 2H), 4.04–3.82 (m, 3H), 3.55–3.43 (m, 4H), 3.30–3.22 (m, 4H), 2.87 (s, 3H), 1.21 (t, J=7.14 Hz, 3H).
MS m/z 404 (M+H)$^+$.

EXAMPLE 7B

Step 1: N-(4-fluorobenzyl)-5-hydroxy-2-[4-(isopropylsulfonyl)-1-methylpiperazin-2-yl]-1-methyl-6-oxo-1,6-dihydropyrimidine-4-carboxamide

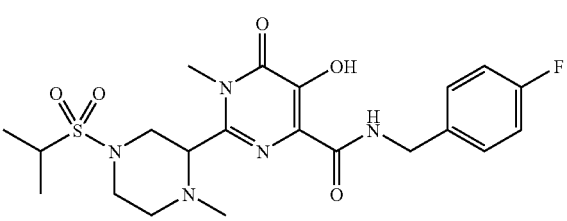

4-fluorobenzyl 2-(1,2-dimethylpiperazin-2-yl) -5-hydroxy-1-methyl -6-oxo-1,6-dihydropyrimidine-4-carboxylate, obtained during the preparation of the compound in example 7 step 4, was dissolved in THF/NaOH 2N (1:1) followed by the addition of iPrSO$_2$Cl (4 eq). After being stirred at room temperature overnight, further addition of iPrSO$_2$Cl (2.4 eq) and NaOH 2N (2.4 eq) were made to complete the reaction. After 3 hours NaOH 2N (10 eq) was added and the reaction mixture was stirred for 10 minutes at room temperature. The title product was isolated by preparative HPLC (Column C18, gradient of $CH_3CN/H_2O$ + 0.01% TFA).

$^1$H NMR (DMSOd$_6$+TFA, 300K, 300 MHz) δ 9.48 (bt, J=6.5 Hz,1H), 7.39–7.35 (m, 2H), 7.7.22–7.12 (m, 2H), 4.96 (d, J=8.4 Hz, 1H), 4.57 (d, J=6.3 Hz, 2H), 4.23 (d, J=14.4 Hz, 1H), 3.96 (d, J=10.8 Hz, 1H), 3.76 (d, J=10.2 Hz, 1H), 3.53 (s, 3H), 3.50–3.35 (m, 3H), 3.23–3.15 (m, 1H), 2.87 (s, 3H), 1.25 (d, J=6.9 Hz, 6H).

MS: m/z 482 (M+H)$^+$.

EXAMPLE 8

N-(4-fluorobenzyl)-5-hydroxy-1-methyl-2-(1-methylpiperidin-2-yl)-6-oxo-1,6-dihydropyrimidine-4-carboxamide

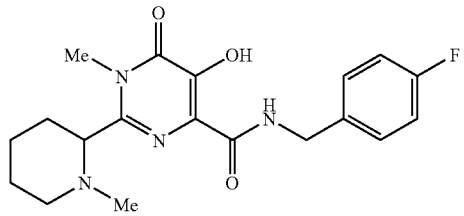

Methyl 5-(benzoyloxy)-1-methyl-6-oxo-2-piperidin-2-yl-1,6-dihydropyrimidine-4-carboxylate (prepared from 1-(benzyloxycarbonyl)piperidine-2-carboxylic acid by procedures similar to those set forth in Examples 1 or 2 in combination with a deprotection step) was suspended in TiF and treated with 3 eq. of triethylamine and 3 eq. of methyl iodide at 40° C. After stirring for 5 h, THF was evaporated and residue poured into EtOAc and washed with brine. Organic phase was dried ($Na_2SO_4$), filtered and concentrated under reduced pressure. The oily residue was taken into EtOAc and treated with 3 eq. of 4-fluorobenzylamine at 90° C. for 0.5 h. The title product was isolated as its trifluoroacetic salt by preparative RP-HPLC (C18, 5 μM, acetonitrile/water containing 0.1% TFA as eluant).

$^1$H NMR (DMSO-d$_6$, 400 MHz) δ 12.28 (bs, 1H), 9.50 (bt, 1H), 9.31 (bs, 1H), 7.37 (dd, J=5.6 Hz, 8.4 Hz, 2H), 7.18 (t, J=8.8 Hz, 2H), 4.8–4.6 (m, 1H), 4.57 (d, J=6.4 Hz, 2H), 3.70–3.60 (m, 1H), 3.50 (s, 3H), 3.4–3.3 (m, 1H), 2.78 (bs, 3H), 2.4–2.3 (m, 1H), 1.92–1.46 (m, 5H).

MS m/z 375 (M+H)$^+$.

EXAMPLE 9

2-(1-Acetylpyrrolidin-2-yl)-N-(4-fluorobenzyl)-5-hydroxy-1-methyl-6-oxo-1,6-dihydropyrimidine-4-carboxamide

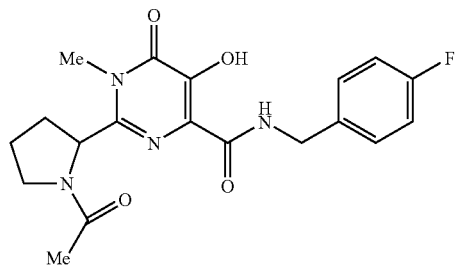

Step 1: Methyl 5-(benzoyloxy)-1-methyl-6-oxo-2-pyrrolidin-2-yl-1,6-dihydropyrimidine-4-carboxylate

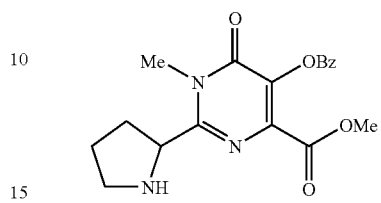

Methyl-5-(benzoyloxy)-2-[1-(tert-butoxycarbonyl)pyrrolidin-2-yl]-6-hydroxypyrimidine-4-carboxylate was treated with TFA:$CH_2Cl_2$ (3:7) at 0° C. The solution was warmed to room temperature and the progress of the reaction was monitored by MS analysis. After 1 h the reaction was complete and the solvent was removed under reduced pressure using a rotatory evaporator. The title product was precipitated with $Et_2O$ and collected by filtration.

$^1$H-NMR (CDCl$_3$, 400 MHz) δ 8.17 (d, J=7.4 Hz, 2H), 7.67 (t, J=7.6 Hz, 1H), 7.52 (t, J=7.6 Hz, 2H), 5.45 (dd, J=7.6, 6.7 Hz, 1H), 3.82 (s, 3H), 3.66 (s, 3H), 3.61 (t, J=7.0 Hz, 2H), 2.78–2.69 (m, 1H), 2.40–2.00 (m, 3H).

MS m/z 358 (M+H)$^+$.

Step 2: 2-(1-Acetylpyrrolidin-2-yl)-N-(4-fluorobenzyl)-5-hydroxy-1-methyl-6-oxo-1,6-dihydropyrimidine-4-carboxamide To a stirred solution of the product of Step 1 (1.0 eq.) in CHCl$_3$, triethylamine (3.0 eq.) was added followed by the addition of acetyl chloride (1.5 eq.). The reaction was stirred at room temperature until the starting material was consumed as determined by MS analysis. The reaction mixture was concentrated and the crude product was used directly in the subsequent step without further purification. A solution of the crude product from above (1.0 eq.) in NMP was treated with 4-fluorobenzylamine (2.0 eq.). The solution was stirred at reflux until the reactants were consumed as determined by MS analysis. The title compound was obtained by RP-HPLC purification (C$_{18}$, eluting with water and acetonitrile containing 0.1% trifluoroacetic acid) as a 4:1 mixture of rotamers by NMR.

$^1$H-NMR (DMSO-d$_6$, 400 MHz) δ 12.11 (bs, 1H), 8.49 (t, J=6.2 Hz, 0.8H), 8.30 (t, J=6.2 Hz, 0.2H), 7.4–7.3 (m, 2H), 7.15 (t, J=8.8 Hz, 2H), 5.22 (dd, J=8.0, 3.2 Hz, 0.2H), 5.02 (dd, J=8.0, 3.2 Hz, 0.8H), 4.60–4.47 (m, 2H), 3.95–3.85 (m, 0.8H), 3.80–3.70 (m, 0.2H), 3.59–3.57 (m, 0.8H), 3.55 (s, 2.4H), 3.52 (s, 0.6H), 3.34-3.37 (m, 0.2H), 2.40–1.7 (m, 4H), 2.5 (s, 2.4H), 1.75 (s, 0.8H).

MS m/z 389 (M+H)$^+$.

EXAMPLE 10

2-(1-benzoyl-2,3-dihydro-1H-indol-2-yl)-N-(4-fluorobenzyl)-5-hydroxy-1-methyl-6-oxo-1,6-dihydropyrimidine-4-carboxamide

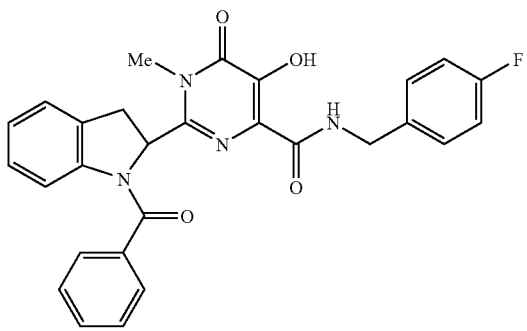

Step 1: Methyl 2-(2,3-dihydro-1H-indol-2-yl)-1-methyl-5-benzoyloxy-6-oxo-1,6-dihydropyrimidine-4-carboxylate

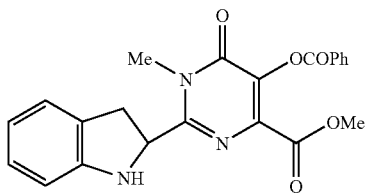

Benzyl 2-[5-(benzoyloxy)-4-(methoxycarbonyl)-1-methyl-6-oxo-1,6-dihydropyrimidi-2-yl]indoline-1-carboxylate was dissolved in EtOAc and hydrogenated at atmospheric pressure on 10% Pd/C overnight. The crude title product was obtained after filtration and evaporation

Step 2: Methyl 2-(1-benzoyl-2,3-dihydro-1H-indol-2-yl)-5-benzoyloxy 1-methyl-6-oxo-1,6-dihydropyrimidine-4-carboxylate

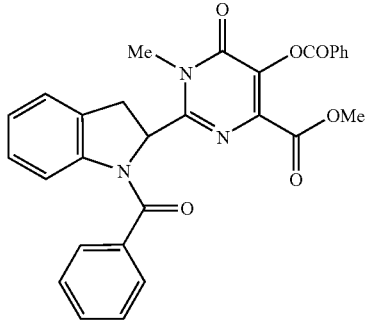

THF was added to the crude product of Step 1, followed by pyridine (2 eq.) and PhCOCl (1 eq.). After being stirred at room temperature overnight, the reaction mixture was evaporated to give the crude title product.

Step 3: 2-(1-benzoyl-2,3-dihydro-1H-indol-2-yl)-N-(4-fluorobenzyl)-5-hydroxy-1-methyl-6-oxo-1,6-dihydropyrimidine-4-carboxamide The crude product of Step 2 was dissolved in MeOH and 4-fluorobenzylamine (3.5 eq.) added. The solution was stirred at 60° C. over night. The title product was obtained by preparative RP-HPLC (C18, gradient of CH$_3$CN/H$_2$O+ 0.01% TFA).

$^1$H NMR (DMSO-d$_6$+TFA, 340 K, 400 MHz) δ 7.75–7.80 (m, 1H), 7.45–6.97 (m, 13 H), 5.77 (dd, J=10, 3.6 Hz, 1H), 4.35–4.50 (m, 2H), 3.72 (dd, J=16, 10 Hz, 1H), 3.35 (s, 3H), 3.16 (dd, J=16, 3.6 Hz, 1H).

MS m/z 499 (M+H)$^+$.

EXAMPLE 11

N-(4-fluorobenzyl)-5-hydroxy-1-methyl-6-oxo-2-[1-(pyridin-2-ylcarbonyl)-1,2,3,4-tetrahydroquinolin-2-yl]-1,6-dihydropyrimidine-4-carboxamide

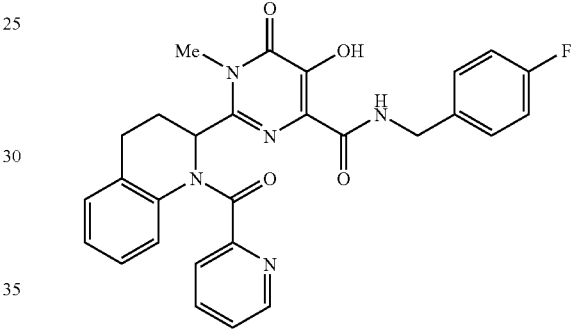

Step 1: Methyl 2-(1,2,3,4-tetrahydroquinolin-2-yl)-1-methyl-5-benzoyloxy-6-oxo-1,6-dihydropyrimidine-4-carboxylate

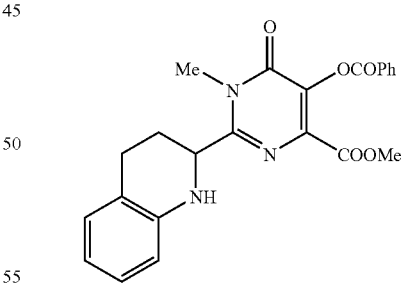

Benzyl 2-[5-(benzoyloxy)-4-(methoxycarbonyl)-1-methyl-6-oxo-1,6-dihydropyrimidi-2-yl]-1,2,3,4-tetrahydroquinoline-1-carboxylate (prepared from tetrahydroquinoline-2-carboxylic acid (Robl et al, *Tetrahedron Letters* 1995, 36: 1593) by protection of the nitrogen and following procedures similar to those set forth in Examples 1 or 2 in combination with a deprotection step) was dissolved in EtOAc and hydrogenated at atmospheric pressure on 10% Pd/C at room temperature overnight. The title product was obtained as the residue after filtration and evaporation of the organic solvent.

Step 2: Methyl 5-benzoyloxy-1-methyl-6-oxo-2-[1-(pyridin-2-ylcarbonyl)-1,2,3,4-tetrahydroquinolin-2-yl]-1,6-dihydropyrimidine-4-carboxylate

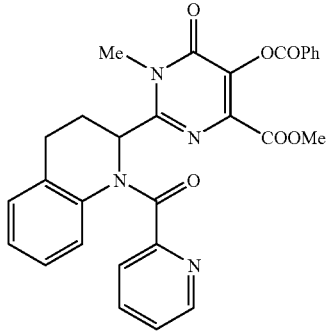

The residue of Step 1 was dissolved in dichloromethane. Pyridine, picolinoyl chloride hydrochloride and a catalytic amount of DMAP were added. A further addition of the reactants was made after two hours. After evaporation of the solvent, the residue was diluted with EtOAc, the organic phase washed with water, dried (Na$_2$SO$_4$) and evaporated to afford the title product.

Step 3: N-(4-fluorobenzyl)-5-hydroxy-1-methyl-6-oxo-2-[1-(pyridin-2-ylcarbonyl)-1,2,3,4-tetrahydroquinolin-2-yl]-1,6-dihydropyrimidine-4-carboxamide The residue of Step 2 was dissolved in DMF and 4-fluorobenzylamine (3 eq.) was added. The reaction mixture was stirred at 90° C. for 1 h. The title compound was purified by preparative HPLC and isolated as its trifluoroacetic salt (C18, gradient of CH$_3$CN/H$_2$O+0.01% TFA).

$^1$H-NMR (DMSO-d$_6$+TFA, 400 MHz, 340 K) δ 8.35 (d, J=4.2 Hz, 1H), 7.81 (t, J=7.4 Hz, 1H), 7.54 (bt, 1 H), 7.49 (d, J=7.7 Hz, 1H), 7.37 (dd, J=5.2 Hz, 7.0 Hz, 1 H), 7.25–7.22 (m, 2H), 7.17–7.09 (m, 3H), 6.90 (t, J=7.3 Hz, 1H), 6.62 (t, J=7.3 Hz, 1H), 6.43 (bs, 1H), 5.74 (t, J=7.6 Hz, 1H), 4.42 (dd, J=6.4 Hz, 14.8 Hz,1H), 4.32 (dd, J=6.4 Hz, 14.8 Hz, 1H), 3.65 (s, 3H), 2.80–2.70 (m, 3H), 1.85–1.75 (m, 1 H).

MS m/z 514 (M+H)$^+$.

EXAMPLE 12

2-[(2S,4R)-1-benzoyl-4-hydroxypyrrolidin-2-yl]-N-(4-fluorobenzyl)-5-hydroxy-1-methyl-6-oxo-1,6-dihydropyrimidine-4-carboxamide

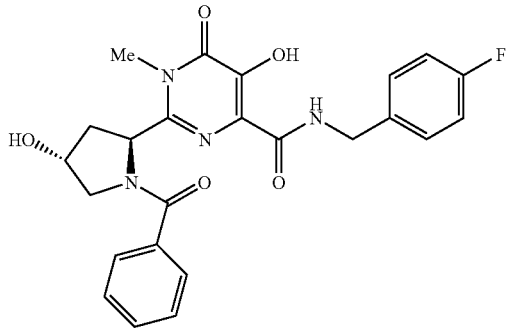

Step 1: Methyl 2-[(2S,4R)-1-benzoyl-4-(benzyloxy)pyrrolidin-2-yl]-5-(benzoyloxy)-1-methyl-6-oxo-1,6-dihydropyrimidine-4-carboxylate

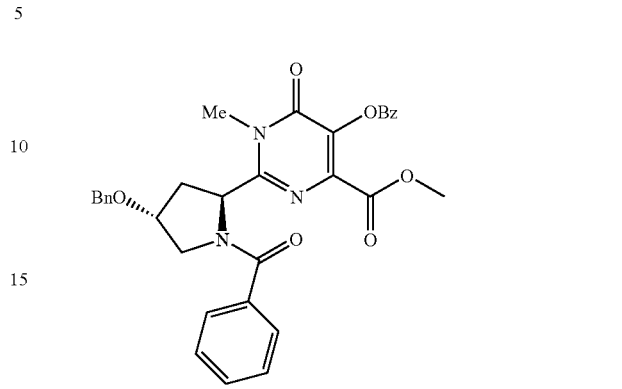

Methyl 2-[(2S,4R)-1-tert-butyloxycarbonyl-4-(benzyloxy)pyrrolidin-2-yl]-5-(benzoyloxy)-1-methyl-6-oxo-1,6-dihydropyrimidine-4-carboxylate [obtained from N-Boc-O-benzyl-L-hydroxyproline using chemistry similar to those set forth in Examples 1 or 2; the stereochemistry of products of Steps 1 to 3 is based on that of starting material] was dissolved in dichloromethane (0.03 M), followed by addition of an excess of TFA. The mixture was stirred at room temperature for 1 hour. The solvent was evaporated in vacuo. To the residue dissolved in pyridine, benzoic anhydride (2 eq.) was added. The mixture was stirred at room temperature for 5 hours. Pyridine was evaporated in vacuo and the residue dissolved in EtOAc was washed with HCl (1M), saturated aqueous NaHCO$_3$ and brine, dried on Na$_2$SO$_4$, filtered and evaporated in vacuo to give the title product as a yellow solid.

$^1$H NMR (DMSO-d$_6$, 400 MHz, 330 K) δ 8.07 (d, J=7.6 Hz, 2H), 7.77 (t, J=7.3 Hz, H), 7.62 (t, J=7.74 Hz, 2H), 7.52–7.49 (m, 5H), 7.33–7.30 (m, 5H), 5.47 (bt, 1H), 4.53 (d, J=12.1 Hz, 1H), 4.44 (d, J=12.0 Hz, 1H), 4.36 (bs, 1H), 3.87–3.84 (m, 1H), 3.76 (s, 3H), 3.73 (s, 3H), 3.57 (d, J=11.2 Hz, 1H) 2.70 (t, J=12.2 Hz, 1H), 2.31–2.28 (m, 1H).

Step 2: 2-[(2S,4R)-1-benzoyl-4-(benzyloxy)pyrrolidin-2-yl]-N-(4-fluorobenzyl)-5-hydroxy-1-methyl-6-oxo-1,6-dihydropyrimidine-4-carboxamide

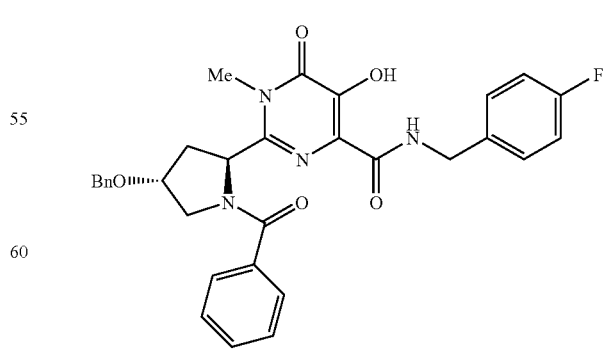

The compound of Step 1 was dissolved in methanol and 4-fluorobenzylamine (5 eq.) was added. The mixture was refluxed overnight. After cooling, the reaction mixture was filtered and washed with ethyl ether to obtain the title product as a white solid.

$^1$H NMR (DMSO-d$_6$, 400 MHz, 300 K) δ 12.15 (s, 1H), 9.00 (br t, 1H), 7.48 (d, J=7.6 Hz, 2H) 7.41–7.20 (m, 10H), 7.12 (t, J=8.8 Hz, 2H), 5.27 (t, J=8 Hz, 1H), 4.63 (dd, J=14.9, 7.3 Hz, 1H), 4.56–4.38 (m, 2H), 4.26 (bs, 1H) 4.25 (d, J=11.4 Hz, 2H) 3.68 (s, 3H), 3.52 (d, J=11.2 Hz, 1H), 2.66–2.63 (m, 1H), 2.26–2.20 (m, 1H).

MS m/z 557 (M+H)$^+$.

Step 3: 2-[(2S,4R)-1-benzoyl-4-hydroxypyrrolidin-2-yl]-N-(4-fluorobenzyl)-5-hydroxy-1-methyl-6-oxo-1,6-dihydropyrimidine-4-carboxamide The title compound of Step 2 was dissolved in AcOH and 10% Pd/C (10% weight) was added. The mixture was stirred under H$_2$ at atmosphere overnight. Pd/C was filtered, AcOH evaporated in vacuo, and the resulting title compound was washed with methanol.

$^1$H NMR (DMSO-d$_6$, 400 MHz) δ 12.1 (s, 1H), 9 (bt, 1H), 7.51–7.47 (m, 3H), 7.41–7.33 (m, 4H) 7.11 (t, J=8.8 Hz, 2H), 5.27 (t, J=8 Hz, 1H), 5.08 (d, J=3.2 Hz, 1H), 4.63 (dd, J=14.8 Hz, 7.3 Hz, 1H), 4.43–4.39 (m, 2H), 4.20 (d, J=7.4 Hz, 1H), 3.67 (s, 3H), 2.41–2.36 (m, 1H), 2.2–2.1 (m, 1H).

MS m/z 467 (M+H)$^+$.

EXAMPLE 13

N$^4$-(4-fluorobenzyl)-5-hydroxy-1-methyl-6-oxo-N$^2$-(pyridin-2-ylmethyl)-1,6-dihydropyrimidine-2,4-dicarboxamide

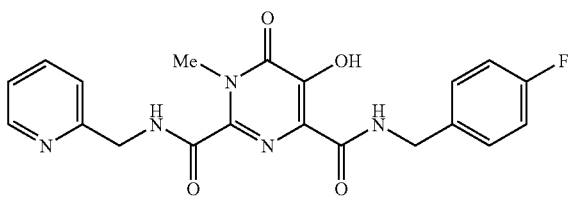

2-Ethyl 4-methyl 5-[(2,2-dimethylpropanoyl)oxy]-1-methyl-6-oxo-1,6-dihydropyrimidine-2,4-dicarboxylate (made by protection and alkylation of the starting material of Example 4, Step 1 using procedures similar to those set forth in Examples 1 or 2) was dissolved in DMF, 4-fluorobenzylamine (3.1 eq.) was added and the mixture was stirred at 90° C. overnight. After concentration of the solvent, the residue was taken into EtOAc, washed with 1 N HCl, dried over Na$_2$SO$_4$ and evaporated to obtain crude N-(4-fluorobenzyl)-2-ethoxycarbonyl-1-methyl-5-hydroxy-6-oxo-1,6-dihydropyrimidine-4-carboxamide. To this crude product was added 2-picolylamine (8 eq.), and the reaction was stirred at 90° C. overnight. The title product was obtained as its trifluoroacetic salt by preparative RP-HPLC purification (C18 gradient of CH$_3$CN/H$_2$O+0.01% TFA).

$^1$H NMR (DMSO-d$_6$, 300K, 400 MHz) δ 12.70 (bs, 1H), 9.75–9.65 (m, 2H), 8.56 (d, J=4.4 Hz, 1H), 7.90–7.80 (m, 1H), 7.44 (d, J=8.0 Hz, 1H), 7.40–7.35 (m, 3H), 7.17 (t, J=9.2 Hz, 2H), 4.60 (d, J=6.0 Hz, 2H), 4.54 (d, J=6.0 Hz, 2H), 3.67 (s, 3H).

MS m/z 412 (M+H)$^+$.

EXAMPLE 14

2-[2-(4-benzoylpiperazin-1-yl)ethyl]-N-(4-fluorobenzyl)-5-hydroxy-1-methyl-6-oxo-1,6-dihydropyrimidine-4-carboxamide

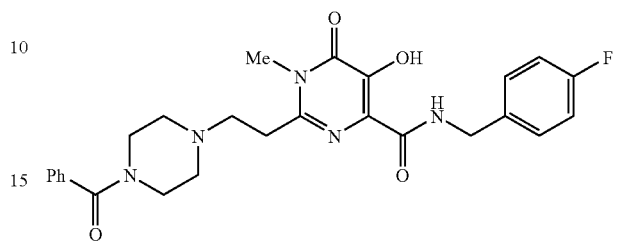

Step 1: 2-(2,2-dimethoxyethyl)-N-(4-fluorobenzyl)-5-hydroxy-1-methyl-6-oxo-1,6-dihydropyrimidine-4-carboxamide

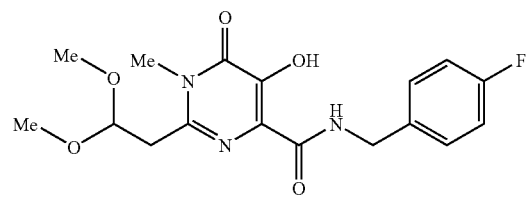

Methyl 2-(2,2-dimethoxyethyl)-5-benzoyloxy-1-methyl-6-oxo-1,6-dihydropyrimidine-4-carboxylate (1.0 eq.) (prepared from 3,3-dimethoxypropionitrile by procedure similar to those set forth in Examples 1 or 2) in dry MeOH was treated with 4-fluorobenzyl amine (2.5 eq.) at reflux for 2 hours. Solvent was removed in vacuo and residue triturated with Et$_2$O to obtain the title product.

$^1$H NMR (DMSO-d$_6$, 300K, 400 MHz) δ: 9.80 (br s, 1H), 7.41–7.38 (m, 2H), 7.15 (t, J=8.7 Hz, 2H), 5.04 (br s, 1H), 4.47 (d, J=6.2 Hz, 2H), 3.46 (s, 3H), 3.28 (s, 6H), 3.01 (d, J=5.5 Hz, 2H).

MS: m/z 366 (M–H)+

Step 2: N-(4-fluorobenzyl)-5-hydroxy-1-methyl-6-oxo-2-(2-oxoethyl)-1,6-dihydropyrimidine-4-carboxamide

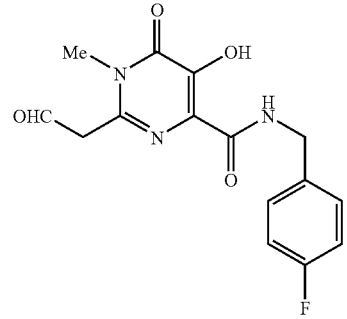

The product of Step 1 was treated with a mixture HCl 1N/THF for 1 hour at 40° C. Organics were removed in vacuo and residue extracted in DCM, dried over $Na_2SO_4$ and concentrated to give the title compound as a foam which was immediately reacted in the following reductive amination.
MS: m/z 320 (M+H)+.

Step 3: 2-[2-(4-benzoylpiperazin-1-yl)ethyl]-N-(4-fluorobenzyl)-5-hydroxy-1-methyl-6-oxo-1,6-dihydropyrimidine4-carboxamide The product of Step 2 was dissolved in MeOH and treated with sodium acetate (1.6 eq.), 1-benzoylpiperazine (2 eq.), and sodium cyanoborohydride (1.43 eq.). The mixture was left stirring at room temperature-for 1 hour. The reaction mixture was concentrated and the title compound was obtained by RP-HPLC purification ($C_{18}$, eluting with water and acetonitrile containing 0.1% TFA).
$^1$H NMR ($CDCl_3$+TFA, 273 K, 600 MHz) δ: 10.431 (br s, 1H), 8.38 (t, J=5.7 Hz, 1H), 7.61 (t, J=6.4 Hz, 1H), 7.52 (t, J=7.7 Hz, 2H), 7.41 (d, J=7.4 Hz, 2H), 7.28 (2H, overlapped by $CHCl_3$), 7.07 (t, J=8.5 Hz, 2H), 4.97 (d, J=14 Hz, 1H), 4.63 (d, J=5.7 Hz, 2H), 4.10 (d, J=14 Hz, 1H), 3.93 (d, J=11.9 Hz, 1H), 3.82–3.74 (m, 4H), 3.61 (s, 3H), 3.47 (t, J=12.6 Hz, 1H), 3.41 (br s, 2H), 3.29–3–26 (m, 1H), 3.15–3.14 (m, 1H).
MS: m/z 494 (M+H)+.

EXAMPLE 15

N-(4-fluorobenzyl)-5-hydroxy-1-(2-hydroxy-3-morpholin-4-ylpropyl)-6-oxo-1,6-dihydropyrimidine-4-carboxamide

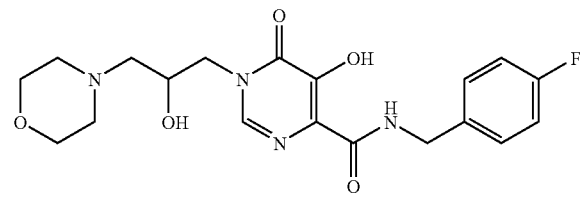

Step 1: Methyl 1-allyl-5-[(2,2-dimethylpropanoyl)oxy]-6-oxo-1,6-dihydropyrimidine-4-carboxylate

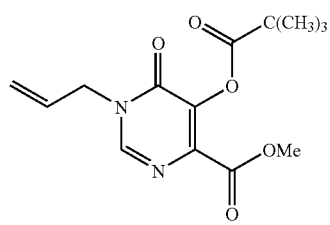

Methyl 5-[(2,2-dimethylpropanoyl)oxy]-6-hydroxy-1,6-dihydropyrimidine-4-carboxylate (see Example 4, Step 3) was dissolved in THF, then allyl bromide (2 eq.) and $Cs_2CO_3$ (2 eq.) were added. The reaction mixture was refluxed for 2 h, then evaporated. The residue was diluted with EtOAc, washed with 1N HCl, dried ($Na_2SO_4$) and the solvent evaporated. The product was-purified by flash chromatography on silica gel eluting with a gradient of petroleum ether/EtOAc.

$^1$H-NMR-(DMSO-$d_6$, 400 MHz, 300K) δ 8.47 (s, 1H), 5.99–5.92 (m, 1H), 5.25–5.14 (m, 2H), 4.58 (d, J=5.5 Hz, 2H), 3.82 (s, 3H), 1.28 (s, 9H).

Step 2: N-(4-fluorobenzyl)-5-hydroxy-1-(2-hydroxy-3-morpholin4-ylpropyl)-6-oxo-1,6-dihydropyrimidine-4-carboxamide 2a. The compound of Step 1 was dissolved in dichloroethane and m-CPBA was added (5 eq.). The reaction mixture was refluxed until the starting material was completely consumed, then evaporated. MS m/z 311 (M+H)+.

2b. Crude material from step 2a was dissolved in MeOH and morpholine (6 eq.) was added. The reaction mixture was refluxed for 3 h, then evaporated. MS (EI+) m/z 398 (M+H)+.

2c. Crude material from step 2b was dissolved in DMF and 4-fluorobenzylamine (3 eq.) was added. The reaction mixture was stirred at 90° C. for 3 h. The title compound was obtained as its trifluoroacetate salt by RP-HPLC purification (gradient of $CH_3CN/H_2O$+0.01% TFA).
$^1$H-NMR (DMSO-$d_6$+TFA, 400 MHz, 340K) δ 9.27 (bt, 1H), 7.94 (s, 1H), 7.40–7.36 (m, 2H), 7.15–7.11 (m, 2H), 4.48 (d, J=6.4 Hz, 2H), 4.30–4.36, (m, 1H), 4.09 (dd, J=13.6, 4.0 Hz, 1H), 3.91–3.86 (m, 5H), 3.34–3.30 (m, 5H), 3.18 (dd, J=13.6 ,4.0 Hz, 1H).
MS m/z 407 (M+H)+.

EXAMPLE 16

2-[(2S ,4S)-1-acetyl-4-fluoropyrrolidin-2-yl]-N-(4-fluorobenzyl)-5-hydroxy-1-methyl-6-oxo-1,6-dihydropyrimidine4-carboxamide

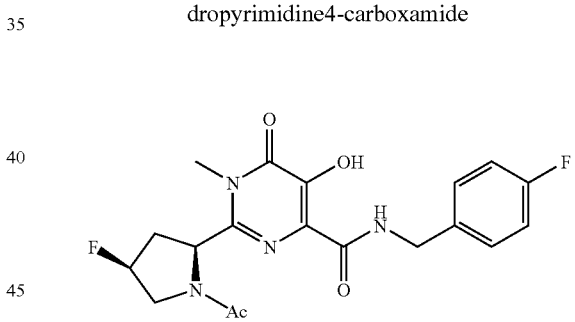

Step 1: 1-Benzyl-2-methyl-(2S,4S)-4-fluoropyrrolidine-1,2-dicarboxylate

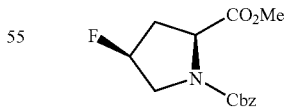

1-benzyl-2-methyl(2S,4R) 4-hydroxypyrrolidine-1,2 dicarboxylate in dichloromethane was added dropwise to a solution, precooled to −78° C., of N,N-diethylaminosulfur trifluoride (1.0 eq.) in dichloromethane. The reaction was stirred while the temperature was allowed to increase to 25° C. The solvent was concentrated under vacuum and the crude was purified by flash chromatography (eluent:petroleum ether:EtOAc=1:1) to give the title compound.

$^1$H NMR (CDCl$_3$, 300 MHz, 300 K) δ 7.42–7.30 (m, 5H), 5.35–5.10 (m, 3H), 4.65 (d, J=9.6 Hz, 0.5H), 4.57 (d, J=9.4Hz, 0.5H), 3.99–3.62 (m, 2H), 3.79 (s, 1.5H), 3.68 (s, 1.5H), 2.62–2.29 (m, 2H).

MS: m/z 282 (M+H)$^+$.

Step 2:
(4S)-1-[(Benzyloxy)carbonyl]-4-fluoro-L-proline

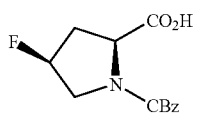

1-Benzyl-2-methyl-(2S,4S)-4-fluoropyrrolidine-1,2-dicarboxylate dissolved in methanol was treated with NaOH 1N (2 eq.) and the reaction mixture was stirred at 50° C. for 3 hours. After concentration of the solvent, HCl 1N was added until pH=1 and the aqueous layer was extracted three times with dichloromethane. The organic phase was washed with brine, dried over Na$_2$SO$_4$ and filtered to give, after concentration, title compound.

$^1$HNMR (CDCl$_3$, 400 MHz, 300 K) δ 7.45–7.30 (m, 5H), 5.33–5.18 (m, 3H), 4.70–4.60 (bm, 1H), 4.00–3.65 (m, 2H), 2.85–2.25 (m, 2H).

MS: m/z 268 (M+H)$^+$.

Step 3: Benzyl-(2S,4S)-2-aminocarbonyl-4-fluoropyrrolidine-1-carboxylate

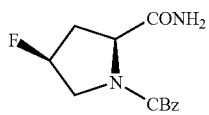

A stirred solution of (4S)-1-[(Benzyloxy)carbonyl]-4-fluoro-L-proline in dioxane was treated with pyridine-(0.7 eq.) and Boc$_2$O (1.3 eq.), then ammonium bicarbonate (1.26 eq.) was added and the mixture was stirred at room temperature for 15 hours. Dioxane was concentrated and the residue was taken up in ethyl acetate, washed with 1 N HCl and brine, dried over Na$_2$SO$_4$ to give, after filtration and concentration, title compound.

$^1$H NMR (DMSO-d$_6$, 400 MHz, 340 K) δ 7.40–7.28 (m, 5H), 5.25 (dt, J$_{H-F}$=53.6 Hz, J=4.5 Hz, 1H), 5.13–5.06 (m, 2H), 4.28 (d, J=9.6 Hz, 1H), 3.80–3.63 (m, 2H), 2.45–2.21 (m, 2H).

MS: m/z 267 (M+H)$^+$.

Step 4: Benzyl-(2S,4S)-2-cyano-4-fluoropyrrolidine-1-carboxylate

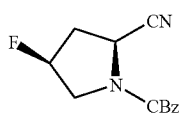

Benzyl-(2S,4S)-2-aminocarbonyl-4-fluoropyrrolidine-1-carboxylate in dichloromethane was treated at 0° C. with Et$_3$N (2.1 eq.) and trifluoroacetic anhydride was added dropwise.

The reaction mixture was stirred at 0° C. for 0.5 hour and 10 minutes at room temperature. Then, it was diluted with dichloromethane, washed with HCl 1N and brine, dried over Na$_2$SO$_4$ and filtered to give, after concentration, title compound.

$^1$H NMR (DMSO-d$_6$, 400 MHz, 340 K) δ 7.42–7.30 (m, 5H), 5.40 (dbt, J$_{H-F}$=52.3 Hz, 1H), 5.20 (d, J=12.7 Hz, 1H), 5.16 (d, J=12.7 Hz, 1H), 4.94 (d, J=8.4 Hz, 1H), 3.68–3.56 (m, 2H), 2.63–2.41 (m, 2H).

MS: m/z 249 (M+H)$^+$.

Step 5: Benzyl-(2S,4S)-2-[amino(hydroxyimino) methyl]-4-fluoropyrrolidine-1-carboxylate

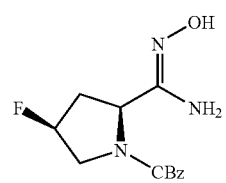

Benzyl-(2S,4S)-2-cyano-4-fluoropyrrolidine-1-carboxylate dissolved in absolute ethanol was treated with triethyl amine (1.5 eq.) and hydroxylamine hydrochloride (1.3 eq.).

The reaction mixture was stirred at 50° C. for 3 hours and then the solvent was removed under reduced pressure. The residue was partitioned between water and dichloromethane and the aqueous layer was extracted with dichloromethane three times. The organic phase was dried over Na$_2$SO$_4$ and filtered. The solid obtained by concentration was then recrystallized from MeOH to give title compound.

$^1$H NMR (DMSO-d$_6$, 400 MHz, 300 K) δ 9.10 (bs, 1H), 7.40–7.25 (m, 5H), 5.35–5.15 (m, 3H), 5.07 (m, 2H), 4.43 (d, J=9.1 Hz, 1H), 3.72–3.56 (m, 2H), 2.45–2.20 (m, 2H).

MS: m/z 282 (M+H)$^+$.

Step 6: Dimethyl-2-{[(amino-{(2S,4S)-1-[(benzyloxy)carbonyl]-4-fluoropyrrolidin-2-yl}methylidene)amino]oxy}but-2-enedioate

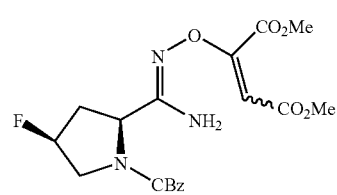

Benzyl-(2S,4S)-2-[amino(hydroxyimino)methyl]-4-fluoropyrrolidine-1-carboxylate in chloroform was treated with dimethylacetylene dicarboxylate for 3 hours at 60° C. The chloroform was then concentrated to give the title compound as a 8:2 mixture of isomers.

¹H NMR (DMSO-d₆, 400 MHz, 300 K) δ 7.45–7.25 (m, 5H), 6.51 (bs, 1.6H), 6.14 (bs, 0.4H), 5.64 (s, 0.8H), 5.61 (s, 0.2H), 5.30 (dt, $J_{H-F}$=53.9 Hz, J=4.6 Hz, 1H), 5.15–5.04 (m, 2H), 4.51 (t, J=8.8 Hz, 0.8H), 4.44 (bt, 0.4H), 3.85–3.48 (m, 8H), 2.67–2.23 (m, 2H).

MS: m/z 424 (M+H)⁺.

Step 7: Methyl-2-{(2S,4S)-1-[(benzyloxy)carbonyl]-4-fluoropyrrolidin-2-yl}-5,6-dihydroxypyrimidine-4-carboxylate

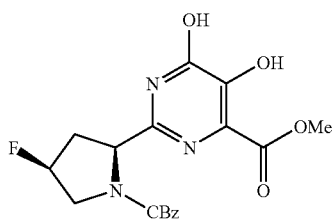

Dimethyl-2-{[(amino-{(2S,4S)-1-[(benzyloxy)carbonyl]-4-fluoropyrrolidin-2-ylmethylidene)amino]oxy}but-2-enedioate was refluxed for 6 hours in ortho-xylene. The reaction mixture was then cooled down to room temperature and petroleum ether was added. A light brown solid precipitated to give after filtration title compound, that was not purified furthermore, but used as such in the following reaction.

Step 8: Methyl-5-(benzoyloxy)-2-{(2S,4S)-1-[(benzyloxy)carbonyl]-4-fluoropyrrolidin-2-yl}-6-hydroxypyrimidine-4-carboxylate

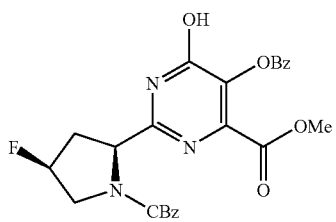

Methyl-2-{(2S,4S)-1-[(benzyloxy)carbonyl]-4-fluoropyrrolidin-2-yl}-5,6-dihydroxypyrimidine-4-carboxylate in pyridine was treated with benzoic anhydride (1.3 eq.) and the reaction mixture was stirred at room temperature overnight. Pyridine was concentrated and the residue was taken up in ethyl acetate and washed with HCl 1N and brine. The organic phase was dried over Na₂SO₄ and filtered to give after concentration a crude that was purified by flash chromatography, (eluent:petroleum ether:ethyl acetate=1:1) to give title compound.

¹H NMR (DMSO-d₆, 400 MHz, 300 K) δ 13.50 (bs, 1H), 8.09 (d, J=7.7 Hz, 2H), 7.80 (t, J=7.35 Hz, 1H), 7.64 (t, J=7.8 Hz, 2H), 7.45–7.15 (m, 5H), 5.36 (dbt, $J_{H-F}$=54 Hz, 1H), 5.14 (m, 2H), 5.02–4.93 (m, 1H), 3.95–3.60 (m, 2H), 3.76 (s, 3H), 2.80–2.36 (m, 2H).

MS: m/z 496 (M+H)⁺.

Step 9: Methyl-5-(benzoyloxy)-2-{(2S,4S)-1-[(benzyloxy)carbonyl]-4-fluoropyrrolidin-2-yl}-1-methyl-6-oxo-1,6-dihydropyrimidine-4-carboxylate

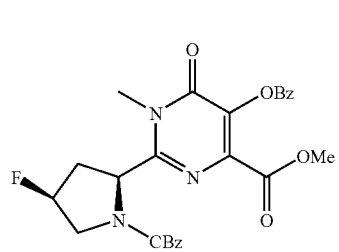

Methyl-5-(benzoyloxy)-2-{(2S,4S)-1-[(benzyloxy)carbonyl]-4-fluoropyrrolidin-2-yl}-6-hydroxypyrimidine-4-carboxylate, dissolved in dry dioxane, was added to a suspension of lithium hydride (1.2 eq.) in dry dioxane. The reaction mixture was stirred at 38° C. for 45 minutes and then cooled down to room temperature. Dimethyl sulfate (1.3 eq.) was added and the mixture was heated to 58° C. and stirred at this temperature for 3 hours. The reaction mixture was then cooled down and glacial acetic acid (0.2 eq.) was added, followed by water and ethyl acetate. The aqueous layer was separated and extracted with ethyl acetate; the organic phase was dried over Na₂SO₄ and filtered to give, after concentration, a crude that was purified by flash chromatography (eluent petroleum ether:ethyl acetate from 4:6 to 2:8) to give the title compound as a 4.6:5.4 mixture of rotamers by NMR.

¹H NMR (DMSO-d₆, 400 MHz, 300 K) δ 8.08 (d, J=7.5 Hz, 2H), 7.79 (t, J=7.3 Hz, 1H), 7.63 (t, J=7.5 Hz, 2H), 7.37–7.11 (m, 5H), 5.48–5.38 (m, 2H), 5.20 (d, J=12.8 Hz, 0.46H), 5.12 (d, J=11.8 Hz, 0.54H), 5.10 (d, J=12.5 Hz, 0.54H), 4.92 (d, J=12.8 Hz, 0.46H), 4.00–3.75 (m, 2H), 3.72 (s, 3H), 3.59 (s, 1.6H), 3.52 (s, 1.4H), 2.90–2.65 (m, 2H).

MS: m/z 510 (M+H)⁺.

Step 10: Methyl-2-[(2S,4S)-1-acetyl-4-fluoropyrrolidin-2-yl]-5-(benzoyloxy)-6-hydroxypyrimidine-4-carboxylate

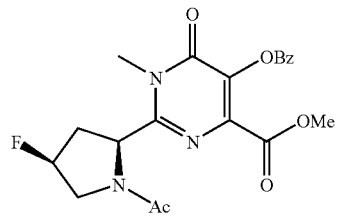

Methyl-5-(benzoyloxy)-2-{(2S,4S)-1-[(benzyloxy)carbonyl]-4-fluoropyrrolidin-2-yl}-1-methyl-6-oxo-1,6-dihydropyrimidine4-carboxylate, dissolved in ethyl acetate was treated with Pd/C 10% (10% w/w) and acetic anhydride (1 eq.) and submitted under H₂ atmosphere at room temperature. The reaction mixture was stirred at room temperature for 18 hours and then the suspension was filtered over celite to give the title compound as a 7:3 mixture of rotamers by NMR.

¹H NMR (DMSO-d₆, 400 MHz, 300 K) δ 8.07 (m, 2H), 7.78 (m, 1H), 7.62 (m, 2H), 5.75–5.26 (m, 2H), 4.13–3.60 (m, 2H), 3.72 (s, 3H), 3.59 (s, 3H), 2.79–2.36 (m, 2H), 2.03 (s, 2.1H), 1.87 (s, 0.9H).

MS: m/z 418 (M+H)⁺.

Step 11: 2-[(2S,4S)-1-acetyl-4-fluoropyrrolidin-2-yl]-N-(4-fluorobenzyl)-5-hydroxy-1-methyl-6-oxo-1,6-dihydropyrimidine-4-carboxamide Methyl-2-[(2S,4S)-1-acetyl4-fluoropyrrolidin-2-yl]-5-(benzoyloxy)-6-hydroxypyrimidine-4-carboxylate was dissolved in MeOH (0.12 N) and treated with 4-F-benzylamine (3 eq.) in a sealed tube. The reaction mixture was stirred at 65° C. for 18 hours, then it was cooled down. The solvent was evaporated and the residue was washed with ethyl ether several times to obtain a solid that was recrystallized from ethanol and washed again with ethyl ether to give the title compound as a 7.3:2.7 mixture of rotamers by NMR.

$^1$H NMR (DMSO-$d_6$, 500 MHz, 300 K) δ 12.01 (bs, 1H), 8.52 (t, J=6.3 Hz, 0.7H), 8.34 (t, J=6.3 Hz, 0.3H), 7.34–7.29 (m, 2H), 7.18–7.12 (m, 2H), 5.39 (dbt, $J_{H-F}$=54.3 Hz, 0.7H), 5.29 (dt, $J_{H-F}$=54.2 Hz, J=4.4 Hz, 0.3H), 5.38 (d, J=8.9 Hz, 0.3H), 5.18 (dd, J=9.2 and 1.6 Hz, 0.7H), 4.55–4.47 (m, 2H), 4.20–3.78 (m, 2H), 3.51 (s, 2.1H), 3.50 (s, 0.9H), 2.75–2.54 (m, 1H), 2.47–2.27 (m, 1H), 2.00 (s, 2.1H), 1.81 (s, 0.9H), MS: m/z 407 (M+H)$^+$.

EXAMPLE 17

2-{(2S,4R)-1-[(dimethylamino)(oxo)acetyl]-4-methoxypyrrolidin-2-yl}-N-(4-fluorobenzyl)-5-hydroxy-1-methyl-6-oxo-1,6-dihydropyrimidine-4-carboxamide

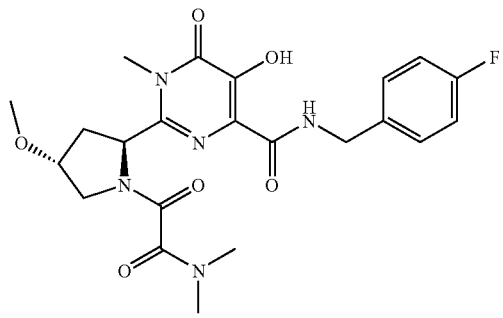

Step 1:
(4R)-1-[(Benzyloxy)carbonyl]-4-methoxy-L-proline

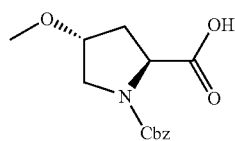

Synthesized following the procedure reported on Journal of Medicinal Chemistry 1988, 31, 875–885.

Step 2: Benzyl-(2S,4R)-2-cyano-4-methoxypyrrolidine-1-carboxylate

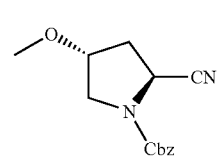

To compound (4R)-1-[(Benzyloxy)carbonyl]-4-methoxy-L-proline dissolved in dioxane, Boc anhydride (1.3 eq), NH$_4$HCO$_3$ (1.26 eq.) and pyridine were added. The mixture was stirred overnight at room temperature. Dioxane was removed in vacuo and the residue, dissolved in ethyl acetate, was washed with HCl 1N, saturated aqueous NaHCO$_3$ and brine, dried over Na$_2$SO$_4$, filtered and concentrated in vacuo to get the primary amide. The crude product was dissolved in dichloromethane and triethylamine (2.1 eq.) was added. The mixture was cooled down to 0° C. and trifluoroacetic anhydride (1.1 eq.) was added. After 1 hour the dichloromethane solution was diluted and washed with HCl 1N, saturated aqueous NaHCO$_3$ and brine, dried over Na$_2$SO$_4$, filtered and evaporated in vacuo. The compound was purified by flash chromatography on silica gel (eluent ethyl acetate:petroleum ether=20%:80%) as a 4:6 mixture of rotamers by NMR.

$^1$H NMR (DMSO-$d_6$, 400 MHz, 300 K) δ 7.45–7.3 (m, 5H), 5.20 (d, J=12 Hz, 0.4H), 5.14 (s, 1.2H), 5.12 (d, J=12 Hz, 0.4H), 4.75 (t, J=7 Hz, 0.4H), 4.64 (t, J=7.8 Hz, 0.6H), 4.02 (bs, 1H), 3.6–3.45 (m, 2H), 3.21 (s, 3H), 2.45–2.40 (partially under DMSO) (m, 1H), 2.40–2.25 (m, 1H).

Step 3: Benzyl-(2S,4R)-2-[amino(hydroxyimino)methyl]-4methoxypyrrolidine-1-carboxylate

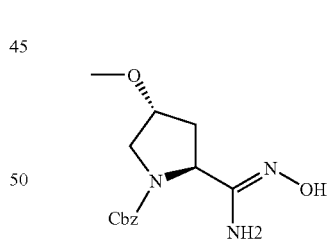

To benzyl-(2S,4R)-2-cyano4-methoxypyrrolidine-1-carboxylate, dissolved in ethanol (0.4 M), hydroxylamine hydrochloride (1.3 eq.) and triethylamine (1.5 eq.) were added. The mixture was stirred at 40° C. for 4 hours then at room temperature overnight. The mixture was concentrated in vacuo and the residue dissolved in ethyl acetate washed with brine, dried over Na$_2$SO$_4$, filtered and concentrated to give title compound.

$^1$H NMR (DMSO-$d_6$, 400 MHz, 300 K) δ 9.05 (bs, 1H), 7.45–7.25 (m, 5H), 5.4 (bs, 2H), 5.10 (d, J=13 Hz, 1H), 5.03 (d, J=13 Hz, 1H), 4.26 (t, J=7.4 Hz, 1H), 3.97 (bs, 1H), 3.63–3.45 (m, 2H), 3.22 (s, 3H) 2.3–2.03 (m, 2H).-

Step 4: Dimethyl-2-{[(amino-{(2S,4R)-1-[(benzyloxy)carbonyl]-4-methoxypyrrolidin-2-yl}methylidene)amino]oxy}but-2-enedioate

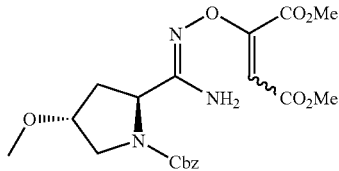

To benzyl-(2S,4R)-2-[amino(hydroxyimino)methyl]-4methoxypyrrolidine-1-carboxylate, dissolved in chloroform, dimethyl acetylendicarboxylate (1.1 eq.) was added. The mixture was refluxed for 1 hour and left stirring at 40° C. overnight. The chloroform was removed in vacuo and the crude product purified by flash chromatography on silica gel (eluent ethyl acetate:petroleum ether=40:60). Two isomers were present in ratio 7:3.

$^1$H NMR (DMSO-$d_6$, 400 MHz, 300 K) δ 7.40–7.23 (m, 5H), 6.7–6.55 (2bs, 1.4H), 6.35–6.2 (bs, 0.6H), 5.61 (s, 0.7H), 5.59 (s, 0.3H), 5.10 (d, J=13 Hz, 0.7H), 5.08 (s, 0,6H), 5.02 (d, J=13 Hz, 0.7H), 4.30–4.20 (m, 1H), 3.97 (bs, 1H) 3.78 (s, 3.73 (s, 0.9H), 3.62 (s, 0.9H), 3.59 (s, 2.1H), 3.65–3.50 (m, 2H), 3.22 (s, 3H), 2.37–2.23 (m, 1H), 2.10–1.95 (m, 1H).

Step 5: Methyl 5-(benzyloxy)-2-{(2S,4R)-1-[(benzyloxy)carbonyl]-4-methoxypyrrolidin-2-yl}-6-hydroxypyrimidine-4-carboxylate

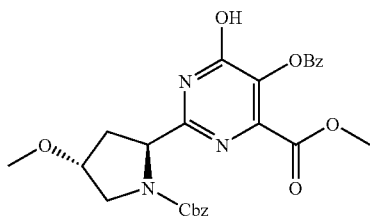

Dimethyl-2-{[(amino-{(2S,4R)-1-[(benzyloxy)carbonyl]-4-methoxypyrrolidin-2-yl}methylidene)amino]oxy}but-2-enedioate were dissolved in xylene and the solution stirred at 150° C. for 3 hours and at room temperature overnight. Xylene was concentrated in vacuo. To the crude compound, dissolved in pyridine, benzoic anhydride (1.3 eq.) was added and the reaction mixture was stirred at room temperature overnight. The solution was concentrated in vacuo and the crude dissolved in ethyl acetate washed with 1 N HCl, saturated aqueous NaHCO$_3$ and brine, dried on Na$_2$SO$_4$, filtered and evaporated in vacuo. The crude product was purified by flash chromatography on silica gel (eluent ethyl acetate:petroleum ether=10:90) and showed a 1:1 mixture of rotamers by NMR.

$^1$H NMR (DMSO-$d_6$, 400 MHz, 300 K) δ 13.5 (s, 1H), 8.09 (t, J=7.0 Hz, 2H), 7.82–7.75 (m, 1H), 7.66–7.61 (m, 2H), 7.40–7.25 (m, 4H), 7.12–7.06 (m, 1H), 5.10 (s, 1H), 5.09 (d, J=12.5 Hz, 0.5H), 4.88 (d, J=12.5 Hz, 0.5H), 4.66 (dd, J=16.2 and 8.0 Hz, 1H), 4.10–4.00 (m, 1H), 3.74 (s, 3H), 3.75–3.60 (m, 2H), 3.25 (s, 3H), 2.45–2.40 (partially under DMSO) (m, 1H), 2.13–2.03 (m, 1H).

Step 6: Methyl-5-(benzoyloxy)-2-{(2S,4R)-1-[(benzyloxy)carbonyl]-4-methoxypyrrolidin-2-yl}-1-methyl-6-oxo-1,6-dihydropyrimidine-4-carboxylate

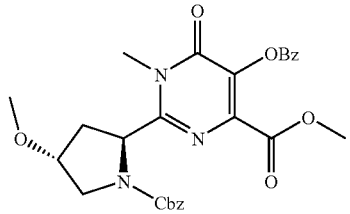

To methyl 5-(benzoyloxy)-2-{(2S,4R)-1-[(benzyloxy)carbonyl]4-methoxypyrrolidin-2-yl}-6-hydroxypyrimidine-4-carboxylate, dissolved in dioxane, LiH (1.4 eq.) was added and the reaction mixture stirred at 38° C. for 40 minutes. The temperature was raised to 60° C. and dimethyl sulphate (1.3 eq.) was added dropwise. After two hours the reaction mixture was cooled down to 0° C. and HCl 1 N was added to quench the reaction. The reaction mixture was extracted with ethyl acetate and the organic phase washed with HCl 1N, saturated aqueous NaHCO$_3$ and brine, dried on Na$_2$SO$_4$, filtered and concentrated in vacuo. The desired product was isolated by flash chromatography on silica gel (eluent ethyl acetate:petroleum ether=30:70) as a 1:1 mixture of rotamers by NMR.

$^1$H NMR (DMSO-$d_6$, 400 MHz, 300 K) δ 8.08 (t, J=6.8, 2H), 7.82–7.75 (m, 1H), 7.66–7.61 (m, 2H), 7.38–7.22 (m, 4H), 7.08–7.02 (m, 1H), 5.18–5.12 (m, 1H), 5.13 (d, J=13.1 Hz, 0.5H), 5.07 (d, J=13.1 Hz, 0.5H), 5.06 (d, J=12.4 Hz, 0.5H), 4.84 (d, J=12.4 Hz, 0.5H), 4.08–4.17 (m, 1H), 3.73 (s, 3H), 3.75–3.55 (m, 2H), 3.65 (s, 1.5H), 3.44 (s, 1.5H), 3.26 (s, 3H), 2.62–2.52 (partially under DMSO) (m, 1H), 2.30–2.15 (m, 1H).

MS: m/z 522 (M+H)$^+$

Step 7: Benzyl-(2S,4R)-2-(4-{[(4-fluorobenzyl)amino]carbonyl}-5-hydroxy-1-methyl-6-oxo-1,6-dihydropyrimidin-2-yl)-4-methoxypyrrolidine-1-carboxylate

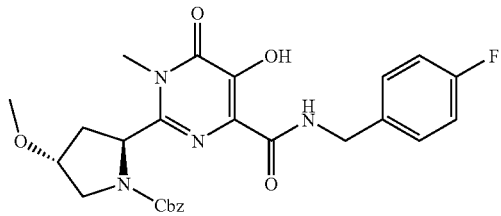

To methyl-5-(benzoyloxy)-2-{(2S,4R)-1-[(benzyloxy)carbonyl]-4-methoxypyrrolidin-2-yl}-1-methyl-6-oxo-1,6-dihydropyrimidine-4-carboxylate,dissolved in methanol, 4-F-benzylamine (3 eq.) was added. The reaction mixture was stirred at reflux overnight. Methanol was removed in vacuo and the residue triturated with ethyl ether to give the title product as a 4:6 mixture of rotamers by NMR:

$^1$H NMR (DMSO-$d_6$+TFA, 400 MHz, 300 K) δ 14.0 (bs, 1H), 8.92 (t, J=6.4 Hz, 0.4H), 8.73 (t, J=5.9 Hz, 0.6H), 7.35–7.25 (m, 4H), 7.20–7.05 (m, 4H), 6.93 (d, J=7.5 Hz, 1H), 5.09–4.95 (m, 1H), 5.09 (d, J=12.3 Hz, 0.6H), 4.75 (d,

J=12.3 Hz, 0.6H), 5.05 (d, J=13 Hz, 0.4H), 4.98 (d, J=13 Hz, 0.4H), 4.52–4.43 (m, 2H), 4.12–4.06 (bm, 0.4H), 4.06–4.02 (bm, 0.6H), 3.87 (dd, J=11.5 and 4.5 Hz, 0.4H), 3.84 (dd, J=12 and 2.7Hz, 0.6H), 3.65–3.55 (m, 1H), 3.59 (s, 1.2H), 3.41 (s, 1.8H), 3.25 (s, 3H), 2.45–2.40 (partially under DMSO) (m, 1H), 2.30–2.15 (m, 1H).

MS: m/z 511 (M+H)+

Step 8: N-(4-fluorobenzyl)-5-hydroxy-2-[(2S,4R)-4-methoxypyrrolidin-2-yl]-1-methyl-6-oxo-1,6-dihydropyrimidine-4-carboxamide

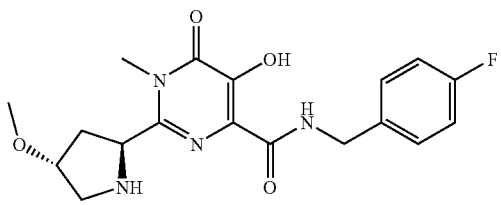

Benzyl-(2S,4R)-2-(4-{[(4-fluorobenzyl)amino]carbonyl}-5-hydroxy-1-methyl-6-oxo-1,6-dihydropyrimidin-2-yl)-4-methoxypyrrolidine-1-carboxylate was dissolved in methanol and Pd/C 10% wt (14% w/w) was added. The mixture was stirred under H$_2$ atmosphere at room temperature. After 2 hours the reaction mixture was filtered and methanol was removed in vacuo to give title compound.

$^1$H NMR (DMSO-d$_6$+TFA, 400 MHz, 300 K) δ 12.58 (bs, 1H), 10.16 (bs, 1H), 9.74 (t, J=6.3 Hz, 1H), 8.90 (bs, 1H), 7.36 (dd, J=8.5 and 5.7 Hz, 2H), 7,19 (t, J=8.8 Hz, 2H), 5.01 (bs, 1H), 4.50–4.60 (m, 2H), 4.19 (bs, 1H), 3.55–3.45 (m, 1H), 3.47 (s, 3H), 3.45–3.35 (m, 1H), 3.32 (s, 3H), 2.74 (dd, J=13.9 and 7.5 Hz, 1H), 2.17–2.10 (m, 1H).

MS: m/z 377 (M+H)+

Step 9: 2-{(2S,4R)-1-[(dimethylamino)(oxo)acetyl]-4-methoxypyrrolidin-2-yl}-N-(4-fluorobenzyl)-5-hydroxy-1-methyl-6-oxo-1,6-dihydropyrimidine-4-carboxamide To N-(4-fluorobenzyl)-5-hydroxy-2-[(2S,4R)-4-methoxypyrrolidin-2-yl]-1-methyl-6-oxo-1,6-dihydropyrimidine4-carboxamide, triethylamine (1 eq.) was added. The reaction mixture was cooled down to 0° C. and methyl chlorooxoacetate (3 eq.) was added. After 1 hour the reaction mixture was concentrated and a big excess of dimethylamine 2M in THF (30 eq.) was added The reaction mixture was concentrated and the desired compound was isolated by HPLC purification (Waters, Symmetry C$_{18}$, 5 um, 19×50 mm eluting with water and acetonitrile containing 0.1% trifluoroacetic acid) as a 2:8 mixture of rotamers by NMR.

$^1$H NMR (DMSO-d$_6$, 400 MHz, 340 K) δ 11.9 (bs, 1H), 8.99 (bs, 0.8H), 8.85 (bs, 0.2H), 7.40–7.30 (m, 2H), 7.14 (t, J=8.8 Hz, 2H), 5.21 (t, J=7.5 Hz, 1H), 4.54 (dd, J=14.9 and 6.7 Hz, 1H),;4.45 (dd, J=14.9 and 6.4 Hz, 1H), 4.10 (bs, 1H), 3.91 (dd, J=11.6 and 4.6 Hz, 0.2H), 3.79 (dd, J=11.2 and 4.4 Hz, 0.8H), 3.60–3.50 (m, 1H), 3.58 (s, 2.4H), 3.48 (s, 0.6H), 3.29 (s, 0.6H), 3.27 (s, 2.4H), 2.87 (s, 2.4H), 2.81 (s, 2.4H), 2.64 (s, 0.6H), 2.57 (s, 0.6H), 2.70–2.50 (m, 1H), 2.30–2.20 (m, 0.8H), 2.20–2.10 (m, 0.2H).

MS: m/z 476, (M+H)+

EXAMPLE 18

N$^1$-[1-(4-{[(4-fluorobenzyl)amino]carbonyl}-5-hydroxy-1-methyl-6-oxo-1,6-dihydropyrimidin-2-yl)-1-methylethyl]-N$^2$,N$^2$-dimethylethanediamide (11)

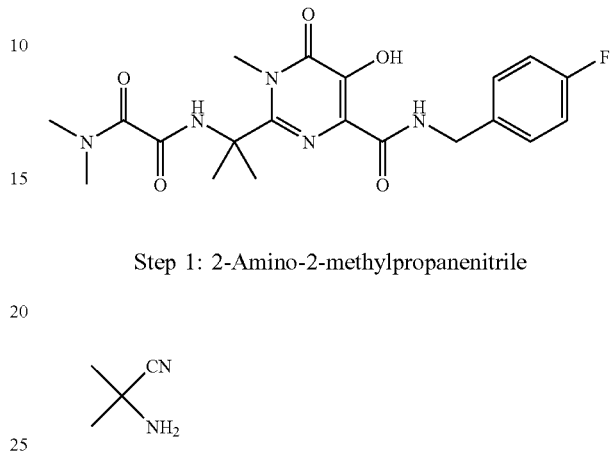

Step 1: 2-Amino-2-methylpropanenitrile

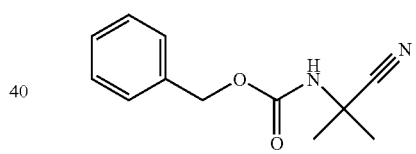

Organic Synthesis Coll. Vol.11 pg 29 Acetone cyanohydrin was diluted with MeOH (approx. 3 mmol/mL). The solution was cooled and saturated with ammonia gas, and the reaction mixture was allowed to stand for one day. The excess of ammonia and methyl alcohol were evaporated by rotary evaporation. Residue consisted in the title product.

Step 2: Benzyl 1-cyano-1-methylethylcarbamate

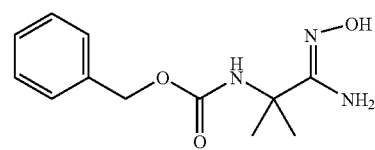

To a suspension of 2-amino-2-methylpropanenitrile in water an equimolar amount of Na$_2$CO$_3$ and a slight excess (1.1 eq) of benzylchloroformate were added, with an external cooling. Reaction mixture was stirred o/n at room temperature, extracted in EtOAc and the organic phase was washed with NaHCO$_3$ss, dried (Na$_2$SO$_4$), filtered and concentrated. Product was obtained as a white solid.

$^1$H-NMR (CDCl$_3$) δ 7.48–7.33 (bs, 5H), 5.15 (s, 2H), 4.98 (bs, 1H), 1.68 (s, 6H);

$^{13}$C-NMR (CDCl$_3$) δ 153.33, 13.81, 127.81, 127.63, 127.55, 120.64, 66.56, 46.19, 26.67; MS (M+1) m/z 219.

Step, 3: Benzyl 2-amino-2-(hydroxyimino)-1,1-dimethylethylcarbamate

Hydroxylamine hydrochloride in methanol was added to an equimolar stirred solution of potassium hydroxide in methanol. The mixture was stirred for 15 min and the precipitated potassium chloride was removed by filtration. The filtrate was added to an equimolar amount of the nitrile and the solution stirred overnight at 40° C., then cooled to room temperature and concentrated. The resulting residue was triturated with water and the white solid, after drying under vacuum, consists mainly in the title product.

$^1$H-NMR (DMSO) δ 9.12 (bs, 1H), 7.48 (bs, 5H), 7.08 (bs, 1H), 5.33 (bs, 2H), 4.98 (s, 2H), 1.39 (s, 6H); MS (M+1) m/z 252.

Step 4: Methyl 2-(1-{[(benzyloxy)carbonyl]amino}-1-methylethyl)-5,6-dihydroxypyrimidine-4-carboxylate

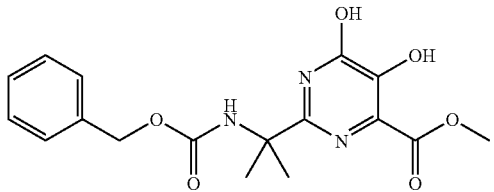

Benzyl 2-amino-2-(hydroxyimino)-1,1-dimethylethylcarbamate was suspended in chloroform and treated with 1.2 eq of dimethylacetylenedicarboxylate and reaction was refluxed overnight. After cooling at room temperature, volatiles were evaporated and the residue was taken into xylene and heated at 145° C. for 48 h. The reaction mixture was stirred at room temperature overnight to allow the precipitation of the product (5) as a light brown solid. This solid was collected by filtration and washed with diethyl ether.

$^1$H-NMR (DMSO) δ 12.54 (s, 1H), 10.21 (s, 1H), 7.44 (bs, 1H), 7.30 (bs, 5H), 4.95 (s, 2H), 3.80 (s, 3H), 1.47 (s, 6H); MS (M+1) m/z 362.

Step 5: Methyl 5-(benzoyloxy)-2-(1-{[(benzyloxy)carbonyl]amino}-1-methylethyl)-6-hydroxypyrimidine-4-carboxylate

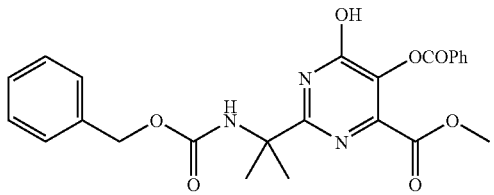

To a stirred solution of methyl 2-(1-{[(benzyloxy)carbonyl]amino}-1-methylethyl)-5,6-dihydroxypyrimidine-4-carboxylate in pyridine, 1.1 eq of benzoic anhydride were added and stirring prolonged at room temperature overnight. Pyridine was evaporated and residue was taken in ethyl acetate and washed with 1 N HCl and brine. Organic layer was separated, dried (Na$_2$SO$_4$), filtered and concentrated by rotary evaporation and residue was purified by flash column chromatography (SiO2, petroleum ether/ethyl acetate 60/40 v/v as eluant). Collection and evaporation of appropriate fractions afforded title product.

$^1$H-NMR (CDCl$_3$) δ 12.2 (bs, 1H), 8.15 (d, J=7.4 Hz, 2H), 7.65 (t, J=7.4 Hz, 1H), 7.50 (t, J=7.5 Hz, 2H), 7.32 (bs, 5H), 5.54 (bs, 1H), 5.05 (s, 2H), 3.82 (s, 3H), 1.67 (s, 6H); MS (M+1) m/z 466.

Step 6: Methyl 5-(benzoyloxy)-2-(1-{[(benzyloxy)carbonyl]amino}-1-methylethyl)-1-methyl-6-oxo-1,6-dihydropyrimidine-4-carboxylate

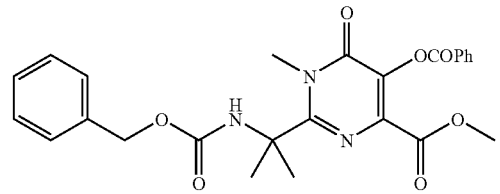

To a stirred solution of LiH (1.1 eq) in dioxane, methyl 5-(benzoyloxy)-2-(1-{[(benzyloxy)carbonyl]amino}-1-methylethyl)-6-hydroxypyrimidine-4-carboxylate was added and the mixture was stirred at 38° C. for 45 min. After cooling down to room temperature, dimethylsulfate (1.3 eq) was added and reaction mixture was heated at 60° C. for 2 h. Mixture was then cooled to room temperature, dioxane evaporated and residue was purified by flash chromatography, eluting with 65/55 v/v petroleum ether/ethyl acetate. Collection and evaporation of appropriate fractions afforded the title product.

$^1$H-NMR (CDCl$_3$) δ 8.19 (d, J=7.3Hz, 2H), 7.65 (t, J=7.3Hz, 1H), 7.51 (t, J=7.6 Hz, 2H), 7.33 (bs, 5H), 5.63 (bs, 1H), 5.03 (s, 2H), 3.80 (s, 3H), 3.63 (bs, 3H), 1.72 (s, 6H); MS (M+1) m/z 480.

Step 8: Benzyl 1-(4-{[(4-fluorobenzyl)amino]carbonyl}-5-hydroxy-1-methyl-6-oxo-1,6-dihydropyrimidin-2-yl)-1-methylethylcarbamate

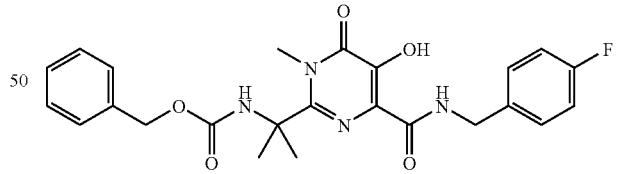

To a methanolic solution of methyl 5-(benzoyloxy)-2-(1-{[(benzyloxy)carbonyl]amino}-1-methylethyl)-1-methyl-6-oxo-1,6-dihydropyrimidine-4-carboxylate, p-fluoro benzylamine (3 eq) was added and mixture was refluxed overnight. After evaporation of methanol, residue was taken in EtOAc, washed with 1N HCl and brine, dried (Na$_2$SO$_4$), filtered and evaporated to obtain the title product.

$^1$H-NMR (CDCl$_3$) δ 11.9 (bs, 1H), 7.79 (bt, 1H), 7.35–7.29 (m, 7H), 7.07 (t, J=8.6 Hz, 2H), 5.27 (bs, 1H), 5.02 (bs, 2H), 4.58 (d, J=6.2 Hz, 2H), 3.67 (s, 3H), 1.70 (s, 6H); MS (M+1) m/z 469.

Step 9: 2-(1-amino-1-methylethyl)-N-(4-fluorobenzyl)-5-hydroxy-1-methyl-6-oxo-1,6-dihydropyrimidine4-carboxamide

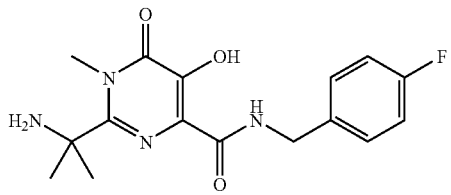

A methanolic solution of Benzyl 1-(4-{[(4-fluorobenzyl)amino]carbonyl}-5-hydroxy-1-methyl-6-oxo-1,6-dihydropyrimidin-2-yl)-1-methylethylcarbamate was stirred over night under a hydrogen atmosphere in the presence of catalytic 10% Pd/C. Catalyst was then filtered off through celite, and the filtrate was concentrated. Product was obtained after trituration with ethyl ether.

$^1$H-NMR (DMSO) δ 12.31 (bs, 1H), 9.68 (bt, J=6.6 Hz, 1H), 8.60 (bs, 2H), 7.43 (dd, J=8.4 Hz, J=5.7 Hz,2H), 7.20 (t, J=8.8 Hz,2H), 4.54 (d, J=6.6 Hz, 2H), 3.56 (s, 3H), 1.73 (s, 6H); MS (M+1) m/z 335.

Step 10: Methyl {[1-(4-{[(4-fluorobenzyl)amino]carbonyl}-5-hydroxy-1-methyl-6-oxo-1,6-dihydropyrimidin-2-yl)-1-methylethyl]amino}(oxo)acetate

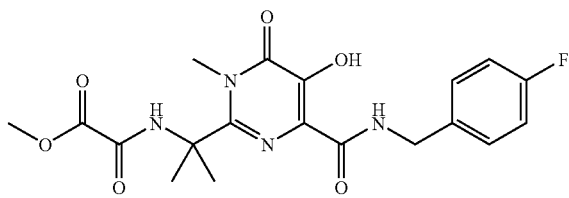

To a stirred mixture of 2-(1-amino-1-methylethyl)-N-(4-fluorobenzyl)-5-hydroxy-1-methyl-6-oxo-1,6-dihydropyrimidine4-carboxamide (4) and triethyl amine (3 eq) in chloroform, methyl chlorooxoacetate (1.5 eq) was added with an external cooling. Finished the addition, the ice bath was removed and the mixture was stirred at room temperature for 3 h. Reaction mixture was then partitioned between chloroform and 1N HCl. Organic layer was separated, washed with brine, dried (Na$_2$SO$_4$), filtered and concentrated to obtain title product.

$^1$H-NMR (DMSO) δ 12.2 (bs, 1H), 9.47 (s, 1H), 9.04 (t, J=6.3 Hz, 1H), 7.38 (dd, J=8.4Hz, J=5.7 Hz, 2H), 7.16 (t, J=8.8 Hz, 2H), 4.50 (d, J=6.3 Hz, 2H), 3.78 (s, 3H), 3.45 (s, 3H), 1.67 (s, 6H); MS (M+1) m/z 421.

Step 11: N$^1$-[1-(4-{[(4-fluorobenzyl)amino]carbonyl}-5-hydroxy-1-methyl-6-oxo-1,6-dihydropyrimidin-2-yl)-1-methylethyl]-N$^2$,N2-dimethylethanediamide (11)

Methyl {[1-(4-{[(4-fluorobenzyl)amino]carbonyl}-5-hydroxy-1-methyl-6-oxo-1,6-dihydropyrimidin-2-yl)-1-methylethyl]amino}(oxo)acetate was refluxed in an excess of 2 M solution of dimethylamine in THF for 2 h. Reaction mixture was cooled to room temperature, evaporated and residue was purified by RP HPLC (C1 8, water/acetonitrile containing 0.1% of trifluoroacetic acid as eluant). Collection and lyophilization of appropriate fractions afforded the title product.

$^1$H-NMR (DMSO) δ 12.19 (s, 1H), 9.32 (s, 1H), 9.06 (t, J=6.4 Hz, 1H), 7.40 (dd, J=8.5 Hz, J=5.7 Hz, 2H), 7.18 (t, J=8.8 Hz, 2H), 4.51 (d, J=6.4 Hz, 2H), 3.55 (s, 3H), 2.93 (s, 3H), 2.87 (s, 3H), 1.68 (s, 6H); $^{13}$C-NMR (DMSO) δ 168.23, 163.76, 163.09, 161.20 (d, J=96.4 Hz), 158.46, 151.90, 145.49, 134.77, 129.40 (d, J=3.2 Hz), 124.29, 115.05 (d, J=8.5 Hz), 56.50, 41.51, 35.46, 33.42, 32.68, 26.85; MS (M+1) m/z 434; MS (M+1) m/z 434.

EXAMPLE 19

Step 1: N-(4-fluorobenzyl)-5-hydroxy-1-methyl-2-(1-methyl-1-{[(5-methyl-1,3,4-oxadiazol-2-yl)carbonyl]amino ethyl})-6-oxo-1,6-dihydropyrimidine-4-carboxamide

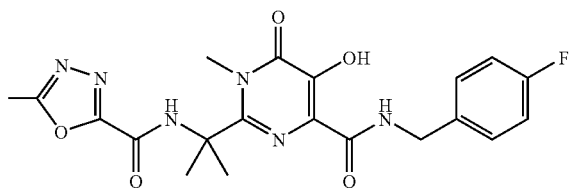

A solution of 5-methyl-1,3,4-oxadiazole-2-carboxylic acid was treated with 1.9 equivalents of oxalyl chloride and a few drops of anhydrous N,N-dimethylformamide. After 1 h, mixture was concentrated, residue was triturated with n-hexane and directly added to an equimolar solution of 2-(1-amino-1-methylethyl)-N-(4-fluorobenzyl)-5-hydroxy-1-methyl-6-oxo-1,6-dihydropyrimidine4-carboxamide (described in step 9, example 18) in acetonitrile. Triethyl amine (3 eq) was added to the mixture and the reaction was stirred overnight at room temperature. Title product was isolated by prep RP HPLC (C18, acetonitrile/water containing 0.1% of trifluoroacetic acid as eluant).

$^1$H-NMR (DMSO) δ 12.2 (bs, 1H), 9.84 (s, 1H), 9.05 (t, J=6.5 Hz, 1H), 7.38 (dd, J=8.4 Hz, J=5.6 Hz, 2H), 7.17 (t, J=8.8 Hz, 2H), 4.50 (d, J=6.5 Hz,2H), 2.56 (s, 3H), 1.74 (s, 6H), one methyl signal obscured by water;

MS (M+1) m/z 445.

EXAMPLE 20

2-{(2S)-1-[(dimethylamino)(oxo)acetyl]-4,4-difluoropyrrolidin-2-yl}-N-(4-fluorobenzyl)-5-hydroxy-1-methyl-6-oxo-1,6-dihydropyrimidine-4-carboxamide

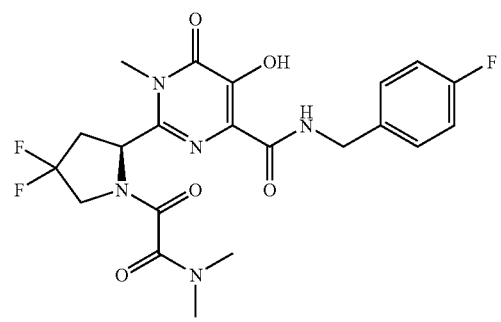

Step 1: 1-Benzyl-2-methyl-(2S)-4-oxopyrrolidine-1,2-dicarboxylate

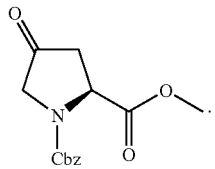

A solution of dimethyl sulfoxide (2.1 eq) in dry dichloromethane was added dropwise to a stirred solution of oxalyl chloride (1.01 eq) in dry dichloromethane (1.25 N) at −78° C. under $N_2$ atmosphere. After 15 min, a solution of the commercially available 1-benzyl-2-methyl-(2S,4R)-4-hydroxypyrrolidine-1,2-dicarboxylate in dry dichloromethane was added slowly, and stirring was continued for 30 min at −78° C. After addition of triethylamine (5 eq), the mixture was gradually warmed up to room temperature. The mixture was quenched with water and aqueous layer was separated and extracted with dichloromethane. The extract was washed with brine and dried over $Na_2SO_4$. Concentration of the solvent in vacuo gave a residue, which was purified by flash cromatography (ethyl acetate:petroleum ether=3:7) to give title product as a yellow oil.

$^1$H NMR (DMSO-$d_6$+TFA, 400 MHz, 330 K) δ 7.40–7.32 (m, 5H), 5.20–5.09 (m, 2H), 4.79 (d, J=9.7 Hz, 1H), 3.95 (d, J=17.9 Hz, 1H), 3.78 (d, J=17.9 Hz, 1H), 3.64 (s, 3H), 3.13 (dd, J=18.7 and 10.6, 1H), 2.62 (dd, J=18.7 and 2.7 Hz, 1H).

MS: m/z 278 (M+H)$^+$

Step 2: 1-Benzyl 2-methyl (2S)-4,4-difluoropyrrolidine-1,2-dicarboxylate

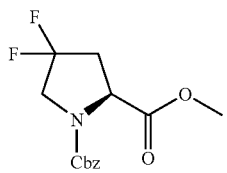

A solution of 1-benzyl-2-methyl-(2S)-4-oxopyrrolidine-1,2-dicarboxylate in dichloromethane was slowly added to a solution of diethylaminosulfur fluoride in dichloromethane precooled to −78° C. The reaction mixture was warmed to room temperature and mixed with cold water. The organic layer was separated, washed with water, dried over $Na_2SO_4$ and evaporated to give title compound as a yellow oil.

$^1$H NMR (DMSO-$d_6$, 400 MHz, 330K) δ 7.40–7.32 (m, 5H), 5.16–5.12 (m, 2H), 4.63 (br s, 1H), 3.96–3.80 (m, 2H), 3.65 (s, 3H), 3.15–2.86 (m, 1H), 2.56–2.45 (partially under DMSO) (m, 1H).

$^{19}$F NMR $^1$H$^{19}$F dec (DMSO-$d_6$, 400 MHz, 330 K) δ −98.13 (d, J=223.7 Hz)±98.72 (d, J=223.6 Hz) (rotamer a), −101.38 (d, J=190.7 Hz)±102.00 (d, J=191.3 Hz) (rotamer b) (2F).

MS m/z 300 (M+H)$^+$.

Step 3: 1-[(Benzyloxy)carbonyl]-4,4-difluoro-L-proline

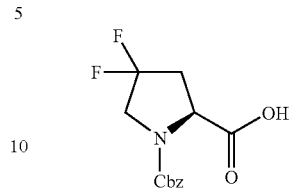

A solution of 1-benzyl 2-methyl (2S)-4,4-difluoropyrrolidine-1,2-dicarboxylate in methanol was refluxed with 2N NaOH (2 eq) for 2 hours. Methanol was removed and pH adjusted to 1 with 3 N HCl obtaining a suspension which was extracted several times with ethyl acetate. Combined organics were dried over $Na_2SO_4$ and evaporated to give title product as a dark brown oil.

$^1$H NMR (DMSO-$d_6$, 400 MHz, 330K) δ 12.96 (br s, 1H), 7.36–7.31 (m, 5H), 5.11 (s, 2H), 4.50 (bs, 1H), 3.91–3.80 (m, 2H), 3.01–2.82 (m, 1H), 2.56–2.41 (partially under DMSO) (m, 1H).

MS: m/z 284 (M−H)$^+$.

Step 4: Benzyl-(2S)-2-aminocarbonyl4,4-difluoropyrrolidine-1-carboxylate

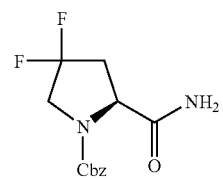

To a stirred solution of 1-[(benzyloxy)carbonyl]4,4-difluoro-L-proline, pyridine (0.6 eq.) and di-t-butyl dicarbonate (1.3 eq) in dioxane, ammonium bicarbonate (1.26 eq) was added and the mixture was stirred at room temperature for 20 hours. Dioxane was concentrated and the residue dissolved in ethyl acetate and washed with HCl 1 N, saturated aqueous $NaHCO_3$ and brine, dried over $Na_2SO_4$, filtered and evaporated in vacuo to obtain a yellow oil.

Two sets of signals, two conformers (ratio 1:1) were present.

$^1$H NMR (DMSO-$d_6$, 400 MHz, 300 K) δ 7.56 (d, J=15.4 Hz, 1H), 7.39–7.34 (m, 5H), 7.17 (d, J=19.3 Hz, 1H), 5.10–5.08 (m, 2H), 4.42 (dd, J=9.3 and 4.7, 0.5H), 4.34 (dd, J=9.2 and 4.6 Hz, 0.5H), 3.92–3.73 (m, 2H), 2.90.2.72 (m, 1H), 2.43–2.30 (m, 1H).

MS: m/z 285 (M+H)$^+$.

Step 5: Benzyl-(2S)-2-cyano-4,4-difluoropyrrolidine-1-carboxylate

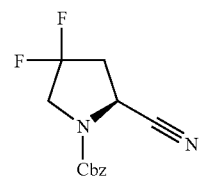

A solution of benzyl-(2S)-2-aminocarbonyl-4,4-difluoropyrrolidine-1-carboxylate and triethylamine (2.1 eq.) in dichloromethane was cooled to 0° C. and trifluoroacetic anhydride (1.1 eq.).was added dropwise under nitrogen. Stirring was continued for 1 hour allowing the mixture to reach room temperature. Volatiles removed in vacuo and residue taken up in ethyl acetate, washed with HCl 1N, brine and dried over $Na_2SO_4$. Evaporation gave title compound as brown oil.

$^1$H NMR (DMSO-$d_6$, 400 MHz, 300 K) δ 7.40–7.34 (m, 5H), 5.20–5.03 (m, 3H), 3.99–3.72 (m, 2H), 3.06–2.69 (m, 2H).

Step 6: Benzyl-(2S)-2-[amino(hydroxyimino)methyl]4,4-difluoropyrrolidine-1-carboxylate

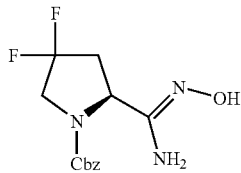

A solution of benzyl-(2S)-2-cyano-4,4-difluoropyrrolidine-1-carboxylate, hydroxylamine hydrochloride (1.4 eq.) and triethylamine (1.7 eq.) in ethanol was refluxed under nitrogen for 5 hours. Mixture was concentrated and residues taken up in ethyl acetate and washed with water and brine. Combined organics were dried over $Na_2SO_4$ and evaporated to give title compound as a foam.

$^1$H NMR (DMSO-$d_6$, 300 MHz, 330 K) δ 9.12 (bs, 1H), 7.38–7.34 (m, 5H), 5.36 (bs, 2H), 5.13 (d, J=14.4 Hz, 1H)+5.09 (d, J=14.4Hz, 1H), 4.56 (dd, J=8.6 and 4.9 Hz, 1H), 4.07–3.76 (m, 2H), 2.80–2.71 (m 1H), 2.60–2.51 (partially under DMSO) (m, 1H).

MS: m/z 300 (M+H)$^+$.

Step 7: Dimethyl-2-{[(amino-(2S)-1-[(benzyloxy)carbonyl]-4,4-difluoropyrrolidin-2-yl}methylidene)amino]oxy}but-2-enedioate

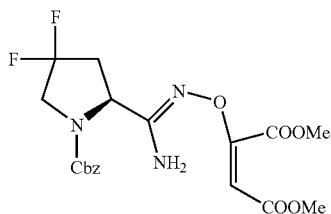

A solution of benzyl-(2S)-2-[amino(hydroxyimino)methyl]4,4-difluoropyrrolidine-1-carboxylate and dimethylacetylendicarboxylate (1.2 eq.) in chloroform was refluxed for 1 hour under nitrogen and the solution was concentrated. Residue was purified by flash chromatography on silica gel, (eluent:petroleum ether:ethyl acetate=7.5:2.5), to give the desired product as a 3:1 mixture of two isomers by $^1$H NMR.

$^1$H NMR (DMSO-$d_6$, 300 MHz, 330 K) δ 7.45–7.25 (m, 5H), 6.63 (bs, 1.5H), 6.30 (bs, 0.5H), 5.62 (s, 0.75H), 5.60 (s, 0.25H), 5.13 (s, 2H),-4.58 (dd, J=9.1 and 4.9 Hz)+4.57 (dd, partially overlapped) (1H), 3.96–3.86 (m, 2H), 3.79 (s, 2.2H), 3.74 (s, 0.8H), 3.66 (s, 0.8H), 3.61 (s, 2.2H), 2.93–2.81 (m, 1H), 2.56–2.43 (partially under DMSO)(m, 1H).

MS: m/z 442 (M+H)$^+$.

Step 8: Methyl-2-{(2S)-1-[(benzyloxy)carbonyl]-4,4-difluoropyrrolidin-2-yl}-5,6-dihydroxypyrimidine-4-carboxylate

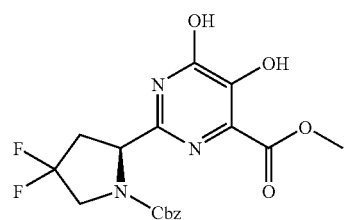

A solution of dimethyl-2-{[(amino-{(2S)-1-[(benzyloxy)carbonyl]-4,4-difluoropyrrolidin-2-yl}methylidene)amino]oxy}but-2-enedioate in o-xylene was refluxed for 6 hours. Then the reaction was cooled down and concentrated at rotavapor. Ethyl ether was added until precipitation of a solid that was filtered, washed with other ethyl ether and dried to give the title pyrimidine as a brown solid. Two sets of signals, two rotamers (ratio 1:1) were present.

$^1$H NMR (DMSO-$d_6$, 400 MHz, 300 K) δ 12.97 (s, 1H), 10.38 (s, 1H), 7.40–7.29 (m, 3H), 7.22–7.15 (m, 1H); 7.10–7.05 (m, 1H), 5.12 (d, J=12.6 Hz, 0.5H) 5.10 (s, 1H) 4.89 (d, J=12.6 Hz, 0.5H), 4.86–4.72 (m, 1H), 4.10–3.86 (m, 2H), 3.81 (s, 3H), 2.90–2.85 (m, 1H), 2.64–2.53 (partially under DMSO) (m, 1H).

MS: n/z 410 (M+H)$^+$.

Step 9: Methyl 5-(benzoyloxy)-2-{(2S)-1-[(benzyloxy)carbonyl]4,4-difluoropyrrolidin-2-yl}-6-hydroxypyrimidine-4-carboxylate

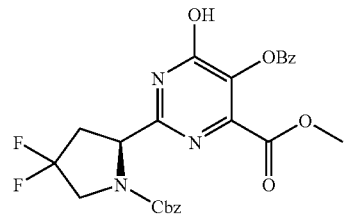

Methyl-2-{(2S)-1-[(benzyloxy)carbonyl]-4,4-difluoropyrrolidin-2-yl}-5,6-dihydroxypyrimidine-4-carboxylate in dry pyridine was treated with benzoic anhydride (2 eq.) overnight at room temperature.

The mixture was evaporated, taken up in ethyl acetate and washed with HCl 1N and brine. Organics were dried over $Na_2SO_4$, filtered and evaporated to obtain an oil which was purified by flash chromatography on silica gel (eluent:ethyl acetate:petroleum ether=7:3).

$^1$H NMR (DMSO-$d_6$, 300 MHz, 330 K) δ 13.51 (bs, 1H), 8.10 (d, J=7.6 Hz, 2H), 7.79 (t, J=7.1 Hz, 1H), 7.64 (t, J=7.6 Hz, 2H), 7.33–7.17 (m, 5H), 5.13 (s, 2H), 4.99 (t, J=7.3 Hz, 1H), 4.09–3.97 (m, 2H), 3.77.(s, 3H), 3.02–2.99 (m, 2H).

MS: m/z 514 (M+H)$^+$.

Step 10: Methyl-5-(benzoyloxy)-2-{(2S)-1-[(benzy-loxy)carbonyl]4,4-difluoropyrrolidin-2-yl}-1-methyl-6-oxo-1,6-dihydropyrimidine-4-carboxylate

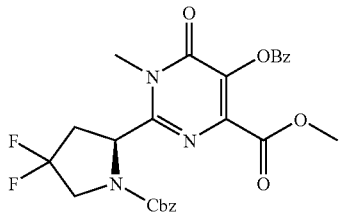

Methyl 5-(benzoyloxy)-2-{(2S)-1-[(benzyloxy)carbonyl] 4,4-difluoropyrrolidin-2-yl}-6-hydroxypyrimidine-4-carboxylate dissolved in dry 1,4-dioxane was added to a suspension of LiH (1.4 eq.) in dioxane. The mixture was stirred at 38° C. for 45 minutes and then cooled down to room temperature. Dimethyl sulphate (1.3 eq.) was added and the mixture was warmed to 58° C. for 1 hour. The reaction mixture was cooled down to 16° C. and glacial acetic acid (0.1 eq) was added, followed by water and ethyl acetate. The combined organic layers were dried (Na$_2$SO$_4$), filtered and concentrated to an oil which was cromatographed through silica gel (eluent:ethyl acetate:petroleum ether=3:7) to give the desired compound as a 1:1 mixture of two rotamers by $^1$H NMR $^1$H NMR (DMSO-d$_6$, 300 MHz, 300 K) δ 8.11–8.08 (m, 2H), 7.80 (t, J=7.7 Hz, 1H), 7.67–7.65 (m, 2H), 7.36–7.10 (m, 5H), 5.50 (dd, J=9.2 and 4.7 Hz, 1H), 5.22 (d, J=12.9 Hz, 0.5H), 5.14–4.95 (m, 1H), 4.93 (d, J=12.3 Hz, 0.5H), 4.16–3.79 (m, 2H), 3.74 (s, 3H), 3.61 (s, 1.5H), 3.45 (s, 1.5H), 3.25–3.11 (m, 1H), 2.89–2.74 (m, 1H). MS: m/z 528 (M+H)$^+$.

Step 11: Benzyl-(2S)-4,4-difluoro-2-(4-{[(4-fluorobenzyl)amino]carbonyl}-5-hydroxy-1-methyl-6-oxo-1,6-dihydropyrimidin-2-yl)pyrrolidine-1-carboxylate

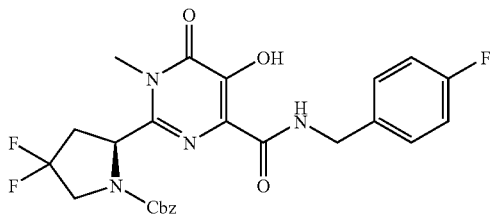

Methyl-5-(benzoyloxy)-2-{(2S)-1-[(benzyloxy)carbonyl] 4,4-difluoropyrrolidin-2-yl}-1-methyl-6-oxo-1,6-dihydropyrimidine-4-carboxylate in dry MeOH was treated with 4-fluorobenzyl amine (2.5 eq.) at reflux for 2 hours. Solvent was removed in vacuo and the residue was taken up in ethyl acetate, washed with HCl 1N, brine, dried over Na$_2$SO$_4$. The filtrate was concentrated in vacuo and triturated with ethyl ether to obtain the title compound as a 1.5:1 mixture of two rotamers by NMR.

$^1$H NMR (DMSO-d$_6$+TFA, 300 MHz, 300 K) δ 8.92 (bt, 0.4H), 8.69 (bt, 0.6H), 7.36–7.31 (m, 4H), 7.20–7.09 (m, 4H), 6.97 (d, J=7.2 Hz, 1H), 5.34–5.25 (m, 1H), 5.14 (d, J=12.4 Hz, 0.4H ), 5.07–4.99 (m, 1.2H), 4.81 (d, J=12.2 Hz, 0.4H), 4.51–4.48 (m, 2H), 4.38–4.21 (m, 1H), 4.07–3.96 (m, 1H), 3.59 (s, 1.2H), 3.48 (s, 1.8H), 3.05–2.95 (m, 1H), 2.78–2.68 (m, 1H).

MS: m/z 517 (M+H)$^+$.

Step 12: (2S)-4,4-difluoro-2-(4-([(4-fluorobenzyl) amino]carbonyl}-5-hydroxy-1-methyl-6-oxo-1,6-dihydropyrimidin-2-yl)pyrrolidinium trifluoroacetate

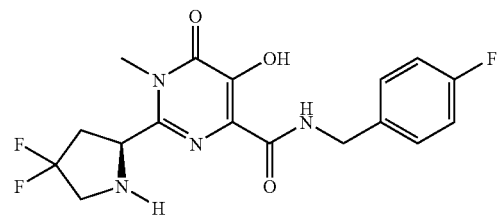

A solution of benzyl-(2S)-4,4-difluoro-2-(4-{[(4-fluorobenzyl)amino]carbonyl}-5-hydroxy-1-methyl-6-oxo-1,6-dihydropyrimidin-2-yl)pyrrolidine-1-carboxylate in MeOH was treated with Pd/C 10% wt (10% w/w) for 3 hours at room temperature under H$_2$ atmosphere. The mixture was filtrated over a celite pad, concentrated in vacuo and treated with trifluoroacetic acid (10 eq.). The acid in excess was removed in vacuo to obtain title product as a pale yellow solid after trituration with ethyl ether.

$^1$H NMR (DMSO-d$_6$+TFA, 300 MHz, 340K) δ 9.60 (bt, 1H), 7.39 (t, J=8 Hz, 2H), 7.17 (t, J=8,8 Hz, 2H), 5.35 (t, J=8.4 Hz, 1H), 4.62 (dd, J=15.3 and 6.6 Hz, 1H), 4.55 (dd, J=15.2 and 6.3 Hz, 1H), 4.05–3.87 (m, 2H), 3.48 (s, 3H), 3.30–3.14 (m, 1H), 2.96–2.78 (m, 1H).

MS: n/z 383 (M+H)$^+$.

Step 13: 2-{(2S)-1-[(dimethylamino)(oxo)acetyl]-4, 4-difluoropyrrolidin-2-yl}-N-(4-fluorobenzyl)-5-hydroxy-1-methyl-6-oxo-1,6-dihydropyrimidine-4-carboxamide A solution of (2S)-4,4-difluoro-2-(4-{[(4-fluorobenzyl) amino]carbonyl}-5-hydroxy-1-methyl-6-oxo-1,6-dihydropyrimidin-2-yl)pyrrolidinium trifluoroacetate in chloroform and triethylamine (1.01 eq.) was treated with methyl chlorooxacetate (2 eq.) at 0° C. The mixture was allowed to reach room temperature for 2 hours. Dimethylamine (30 eq.) was added at room temperature and the mixture left stirring over night. The mixture was concentrated in vacuo and purified by preparative HPLC (Column: C$_{18}$, eluent:acetonitrile and water containing 0.1% trifluoroacetic acid). To obtain the title product two rotamers (ratio 4:1) were found in $^1$H NMR.

$^1$H NMR (DMSO-d$_6$+TFA, 300 MHz, 300 K) δ 9.23 (t, J=6.5 Hz, 0.8H), 9.10 (bt, 0.2H), 7.34–7.31 (m, 2H), 7.11 (t, J=8.8 Hz, 2H), 5.48 (dd, J=8.9 and 5.7 Hz, 1H), 4.53 (dd, J=15.0 and 6.7 Hz, 1H), 4.42 (dd, J=15.0 and 6.2 Hz, 1H), 4.24–4.16 (m, 1H), 4.05–4.02 (t, J=11.8 Hz, 1H), 3.52 (s, 2.4H), 3.45 (s, 0.6H), 3.15–3.04 (m, 1.6H), 2.84 (s, 2.4H), 2.80 (s, 2.4H), 2.79–2.65 (m, 0.4H), 2.63 (s, 0.6H), 2.57 (s, 0.6H).

MS: m/z 482 (M+H)$^+$.

EXAMPLE 21

2-[1,2-dimethyl4-(methylsulfonyl)piperazin-2-yl]-N-(4-fluorobenzyl)-5-hydroxy-1-methyl-6-oxo-1,6-dihydropyrimidine-4-carboxamide

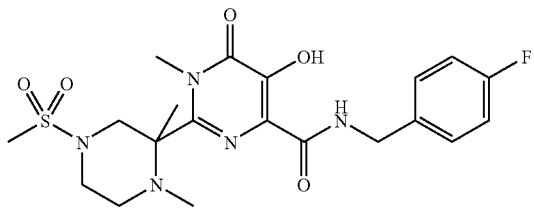

Step 1: 1-benzyl 4-tert-butyl 2-cyano-2-methylpiperazine-1,4-dicarboxylate

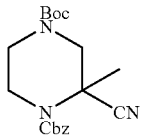

To a cooled (−75° C.) solution of LDA 2M in heptane/THF (1.5 eq) in THF, a solution of 1-[(benzyloxy)carbonyl]-4-(tert-butoxycarbonyl)piperazine-2-carboxylic acid (Bigge et al, *Tetrahedron Lett.* 1989, 30: 5193) in THF was added dropwise at −75° C. After being stirred for 1 hour at −75° C., MeI (1.5 eq) was added. After 2 hours at −75°C. the reaction mixture was left warming to r.t., evaporated, diluted with AcOEt, washed with NaHCO$_3$, water, brine and dried over Na$_2$SO4. The crude was purified by flash chromatography on silica gel (petroleum ether/AcOEt, 85:15) to obtain the title compound.

$^1$H NMR (DMSOd$_6$, 340K, 300 MHz) δ 7.45–7.30 (m, 5H), 5.19 (AA' system, J=13 Hz, 2H), 4.05 (d, J=14 Hz, 1H), 3.87–3.78 (m, 1H), 3.66 (d, J=14 Hz, 1H), 3.62–3.35 (m, 3H), 1.66 (s, 3H), 1.45 (s, 9H).

MS: m/z 360 (M+H)$^+$.

Step 2: 1-benzyl 4-tert-butyl 2-[(Z)-amino({[(1E)-3-methoxy-1-(methoxycarbonyl)-3-oxoprop-1-enyl]oxy}imino)methyl]-2-methyl piperazine-1,4-dicarboxylate

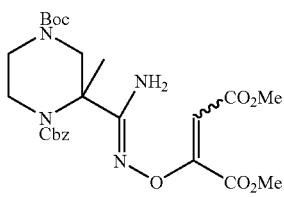

A solution of 1-benzyl 4-tert-butyl 2-cyano-2-methylpiperazine-1,4-dicarboxylate in EtOH was added to a solution of Et$_3$N (3.2 eq) and NH$_2$OH HCl (3 eq) in EtOH. The mixture was stirred 2 hr at 40° C. After evaporation of the solvent, the residue was diluted with AcOEt, washed with water, dried over Na$_2$SO$_4$, filtered and concentrated. The residue was further dissolved in chloroform and dimethylacetylenedicarboxylate (1.5 eq) added to the stirred solution. Reaction was refluxed over night. The mixture was evaporated and the residue was purified by flash chromatography on silica gel (petroleum ether/AcOEt, 65:35) affording the title compound as mixture of isomers in 3.5:1 ratio.

$^1$H NMR (DMSOd$_6$, 340K, 300 MHz). Two sets of signals were observed due to the presence of the geometric isomers-δ 7.48–7.25 (m, 5H), 6.31 (bs, 1.56H), 6.01 (bs, 0.44H), 5.63 (s, 0.78H), 5.55 (s, 0.22H), 5.12–5.02 (m, 2H), 3.85–3.60 (m, 9H), 3.60–3.45 (m, 2H), 3.45–3.31 (m, 1H), 1.51 (s, 2.4H), 1.45 (s, 0.66H), 1.41 (s, 9H).

MS: m/z 535 (M+H)$^+$.

Step3: 1-benzyl 4-tert-butyl 2-[5-(benzoyloxy)-4-hydroxy-6-(methoxycarbonyl) pyrimidin-2-yl]-2-methylpiperazine-1,4-dicarboxylate

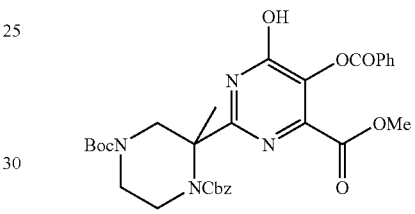

1-benzyl 4-tert-butyl 2-[(Z)-amino({[(1E)-3-methoxy-1-(methoxycarbonyl)-3-oxoprop-1-enyl]oxy}imino)methyl]-2-methylpiperazine-1,4-dicarboxylate was dissolved in xylene and stirred at 155° C. for 8 h. After evaporation of the solvent, the residue was dissolved in pyridine and benzoic anhydride (1.5 eq) was added. The reaction mixture was stirred at room temperature over night, then pyridine was evaporated. The residue was diluted with AcOEt, the organic phase washed with HCl 1N, dried (Na$_2$SO$_4$) and evaporated. The title product was obtained by flash chromatography (eluent:petroleum ether/AcOEt 70/30).

$^1$H-NMR (DMSOd$_6$, 340K, 400 MHz) δ 12.96 (bs, 1H), 8.07 (d, J=7.2 Hz, 2H), 7.76 (t, J=7.6 Hz, 1H), 7.62 (t, J=7.6 Hz, 2H), 7.37–7.22 (m, 5H), 5.03 (s, 2H), 3.96 (dt, J$_1$32 13.6 Hz, J$_2$=5.8 Hz, 1H), 3.80–3.52 (m, 7H), 3.47–3.40 (m, 1H), 1.65 (s, 3H), 1.35 (s, 9H).

MS: m/z 607 (M+H)$^+$.

Step 4: 1-benzyl 4-tert-butyl 2-[5-(benzoyloxy)-4-(methoxycarbonyl)-1-methyl-6-oxo-1,6-dihydropyrimidin-2-yl]-2-methylpiperazine-1,4-dicarboxylate

A

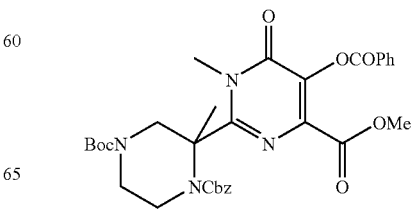

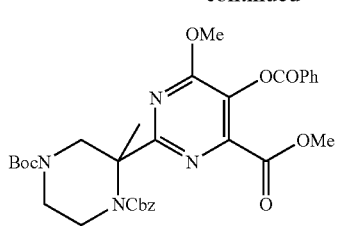

1-Benzyl 4-tert-butyl 2-[5-(benzoyloxy)-4-hydroxy-6-(methoxycarbonyl) pyrimidin-2-yl]-2-methylpiperazine-1,4-dicarboxylate was added to a suspension of LiH (1.1 eq) in dioxane (7 ml/mmol) at room temperature. The mixture was stirred at 40° C. for 45 min, then dimethylsulfate (1.3 eq) was added and the temperature was raised to 60° C. After 1 h glacial acetic acid (0.1 eq) was added to the reaction mixture, followed by water (7 ml/mmol) and EtOAc (7 ml/mmol). The aqueous layer was separated and extracted with EtOAc. The combined organic layers were dried ($Na_2SO_4$) and concentrated. The crude was purified by flash chromatography on silica gel (AcOEt/petroleum ether, 1:4) to separate the title compound A from B (ratio A/B 1.3/1).

A: $^1$H NMR ($CD_3CN$, 320K, 300 MHz) δ 8.18 (d, J=7.2 Hz, 2H), 7.80 (t, J=7.5 Hz, 1H), 7.63 (t, J=7.8 Hz, 2H), 7.45–7.22 (m, 5H), 5.08 (AA' system, J=12 Hz, 2H), 4.18–3.88 (m, 3H), 3.81 (s, 3H), 3.68–3.46 (m, 5H, at 3.58 (s)), 3.40–3.22 (m, 1H), 1.75 (s, 3H), 1.49 (s, 9H).

MS: m/z 621 (M+H)$^+$.

Step 5: Methyl 5-(benzoyloxy)-2-[4-(tert-butoxycarbonyl)-2-methylpiperazin-2-yl]-1-methyl-6-oxo-1,6-dihydropyrimidine4-carboxylate

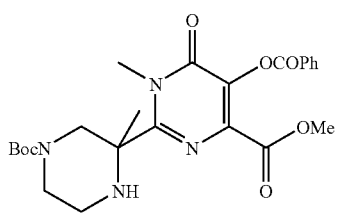

1-Benzyl 4-tert-butyl 2-[5-(benzoyloxy)-4-(methoxycarbonyl)-1-methyl-6-oxo-1,6-dihydropyrimidin-2-yl]-2-methylpiperazine-1,4-dicarboxylate was dissolved in AcOEt (20 ml/mmol) and hydrogenated at atm pressure on 10% (w/w) Pd/C over night. After filtration of the catalyst, solvent was evaporated to give crude product.

$^1$H NMR ($DMSOd_6$ +TFA, 340K, 400 MHz) δ 8.08 (d, J=7.1 Hz, 2H), 7.787 (t, J=7.4 Hz, 1H), 7.63 (t, J=7.8 Hz, 2H), 4.30 (d, J=15.2 Hz, 1H), 3.90–3.50 (m, 10H), 3.35–3.25 (m, 1H), 1.81 (s, 3H), 1.37 (s, 9H).

MS (EI+) m/z 487 (M+H)$^+$.

Step 6: 2-[1,2-dimethyl4-(methylsulfonyl)piperazin-2-yl]-N-(4-fluorobenzyl)-5-hydroxy-1-methyl-6-oxo-1,6-dihydropyrimidine-4-carboxamide Crude methyl 5-(benzoyloxy)-2-[4-(tert-butoxycarbonyl)-2-methylpiperazin-2-yl]-1-methyl-6-oxo-1,6-dihydropyrimidine-4-carboxylate was dissolved in MeOH, p-fluorobenzylamine (3.0 eq) was added and the mixture was refluxed over night. Evaporation of the solvent afforded crude product.

MS: m/z 476 (M+H)$^+$.

Crude obtained in the previous step was dissolved in MeOH (20 ml/mmol) and $NaCNBH_3$ (2.8 eq), AcONa (3.2 eq) and HCHO 37% in $H_2O$ (4 eq) were added. The reaction mixture was stirred at room temperature over night, evaporated and the crude solid (4-fluorobenzyl 2-[4-(tert-butoxycarbonyl)-1,2-dimethylpiperazin-2-yl]-5-hydroxy-1-methyl-6-oxo-1,6-dihydropyrimidine4-carboxylate) obtained washed with $Et_2O$.

MS (EI+) m/z 490 (M+H)$^+$.

Deprotection of Boc group was carried out in DCM/TFA (1:1, 10 ml/mmol) for 1 hour.

MS (EI+) m/z 390 (M+H)$^+$. The crude product was dissolved in DCM, $Et_3N$ (3.3 eq) and $MeSO_2Cl$ (2.6 eq) were added and the reaction was stirred at room temperature over night. The reaction mixture was evaporated and the crude residue purified by preparative HPLC (C18, gradient of $CH_3CN/H_2O$+0.01% TFA) to obtain the title product.

$^1$H NMR ($CD_3CN$ +TFA, 320K, 400 MHz) δ 8.51 (bs, 1H), 7.46–7.36 (m, 2H), 7.15–7.10 (m, 2H), 4.64 (d, J=6.4 Hz, 2H), 4.04 (dd, $J_1$=14.4 Hz, $J_2$=2.2 Hz, 1H), 3.88–3.80 (m, 1H), 3.68 (dt, $J_1$=13.6 Hz, $J_2$=3.3 Hz, 1H), 3.61 (s, 3H), 3.60–3.50 (m, 1H) 3.42–3.31 (m, 2H), 2.94 (s, 3H), 2.81 (s, 3H), 1.92 (s, 3H).

MS: m/z 468 (M+H)$^+$.

Tables 1 and 2 below list compounds of the present invention which have been prepared. The tables provide the structure and name of each compound, the mass of its molecular ion plus 1 (M$^+$) or molecular ion minus 1 (M$^-$) as determined via FIA-MS, and the synthetic scheme employed to prepare the compound. When the compound was prepared as a salt, the identity of the salt is included with the compound name. The synthetic scheme identified as "1*" in Table 1 is identical to Scheme 1 above, except for an additional deprotection step to remove Boc, Cbz, or benzyl present in the 2-substituent in the pyrimidinone ring.

TABLE 1

| Exp | Structure | Name | M+ | Scheme |
|---|---|---|---|---|
| 1 | 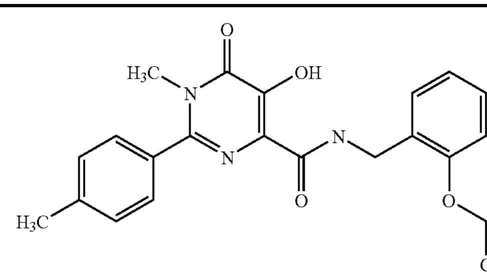 | N-(2-ethoxybenzyl)-5-hydroxy-1-methyl-2-(4-methylphenyl)-6-oxo-1,6-dihydropyrimidine-4-carboxamide | 394 | 1 |

TABLE 1-continued

| Exp | Structure | Name | M+ | Scheme |
|---|---|---|---|---|
| 2 | 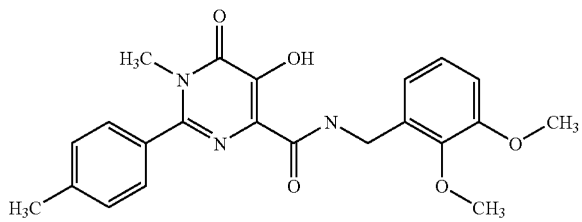 | N-(2,3-dimethoxybenzyl)-5-hydroxy-1-methyl-2-(4-methylphenyl)-6-oxo-1,6-dihydropyrimidine-4-carboxamide | 410 | 1 |
| 3 | 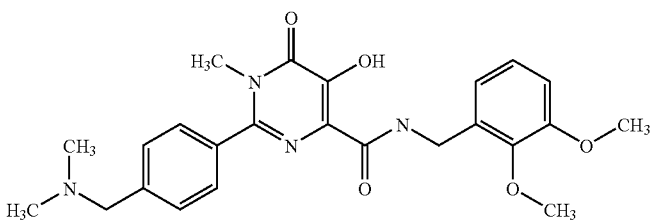 | N-(2,3-dimethoxybenzyl)-2-{4-[(dimethylamino)methyl]phenyl}-5-hydroxy-1-methyl-6-oxo-1,6-dihydropyrimidine-4-carboxamide (TFA salt) | 453 | 3 |
| 4 | 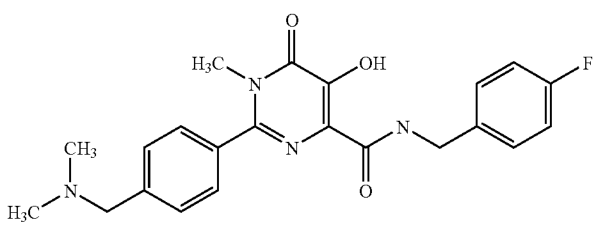 | N-(4-fluorobenzyl)-2-{4-[(dimethylamino)methyl]phenyl}-5-hydroxy-1-methyl-6-oxo-1,6-dihydropyrimidine-4-carboxamide (TFA salt) | 411 | 3 |
| 5 | 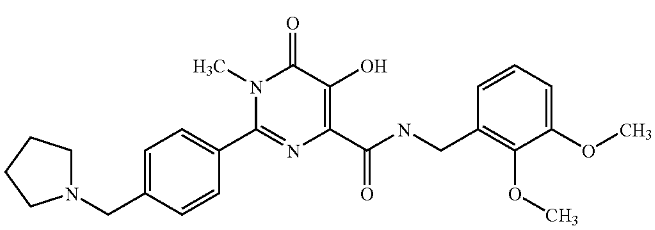 | N-(2,3-dimethoxybenzyl)-5-hydroxy-1-methyl-6-oxo-2-[4-(pyrrolidin-1-ylmethyl)phenyl]-1,6-dihydropyrimidine-4-carboxamide (TFA salt) | 479 | 3 |
| 6 | 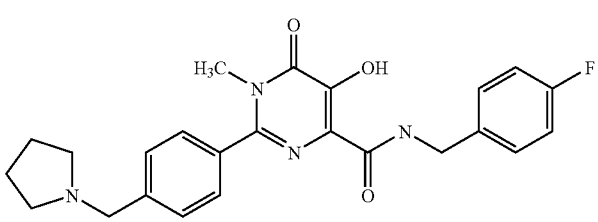 | N-(4-fluorobenzyl)-5-hydroxy-1-methyl-6-oxo-2-[4-(pyrrolidin-1-ylmethyl)phenyl]-1,6-dihydropyrimidine-4-carboxamide (TFA salt) | 437 | 3 |
| 7 | 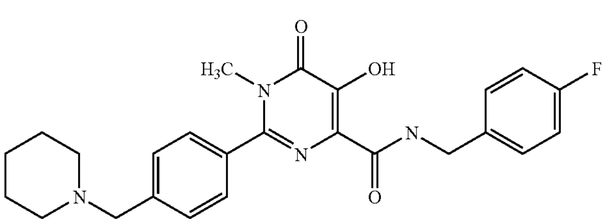 | N-(4-fluorobenzyl)-5-hydroxy-1-methyl-6-oxo-2-[4-(piperidin-1-ylmethyl)phenyl]-1,6-dihydropyrimidine-4-carboxamide (TFA salt) | 451 | 3 |

TABLE 1-continued

| Exp | Structure | Name | M+ | Scheme |
|---|---|---|---|---|
| 8 | 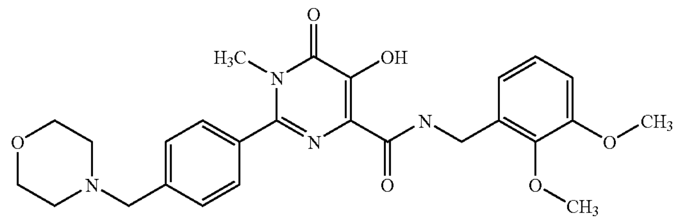 | N-(2,3-dimethoxybenzyl)-5-hydroxy-1-methyl-2-[4-(morpholin-4-ylmethyl)phenyl]-6-oxo-1,6-dihydropyrimidine-4-carboxamide (TFA salt) | 495 | 3 |
| 9 | 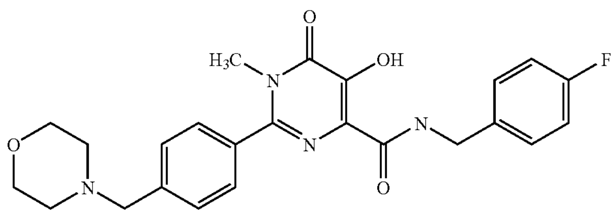 | N-(4-fluorobenzyl)-5-hydroxy-1-methyl-2-[4-(morpholin-4-ylmethyl)phenyl]-6-oxo-1,6-dihydropyrimidine-4-carboxamide (TFA salt) | 453 | 3 |
| 10 | 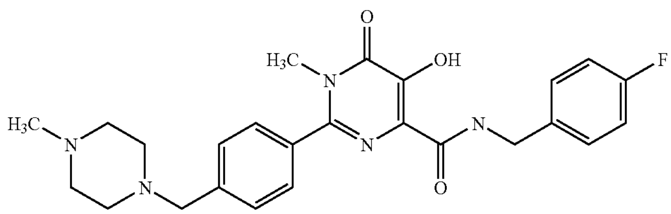 | N-(4-fluorobenzyl)-5-hydroxy-1-methyl-2-{4-[(4-methylpiperazin-1-yl)methyl]phenyl}-6-oxo-1,6-dihydropyrimidine-4-carboxamide (TFA salt) | 466 | 3 |
| 11 | 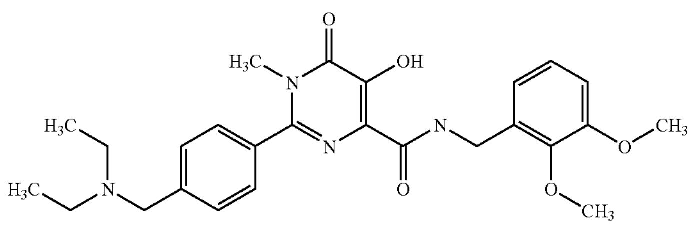 | 2-{4-[(diethylamino)methyl]phenyl}-N-(2,3-dimethoxybenzyl)-5-hydroxy-1-methyl-6-oxo-1,6-dihydropyrimidine-4-carboxamide (TFA salt) | 481 | 3 |
| 12 | 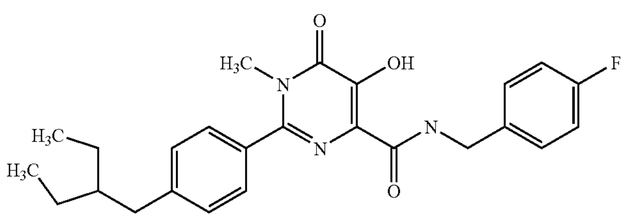 | 2-{4-[(diethylamino)methyl]phenyl}-N-(4-fluorobenzyl)-5-hydroxy-1-methyl-6-oxo-1,6-dihydropyrimidine-4-carboxamide (TFA salt) | 439 | 3 |
| 13 | 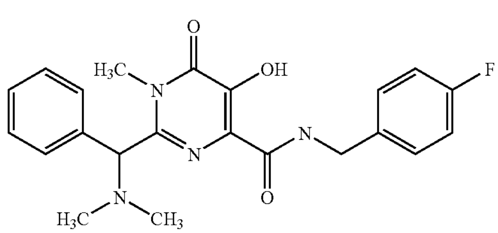 | 2-[(dimethylamino)(phenyl)methyl]-N-(4-fluorobenzyl)-5-hydroxy-1-methyl-6-oxo-1,6-dihydropyrimidine-4-carboxamide (TFA salt) | 411 | 3 |

TABLE 1-continued

| Exp | Structure | Name | M+ | Scheme |
|---|---|---|---|---|
| 14 | 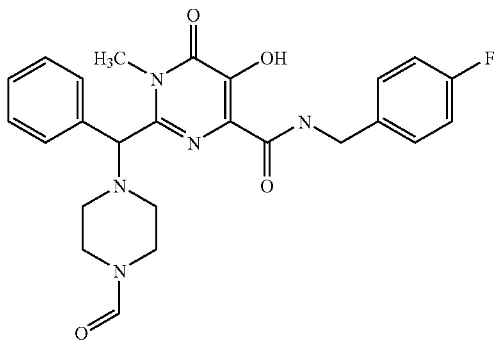 | N-(4-fluorobenzyl)-2-[(4-formylpiperazin-1-yl)(phenyl)methyl]-5-hydroxy-1-methyl-6-oxo-1,6-dihydropyrimidine-4-carboxamide (TFA salt) | 480 | 3 |
| 15 | 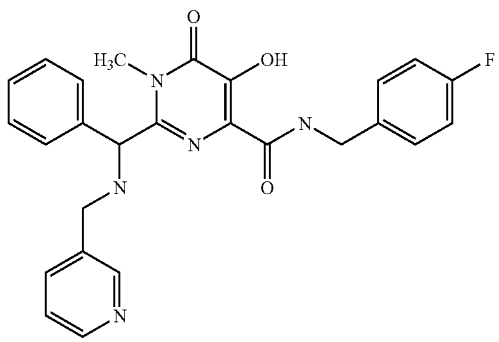 | N-(4-fluorobenzyl)-5-hydroxy-1-methyl-6-oxo-2-{phenyl[(pyridin-3-ylmethyl)amino]methyl}-1,6-dihydropyrimidine-4-carboxamide (TFA salt) | 474 | 3 |
| 16 | 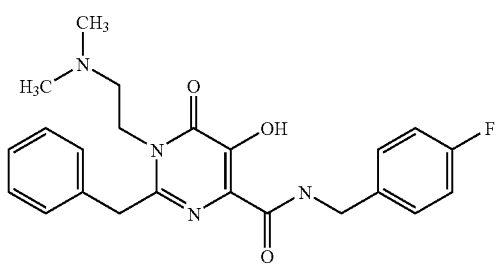 | 2-benzyl-1-[2-(dimethylamino)ethyl]-N-(4-fluorobenzyl)-5-hydroxy-6-oxo-1,6-dihydropyrimidine-4-carboxamide (TFA salt) | 425 | 1 |
| 17 | 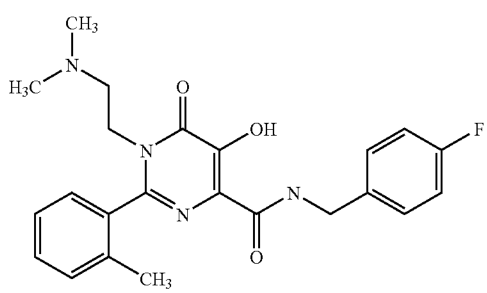 | 1-[2-(dimethylamino)ethyl]-N-(4-fluorobenzyl)-5-hydroxy-2-(2-methylphenyl)-6-oxo-1,6-dihydropyrimidine-4-carboxamide (TFA salt) | 425 | 1 |
| 18 | 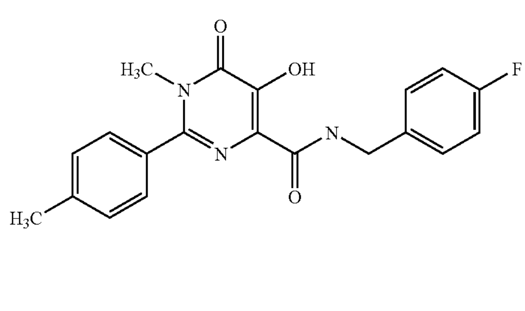 | N-(4-fluorobenzyl)-5-hydroxy-1-methyl-2-(4-methylphenyl)-6-oxo-1,6-dihydropyrimidine-4-carboxamide | 368 | 1 |

TABLE 1-continued

| Exp | Structure | Name | M+ | Scheme |
|---|---|---|---|---|
| 19 | 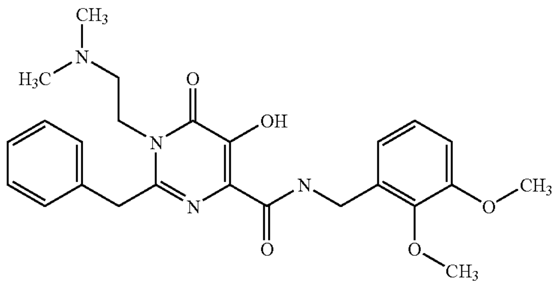 | 2-benzyl-N-(2,3-dimethoxybenzyl)-1-[2-(dimethylamino)ethyl]-5-hydroxy-6-oxo-1,6-dihydropyrimidine-4-carboxamide (TFA salt) | 467 | 1 |
| 20 | 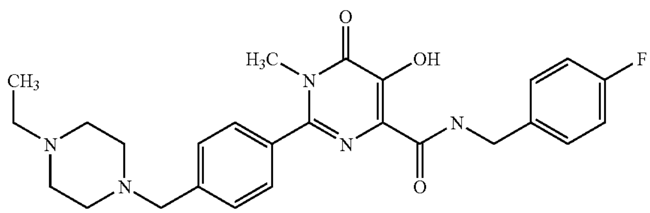 | 2-{4-[(4-ethylpiperazin-1-yl)methyl]phenyl}-N-(4-fluorobenzyl)-5-hydroxy-1-methyl-6-oxo-1,6-dihydropyrimidine-4-carboxamide (TFA salt) | 480 | 3 |
| 21 | 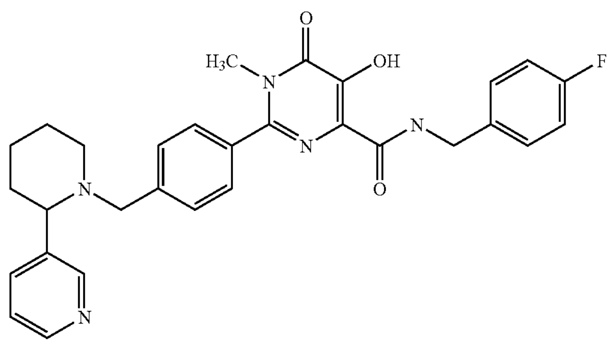 | N-(4-fluorobenzyl)-5-hydroxy-1-methyl-6-oxo-2-{4-[(2-pyridin-3-ylpiperidin-1-yl)methyl]phenyl}-1,6-dihydropyrimidine-4-carboxamide (TFA salt) | 528 | 3 |
| 22 | 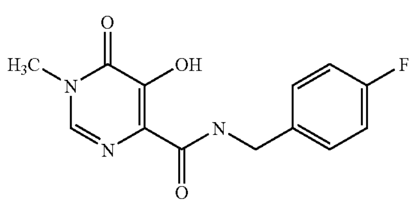 | N-(4-fluorobenzyl)-5-hydroxy-1-methyl-6-oxo-1,6-dihydropyrimidine-4-carboxamide | 276 (M−) | 1 |
| 23 | 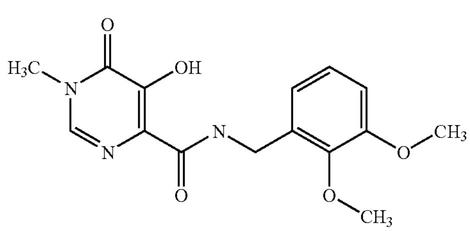 | N-(2,3-dimethoxybenzyl)-5-hydroxy-1-methyl-6-oxo-1,6-dihydropyrimidine-4-carboxamide | 320 | 1 |
| 24 | 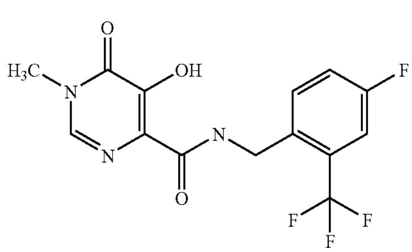 | N-[4-fluoro-2-(trifluoromethyl)benzyl]-5-hydroxy-1-methyl-6-oxo-1,6-dihydropyrimidine-4-carboxamide | (M−) 344 | 1 |

TABLE 1-continued

| Exp | Structure | Name | M+ | Scheme |
|---|---|---|---|---|
| 25 | 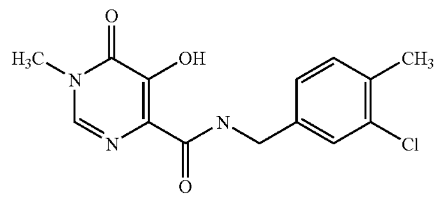 | N-(3-chloro-4-methylbenzyl)-5-hydroxy-1-methyl-6-oxo-1,6-dihydropyrimidine-4-carboxamide | 308 | 1 |
| 26 | Chiral | 5-hydroxy-N-[(1R,2S)-2-hydroxy-2,3-dihydro-1H-inden-1-yl]-1-methyl-2-{4-[(4-methylpiperazin-1-yl)methyl]phenyl}-6-oxo-1,6-dihydropyrimidine-4-carboxamide (TFA salt) | 490 | 3 |
| 27 | Chiral | N-(4-fluorobenzyl)-5-hydroxy-2 (4-{[(2R)-2-(methoxymethyl)pyrrolidin-1-yl]methyl}phenyl)-1-methyl-6-oxo-1,6-dihydropyrimidine-4-carboxamide (TFA salt) | 481 | 3 |
| 28 | Chiral | N-(4-fluorobenzyl)-5-hydroxy-2 (4-{[(2S)-2-(methoxymethyl)pyrrolidin-1-yl]methyl}phenyl)-1-methyl-6-oxo-1,6-dihydropyrimidine-4-carboxamide (TFA salt) | 481 | 3 |
| 29 | 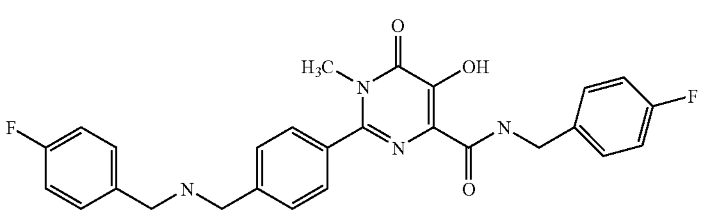 | N-(4-fluorobenzyl)-2-(4-{[(4-fluorobenzyl)amino]methyl}phenyl)-5-hydroxy-1-methyl-6-oxo-1,6-dihydropyrimidine-4-carboxamide (TFA salt) | 491 | 3 |
| 30 | 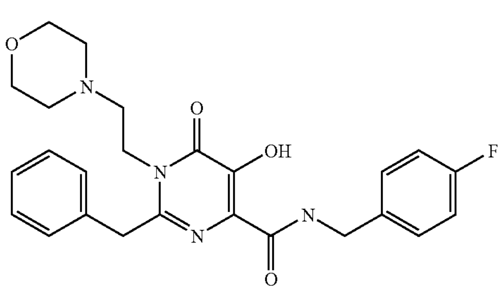 | 2-benzyl-N-(4-fluorobenzyl)-5-hydroxy-1-(2-morpholin-4-ylethyl)-6-oxo-1,6-dihydropyrimidine-4-carboxamide (TFA salt) | 467 | 1 |

TABLE 1-continued

| Exp | Structure | Name | M+ | Scheme |
|---|---|---|---|---|
| 31 | 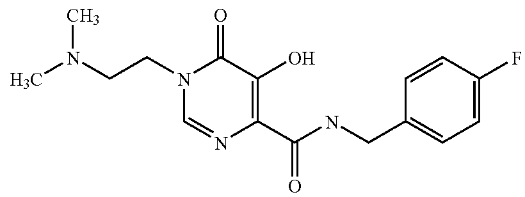 | 1-[2-(dimethylamino)ethyl]-N-(4-fluorobenzyl)-5-hydroxy-6-oxo-1,6-dihydropyrimidine-4-carboxamide (TFA salt) | 335 | 1 |
| 32 | 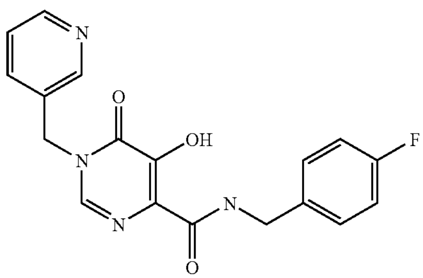 | N-(4-fluorobenzyl)-5-hydroxy-6-oxo-1-(pyridin-3-ylmethyl)-1,6-dihydropyrimidine-4-carboxamide (TFA salt) | 355 | 1 |
| 33 | 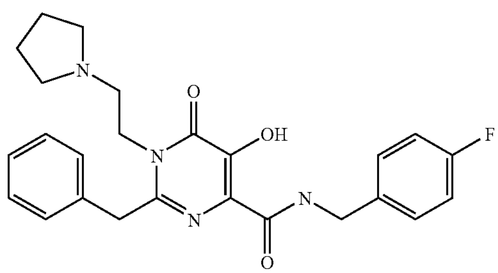 | 2-benzyl-N-(4-fluorobenzyl)-5-hydroxy-6-oxo-1-(2-pyrrolidin-1-ylethyl)-1,6-dihydropyrimidine-4-carboxamide (TFA salt) | 451 | 1 |
| 34 | 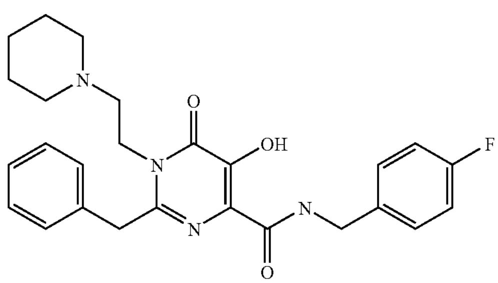 | 2-benzyl-N-(4-fluorobenzyl)-5-hydroxy-6-oxo-1-(2-piperidin-1-ylethyl)-1,6-dihydropyrimidine-4-carboxamide (TFA salt) | 465 | 1 |
| 35 | 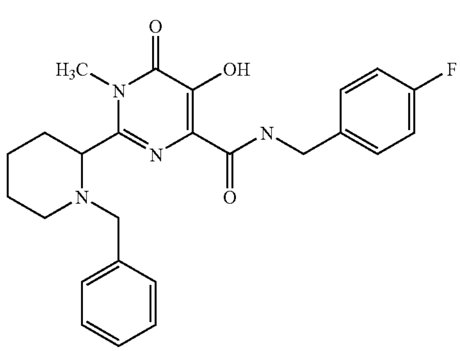 | 2-(1-benzylpiperidin-2-yl)-N-(4-fluorobenzyl)-5-hydroxy-1-methyl-6-oxo-1,6-dihydropyrimidine-4-carboxamide (TFA salt) | 451 | 4 |

TABLE 1-continued

| Exp | Structure | Name | M+ | Scheme |
|---|---|---|---|---|
| 36 | 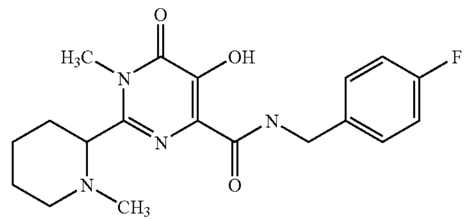 | N-(4-fluorobenzyl)-5-hydroxy-1 methyl-2-(1-methylpiperidin-2-yl)-6-oxo-1,6 dihydropyrimidine-4-carboxamide (TFA salt) | 375 | 4 |
| 37 | 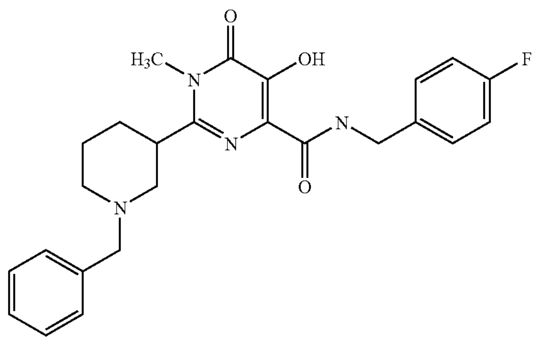 | 2-(1-benzylpiperidin-3-yl)-N-(4-fluorobenzyl)-5-hydroxy-1-methyl-6-oxo-1,6-dihydropyrimidine-4-carboxamide (TFA salt) | 451 | 4 |
| 38 | 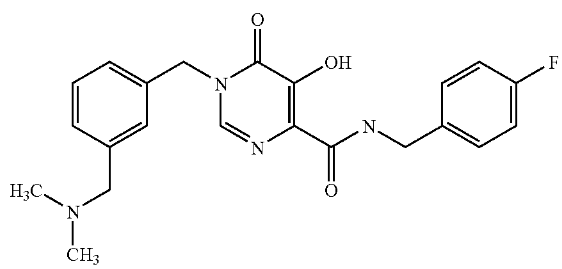 | 1-{3-[(dimethylamino)methyl]benzyl}-N-(4-fluorobenzyl)-5-hydroxy 6-oxo-1,6-dihydropyrimidine-4-carboxamide (TFA salt) | 411 | 3 |
| 39 | 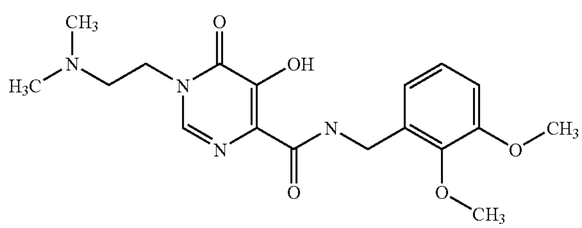 | N-(2,3-dimethoxybenzyl)-1-[2-(dimethylamino)ethyl]-5-hydroxy-6-oxo-1,6-dihydropyrimidine-4-carboxamide (TFA salt) | 377 | 1 |
| 40 | 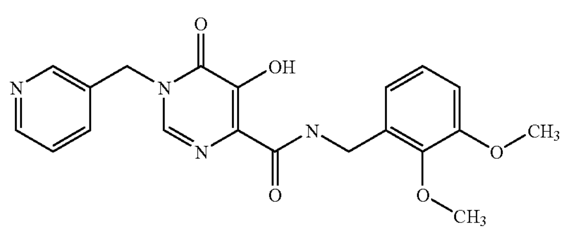 | N-(2,3-dimethoxybenzyl)-5-hydroxy-6-oxo-1-(pyridin-3-ylmethyl)-1,6-dihydropyrimidine-4-carboxamide (TFA salt) | 397 | 1 |
| 41 | 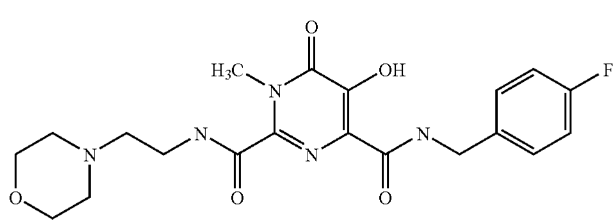 | N4-(4-fluorobenzyl)-5-hydroxy-1-methyl-N2-(2-morpholin-4-ylethyl)-6-oxo-1,6-dihydropyrimidine-2,4-dicarboxamide (TFA salt) | 434 | 6 |

TABLE 1-continued

| Exp | Structure | Name | M+ | Scheme |
|---|---|---|---|---|
| 42 | 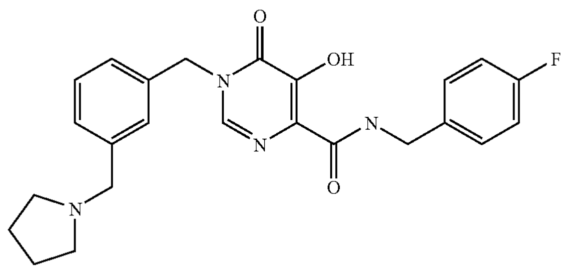 | N-(4-fluorobenzyl)-5-hydroxy-6-oxo-1-[3-(pyrrolidin-1-ylmethyl)benzyl]-1,6-dihydropyrimidine-4-carboxamide (TFA salt) | 437 | 3 |
| 43 | 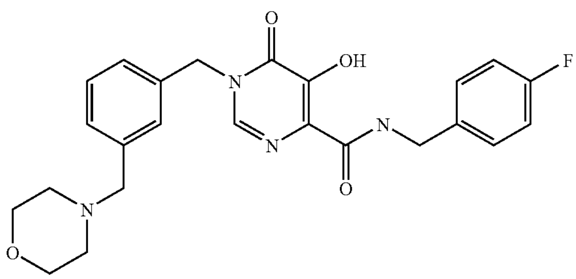 | N-(4-fluorobenzyl)-5-hydroxy-1-[3-(morpholin-4-ylmethyl)benzyl]-6-oxo-1,6-dihydropyrimidine-4-carboxamide (TFA salt) | 453 | 3 |
| 44 | 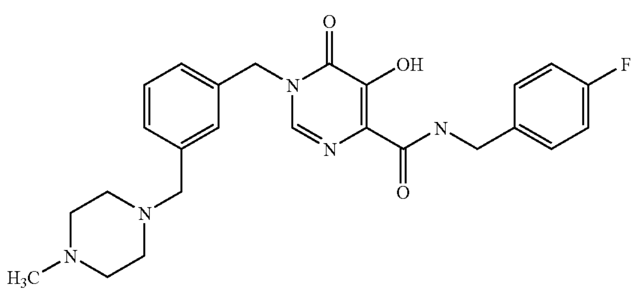 | N-(4-fluorobenzyl)-5-hydroxy-1-{3-[(4-methylpiperazin-1-yl)methyl]benzyl}-6-oxo-1,6-dihydropyrimidine-4-carboxamide (TFA salt) | 466 | 3 |
| 45 | 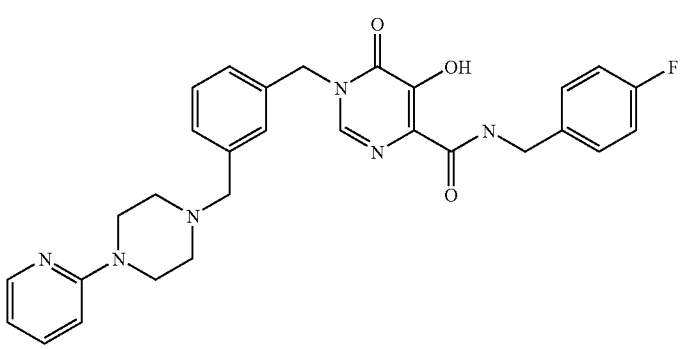 | N-(4-fluorobenzyl)-5-hydroxy-6-oxo-1-{3-[(4-pyridin-2-ylpiperazin-1-yl)methyl]benzyl}1,6-dihydropyrimidine-4-carboxamide (TFA salt) | 529 | 3 |
| 46 | 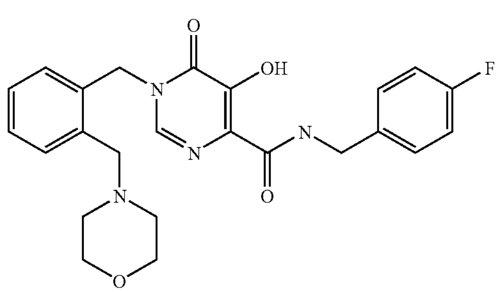 | N-(4-fluorobenzyl)-5-hydroxy-1-[2-(morpholin-4-ylmethyl)benzyl]-6-oxo-1,6-dihydropyrimidine-4-carboxamide (TFA salt) | 453 | 3 |

TABLE 1-continued

| Exp | Structure | Name | M+ | Scheme |
|---|---|---|---|---|
| 47 | 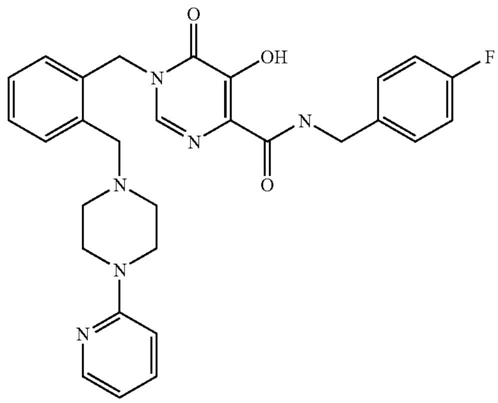 | N-(4-fluorobenzyl)-5-hydroxy-6-oxo-1-{2-[(4-pyridin-2-ylpiperazin-1-yl)methyl]benzyl}-1,6-dihydropyrimidine-4-carboxamide (TFA salt) | 529 | 3 |
| 48 | 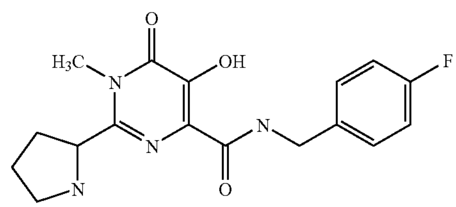 | N-(4-fluorobenzyl)-5-hydroxy-1-methyl-6-oxo-2-pyrrolidin-2-yl-1,6-dihydropyrimidine-4-carboxamide (TFA salt) | 347 | 1* |
| 49 | 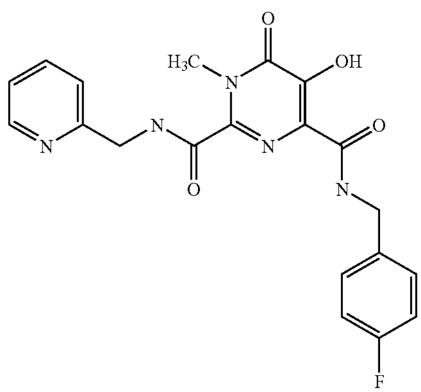 | N4-(4-fluorobenzyl)-5-hydroxy-1-methyl-6-oxo-N2-(pyridin-2-ylmethyl)-1,6-dihydropyrimidine-2,4-dicarboxamide (TFA salt) | 412 | 6 |
| 50 | 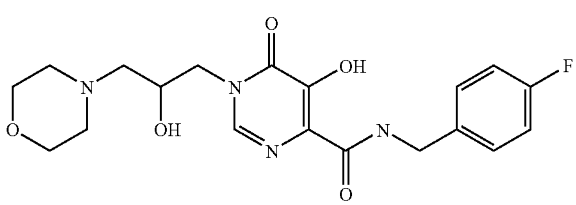 | N-(4-fluorobenzyl)-5-hydroxy-1-(2-hydroxy-3-morpholin-4-ylpropyl)-6-oxo-1,6-dihydropyrimidine-4-carboxamide (TFA salt) | 407 | I |
| 51 | 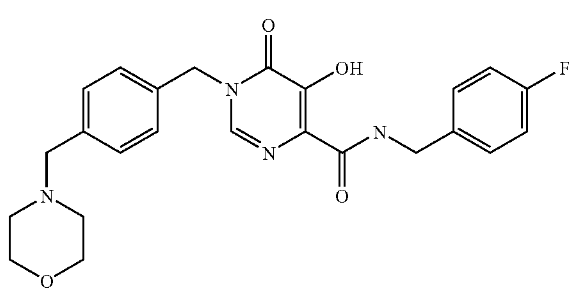 | N-(4-fluorobenzyl)-5-hydroxy-1-[4-(morpholin-4-ylmethyl)benzyl]-6-oxo-1,6-dihydropyrimidine-4-carboxamide (TFA salt) | 453 | 3 |

TABLE 1-continued

| Exp | Structure | Name | M+ | Scheme |
|---|---|---|---|---|
| 52 | 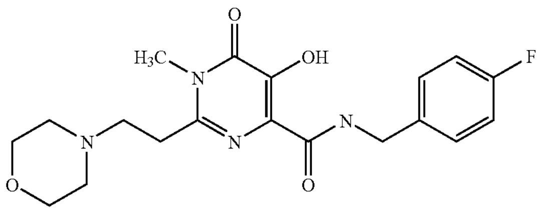 | N-(4-fluorobenzyl)-5-hydroxy-1 methyl-2-(2-morpholin-4-ylethyl)-6-oxo-1,6-dihydropyrimidine-4-carboxamide (TFA salt) | 390.9 | 7 |
| 53 | 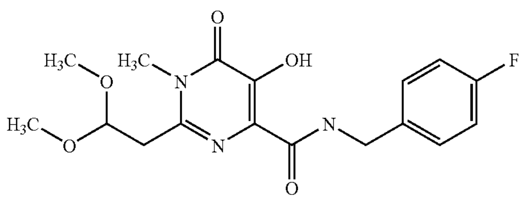 | 2-(2,2-dimethoxyethyl)-N-(4-fluorobenzyl)-5-hydroxy-1-methyl-6-oxo-1,6-dihydropyrimidine-4-carboxamide | 366 | 1 |
| 54 | 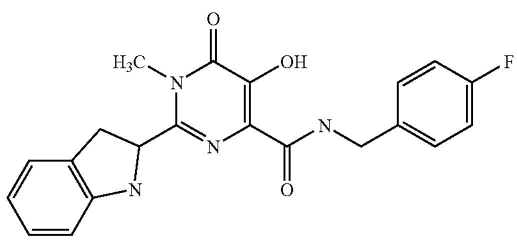 | 2-(2,3-dihydro-1H-indol-2-yl)-N-(4-fluorobenzyl)-5-hydroxy-1 methyl-6-oxo-1,6-dihydropyrimidine-4-carboxamide (HCl salt) | 395 | 1* |
| 55 | 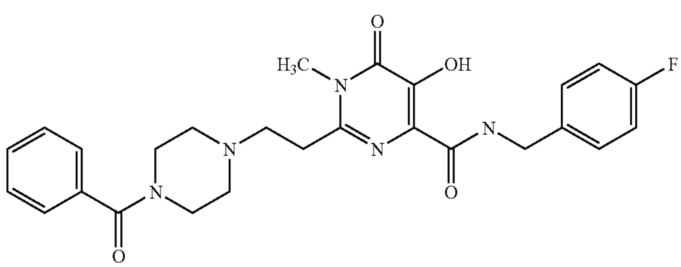 | 2-[2-(4-benzoylpiperazin-1-yl)ethyl]-N-(4-fluorobenzyl)-5-hydroxy-1-methyl-6-oxo-1,6-dihydropyrimidine-4-carboxamide | 494 | 7 |
| 56 | 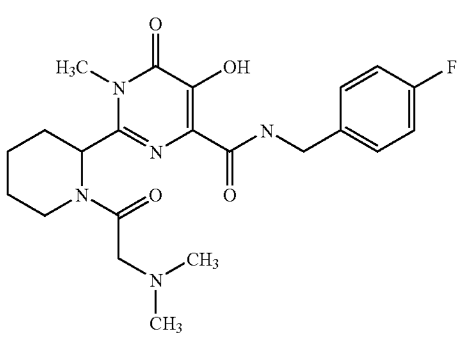 | 2-[1-(N,N-dimethylglycyl)piperidin-2-yl]-N-(4-fluorobenzyl)-5-hydroxy-1 methyl-6-oxo-1,6-dihydropyrimidine-4-carboxamide (TFA salt) | 446 | 5 |
| 57 | 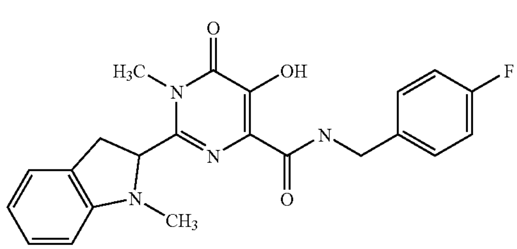 | N-(4-fluorobenzyl)-5-hydroxy-1 methyl-2-(1-methyl-2,3-dihydro 1H-indol-2-yl)-6-oxo-1,6-dihydropyrimidine-4-carboxamide (HCL salt) | 409 | 4 |

TABLE 1-continued

| Exp | Structure | Name | M+ | Scheme |
|---|---|---|---|---|
| 58 | 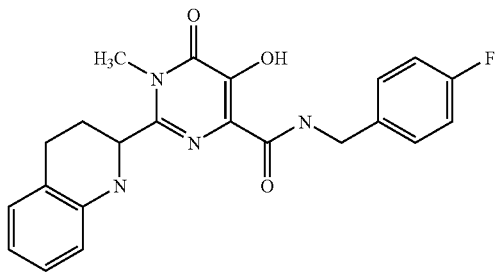 | N-(4-fluorobenzyl)-5-hydroxy-1-methyl-6-oxo-2-(1,2,3,4-tetrahydroquinolin-2-yl)-1,6-dihydropyrimidine-4-carboxamide (TFA salt) | 409 | 1* |
| 59 | 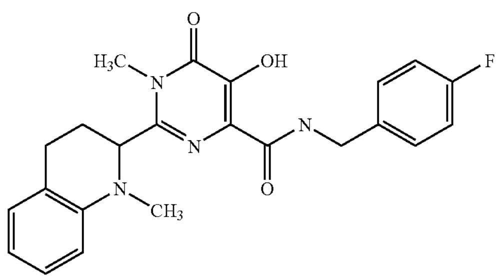 | N-(4-fluorobenzyl)-5-hydroxy-1-methyl-2-(1-methyl-1,2,3,4-tetrahydroquinolin-2-yl)-6-oxo-1,6-dihydropyrimidine-4-carboxamide (TFA salt) | 423 | 4 |
| 60 | Chiral | tert-butyl (2S,4R)-4-(benzyloxy)-2-(4-{[(4-fluorobenzyl)amino]carbonyl}-5-hydroxy-1-methyl-6-oxo-1,6-dihydropyrimidin-2-yl)pyrrolidine-1-carboxylate | 552.8 | 1 |
| 61 | Chiral | tert-butyl (2S,4R)-2-(4-{[(4-fluorobenzyl)amino]carbonyl}-5-hydroxy-1-methyl-6-oxo-1,6-dihydropyrimidin-2-yl)-4-hydroxypyrrolidine-1-carboxylate | 463.2 | 1* |
| 62 | Chiral | 2-[(2S,4R)-4-(benzyloxy)pyrrolidin-2-yl]-N-(4-fluorobenzyl)-5-hydroxy-1-methyl-6-oxo-1,6-dihydropyrimidine-4-carboxamide (TFA salt) | 453 | 1* |
| 63 | Chiral | N-(4-fluorobenzyl)-5-hydroxy-2-[(2S,4R)-4-hydroxypyrrolidin-2-yl]-1-methyl-6-oxo-1,6-dihydropyrimidine-4-carboxamide (HCl salt) | 362.8 | 1* |

TABLE 1-continued

| Exp | Structure | Name | M+ | Scheme |
|---|---|---|---|---|
| 64 | Chiral | N-(4-fluorobenzyl)-5-hydroxy-2-[(2S,4R)-4-hydroxy-1-methylpyrrolidin-2-yl]-1-methyl 6-oxo-1,6-dihydropyrimidine-4-carboxamide (TFA salt) | 376.8 | 4 |
| 65 | Chiral | 2-[(2S,4R)-4-(benzyloxy)-1-methylpyrrolidin-2-yl]-N-(4-fluorobenzyl)-5-hydroxy-1-methyl-6-oxo-1,6-dihydropyrimidine-4-carboxamide (TFA salt) | 466.6 | 4 |
| 66 | Chiral | 2-[(2S,4R)-1-benzoyl-4-(benzyloxy)pyrrolidin-2-yl]-N-(4-fluorobenzyl)-5-hydroxy-1-methyl-6-oxo-1,6-dihydropyrimidine-4-carboxamide | 557 | 5 |
| 67 | 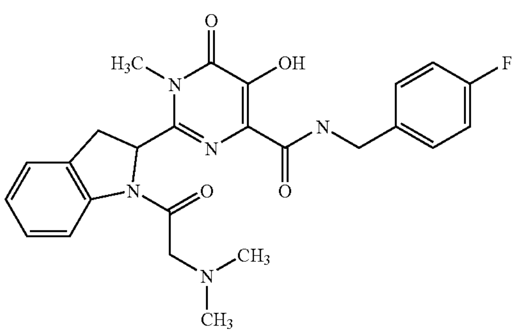 | 2-[1-(N,N-dimethylglycyl)-2,3-dihydro-1H-indol-2-yl]-N-(4-fluorobenzyl)-5-hydroxy-1-methyl-6-oxo-1,6-dihydropyrimidine-4-carboxamide (TFA salt) | 480 | 5 |
| 68 | 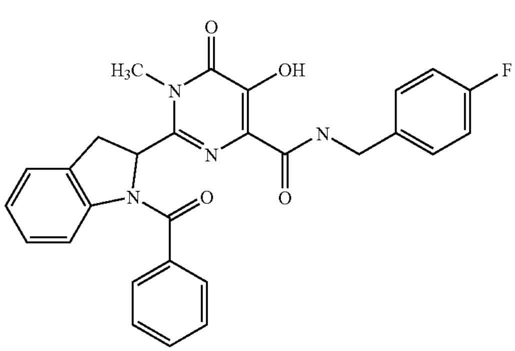 | 2-(1-benzoyl-2,3-dihydro-1H-indol-2-yl)-N-(4-fluorobenzyl)-5-hydroxy-1-methyl-6-oxo-1,6-dihydropyrimidine-4-carboxamide | 499 | 5 |

TABLE 1-continued

| Exp | Structure | Name | M+ | Scheme |
|---|---|---|---|---|
| 69 | 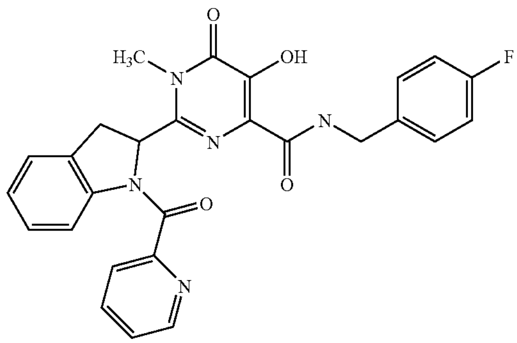 | N-(4-fluorobenzyl)-5-hydroxy-1-methyl-6-oxo-2-[1-(pyridin-2-ylcarbonyl)-2,3-dihydro-1H-indol-2-yl]-1,6-dihydropyrimidine-4-carboxamide (TFA salt) | 500 | 5 |
| 70 | 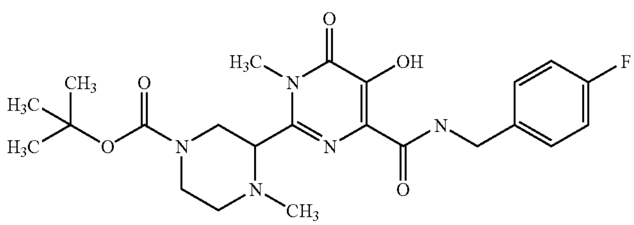 | tert-butyl 3-(4-{[(4-fluorobenzyl)amino]carbonyl}-5-hydroxy-1-methyl-6-oxo-1,6-dihydropyrimidin-2-yl)-4-methylpiperazine-1-carboxylate (TFA salt) | 476 | 4 |
| 71 | 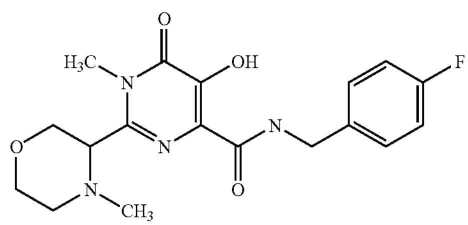 | N-(4-fluorobenzyl)-5-hydroxy-1-methyl-2-(4-methylmorpholin-3-yl)-6-oxo-1,6-dihydropyrimidine-4-carboxamide (TFA salt) | 377 | 4 |
| 72 | 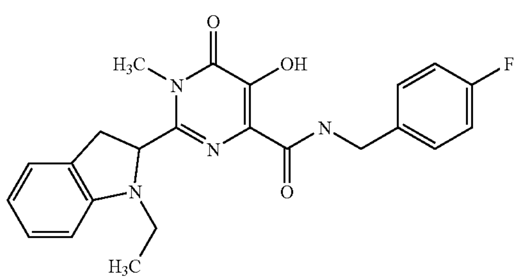 | 2-(1-ethyl-2,3-dihydro-1H-indol-2-yl)-N-(4-fluorobenzyl)-5-hydroxy-1-methyl-6-oxo-1,6-dihydropyrimidine-4-carboxamide (TFA salt) | 423 | 4 |
| 73 | 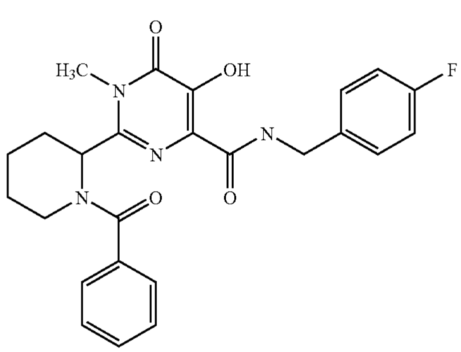 | 2-(1-benzoylpiperidin-2-yl)-N-(4-fluorobenzyl)-5-hydroxy-1-methyl-6-oxo-1,6-dihydropyrimidine-4-carboxamide | 465 | 5 |

TABLE 1-continued

| Exp | Structure | Name | M+ | Scheme |
|---|---|---|---|---|
| 74 | 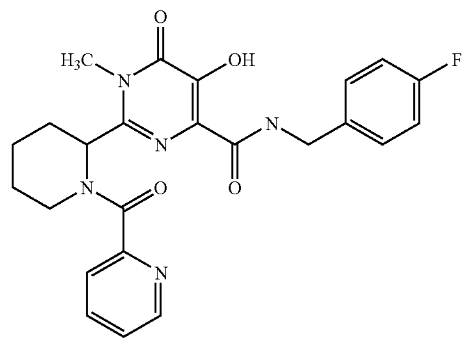 | N-(4-fluorobenzyl)-5-hydroxy-1-methyl-6-oxo-2-[1-(pyridin-2-ylcarbonyl)piperidin-2-yl]-1,6-dihydropyrimidine-4-carboxamide (TFA salt) | 466 | 5 |
| 75 | 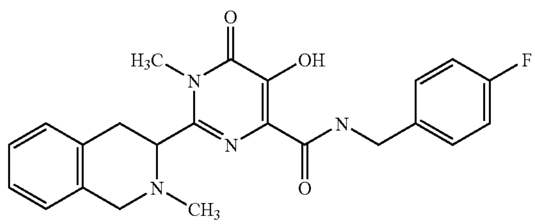 | N-(4-fluorobenzyl)-5-hydroxy-1-methyl-2-(2-methyl-1,2,3,4-tetrahydroisoquinolin-3-yl)-6-oxo-1,6-dihydropyrimidine-4-carboxamide (TFA salt) | 423 | 4 |
| 76 | 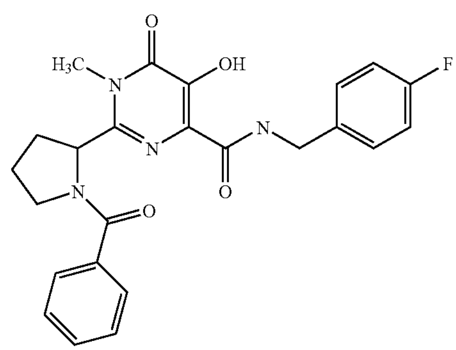 | 2-(1-benzoylpyrrolidin-2-yl)-N-(4-fluorobenzyl)-5-hydroxy-1-methyl-6-oxo-1,6-dihydropyrimidine-4-carboxamide | 451 | 5 |
| 77 | 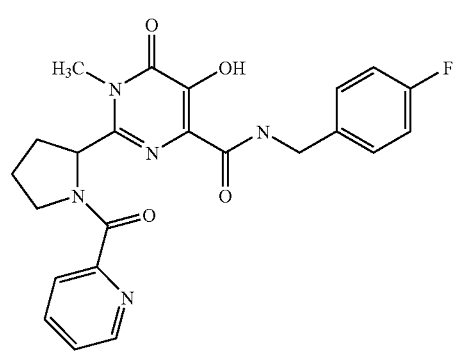 | N-(4-fluorobenzyl)-5-hydroxy-1-methyl-6-oxo-2-[1-(pyridin-2-ylcarbonyl)pyrrolidin-2-yl]-1,6-dihydropyrimidine-4-carboxamide (TFA salt) | 452 | 5 |
| 78 | 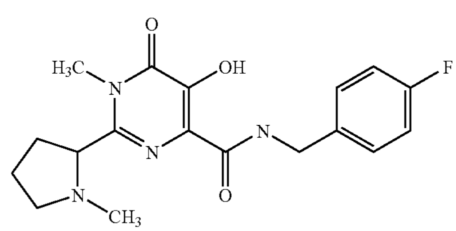 | N-(4-fluorobenzyl)-5-hydroxy-1-methyl-2-(1-methylpyrrolidin-2-yl)-6-oxo-1,6-dihydropyrimidine-4-carboxamide (TFA salt) | 361 | 4 |

TABLE 1-continued

| Exp | Structure | Name | M+ | Scheme |
|---|---|---|---|---|
| 79 | Chiral | 2-[(2S,4R)-4-(benzyloxy)-1-(pyridin-2-ylcarbonyl)pyrrolidin 2-yl]-N-(4-fluorobenzyl)-5-hydroxy-1-methyl-6-oxo-1,6-dihydropyrimidine-4-carboxamide (TFA salt) | 558 | 5 |
| 80 | 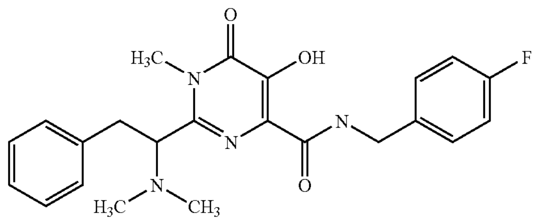 | 2-[1-(dimethylamino)-2-phenylethyl]-N-(4-fluorobenzyl)-5-hydroxy-1-methyl-6-oxo-1,6-dihydropyrimidine-4-carboxamide (TFA salt) | 425 | 4 |
| 81 | Chiral | 2-[(2S,4R)-1-benzoyl-4-hydroxypyrrolidin-2-yl]-N-(4-fluorobenzyl)-5-hydroxy-1-methyl-6-oxo-1,6-dihydropyrimidine-4-carboxamide | 467 | 1* |
| 82 | 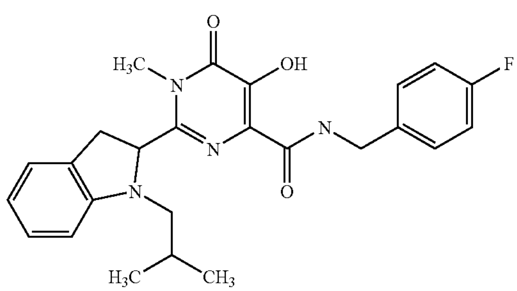 | N-(4-fluorobenzyl)-5-hydroxy-2-(1-isobutyl-2,3-dihydro-1H-indol-2-yl)-1-methyl-6-oxo-1,6-dihydropyrimidine-4-carboxamide (TFA salt) | 451 | 4 |
| 83 | 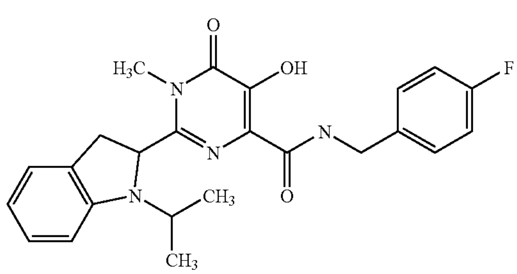 | N-(4-fluorobenzyl)-5-hydroxy-2-(1-isopropyl-2,3-dihydro-1H-indol-2-yl)-1-methyl-6-oxo-1,6-dihydropyrimidine-4-carboxamide (TFA salt) | 437 | 4 |

TABLE 1-continued

| Exp | Structure | Name | M+ | Scheme |
|---|---|---|---|---|
| 84 | 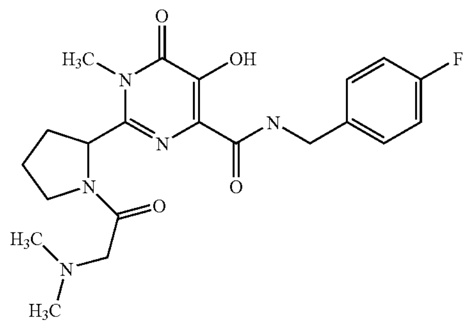 | 2-[1-(N,N-dimethylglycyl)pyrrolidin-2-yl]-N-(4-fluorobenzyl)-5-hydroxy-1-methyl-6-oxo-1,6-dihydropyrimidine-4-carboxamide (TFA salt) | 432 | 5 |
| 85 | 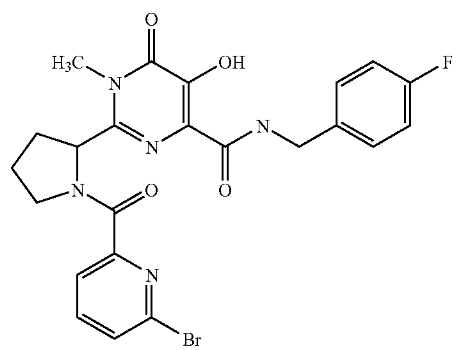 | 2-{1-[(6-bromopyridin-2-yl)carbonyl]pyrrolidin-2-yl}-N-(4-fluorobenzyl)-5-hydroxy-1-methyl-6-oxo-1,6-dihydropyrimidine-4-carboxamide (TFA salt) | 531 | 5 |
| 86 | 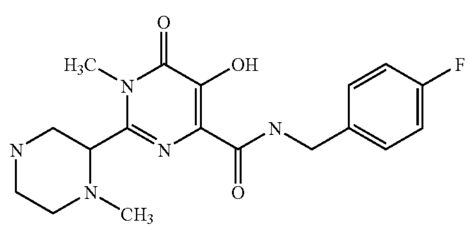 | N-(4-fluorobenzyl)-5-hydroxy-1-methyl-2-(1-methylpiperazin-2-yl)-6-oxo-1,6-dihydropyrimidine-4-carboxamide (TFA salt) | 376 | 1* |
| 87 | 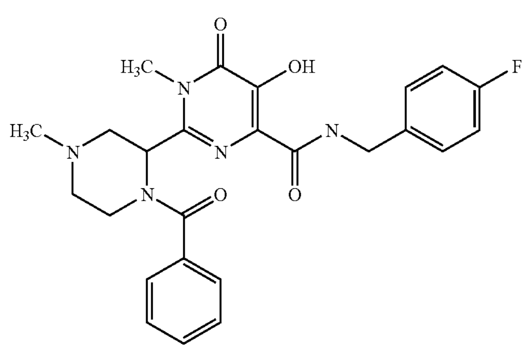 | 2-(1-benzoyl-4-methylpiperazin-2-yl)-N-(4-fluorobenzyl)-5-hydroxy-1-methyl-6-oxo-1,6-dihydropyrimidine-4-carboxamide (TFA salt) | 480 | 4 |
| 88 | 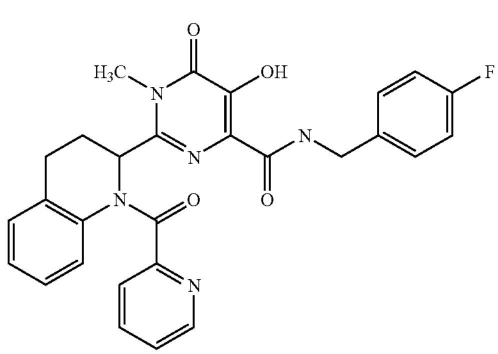 | N-(4-fluorobenzyl)-5-hydroxy-1-methyl-6-oxo-2-[1-(pyridin-2-ylcarbonyl)-1,2,3,4-tetrahydroquinolin-2-yl]-1,6-dihydropyrimidine-4-carboxamide (TFA salt) | 514 | 5 |

TABLE 1-continued

| Exp | Structure | Name | M+ | Scheme |
|---|---|---|---|---|
| 89 | 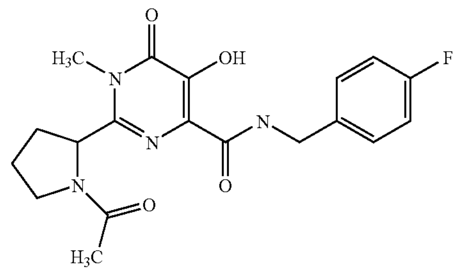 | 2-(1-acetylpyrrolidin-2-yl)-N-(4 fluorobenzyl)-5-hydroxy-1-methyl-6-oxo-1,6-dihydropyrimidine-4-carboxamide | 389 | 5 |
| 90 | 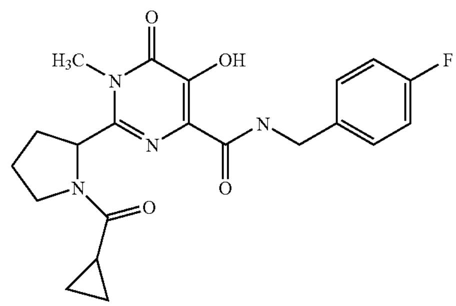 | 2-[1-(cyclopropylcarbonyl)pyrrolidin 2-yl]-N-(4-fluorobenzyl)-5-hydroxy-1-methyl-6-oxo-1,6-dihydropyrimidine-4-carboxamide | 415 | 5 |
| 91 | 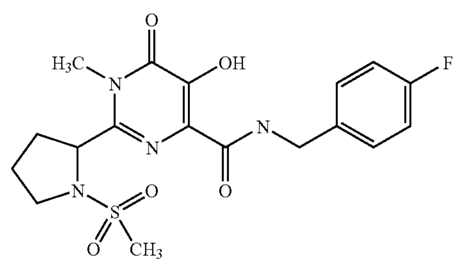 | N-(4-fluorobenzyl)-5-hydroxy-1 methyl-2-[1-(methylsulfonyl)pyrrolidin-2-yl] 6-oxo-1,6-dihydropyrimidine-4-carboxamide | 425 | 5 |
| 92 | 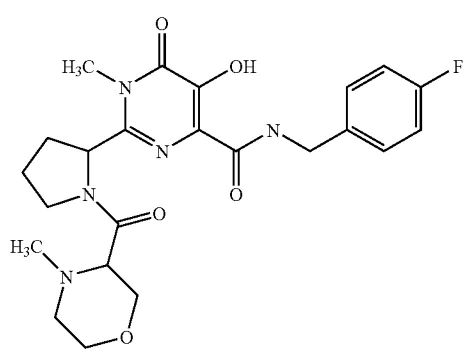 | N-(4-fluorobenzyl)-5-hydroxy-1 methyl-2-{1-[(4-methylmorpholin-3-yl)carbonyl]pyrrolidin-2-yl}-6-oxo-1,6-dihydropyrimidine-4-carboxamide (TFA salt) | 474 | 5 |
| 93 | 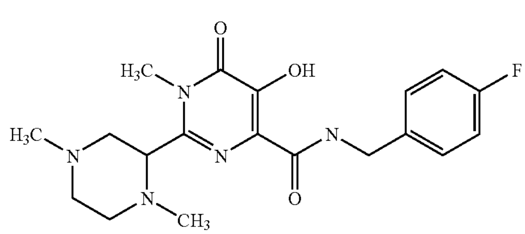 | 2-(1,4-dimethylpiperazin-2-yl)-N-(4-fluorobenzyl)-5-hydroxy-1 methyl-6-oxo-1,6-dihydropyrimidine-4-carboxamide (TFA salt) | 390 | 4 |

TABLE 1-continued

| Exp | Structure | Name | M+ | Scheme |
|---|---|---|---|---|
| 94 | 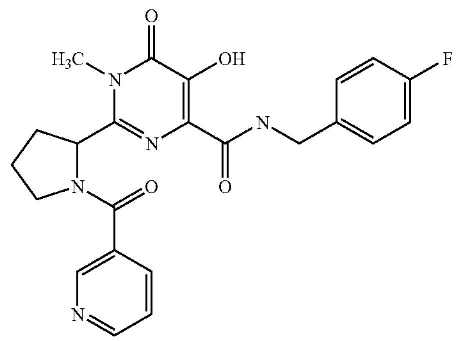 | N-(4-fluorobenzyl)-5-hydroxy-1-methyl-6-oxo-2-[1-(pyridin-3-ylcarbonyl)pyrrolidin-2-yl]-1,6-dihydropyrimidine-4-carboxamide (TFA salt) | 452 | 5 |
| 95 | 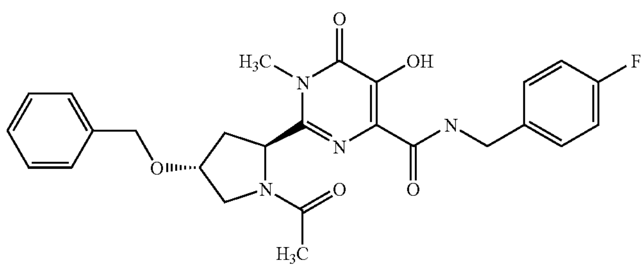 | 2-[(2S,4R)-1-acetyl-4-(benzyloxy)pyrrolidin-2-yl]-N-(4-fluorobenzyl)-5-hydroxy-1-methyl-6-oxo-1,6-dihydropyrimidine-4-carboxamide | 495 | 5 |
| 96 | 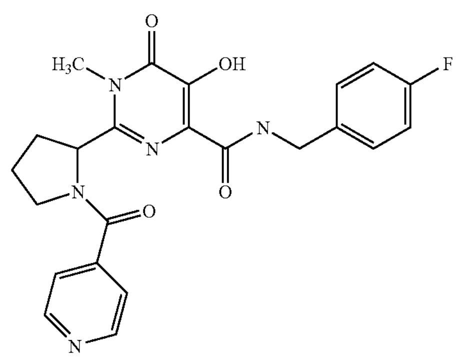 | N-(4-fluorobenzyl)-5-hydroxy-2-(1-isonicotinoylpyrrolidin-2-yl)-1-methyl-6-oxo-1,6-dihydropyrimidine-4-carboxamide (TFA salt) | 452 | 5 |
| 97 | 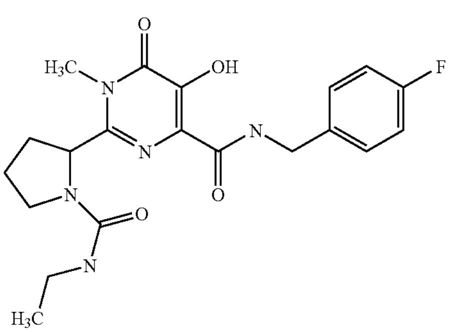 | 2-{1-[(ethylamino)carbonyl]-pyrrolidin-2-yl}-N-(4-fluorobenzyl)-5-hydroxy-1-methyl-6-oxo-1,6-dihydropyrimidine-4-carboxamide | 418 | 5 |

TABLE 1-continued

| Exp | Structure | Name | M+ | Scheme |
|---|---|---|---|---|
| 98 | 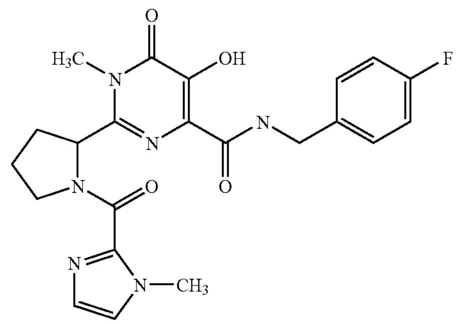 | N-(4-fluorobenzyl)-5-hydroxy-1-methyl-2-{1-[(1-methyl-1H-imidazol-2-yl)carbonyl]pyrrolidin-2-yl}-6-oxo-1,6-dihydropyrimidine-4-carboxamide (TFA salt) | 455 | 5 |
| 99 | Chiral | 2-[(2S,4R)-1-acetyl-4-hydroxypyrrolidin-2-yl]-N-(4-fluorobenzyl)-5-hydroxy-1-methyl-6-oxo-1,6-dihydropyrimidine-4-carboxamide | 405 | 1* |
| 100 | 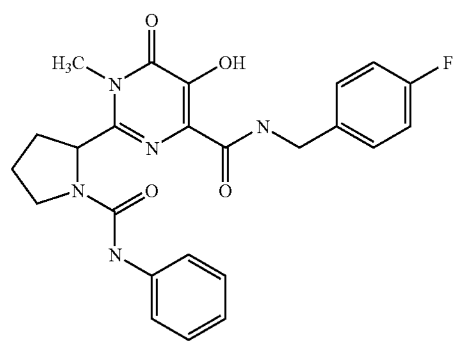 | 2-[1-(anilinocarbonyl)pyrrolidin-2-yl]-N-(4-fluorobenzyl)-5-hydroxy-1-methyl-6-oxo-1,6-dihydropyrimidine-4-carboxamide | 466 | 5 |
| 101 | 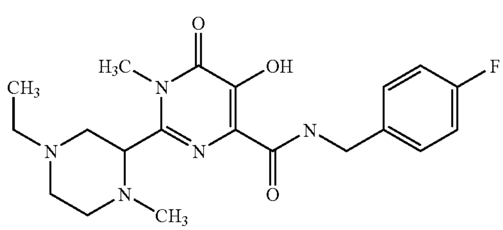 | 2-(4-ethyl-1-methylpiperazin-2-yl)-N-(4-fluorobenzyl)-5-hydroxy-1-methyl-6-oxo-1,6-dihydropyrimidine-4-carboxamide (TFA salt) | 404 | 4 |
| 102 | 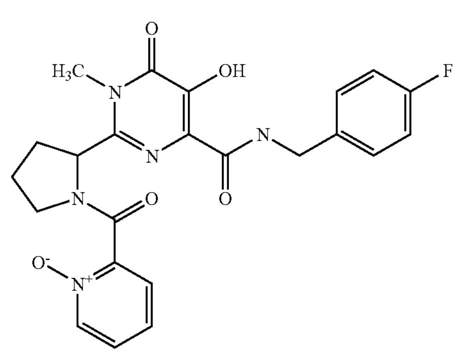 | N-(4-fluorobenzyl)-5-hydroxy-1-methyl-2-{1-[(1-oxidopyridin-2-yl)carbonyl]pyrrolidin-2-yl}-6-oxo-1,6-dihydropyrimidine-4-carboxamide | 468 | 5 |

TABLE 1-continued

| Exp | Structure | Name | M+ | Scheme |
|---|---|---|---|---|
| 103 | 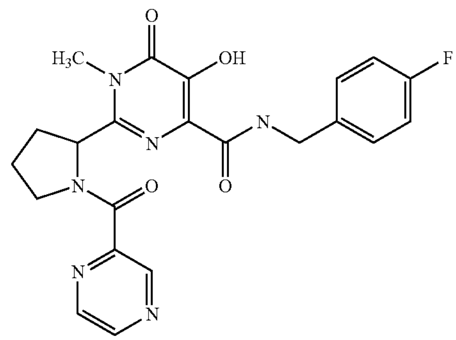 | N-(4-fluorobenzyl)-5-hydroxy-1 methyl-6-oxo-2-[1-(pyrazin-2-ylcarbonyl)pyrrolidin-2-yl]-1,6-dihydropyrimidine-4-carboxamide (TFA salt) | 453 | 5 |
| 104 | Chiral | 2-[(4R)-3-acetyl-1,3-thiazolidin-4-yl]-N-(4-fluorobenzyl)-5-hydroxy-1-methyl-6-oxo-1,6-dihydropyrimidine-4-carboxamide | 407 | 5 |

TABLE 2

| Exp. | STRUCTURE | Name | M + 1 | Scheme |
|---|---|---|---|---|
| 1 | 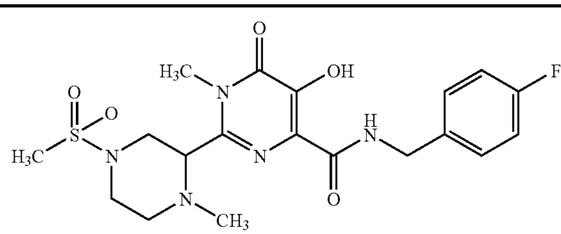 | N-(4-fluorobenzyl)-5-hydroxy-1-methyl-2-[1-methyl-4-(methylsulfonyl)piperazin-2-yl]-6-oxo-1,6-dihydropyrimidine-4-carboxamide | 454 | 5 |
| 2 | 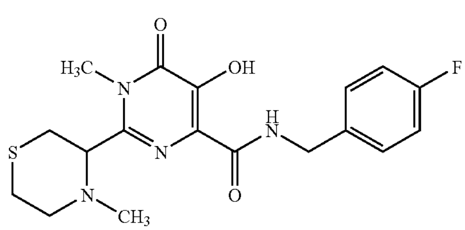 | N-(4-fluorobenzyl)-5-hydroxy-1-methyl-2-(4-methylthiomorpholin-3 yl)-6-oxo-1,6-dihydropyrimidine-4-carboxamide | 393 | 4 |
| 3 | 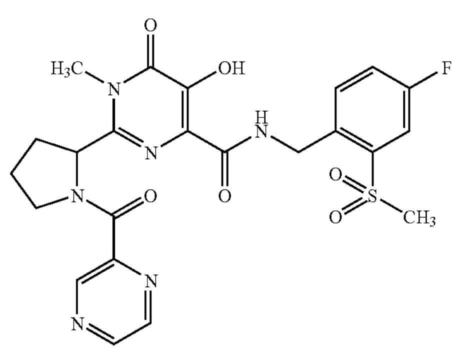 | N-[4-fluoro-2-(methylsulfonyl)benzyl]-5-hydroxy-1-methyl-6-oxo-2-[1-(pyrazin-2-ylcarbonyl)pyrrolidin-2-yl]-1,6-dihydropyrimidine-4-carboxamide | 531 | 1 |

TABLE 2-continued

| Exp. | STRUCTURE | Name | M + 1 | Scheme |
|---|---|---|---|---|
| 4 | 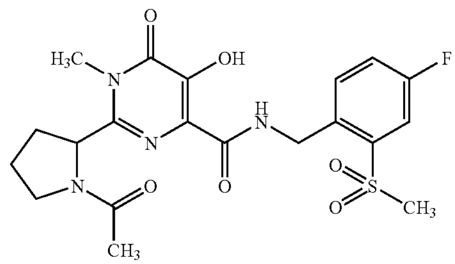 | 2-(1-acetylpyrrolidin-2-yl)-N-[4-fluoro-2-(methylsulfonyl)benzyl]-5-hydroxy-1-methyl-6-oxo-1,6-dihydropyrimidine-4-carboxamide | 467 | 1 |
| 5 | 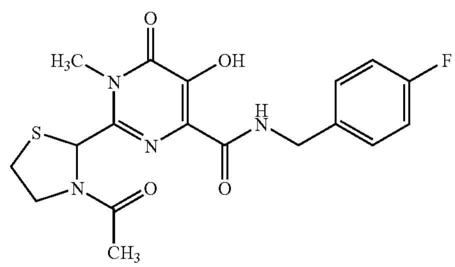 | 2-(3-acetyl-1,3-thiazolidin-2-yl)-N-(4-fluorobenzyl)-5-hydroxy-1-methyl-6-oxo-1,6-dihydropyrimidine-4-carboxamide | 407 | 1 |
| 6 | 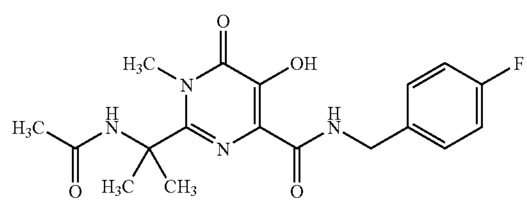 | 2-[1-(acetylamino)-1-methylethyl]-N-(4-fluorobenzyl)-5-hydroxy-1-methyl-6-oxo-1,6-dihydropyrimidine-4-carboxamide | 377 | 1 |
| 7 | 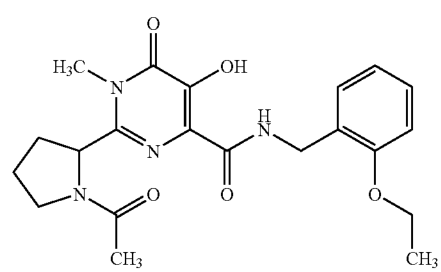 | 2-(1-acetylpyrrolidin-2-yl)-N-(2-ethoxybenzyl)-5-hydroxy-1-methyl-6-oxo-1,6-dihydropyrimidine-4-carboxamide | 415 | 1 |
| 8 | 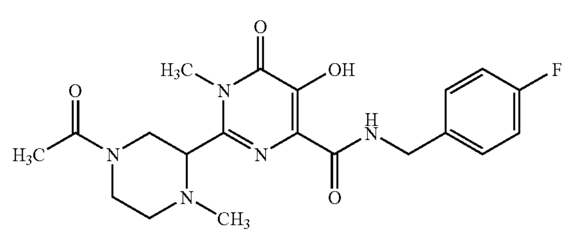 | 2-(4-acetyl-1-methylpiperazin-2-yl)-N-(4-fluorobenzyl)-5-hydroxy-1-methyl-6-oxo-1,6-dihdropyrimidine-4-carboxamide | 418 | 5 |
| 9 | 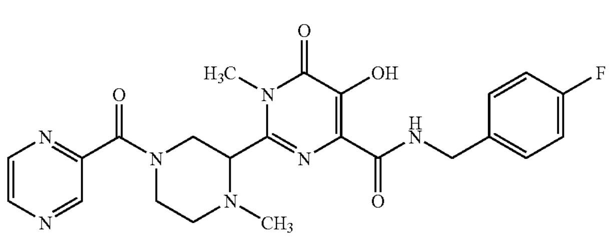 | N-(4-fluorobenzyl)-5-hydroxy-1-methyl-2-[1-methyl-4-(pyrazin-2-ylcarbonyl)piperazin-2-yl]-6-oxo-1,6-dihydropyrimidine-4-carboxamide | 482 | 5 |

TABLE 2-continued

| Exp. | STRUCTURE | Name | M + 1 | Scheme |
|---|---|---|---|---|
| 10 | 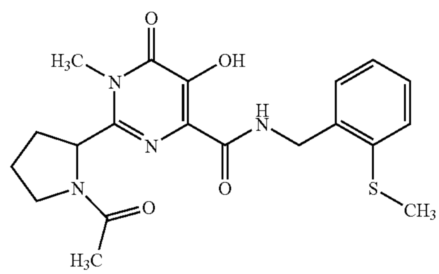 | 2-(1-acetylpyrrolidin-2-yl)-5-hydroxy-1-methyl-N-[2-(methylthio)benzyl]-6-oxo-1,6-dihydropyrimidine-4-carboxamide | 417 | 1 |
| 11 | 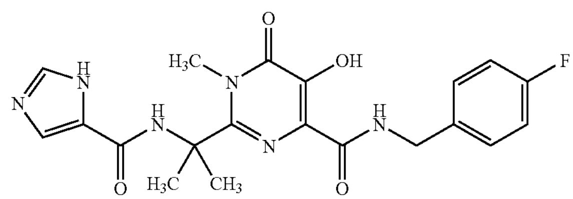 | N-(4-fluorobenzyl)-5-hydroxy-2-{1-[(1H-imidazol-5-ylcarbonyl)amino]-1-methylethyl}-1-methyl-6-oxo-1,6-hydropyrimidine-4-carboxamide | 429 | 5 |
| 12 | 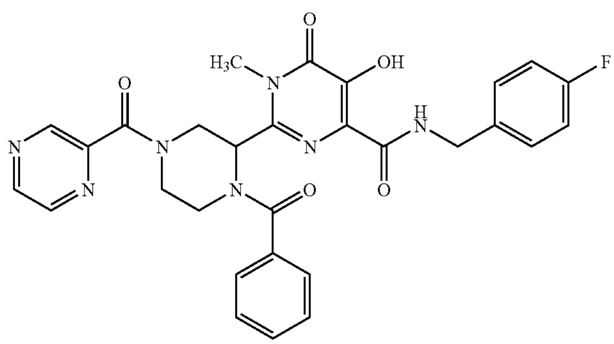 | 2-[1-benzoyl-4-(pyrazin-2-ylcarbonyl)piperazin-2-yl]-N-(4-fluorobenzyl)-5-hydroxy-1-methyl-6-oxo-1,6-dihydropyrimidine-4-carboxamide | 572 | 5 |
| 13 | 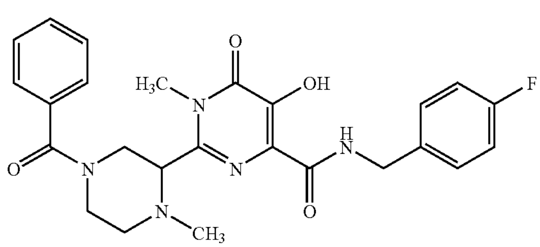 | 2-(4-benzoyl-1-methylpiperazin-2-yl)-N-(4-fluorobenzyl)-5-hydroxy-1-methyl-6-oxo-1,6-dihydropyrimidine-4-carboxamide | 480 | 5 |
| 14 | 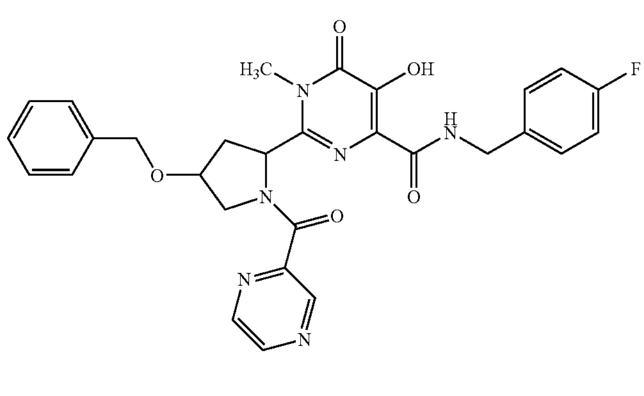 | 2-[4-(benzyloxy)-1-(pyrazin-2-ylcarbonyl)pyrrolidin-2-yl]-N-(4-fluorobenzyl)-5-hydroxy-1-methyl-6-oxo-1,6-dihydropyrimidine-4-carboxamide | 559 | 5 |

TABLE 2-continued

| Exp. | STRUCTURE | Name | M + 1 | Scheme |
|---|---|---|---|---|
| 15 | 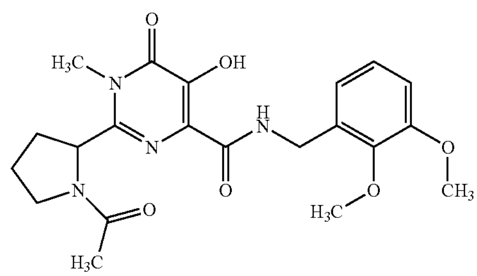 | 2-(1-acetylpyrrolidin-2-yl)-N-(2,3-dimethoxybenzyl)-5-hydroxy-1-methyl-6-oxo-1,6-dihydropyrimidine-4-carboxamide | 431 | 1 |
| 16 | 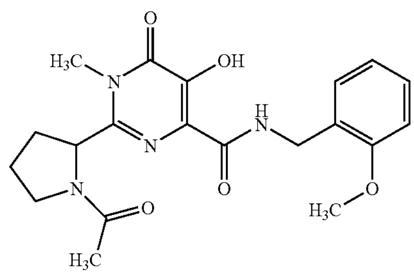 | 2-(1-acetylpyrrolidin-2-yl)-5-hydroxy-N-(2-methoxybenzyl)-1-methyl-6-oxo-1,6-dihydropyrimidine-4-carboxamide | 401 | 1 |
| 17 | 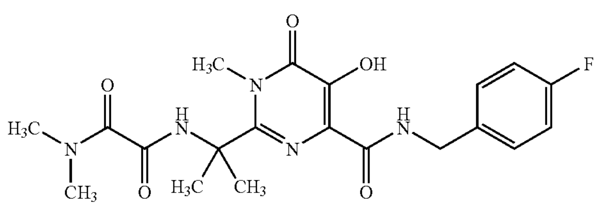 | N-1-[1-(4-{[(4-fluorobenzyl)amino]carbonyl}-5-hydroxy-1-methyl-6-oxo-1,6-dihydropyrimidin-2-yl)-1-methylethyl]-N-2-,N-2-dihydropyrimidine-4-carboxamide | 434 | 8 |
| 18 | 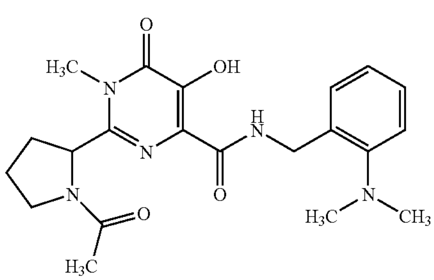 | 2-(1-acetylpyrrolidin-2-yl)-N-[2-(dimethylamino)benzyl]-5-hydroxy-1-methyl-6-oxo-1,6 dihydropyrimidine-4-carboxamide | 414 | 4 |
| 19 | 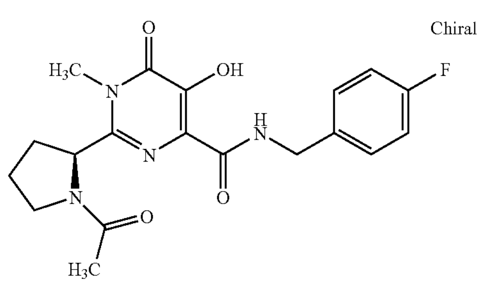 | 2-[(2S)-1-acetylpyrrolidin-2-yl]-N-(4-fluorobenzyl)-5-hydroxy-1-methyl-6-oxo-1,6-dihydropyrimidine-4-carboxamide | 389 | 1 |

TABLE 2-continued

| Exp. | STRUCTURE | Name | M + 1 | Scheme |
|---|---|---|---|---|
| 20 | 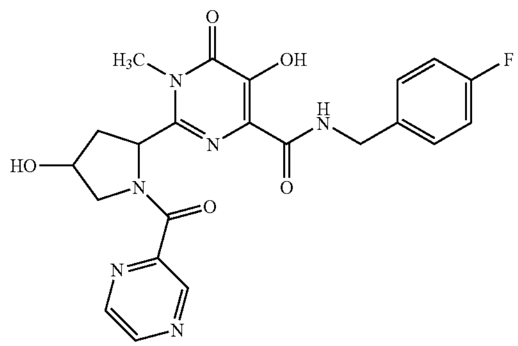 | N-(4-fluorobenzyl)-5-hydroxy-2-[4-hydroxy-1-(pyrazin-2-ylcarbonyl)pyrrolidin-2-yl]-1-methyl-6-oxo-1,6-dihydropyrimidine-4-carboxamide | 469 | 5* |
| 21 | 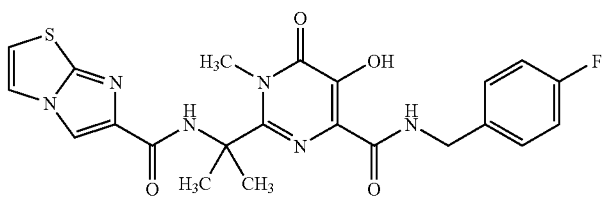 | N-[1-(4-{[(4-fluorobenzyl)amino]carbonyl}-5-hydroxy-1-methyl-6-oxo-1,6-dihydropyrimidin-2-yl)-1-methylethyl]imidazo[2,1-b][1,3]thiazole-6-carboxamide | 485 | 5 |
| 22 | 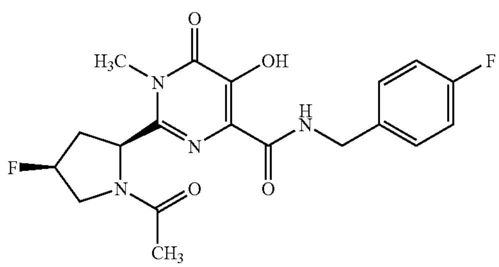 | 2-[(2S,4S)-1-acetyl-4-fluoropyrrolidin-2-yl]-N-(4-fluorobenzyl)-5-hydroxy-1-methyl-6-oxo-1,6-dihydropyrimidine-4-carboxamide | 407 | 1 |
| 23 | 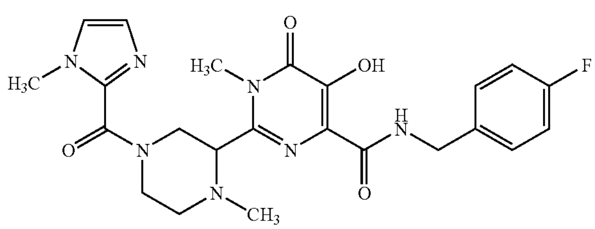 | N-(4-fluorobenzyl)-5-hydroxy-1-methyl-2-{1-methyl-4-[(1-methyl-1H-imidazol-2-yl)carbonyl]piperazin-2-yl}-6-oxo-1,6-dihydropyrimidine-4-carboxamide | 484 | 5 |
| 24 | 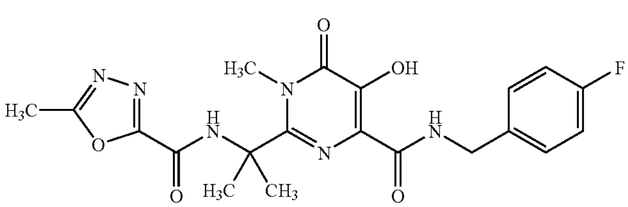 | N-(4-fluorobenzyl)-5-hydroxy-1-methyl-2-(1-methyl-1-{[(5-methyl-1,3,4-oxadiazol-2-yl)carbonyl]amino}ethyl)-6-oxo-1,6 dihyropyrimidine-4-carboxamide | 445 | 5 |
| 25 | 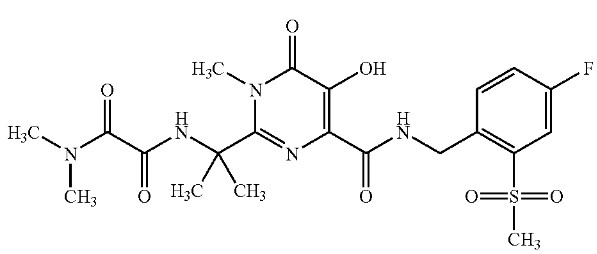 | N-1-{1-[4-({[4-fluoro-2-(methylsulfonyl)benzyl]amino}carbonyl)-5-hydroxy-1-methyl-6-oxo-1,6-dihydropyrimidin-2-yl]-1-methylethyl}-N-2,N-2-dimethylethanediamide | 512 | 8 |

TABLE 2-continued

| Exp. | STRUCTURE | Name | M + 1 | Scheme |
|---|---|---|---|---|
| 26 | 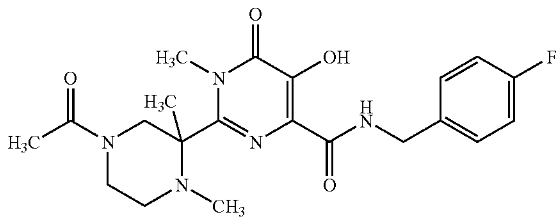 | 2-(4-acetyl-1,2-dimethylpiperazin-2-yl)-N-(4-fluorobenzyl)-5-hydroxy-1-methyl-6-oxo-1,6-dihydropyrimidine-4-carboxamide | 432 | 5 |
| 27 | 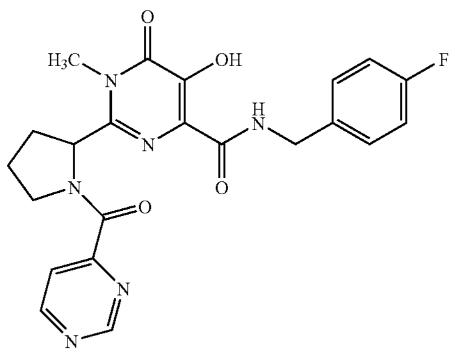 | N-(4-fluorobenzyl)-5-hydroxy-1-methyl-6-oxo-2-[1-(pyrimidin-4-ylcarbonyl)pyrrolidin-2-yl]-1,6 dihydropyrimidine-4-carboxamide | 453 | 1 |
| 28 | 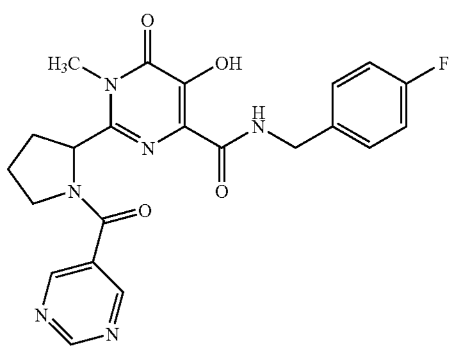 | N-(4-fluorobenzyl)-5-hydroxy-1-methyl-6-oxo-2-[1-(pyrimidin-5-ylcarbonyl)pyrrolidin-2-yl]-1,6-dihydropyrimidine-4-carboxamide | 453 | 1 |
| 29 | 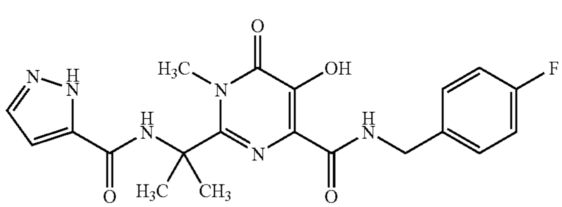 | N-(4-fluorobenzyl)-5-hydroxy-1-methyl-2-{1-methyl-1-[(1H-pyrazol 5-ylcarbonyl)amino]ethyl}-6-oxo-1,6-dihydropyrimidine-4-carboxamide | 429 | 5 |
| 30 | 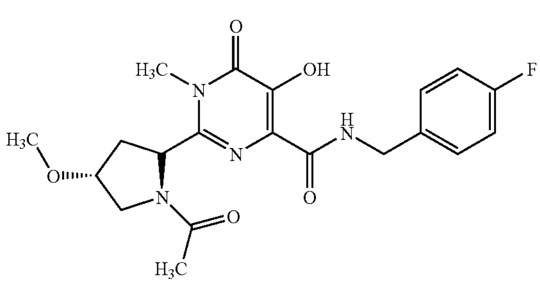 | 2-[(2R,4R)-1-acetyl-4-methoxypyrrolidin-2-yl]-N-(4-fluorobenzyl)-5-hydroxy-1-methyl-6-oxo-1,6-dihydropyrimidine-4-carboxamide | 419 | 1 |

TABLE 2-continued

| Exp. | STRUCTURE | Name | M + 1 | Scheme |
|---|---|---|---|---|
| 31 | 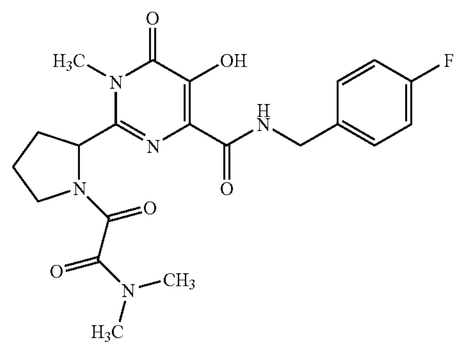 | 2-{1-[(dimethylamino)(oxo)acetyl]pyrrolidin-2-yl}-N-(4-fluorobenzyl)-5-hydroxy-1-methyl-6-oxo-1,6-dihydropyrimidine-4-carboxamide | 446 | 8 |
| 32 | 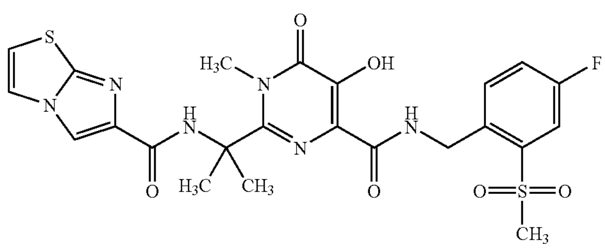 | N-{1-[4-({[4-fluoro-2-(methylsulfonyl)benzyl]amino}carbonyl)-5-hydroxy-1-methyl-6-oxo-1,6-dihydropyrimidin-2-yl]-1-methylethyl}imidazo[2,1-b][1,3]thiazole-6-carboxamide | 563 | 5 |
| 33 | 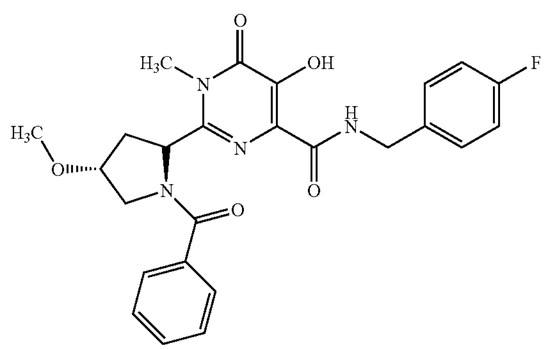 | 2-[(2R,4R)-1-benzoyl-4-methoxypyrrolidin-2-yl]-N-(4-fluorobenzyl)-5-hydroxy-1-methyl-6-oxo-1,6-dihydropyrimidine-4-carboxamide | 481 | 5* |
| 34 | 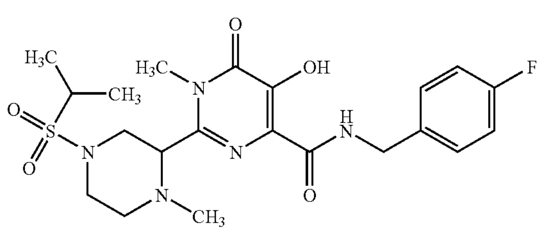 | N-(4-fluorobenzyl)-5-hydroxy-2-[4-(isopropylsulfonyl)-1-methylpiperazin-2-yl]-1-methyl-6-oxo-1,6-dihydropyrimidine-4-carboxamide | 482 | 5 |
| 35 | 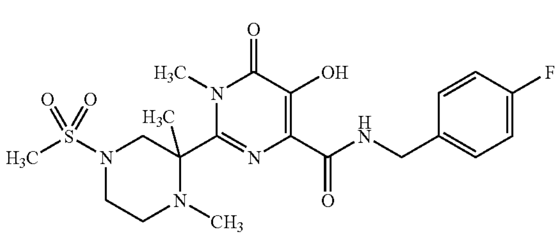 | 2-[1,2-dimethyl-4-(methylsulfonyl)piperazin-2-yl]-N-(4-fluorobenzyl)-5-hydroxy-1-methyl-6-oxo-1,6-dihydropyrimidine-4-carboxamide | 468 | 5 |

TABLE 2-continued

| Exp. | STRUCTURE | Name | M + 1 | Scheme |
|---|---|---|---|---|
| 36 | 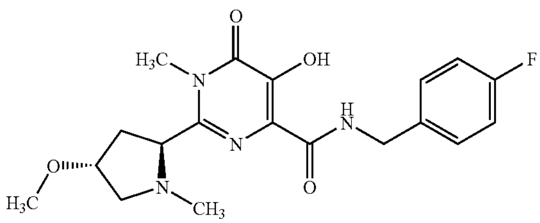 | N-(4-fluorobenzyl)-5-hydroxy-2-[(2S,4R)-4-methoxy-1-methylpyrrolidin-2-yl]-1-methyl-6-oxo-1,6-dihydropyrimidine-4-carboxamide | 391 | 4 |
| 37 | 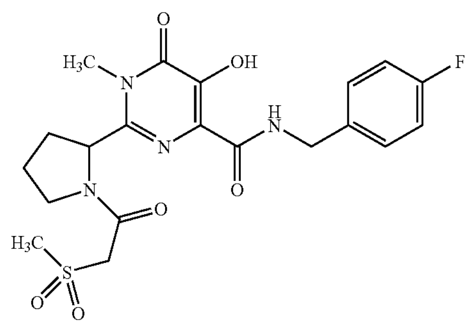 | N-(4-fluorobenzyl)-5-hydroxy-1-methyl-2-{1-[(methylsulfonyl)acetyl]pyrrolidin-2-yl}-6-oxo-1,6-dihydropyrimidine-4-carboxamide | 467 | 1 |
| 38 | 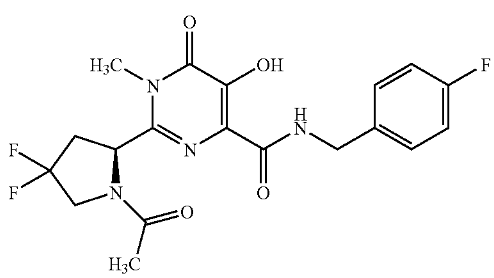 | 2-[(2S)-1-acetyl-4,4-difluoropyrrolidin-2-yl]-N-(4-fluorobenzyl)-5-hydroxy-1-methyl-6-oxo-1,6-dihydropyrimidine-4-carboxamide | 425 | 1 |
| 39 | 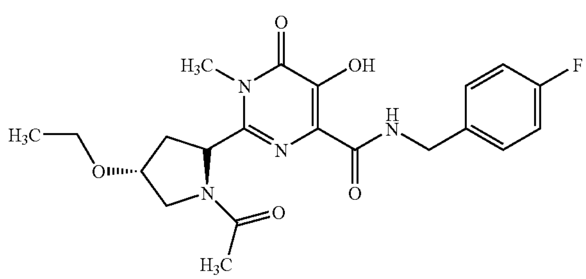 | 2-[(2R,4R)-1-acetyl-4-ethoxypyrrolidin-2-yl]-N-(4-fluorobenzyl)-5-hydroxy-1-methyl-6-oxo-1,6-dihydropyrimidine-4-carboxamide | 433 | 1 |
| 40 | 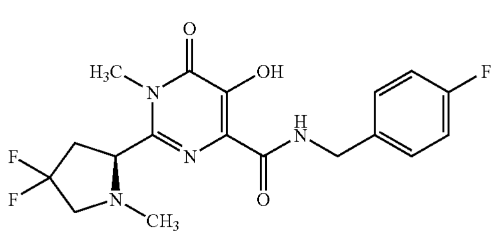 | 2-[(2S)-4,4-difluoro-1-methylpyrrolidin-2-yl]-N-(4-fluorobenzyl)-5-hydroxy-1-methyl-6-oxo-1,6-dihydropyrimidine-4-carboxamide | 397 | 4 |

TABLE 2-continued

| Exp. | STRUCTURE | Name | M + 1 | Scheme |
|---|---|---|---|---|
| 41 | 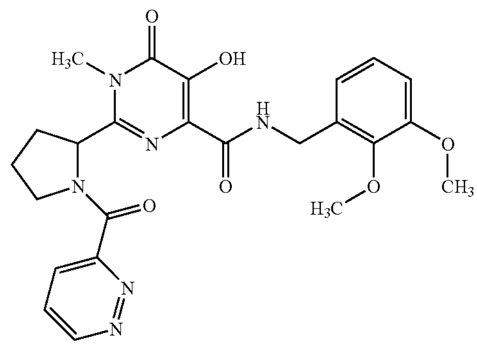 | N-(2,3-dimethoxybenzyl)-5-hydroxy-1-methyl-6-oxo-2-[1-(pyridazin-3-ylcarbonyl)pyrrolidin-2-yl]-1,6-dihydropyrimidine-4-carboxamide | 495 | 1 |
| 42 | 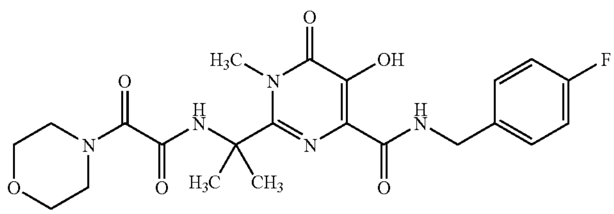 | N-(4-fluorobenzyl)-5-hydroxy-1-methyl-2-(1-methyl-1-{[morpholin-4-yl(oxo)acetyl]amino}ethyl)-6-oxo 1,6-dihydropyrimidine-4-carboxamide | 476 | 8 |
| 43 | 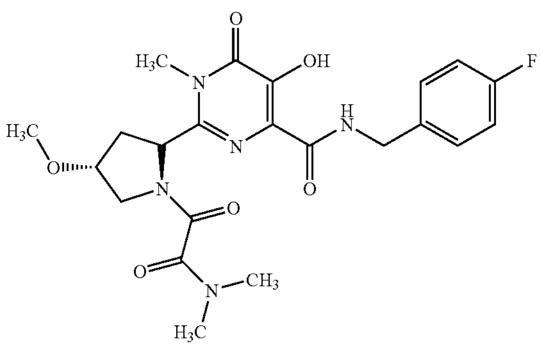 | 2-{(2R,4R)-1-[(dimethylamino)(oxo)acetyl]-4-methoxypyrrolidin-2-yl}-N-(4-fluorobenzyl)-5-hydroxy-1-methyl-6-oxo-1,6-dihydropyrimidine-4-carboxamide | 476 | 8 |
| 44 | 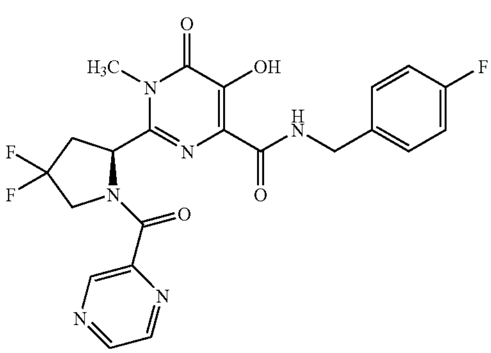 | 2-[(2S)-4,4-difluoro-1-(pyrazin-2-ylcarbonyl)pyrrolidin-2-yl]-N-(4-fluorobenzyl)-5-hydroxy-1-methyl-6-oxo-1,6-dihydropyrimidine-4-carboxamide | 489 | 5 |
| 45 | 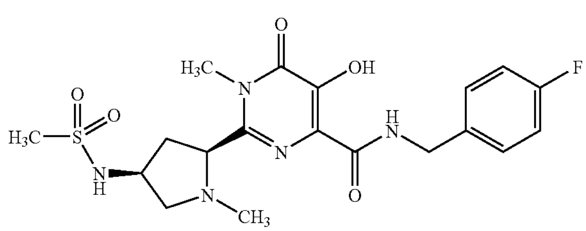 | N-(4-fluorobenzyl)-5-hydroxy-1-methyl-2-{(2S,4S)-1-methyl-4-[(methylsulfonyl)amino]pyrrolidin-2-yl}-6-oxo-1,6-dihydropyrimidine-4-carboxamide | 454 | 4 |

TABLE 2-continued

| Exp. | STRUCTURE | Name | M + 1 | Scheme |
|---|---|---|---|---|
| 46 | 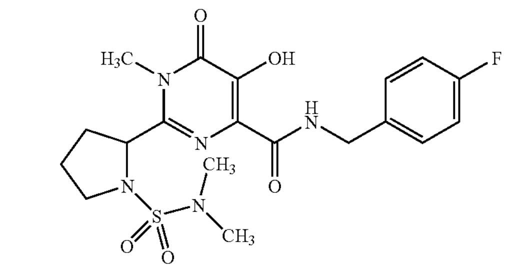 | 2-{1-[(dimethylamino)sulfonyl]pyrrolidin-2-yl}-N-(4-fluorobenzyl)-5-hydroxy-1-methyl-6-oxo-1,6-dihydropyrimidine-4-carboxamide | 454 | 5 |
| 47 | 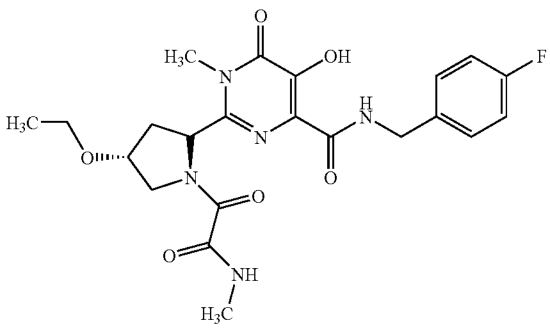 | 2-{(2R,4R)-4-ethoxy-1-[(methylamino)(oxo)acetyl]pyrrolidin-2-yl}-N-(4-fluorobenzyl)-5-hydroxy-1-methyl-6-oxo-1,6-dihydropyrimidine-4-carboxamide | 476 | 8 |
| 48 | 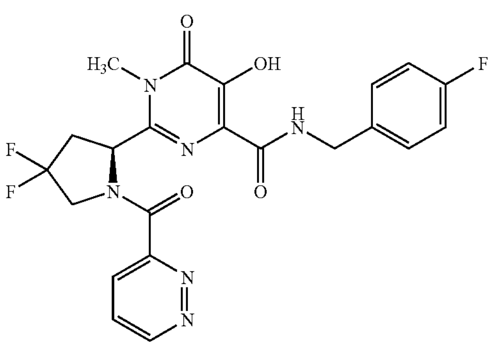 | 2-[(2S)-4,4-difluoro-1-(pyridazin-3-ylcarbonyl)pyrrolidin-2-yl]-N-(4-fluorobenzyl)-5-hydroxy-1-methyl-6-oxo-1,6-dihydropyrimidine-4-carboxamide | 489 | 5 |
| 49 | 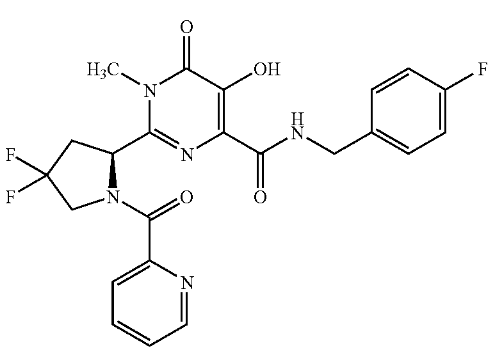 | 2-[(2S)-4,4-difluoro-1-(pyridin-2-ylcarbonyl)pyrrolidin-2-yl]-N-(4-fluorobenzyl)-5-hydroxy-1-methyl-6-oxo-1,6-dihydropyrimidine-4-carboxamide | 488 | 5 |

TABLE 2-continued

| Exp. | STRUCTURE | Name | M + 1 | Scheme |
|---|---|---|---|---|
| 50 | 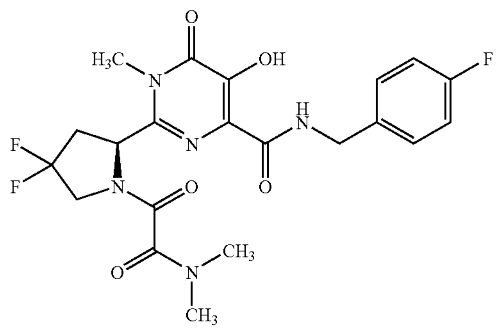 | 2-{(2S)-1-[(dimethylamino)(oxo)acetyl]-4,4-difluoropyrrolidin-2-yl}-N-(4-fluorobenzyl)-5-hydroxy-1-methyl-6-oxo-1,6-dihydropyrimidine-4-carboxamide | 482 | 8 |
| 51 | 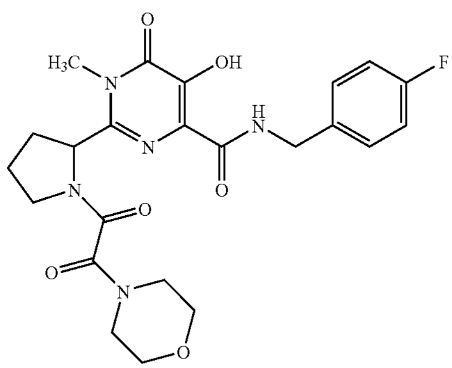 | N-(4-fluorobenzyl)-5-hydroxy-1-methyl-2-{1-[morpholin-4-yl(oxo)acetyl]pyrrolidin-2-yl}-6-oxo-1,6-dihydropyrimidine-4-carboxamide | 488 | 8 |
| 52 | | 2-{(2S)-1-[(dimethylamino)(oxo)acetyl]pyrrolidin-2-yl}-N-(4-fluorobenzyl)-5-hydroxy-1-methyl-6-oxo-1,6-dihydropyrimidine-4-carboxamide | 446 | 8 |
| 52 | | 2-{(2S)-1-[(dimethylamino)(oxo)acetyl]pyrrolidin-2-yl}-N-(4-fluoro-2-methoxybenzyl)-5-hydroxy-1-methyl-6-oxo-1,6-dihydropyrimidine-4-carboxamide | 476 | 8 |

TABLE 2-continued

| Exp. | STRUCTURE | Name | M + 1 | Scheme |
|---|---|---|---|---|
| 54 | 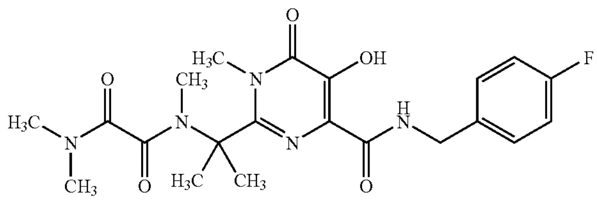 | N1-[1-(4-{[(4-fluorobenzyl)amino]carbonyl}-5-hydroxy-1-methyl-6-oxo-1,6-dihydropyrimidin-2-yl)-1-methylethyl]-N1,N2,N2-trimethylethanediamide | 448 | 8 |
| 55 | 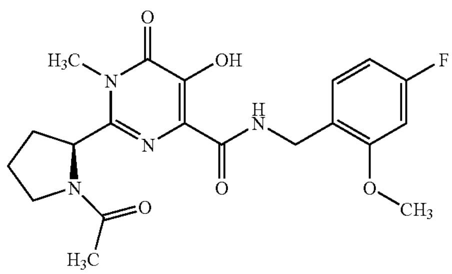 | 2-[(2S)-1-acetylpyrrolidin-2-yl]-N-(4-fluoro-2-methoxybenzyl)-5-hydroxy-1-methyl-6-oxo-1,6-dihydropyrimidine-4-carboxamide | 419 | 1 |
| 56 | 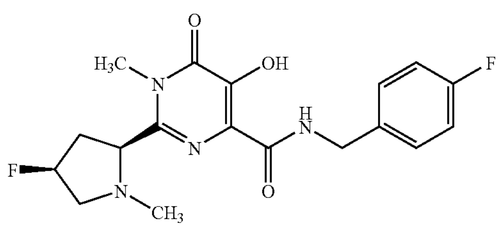 | N-(4-fluorobenzyl)-2-[(2S,4S)-4-fluoro-1-methylpyrrolidin-2-yl]-5-hydroxy-1-methyl-6-oxo-1,6-dihydropyrimidine-4-carboxamide | 379 | 4 |
| 57 | 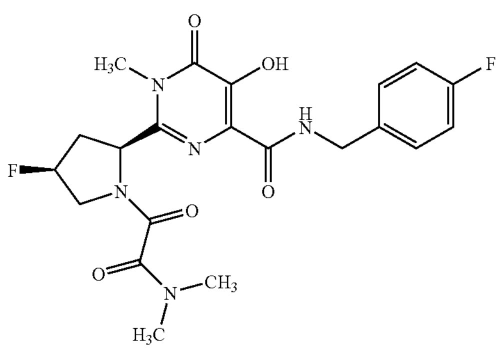 | 2-{(2S,4S)-1-[(dimethylamino)(oxo)acetyl]-4-fluoropyrrolidin-2-yl}-N-(4-fluorobenzyl)-5-hydroxy-1-methyl-6-oxo-1,6-dihydropyrimidine-4-carboxamide | 464 | 8 |
| 58 | 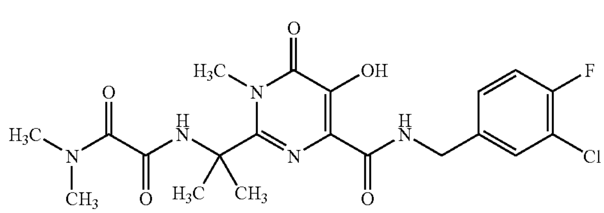 | N1-[1-(4-{[(3-chloro-4-fluorobenzyl)amino]carbonyl}-5-hydroxy-1-methyl-6-oxo-1,6-dihydropyrimidin-2-yl)-1-methylethyl]-N2,N2-dimethylethanediamide | 468 | 8 |

While the foregoing specification teaches the principles of the present invention, with examples provided for the purpose of illustration, the practice of the invention encompasses all of the usual variations, adaptations and/or modifications that come within the scope of the following claims.

What is claimed is:

1. A method for treating infection by HIV or for treating or delaying the onset of AIDS in a subject in need thereof which comprises administering to the subject a therapeutically effective amount of a compound of Formula I:

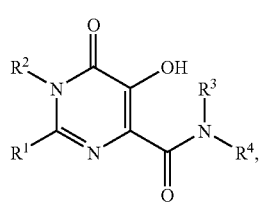

(I)

or a pharmaceutically acceptable salt thereof; wherein
$R^1$ is
(1) —H,
(2) —$C_{1-6}$ alkyl, which is optionally substituted with one or more substituents each of which is independently halogen, —OH, —CN, —O—$C_{1-6}$ alkyl, —O—$C_{1-6}$ haloalkyl, —C(=O)$R^a$, —CO$_2R^a$, —S$R^a$, —S(=O)$R^a$, —N($R^aR^b$), —C(=O)—$C_{0-6}$ alkyl-N($R^aR^b$), N($R^a$)—C(=O)—$C_{0-6}$ alkyl-N($R^bR^c$), —SO$_2R^a$, —N($R^a$)SO$_2R^b$, —SO$_2$N($R^aR^b$), —N($R^a$)—C(=O)$R^b$,

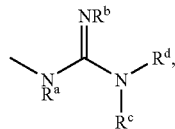

or —N($R^a$)C(=O)C(=O)N($R^aR^b$),
(3) —$R^k$,
(4) —$C_{1-6}$ alkyl-$R^k$, wherein:
  (i) the alkyl is optionally substituted with one or more substituents each of which is independently halogen, —OH, —CN, —O—$C_{1-6}$ alkyl, —O—$C_{1-6}$ haloalkyl, —N($R^aR^b$), —N($R^a$)CO$_2R^b$, —N($R^a$)C(=O)—$C_{0-6}$ alkyl-N($R^aR^c$), or —N($R^a$)—$C_{2-6}$ alkyl-OH with the proviso that the —OH is not attached to the carbon alpha to N($R^a$); and
  (ii) the alkyl is optionally mono-substituted with —$R^s$, —$C_{1-6}$ alkyl-$R^s$, —N($R^a$)—C(=O)—$C_{0-6}$ alkyl-$R^s$, —N($R^a$)—$C_{0-6}$ alkyl-$R^s$, —O—$C_{0-6}$ alkyl-$R^s$, or —N($R^a$)—C(=)—$C_{0-6}$ alkyl-$R^s$; wherein $R^s$ is
    (a) aryl which is optionally substituted with one or more substituents each of which is independently halogen, —OH, —$C_{1-6}$ alkyl, —$C_{1-6}$ alkyl-O$R^a$, —$C_{1-6}$ haloalkyl —O—$C_{1-6}$ alkyl, —O—$C_{1-6}$ haloalkyl, methylenedioxy attached to two adjacent carbon atoms, or aryl;
    (b) a 4- to 8-membered saturated heterocyclic ring containing from 1 to 4 heteroatoms independently selected from N, O and S; wherein the saturated heterocyclic ring is optionally substituted with one or more substituents each of which is independently halogen, —$C_{1-6}$ alkyl, —$C_{1-6}$ alkyl-O$R^a$, —$C_{1-6}$ haloalkyl, —O—$C_{1-6}$ alkyl, —O—$C_{1-6}$ haloalkyl, —C(=O)$R^a$, —CO$_2R^a$, —C(=O)—$C_{0-6}$ alkyl-N($R^aR^b$), —SO$_2R^a$, oxo, aryl, or —$C_{1-6}$ alkyl-aryl; or
    (c) a 5- to 7-membered heteroaromatic ring containing from 1 to 4 heteroatoms independently selected from N, O and S; wherein the heteroaromatic ring is optionally substituted with one or more substituents each of which is independently halogen, —$C_{1-6}$ alkyl, —$C_{1-6}$ alkyl-O$R^a$, —$C_{1-6}$ haloalkyl, —O—$C_{1-6}$ alkyl, —O—$C_{1-6}$ haloalkyl, oxo, or aryl;
(5) —$C_{0-6}$ alkyl-O—$C_{0-6}$ alkyl-$R^k$,
(6) —$C_{0-6}$ alkyl-S(O)$_n$—$C_{0-6}$ alkyl-$R^k$,
(7) —O—$C_{1-6}$ alkyl-O$R^k$,
(8) —O—$C_{1-6}$alkyl-O—$C_{1-6}$alkyl-$R^k$,
(9) —O—$C_{1-6}$ alkyl-S(O)$_nR^k$,
(10) —$C_{0-6}$ alkyl-N($R^a$)—$R^k$,
(11) —$C_{0-6}$ alkyl-N($R^a$)—$C_{1-6}$ alkyl-$R^k$,
(12) —$C_{0-6}$ alkyl-N($R^a$)—$C_{1-6}$ alkyl-O$R^k$,
(13) —$C_{0-6}$ alkyl-C(=O)-$R^k$,
(14) —$C_{0-6}$ alkyl-C(=O)N($R^a$)—$C_{0-6}$ alkyl-$R^k$,
(15) —$C_{0-6}$ alkyl-N($R^a$)C(=O)—$C_{0-6}$ alkyl-$R^k$,
(16) —$C_{0-6}$ alkyl-N($R^a$)C(=O)—O—$C_{0-6}$ alkyl-$R^k$, or
(17) —$C_{0-6}$ alkyl-N($R^a$)C(=O)C(=O)$R^k$;
$R^2$ is —$C_{1-6}$ alkyl which is optionally substituted with one or more substituents each of which is independently
(1) halogen,
(2) —OH,
(3) —CN,
(4) —O—$C_{1-6}$ alkyl,
(5) —O—$C_{1-6}$ haloalkyl,
(6) —C(=O)$R^a$,
(7) —CO$_2R^a$,
(8) —S$R^a$,
(9) —S(=O)$R^a$,
(10) —N($R^aR^b$),
(11) —C(=O)N($R^aR^b$),
(12) —N($R^a$)—C(=O)—$C_{1-6}$ alkyl-N($R^bR^c$),
(13) —SO$_2R^a$,
(14) —N($R^a$)SO$_2R^b$,
(15) —SO$_2$N($R^aR^b$),
(16) —N($R^a$)—C($R^b$)=O,
(17) —$C_{3-8}$ cycloalkyl,
(18) aryl, wherein the aryl is optionally substituted with one or more substituents each of which is independently halogen, —$C_{1-6}$ alkyl, —$C_{1-6}$ haloalkyl, —O—$C_{1-6}$ alkyl, —O—$C_{1-6}$ haloalkyl, —$C_{0-6}$ alkyl-N($R^aR^b$), or —$C_{1-6}$ alkyl substituted with a 5- or 6-membered saturated heterocyclic ring containing from 1 to 4 heteroatoms independently selected from N, O and S;
  wherein the saturated heterocyclic ring is optionally substituted with from 1 to 3 substituents each of which is independently —$C_{1-6}$ alkyl, oxo, or a 5- or 6-membered heteroaromatic ring containing from 1 to 4 heteroatoms independently selected from N, O and S; or
(19) a 5- to 8-membered monocyclic heterocycle which is saturated or unsaturated and contains from 1 to 4 heteroatoms independently selected from N, O and S; wherein the heterocycle is optionally substituted with one or more substituents each of which is independently —$C_{1-6}$ alkyl, —O—$C_{1-6}$ alkyl, oxo, phenyl, or naphthyl;

with the proviso that none of the following substituents is attached to the carbon atom in the —$C_{1-6}$ alkyl group that is attached to the ring nitrogen: halogen, —OH, —O—$C_{1-6}$ alkyl, —O—$C_{1-6}$ haloalkyl, —$SR^a$, —S(=O)$R^a$, or —N($R^a$)—C($R^b$)=O;

$R^3$ is —H or —$C_{1-6}$ alkyl;

$R^4$ is (1) H, (2) $C_{1-6}$ alkyl which is optionally substituted with one or more substituents each of which is independently halogen, —OH, O—$C_{1-6}$ alkyl, —O—$C_{1-6}$ haloalkyl, —$NO_2$, —N($R^aR^b$), —C(=O)$R^a$, —$CO_2R^a$, —$SR^a$, —S(=O)$R^a$, —$SO_2R^a$, or —N($R^a$)$CO_2R^b$, (3) $C_{1-6}$ alkyl which is optionally substituted with one or more substituents each of which is independently halogen, —OH, or O—$C_{1-4}$ alkyl, and which is substituted with 1 or 2 substituents each of which is independently:

(i) $C_{3-8}$ cycloalkyl, (ii) aryl, (iii) a fused bicyclic carbocycle consisting of a benzene ring fused to a $C_{5-7}$ cycloalkyl, (iv) a 5- or 6-membered saturated heterocyclic ring containing from 1 to 4 heteroatoms independently selected from N, O and S, (v) a 5- or 6-membered heteroaromatic ring containing from 1 to 4 heteroatoms independently selected from N, O and S, or (vi) a 9- or 10-membered fused bicyclic heterocycle containing from 1 to 4 heteroatoms independently selected from N, O and S, wherein at least one of the rings is aromatic, (4) $C_{2-5}$ alkynyl optionally substituted with aryl, (5) $C_{3-8}$ cycloalkyl optionally substituted with aryl, (6) aryl, (7) a fused bicyclic carbocycle consisting of a benzene ring fused to a $C_{5-7}$ cycloalkyl, (8) a 5- or 6-membered saturated heterocyclic ring containing from 1 to 4 heteroatoms independently selected from N, O and S, (9) a 5- or 6-membered heteroaromatic ring containing from 1 to 4 heteroatoms independently selected from N, O and S, or

(10) a 9- or 10-membered fused bicyclic heterocycle containing from 1 to 4 heteroatoms independently selected from N, O and S, wherein at least one of the rings is aromatic;

wherein each aryl in (3)(ii) or the aryl in (4), (5) or (6) or each fused carbocycle in (3)(iii) or the fused carbocycle in (7) is optionally substituted with one or more substituents each of which is independently halogen, —OH, —$C_{1-6}$ alkyl, —$C_{1-6}$ alkyl-$OR^a$, —$C_{1-6}$ haloalkyl, —O—$C_{1-6}$ alkyl, —O—$C_{1-6}$ haloalkyl, —CN, —$NO_2$, —N($R^aR^b$), —$C_{1-6}$ alkyl-N($R^aR^b$), —C(=O)N($R^aR^b$), —C(=O)$R^a$, —$CO_2R^a$, —$C_{1-6}$ alkyl-$CO_2R^a$, —$OCO_2R^a$, —$SR^a$, —S(=O)$R^a$, —$SO_2R^a$, —N($R^a$)$SO_2R^b$, —$SO_2$N($R^aR^b$), —N($R^a$)C(=O)$R^b$, —N($R^a$)$CO_2R^b$, —$C_{1-6}$ alkyl-N($R^a$)$CO_2R^b$, aryl, —$C_{1-6}$ alkyl-aryl, —O-aryl, or —$C_{0-6}$ alkyl-het wherein het is a 5- or 6-membered heteroaromatic ring containing from 1 to 4 heteroatoms independently selected from N, O and S, and het is optionally fused with a benzene ring, and is optionally substituted with one or more substituents each of which is independently —$C_{1-6}$ alkyl, —$C_{1-6}$ haloalkyl, —O—$C_{1-6}$ alkyl, —O—$C_{1-6}$ haloalkyl, oxo, or —$CO_2R^a$;

each saturated heterocyclic ring in (3)(iv) or the saturated heterocyclic ring in (8) is optionally substituted with one or more substituents each of which is independently halogen, —$C_{1-6}$ alkyl, —$C_{1-6}$ haloalkyl, —O—$C_{1-6}$alkyl, —O—$C_{1-6}$ haloalkyl, oxo, aryl, or a 5- or 6-membered heteroaromatic ring containing from 1 to 4 heteroatoms independently selected from N, O and S; and each heteroaromatic ring in (3)(v) or the heteroaromatic ring in (9) or each fused bicyclic heterocycle in (3)(vi) or the fused bicyclic heterocycle in (10) is optionally substituted with one or more substituents each of which is independently halogen, —$C_{1-6}$ alkyl, —$C_{1-6}$ haloalkyl, —O—$C_{1-6}$ alkyl, —O—$C_{1-6}$ haloalkyl, oxo, aryl, or —$C_{1-6}$ alkyl-aryl;

or alternatively $R^3$ and $R^4$ together with the N to which both are attached form a $C_{3-7}$ azacycloalkyl which is optionally substituted with one or more substituents each of which is independently —$C_{1-6}$ alkyl or oxo;

each $R^a$, $R^b$, $R^c$ and $R^d$ is independently —H or —$C_{1-6}$ alkyl;

$R^k$ is carbocycle or heterocycle, wherein the carbocycle or heterocycle is optionally substituted with one or more substituents each of which is independently (1) halogen, (2) —OH, (3) —CN, (4) —$C_{1-6}$ alkyl, which is optionally substituted with one or more substituents each of which is independently halogen, —OH, —CN, —O—$C_{1-6}$ alkyl, —O—$C_{1-6}$ haloalkyl, —C(=O)$R^a$, —$CO_2R^a$, —$SR^a$, —S(=O)$R^a$, —N($R^aR^b$), —C(=O)—$(CH_2)_{0-2}$N($R^aR^b$), N($R^a$)—C(=O)—$(CH_2)_{0-2}$N($R^bR^c$), —$SO_2R^a$, —N($R^a$)$SO_2R^b$, —$SO_2$N($R^aR^b$), or —N($R^a$)—C($R^b$)=O, (5) —O—$C_{1-6}$ alkyl, which is optionally substituted with one or more substituents each of which is independently halogen, —OH, —CN, —O—$C_{1-6}$ alkyl, —O—$C_{1-6}$ haloalkyl, —C(=O)$R^a$, —$CO_2R^a$, —$SR^a$, —S(=O)$R^a$, —N($R^aR^b$), —C(=O)—$(CH_2)_{0-2}$N($R^aR^b$), N($R^a$)—C(=O)—$(CH_2)_{0-2}$N($R^bR^c$), —$SO_2R^a$, —N($R^a$)$SO_2R^b$, —$SO_2$N($R^aR^b$), or —N($R^a$)—C($R^b$)=O, (6) —$NO_2$, (7) oxo, (8) —C(=O)$R^a$, (9) —$CO_2R^a$,

(10) —$SR^a$,

(11) —S(=O)$R^a$,

(12) —N($R^aR^b$),

(13) —C(=O)N($R^aR^b$),

(14) —C(=O)—$C_{1-6}$ alkyl-N($R^aR^b$),

(15) —N($R^a$)C(=O)$R^b$,

(16) —$SO_2R^a$,

(17) —$SO_2$N($R^aR^b$),

(18) —N($R^a$)$SO_2R^b$,

(19) —$R^m$,

(20) —$C_{1-6}$ alkyl-$R^m$, wherein the alkyl is optionally substituted with one or more substituents each of which is independently halogen, —OH, —CN, —$C_{1-6}$ haloalkyl, —O—$C_{1-6}$ alkyl, —O—$C_{1-6}$ haloalkyl, —C(=O)$R^a$, —$CO_2R^a$, —$SR^a$, —S(=O)R$^a$, —N(R$^a$R$^b$), —N(R$^a$)CO$_2$R$^b$, —SO$_2$R$^a$, —N(R$^a$)SO$_2$R$^b$, —SO$_2$N(R$^a$R$^b$), or —N(R$^a$)—C(R$^b$)=O,

(21) —C$_{0-6}$ alkyl-N(R$^a$)—C$_{0-6}$ alkyl-R$^m$,
(22) —C$_{0-6}$ alkyl-O—C$_{0-6}$ alkyl-R$^m$,
(23) —C$_{0-6}$ alkyl-S—C$_{0-6}$ alkyl-R$^m$,
(24) —C$_{0-6}$ alkyl-C(=O)—C$_{0-6}$ alkyl-R$^m$,
(25) —C(=O)—O—C$_{0-6}$ alkyl-R$^m$,
(26) —C(=O)N(R$^a$)—C$_{0-6}$ alkyl-R$^m$,
(27) —N(R$^a$)C(=O)—R$^m$,
(28) —N(R$^a$)C(=O)—C$_{1-6}$ alkyl-R$^m$, wherein the alkyl is optionally substituted with one or more substituents each of which is independently halogen, —OH, —CN, —C$_{1-6}$ haloalkyl, —O—C$_{1-6}$ alkyl, —O—C$_{1-6}$ haloalkyl, —C(=O)R$^a$, —CO$_2$R$^a$, —SR$^a$, —S(=O)R$^a$, —N(R$^a$R$^b$), —N(R$^a$)CO$_2$R$^b$, —SO$_2$R$^a$, —N(R$^a$)SO$_2$R$^b$, —SO$_2$N(R$^a$R$^b$), or —N(R$^a$)—C(R$^b$)=O,
(29) —N(R$^a$)—C(=O)—N(R$^b$)—C$_{0-6}$ alkyl-R$^m$,
(30) —N(R$^a$)—C(=O)—O—C$_{0-6}$ alkyl-R$^m$,
(31) —N(R$^a$)—C(=O)—N(R$^b$)—SO$_2$—C$_{0-6}$ alkyl-R$^m$,
(32) —C(=O)—C(=O)—N(R$^a$R$^b$),
(33) —C(=O)—C$_{1-6}$ alkyl-SO$_2$R$^a$, or
(34) —C(=O)—C(=O)R$^m$, carbocycle in R$^k$ is (i) a C$_3$ to C$_8$ monocyclic saturated or unsaturated ring, (ii) a C$_7$ to C$_{12}$ bicyclic ring system, or (iii) a C$_{11}$ to C$_{16}$ tricyclic ring system, wherein each ring in (ii) or (iii) is independent of or fused to the other ring or rings and each ring is saturated or unsaturated;

heterocycle in R$^k$ is (i) a 4- to 8-membered, saturated or unsaturated monocyclic ring, (ii) a 7- to 12-membered bicyclic ring system, or (iii) an 11 to 16-membered tricyclic ring system; wherein each ring in (ii) or (iii) is independent of or fused to the other ring or rings and each ring is saturated or unsaturated; the monocyclic ring, bicyclic ring system or tricyclic ring system contains from 1 to 6 heteroatoms selected from N, O and S and a balance of carbon atoms; and wherein any one or more of the nitrogen and sulfur heteroatoms is optionally be oxidized, and any one or more of the nitrogen heteroatoms is optionally quaternized;

each R$^m$ is independently C$_{3-8}$ cycloalkyl; aryl; a 5- to 8-membered monocyclic heterocycle which is saturated or unsaturated and contains from 1 to 4 heteroatoms independently selected from N, O and S; or a 9- to 10-membered bicyclic heterocycle which is saturated or unsaturated and contains from 1 to 4 heteroatoms independently selected from N, O and S; wherein any one or more of the nitrogen and sulfur heteroatoms in the heterocycle or bicyclic heterocycle is optionally oxidized and any one or more of the nitrogen heteroatoms is optionally quaternized; and wherein the cycloalkyl or the aryl defined in R$^m$ is optionally substituted with one or more substituents each of which is independently halogen, —C$_{1-6}$ alkyl optionally substituted with —O—C$_{1-4}$ alkyl, —C$_{1-6}$ haloalkyl, —O—C$_{1-6}$ alkyl, —O—C$_{1-6}$ haloalkyl, —N(R$^a$R$^b$), aryl, or —C$_{1-6}$ alkyl-aryl; and the monocyclic or bicyclic heterocycle defined in R$^m$ is optionally substituted with one or more substituents each of which is independently halogen, —C$_{1-6}$ alkyl, —C$_{1-6}$ haloalkyl, —O—C$_{1-6}$ alkyl, —O—C$_{1-6}$ haloalkyl, oxo, aryl, —C$_{1-6}$ alkyl-aryl, —C(=O)-aryl, —CO$_2$-aryl, —CO$_2$—C$_{1-6}$ alkyl-aryl, a 5- or 6-membered saturated heterocyclic ring containing from 1 to 4 heteroatoms independently selected from N, O and S, or a 5- or 6-membered heteroaromatic ring containing from 1 to 4 heteroatoms independently selected from N, O and S; and each n is independently an integer equal to zero, 1 or 2.

2. The method according to claim 1, wherein the compound of Formula I is a compound selected from the group consisting of:

N1-[1-(4-{[(4-fluorobenzyl)amino]carbonyl}-5-hydroxy-1-methyl-6-oxo-1,6-dihydropyrimidin-2-yl)-1-methylethyl]-N2,N2-dimethylethanediamide;

N-(4-fluorobenzyl)-5-hydroxy-1-methyl-2-(1-methyl-1-{[(5-methyl-1,3,4-oxadiazol-2-yl)carbonyl]amino}ethyl)-6-oxo-1,6-dihydropyrimidine-4-carboxamide;

and pharmaceutically acceptable salts thereof.

3. The method according to claim 2, wherein the compound of Formula I is N1-[1-(4-{[(4-fluorobenzyl)amino]carbonyl}-5-hydroxy-1-methyl-6-oxo-1,6-dihydropyrimidin-2-yl)-1-methylethyl]-N2,N2-dimethylethanediamide or a pharmaceutically acceptable salt thereof.

4. The method according to claim 2, wherein the compound of Formula I is N-(4-fluorobenzyl)-5-hydroxy-1-methyl-2-(1-methyl-1-{[(5-methyl-1,3,4-oxadiazol-2-yl)carbonyl]amino}ethyl)-6-oxo-1,6-dihydropyrimidine-4-carboxamide or a pharmaceutically acceptable salt thereof.

5. The method according to claim 1, wherein in the compound of Formula I or a pharmaceutically acceptable salt thereof:

R$^1$ is:
(1) —H.
(2) —C$_{1-6}$ alkyl, which is optionally substituted with from 1 to 4 substituents each of which is independently halogen, —OH, —CN, —O—C$_{1-4}$ alkyl, —O—C$_{1-4}$ haloalkyl, —C(=O)R$^a$, —CO$_2$R$^a$, —SR$^a$, —S(=O)R$^a$, —N(R$^a$R$^b$), —C(=O)—C$_{0-4}$ alkyl-N(R$^a$R$^b$), N(R$^a$)—C(=O)—C$_{0-4}$ alkyl-N(R$^b$R$^c$), —SO$_2$R$^a$, —N(R$^a$)SO$_2$R$^b$, —SO$_2$N(R$^a$R$^b$), —N(R$^a$)—C(=O)R$^b$,

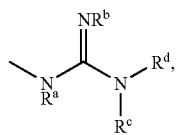

or —N(R$^2$)C(=O)C(=O)N(R$^a$R$^b$),
(3) —R$^k$,
(4) —C$_{1-4}$ alkyl-R$^k$, wherein:
(i) the alkyl is optionally substituted with from 1 to 4 substituents each of which is independently halogen, —OH, —CN, —O—C$_{1-4}$ alkyl, —O—C$_{1-4}$ haloalkyl, —N(R$^a$R$^b$), —N(R$^a$)CO$_2$R$^b$, —N(R$^a$)C(=O)—C$_{0-4}$ alkyl-N(R$^b$R$^c$), or —N(R$^a$)—(CH$_2$)$_{2-4}$—OH; and
(ii) the alkyl is optionally mono-substituted with —R$^s$, —N(R$^a$)—C(=O)—C$_{0-4}$ alkyl-R$^s$; wherein R$^2$ is
(a) aryl which is optionally substituted with from 1 to 3 substituents each of which is independently halogen, —OH, —C$_{1-4}$ alkyl, —C$_{1-4}$ alkyl-OR$^a$, —C$_{1-4}$ haloalkyl —O—C$_{1-6}$ alkyl, —O—C$_{1-4}$ haloalkyl, methylenedioxy attached to two adjacent carbon atoms, or phenyl;
(b) a 5- to 6-membered heterocyclic ring containing from 1 to 4 heteroatoms independently selected from N, O and S; wherein the heteroaromatic ring is optionally substituted with from 1 to 3 substituents each of which is independently halogen, —$C_{1-4}$ alkyl, —$C_{1-4}$ alkyl-$OR^a$, —$C_{1-4}$ haloalkyl, —O—$C_{1-4}$ alkyl, —O—$C_{1-4}$ haloalkyl, oxo, or phenyl; or (c) a 5- to 6-membered saturated heteroaromatic ring containing from 1 to 4 heteroatoms independently selected from N, O and S; wherein the saturated heterocyclic ring is optionally substituted with from 1 to 3 substituents each of which is independently halogen, —$C_{1-4}$ alkyl, —$C_{1-4}$ alkyl-$OR^a$, —$C_{1-4}$ haloalkyl, —O—$C_{1-4}$ alkyl, —O—$C_{1-4}$ haloalkyl, —C(=O)$R^a$, —$CO_2R^a$, —$C_{1-4}$ alkyl-N($R^aR^b$), —$SO_2R^a$, oxo, or phenyl, (5) —$(CH_2)_{0-3}$—C(=O)N($R^a$)—$(CH_2)_{0-3}$—$R^k$,
(6) —C($C_{1-4}$ alkyl)$_2$N($R^a$)C(=O)$R^b$,
(7) —C($C_{1-4}$ alkyl)$_2$N($R^a$)C(=O)$R^k$, or
(8) —C($C_{1-4}$ alkyl)$_2$N($R^a$)C(=O)C(=O)N($R^bR^c$).

6. The method according to claim 5, wherein in the compound of Formula I or a pharmaceutically acceptable salt thereof:
$R^2$ is methyl
$R^3$ is —H; and
$R^4$ is —$CH_2$-phenyl, wherein the phenyl is optionally substituted with from 1 to 3 substituents, each of which is independently —F, —Br, —Cl, —OH, —$C_{1-4}$ alkyl, —$C_{1-4}$ fluoroalkyl, —O—$C_{1-4}$ alkyl, —$SO_2$—$C_{1-4}$ alkyl, —S—$C_{1-4}$ alkyl, —N(CH$_3$)$_2$, or —O—$C_{1-4}$ fluoroalkyl.

7. The method according to claim 6, wherein in the compound of Formula I or a pharmaceutically acceptable salt thereof:
$R^k$ is phenyl; a 5- or 6-membered saturated heterocyclic ring containing 1 or 2 heteroatoms selected from 1 or 2 N atoms, 0 or 1 O atoms, and 0 or 1 S atoms; a 5- or 6-membered heteroaromatic ring containing 1 or 2 heteroatoms selected from 1 or 2 N atoms, 0 or 1 O atoms, and 0 or 1 S atoms; or a bicyclic heterocycle which is a benzene ring fused to a 5- or 6-membered saturated heterocyclic ring containing 1 or 2 nitrogen atoms; wherein:
(a) the phenyl, the saturated heterocyclic ring, heteroaromatic ring, or bicyclic heterocycle is optionally substituted with from 1 to 3 substituents each of which is independently
(1) fluoro,
(2) chloro,
(3) bromo,
(4) —OH
(5) —CF$_3$,
(6) —$C_{1-4}$ alkyl, which is optionally substituted with 1 or 2 substituents each of which is independently —OH, —CN, —O—$C_{1-4}$ alkyl, —OCF$_3$, —N($R^aR^b$), —C(=O)N($R^aR^b$), or N($R^a$)—C(=O)—$(CH_2)_{0-2}$N($R^bR^c$),
(7) —OCF$_3$,
(8) —O—$C_{1-4}$ alkyl
(9) —C(=O)$R^a$,
(10) —$CO_2R^a$,
(11) —$SR^a$,
(12) —$SR^a$,
(13) —N($R^aR^b$),
(14) —C(=O)N($R^aR^b$),
(15) —C(=O)—$(CH_2)_{1-2}$—N($R^aR^b$),
(16) —N($R^a$)C(=O)$R^b$, or
(17) —$SO_2R^a$;
(b) the phenyl is optionally mono-substituted with
(1) —$(CH_2)_{1-2}$—$R^m$, or (2) —$(CH_2)$0-2—N($R^a$)—$(CH_2)_{0-2}$—$R^m$; and
(c) the saturated heterocyclic ring, heteroaromatic ring, or bicyclic heterocycle is optionally mono- or di-substituted with
(1) oxo
(2) —$(CH_2)_{1-2}$—$R^m$,
(3) —O—$(CH_2)_{1-2}$—$R^m$, or
(4) —$(CH_2)_{0-1}$—C(=O)—$(CH_2)_{0-2}$—$R^m$; and each $R^m$ is independently cyclopropyl; phenyl; a 5- or 6-membered saturated heterocyclic ring selected from pyrrolidinyl, imidazolidinyl, pyrazolidinyl, piperidinyl, piperazinyl, and morpholinyl; or a 5- or 6-membered heteroaromatic ring selected from thienyl, pyridyl optionally in the form of an N-oxide, imidazolyl, pyrrolyl, pyrazolyl, thiazolyl, isothiazolyl, oxazolyl, isooxazolyl, oxadiazolyl, thiadiazolyl, pyrazinyl, pyrimidinyl, triazolyl, tetrazolyl, furanyl, and pyridazinyl; wherein
the cyclopropyl is unsubstituted;
the phenyl is optionally substituted with from 1 to 3 substituents each of which is independently halogen, —$C_{1-4}$ alkyl, —CF$_3$, —O—$C_{1-4}$ alkyl, —OCF$_3$, or —N($R^aR^b$);
the saturated heterocyclic ring is optionally substituted with 1 or 2 substituents each of which is independently —$C_{1-4}$ alkyl, —CF$_3$, —O—$C_{1-4}$ alkyl, —OCF$_3$, oxo, phenyl, —$(CH_2)_{1-2}$-phenyl, —C(=O)-phenyl, —$CO_2$-phenyl, or —$C_2$—$CH_2$-phenyl; and
the heteroaromatic ring is optionally substituted with 1 or 2 substituents each of which is independently —$C_{1-4}$ alkyl, —CF$_3$, —O—$C_{1-4}$ alkyl, —OCF$_3$, oxo, phenyl, or —$(CH_2)_{1-2}$-phenyl.

8. The method according to claim 7, wherein in the compound of Formula I or a pharmaceutically acceptable salt thereof:
$R^1$ is:
(1) —H,
(2) —$C_{1-4}$ alkyl, which is optionally substituted with from 1 to 3 substituents each of which is independently halogen, —O—$C_{1-4}$ alkyl, —O—$C_{1-4}$ haloalkyl, —C(=O)$R^a$, —$CO_2R^a$, —N($R^aR^b$), or —C(=O)—$(CH_2)_{0-2}$—N($R^aR^b$),
(3) —$R^k$,
(4) —$(CH_2)_{1-4}$—$R^k$, wherein:
(i) the —$(CH_2)_{1-4}$-moiety is optionally substituted with 1 or 2 substituents each of which is independently halogen, —OH, —O—$C_{1-4}$ alkyl, —O—$C_{1-4}$ haloalkyl, or —N($R^aR^b$); and
(ii) the —$(CH_2)_{1-4}$-moiety is optionally mono-substituted with —$R^s$ or —N($R^a$)—$(CH_2)_{1-2}$—$R^s$; wherein $R^s$ is
(a) phenyl which is optionally substituted with from 1 to 3 substituents each of which is independently halogen, —$C_{1-4}$ alkyl, —$C_{1-4}$ alkyl-$OR^a$, —$C_{1-4}$ haloalkyl, —O—$C_{1-4}$ alkyl, or —O—$C_{1-4}$ haloalkyl; or
(b) a 5- or 6-membered heteroaromatic ring containing from 1 to 4 heteroatoms independently selected from N, O and S; wherein the heteroaromatic ring is optionally substituted with from 1 to 3 substituents each of which is independently halogen, —$C_{1-4}$ alkyl, —$C_{1-4}$ alkyl-OR$^a$, —C$_{1-4}$ haloalkyl, —O—C$_{1-4}$ alkyl, or —O—C$_{1-4}$ haloalkyl; or
(c) a 5- or 6-membered saturated heterocyclic ring containing from 1 to 4 heteroatoms independently selected from N, O and S; wherein the saturated heterocyclic ring is optionally substituted with from 1 to 3 substituents each of which is independently halogen, —C$_{1-4}$ alkyl, —C$_{1-4}$ alkyl-OR$^a$, —C$_{1-4}$ haloalkyl, —O—C$_{1-4}$ alkyl, —O—C$_{1-4}$ haloalkyl, —C(=O)R$^a$, or —CO$_2$R$^a$, (5) —C(=O)N(R$^a$)—(CH$_2$)$_{0-3}$—R$^k$,
(6) —C(CH$_3$)$_2$N(R$^a$)C(=O)R$^b$,
(7) —C(CH$_3$)$_2$N(R$^a$)C(=O)R$^k$, or
(8) —C(CH$_3$)$_2$N(R$^a$)C(=O)C(=O)N(R$^b$R$^c$).

9. The method according to claim 1, which is a method for treating infection by HIV.

10. The method according to claim 9, which is a method for treating infection by HIV-1.

11. The method according to claim 10, wherein the compound of Formula I is a compound selected from the group consisting of:

N1-[1-(4-{[(4-fluorobenzyl)amino]carbonyl}-5-hydroxy-1-methyl-6-oxo-1,6-dihydropyrimidin-2-yl)-1-methyl-ethyl]-N2,N2-dimethylethanediamide;

N-(4-fluorobenzyl)-5-hydroxy-1-methyl-2-(1-methyl-1-{[(5-methyl-1,3,4-oxadiazol-2-yl)carbonyl]amino}ethyl)-6-oxo-1,6-dihydropyrimidine-4-carboxamide;

and pharmaceutically acceptable salts thereof.

12. The method according to claim 11, wherein the compound of Formula I is N-(4-fluorobenzyl)-5-hydroxy-1-methyl-2-(1-methyl-1-{[(5-methyl-1,3,4-oxadiazol-2-yl)carbonyl]amino}ethyl)-6-oxo-1,6-dihydropyrimidine-4-carboxamide or a pharmaceutically acceptable salt thereof.

* * * * *

UNITED STATES PATENT AND TRADEMARK OFFICE
CERTIFICATE OF CORRECTION

PATENT NO. : 7,217,713 B2
APPLICATION NO. : 11/491815
DATED : May 15, 2007
INVENTOR(S) : Crescenzi et al.

It is certified that error appears in the above-identified patent and that said Letters Patent is hereby corrected as shown below:

In claim 1, column 165, line 56, replace "-N($R^a$)-C(=)-$C_{0-6}$ alkyl-$R^s$;" with -- -N($R^a$)-C(=O)-$C_{0-6}$ alkyl-$R^s$; --.

In claim 1, column 165, line 61, replace "-$C_{1-6}$ haloalkyl-O-$C_{1-6}$ alkyl," with -- -$C_{1-6}$ haloalkyl, -O-$C_{1-6}$ alkyl, --.

In claim 1, column 167, line 57, replace "-C(=0)$R^a$," with -- -C(=O)$R^a$, --.

In claim 5, column 170, line 31, replace "-$C_{1-6}$ alkyl," with -- -$C_{1-4}$ alkyl, --.

In claim 5, column 170, line 58, replace "-N($R^a$)-C(=O)-$C_{0-4}$ alkyl-$R^s$;" with -- -N($R^a$)-C(=O)-$C_{0-4}$ alkyl-$R^s$, -N($R^a$)-$C_{0-4}$ alkyl-$R^s$, -O-$C_{0-4}$ alkyl-$R^s$, or -N($R^a$)-C(=O)-$C_{0-4}$ alkyl-$R^s$; --.

In claim 5, column 170, line 59, replace "$R^2$" with -- $R^s$ --.

In claim 5, column 170, line 63, replace "-$C_{1-4}$ haloalkyl -O-$C_{1-6}$ alkyl," with -- -$C_{1-4}$ haloalkyl, -O-$C_{1-4}$ alkyl, --.

In claim 5, column 171, line 15, replace "-$C_{1-4}$ alkyl-N($R^a R^b$)," with -- -C(=O)-$C_{0-4}$ alkyl-N($R^a R^b$), --.

In claim 7, column 172, line 4, replace "-(CH$_2$)0-2-N($R^a$)-" with -- -(CH$_2$)$_{0-2}$-N($R^a$)- --.

In claim 7, column 172, line 31, replace "-$C_2$-" with -- -$CO_2$- --.

In claim 8, column 172, line 54, replace "-(CH$_2$)$_{14}$-moiety" with -- -(CH$_2$)$_{1-4}$- moiety --.

UNITED STATES PATENT AND TRADEMARK OFFICE
CERTIFICATE OF CORRECTION

PATENT NO. : 7,217,713 B2
APPLICATION NO. : 11/491815
DATED : May 15, 2007
INVENTOR(S) : Crescenzi et al.

It is certified that error appears in the above-identified patent and that said Letters Patent is hereby corrected as shown below:

In claim 5, column 170, line 48, replace "-N(R$^2$)C(=O)C(=O)N(R$^a$R$^b$)," with -- -N(R$^a$)C(=O)C(=O)N(R$^a$R$^b$), --.

Signed and Sealed this

Sixteenth Day of October, 2007

JON W. DUDAS
*Director of the United States Patent and Trademark Office*

UNITED STATES PATENT AND TRADEMARK OFFICE
CERTIFICATE OF CORRECTION

PATENT NO. : 7,217,713 B2 Page 1 of 1
APPLICATION NO. : 11/491815
DATED : May 15, 2007
INVENTOR(S) : Creszenci et al.

It is certified that error appears in the above-identified patent and that said Letters Patent is hereby corrected as shown below:

On the title page, in the second line of Part (62), replace "PCT/GB02/004743" with -- PCT/GB02/04753 --.

On the title page, on page 1, in the second line of Part (60), replace "60/339,658" with -- 60/339,568 --.

In column 1, line 7, replace "PCT/GB02/004743" with -- PCT/GB02/04753 --.

In column 1, line 9, replace "60/339,658" with -- 60/339,568 --.

Signed and Sealed this

Eighteenth Day of March, 2008

JON W. DUDAS
*Director of the United States Patent and Trademark Office*